United States Patent
Khattak et al.

(10) Patent No.: US 10,272,434 B2
(45) Date of Patent: Apr. 30, 2019

(54) CARTRIDGES, KITS, AND METHODS FOR AMPLIFICATION AND DETECTION OF ANALYTES

(71) Applicant: CUE HEALTH INC., San Diego, CA (US)

(72) Inventors: Ayub Khattak, San Diego, CA (US); Clinton Sever, San Diego, CA (US); Paul Nelson, San Diego, CA (US); Ryan Cooper, San Diego, CA (US); Thomas Congdon, San Diego, CA (US); Justin DeMartino, San Diego, CA (US); Raphael Shapiro, San Diego, CA (US); Mark Duncan, San Diego, CA (US)

(73) Assignee: CUE HEALTH INC., San Diego, CA (US)

( * ) Notice: Subject to any disclaimer, the term of this patent is extended or adjusted under 35 U.S.C. 154(b) by 0 days.

(21) Appl. No.: 15/945,646

(22) Filed: Apr. 4, 2018

(65) Prior Publication Data
US 2018/0229231 A1    Aug. 16, 2018

Related U.S. Application Data

(60) Division of application No. 15/487,956, filed on Apr. 14, 2017, now Pat. No. 9,962,703, which is a
(Continued)

(51) Int. Cl.
*C12M 1/34*      (2006.01)
*B01L 3/00*      (2006.01)
(Continued)

(52) U.S. Cl.
CPC ........... *B01L 3/508* (2013.01); *B01F 11/0266* (2013.01); *B01L 3/5027* (2013.01);
(Continued)

(58) Field of Classification Search
CPC ............... B01L 3/508; B01L 3/502715; B01L 3/502738; B01L 7/52; B01L 3/5027;
(Continued)

(56) References Cited

U.S. PATENT DOCUMENTS

| D115,326 S | 6/1939 | Chott |
|---|---|---|
| 3,915,806 A | 10/1975 | Horlach |

(Continued)

FOREIGN PATENT DOCUMENTS

| CN | 104232622 A | 12/2014 |
|---|---|---|
| EP | 1183102 B1 | 12/2003 |

(Continued)

OTHER PUBLICATIONS

U.S. Appl. No. 14/479,158, filed Sep. 5, 2014, Khattak et al.
(Continued)

*Primary Examiner* — Dennis White
(74) *Attorney, Agent, or Firm* — Foley & Lardner LLP; Antoinette F. Konski; Christopher C. Bolten

(57) ABSTRACT

Devices, systems, and methods for detecting molecules of interest within a collected sample are described herein. In certain embodiments, self-contained sample analysis systems are disclosed, which include a reusable reader component, a disposable cartridge component, and a disposable sample collection component. The reader component may communicate with a remote computing device for the digital transmission of test protocols and test results. In various disclosed embodiments, the systems, components, and methods are configured to identify the presence, absence, and/or quantity of particular nucleic acids, proteins, or other analytes of interest, for example, in order to test for the presence of one or more pathogens or contaminants in a sample.

30 Claims, 50 Drawing Sheets

Related U.S. Application Data continuation of application No. 15/336,735, filed on Oct. 27, 2016, now Pat. No. 9,623,409, which is a continuation of application No. PCT/US2016/042688, filed on Jul. 16, 2016.

(60) Provisional application No. 62/194,101, filed on Jul. 17, 2015.

(51) Int. Cl.

| | |
|---|---|
| *B05D 3/00* | (2006.01) |
| *C12Q 1/6825* | (2018.01) |
| *F16K 99/00* | (2006.01) |
| *G01N 27/28* | (2006.01) |
| *G01N 27/327* | (2006.01) |
| *G01N 33/543* | (2006.01) |
| *G01N 33/58* | (2006.01) |
| *G01N 35/00* | (2006.01) |
| *H04M 1/725* | (2006.01) |
| *B01L 7/00* | (2006.01) |
| *B01F 11/02* | (2006.01) |
| *G01N 1/02* | (2006.01) |
| *G01N 21/78* | (2006.01) |
| *G01N 35/10* | (2006.01) |

(52) U.S. Cl.
CPC ... *B01L 3/502715* (2013.01); *B01L 3/502723* (2013.01); *B01L 3/502738* (2013.01); *B01L 7/52* (2013.01); *B05D 3/002* (2013.01); *C12Q 1/6825* (2013.01); *F16K 99/0032* (2013.01); *F16K 99/0036* (2013.01); *G01N 27/28* (2013.01); *G01N 27/3271* (2013.01); *G01N 27/3273* (2013.01); *G01N 33/54306* (2013.01); *G01N 33/54326* (2013.01); *G01N 33/54333* (2013.01); *G01N 33/54366* (2013.01); *G01N 33/54373* (2013.01); *G01N 33/581* (2013.01); *G01N 35/00029* (2013.01); *G01N 35/0098* (2013.01); *H04M 1/72527* (2013.01); *B01L 3/5029* (2013.01); *B01L 2200/025* (2013.01); *B01L 2200/026* (2013.01); *B01L 2200/027* (2013.01); *B01L 2200/028* (2013.01); *B01L 2200/0668* (2013.01); *B01L 2200/0684* (2013.01); *B01L 2200/0689* (2013.01); *B01L 2200/087* (2013.01); *B01L 2200/10* (2013.01); *B01L 2200/16* (2013.01); *B01L 2300/023* (2013.01); *B01L 2300/025* (2013.01); *B01L 2300/04* (2013.01); *B01L 2300/044* (2013.01); *B01L 2300/06* (2013.01); *B01L 2300/0627* (2013.01); *B01L 2300/0645* (2013.01); *B01L 2300/0681* (2013.01); *B01L 2300/087* (2013.01); *B01L 2300/0816* (2013.01); *B01L 2300/0838* (2013.01); *B01L 2300/0864* (2013.01); *B01L 2300/0867* (2013.01); *B01L 2300/12* (2013.01); *B01L 2300/161* (2013.01); *B01L 2300/1827* (2013.01); *B01L 2400/0406* (2013.01); *B01L 2400/0439* (2013.01); *B01L 2400/0487* (2013.01); *B01L 2400/0677* (2013.01); *B01L 2400/0683* (2013.01); *B05D 2518/00* (2013.01); *F16K 2099/0084* (2013.01); *G01N 1/02* (2013.01); *G01N 21/78* (2013.01); *G01N 27/3272* (2013.01); *G01N 35/1095* (2013.01); *G01N 2001/027* (2013.01); *G01N 2001/028* (2013.01); *G01N 2035/00277* (2013.01); *G01N 2035/00554* (2013.01); *G01N 2458/30* (2013.01); *Y10T 137/1797* (2015.04)

(58) Field of Classification Search
CPC .......... B01L 3/502723; B01L 2300/12; B01L 2200/026; B01L 2200/028; B01L 2200/0668; B01L 2200/0684; B01L 2200/0689; B01L 2200/087; B01L 2200/10; B01L 2200/16; B01L 2300/023; B01L 2300/025; B01L 2200/025; B01L 2300/044; B01L 2300/06; B01L 2300/0627; B01L 2300/0645; B01L 2300/0681; B01L 2300/087; B01L 2300/0816; B01L 2300/0838; B01L 2300/0864; B01L 2300/0867; B01L 2200/027; B01L 2300/161; B01L 2300/1827; B01L 2400/0406; B01L 2400/0439; B01L 2400/0487; B01L 2400/0677; B01L 2400/0683; B01L 3/5029; B01L 2300/04; B05D 3/002; B05D 2518/00; C12Q 1/6825; F16K 99/0032; F16K 99/0036; F16K 2099/0084; G01N 27/28; G01N 27/3271; G01N 27/3273; G01N 33/54306; G01N 33/54326; G01N 33/54333; G01N 33/54366; G01N 33/54373; G01N 33/581; G01N 35/00029; G01N 35/0098; G01N 1/02; G01N 21/78; G01N 27/3272; G01N 35/1095; G01N 2001/027; G01N 2001/028; G01N 2035/00277; G01N 2035/00554; G01N 2458/30; H04M 1/72527; Y10T 137/1797
See application file for complete search history.

(56) References Cited

U.S. PATENT DOCUMENTS

| | | |
|---|---|---|
| D249,062 S | 8/1978 | Crafoord et al. |
| D298,166 S | 10/1988 | Chennault |
| D302,585 S | 8/1989 | Elliott |
| D303,288 S | 9/1989 | Harboe et al. |
| D306,067 S | 2/1990 | Bogdanoff et al. |
| 5,223,414 A | 6/1993 | Zarling et al. |
| 5,273,881 A | 12/1993 | Sena et al. |
| D343,679 S | 1/1994 | Wong |
| 5,455,166 A | 10/1995 | Walker |
| 5,470,723 A | 11/1995 | Walker et al. |
| 5,498,392 A | 3/1996 | Wilding |
| D379,230 S | 5/1997 | Mark |
| 5,708,247 A | 1/1998 | McAleer et al. |
| 5,714,320 A | 2/1998 | Kool |
| D402,753 S | 12/1998 | White |
| 5,935,804 A | 8/1999 | Laine et al. |
| 6,146,590 A | 11/2000 | Mazurek et al. |
| 6,235,502 B1 | 5/2001 | Weissman et al. |
| D458,456 S | 6/2002 | Dragan et al. |
| 6,410,278 B1 | 6/2002 | Notomi et al. |
| 6,514,415 B2 | 2/2003 | Hatch et al. |
| 6,523,560 B1 | 2/2003 | Williams et al. |
| D472,975 S | 4/2003 | Iori et al. |
| 6,686,195 B1 | 2/2004 | Colin et al. |
| 6,893,879 B2 | 5/2005 | Petersen et al. |
| 6,929,915 B2 | 8/2005 | Benkovic et al. |
| D518,597 S | 4/2006 | Sommers |
| 7,118,667 B2 | 10/2006 | Lee |
| 7,195,036 B2 | 3/2007 | Burns et al. |
| D542,931 S | 5/2007 | Pukall et al. |
| 7,282,328 B2 | 10/2007 | Kong et al. |
| 7,285,412 B2 | 10/2007 | Casagrande et al. |
| 7,291,497 B2 | 11/2007 | Holmes et al. |
| 7,399,590 B2 | 7/2008 | Piepenburg et al. |
| 7,432,106 B2 | 10/2008 | Cox |
| 7,466,908 B1 | 12/2008 | Lem et al. |
| 7,478,792 B2 | 1/2009 | Oh et al. |

(56) References Cited

U.S. PATENT DOCUMENTS

| | | | |
|---|---|---|---|
| D591,864 S | 5/2009 | Schmidt | |
| D600,578 S | 9/2009 | Tsuji | |
| 7,635,594 B2 | 12/2009 | Holmes et al. | |
| 7,723,099 B2 | 5/2010 | Miller et al. | |
| 7,888,125 B2 | 2/2011 | Gibbons et al. | |
| 7,981,696 B2 | 7/2011 | Moreland et al. | |
| 8,007,999 B2 | 8/2011 | Holmes et al. | |
| 8,008,034 B2 | 8/2011 | Gibbons et al. | |
| 8,012,744 B2 | 9/2011 | Gibbons et al. | |
| D646,189 S | 10/2011 | Dinter et al. | |
| 8,071,054 B2 | 12/2011 | Oh et al. | |
| 8,071,308 B2 | 12/2011 | Piepenburg et al. | |
| 8,101,402 B2 | 1/2012 | Holmes | |
| 8,202,697 B2 | 6/2012 | Holmes | |
| 8,216,832 B2 | 7/2012 | Battrell et al. | |
| 8,265,955 B2 | 9/2012 | Michelson et al. | |
| 8,283,155 B2 | 10/2012 | Holmes et al. | |
| 8,361,808 B2 | 1/2013 | Wang | |
| D679,025 S | 3/2013 | Motadel et al. | |
| 8,435,738 B2 | 5/2013 | Holmes | |
| 8,449,842 B2 | 5/2013 | Knopp et al. | |
| 8,470,524 B2 | 6/2013 | Gibbons et al. | |
| 8,475,739 B2 | 7/2013 | Holmes et al. | |
| 8,528,777 B2 | 9/2013 | Harder et al. | |
| 8,551,714 B2 | 10/2013 | Jovanovich et al. | |
| 8,562,918 B2 | 10/2013 | Jovanovich et al. | |
| D698,036 S | 1/2014 | Dickinson | |
| 8,637,253 B2 | 1/2014 | Piepenburg et al. | |
| 8,669,047 B2 | 3/2014 | Holmes et al. | |
| 8,679,407 B2 | 3/2014 | Holmes et al. | |
| 8,724,833 B1 | 5/2014 | Shain et al. | |
| 8,735,104 B2 | 5/2014 | Harder et al. | |
| D707,847 S | 6/2014 | Motadel et al. | |
| 8,741,230 B2 | 6/2014 | Holmes et al. | |
| 8,778,665 B2 | 7/2014 | Gibbons et al. | |
| 8,802,445 B2 | 8/2014 | Linder et al. | |
| D718,462 S | 11/2014 | Cook et al. | |
| 8,883,518 B2 | 11/2014 | Roy et al. | |
| D719,666 S | 12/2014 | Manian | |
| 8,945,880 B2 | 2/2015 | Cloake et al. | |
| 9,028,773 B2 | 5/2015 | Ganesan | |
| 9,034,168 B2 | 5/2015 | Khattak et al. | |
| 9,052,275 B2 | 6/2015 | Khattak et al. | |
| 9,086,417 B2 | 7/2015 | Khattak et al. | |
| 9,176,126 B2 | 11/2015 | Holmes et al. | |
| D745,185 S | 12/2015 | Kimura et al. | |
| D745,423 S | 12/2015 | Khattak et al. | |
| 9,207,244 B2 | 12/2015 | Khattak et al. | |
| 9,207,245 B2 | 12/2015 | Khattak | |
| 9,310,231 B2 | 4/2016 | Bloss et al. | |
| 9,360,491 B2 | 6/2016 | Sever et al. | |
| 9,435,793 B2 | 9/2016 | Burd et al. | |
| D774,407 S | 12/2016 | Khattak et al. | |
| 9,522,397 B2 | 12/2016 | Khattak et al. | |
| 9,623,409 B2 | 4/2017 | Khattak et al. | |
| 9,636,676 B2 | 5/2017 | Sever et al. | |
| D789,815 S | 6/2017 | Khattak et al. | |
| 9,718,058 B2 | 8/2017 | Khattak et al. | |
| 9,724,691 B2 | 8/2017 | Khattak et al. | |
| 9,789,483 B2 | 10/2017 | Khattak et al. | |
| 9,808,804 B2 | 11/2017 | Khattak et al. | |
| 9,962,703 B2 | 5/2018 | Khattak et al. | |
| D820,130 S | 6/2018 | Khattak et al. | |
| D821,602 S | 6/2018 | Sever et al. | |
| 2002/0002326 A1 | 1/2002 | Causey et al. | |
| 2002/0123048 A1 | 9/2002 | Gau, Jr. | |
| 2002/0137234 A1 | 9/2002 | Wohlstadter et al. | |
| 2003/0019522 A1 | 1/2003 | Parunak | |
| 2004/0082878 A1 | 4/2004 | Baldwin et al. | |
| 2004/0173456 A1 | 9/2004 | Boos et al. | |
| 2004/0189311 A1 | 9/2004 | Glezer et al. | |
| 2004/0214200 A1 | 10/2004 | Brown et al. | |
| 2004/0219732 A1 | 11/2004 | Burns et al. | |
| 2005/0136529 A1 | 6/2005 | Yang et al. | |
| 2005/0171528 A1* | 8/2005 | Sartor | A61B 18/042 606/41 |
| 2005/0178700 A1 | 8/2005 | Tyvoll et al. | |
| 2005/0200643 A1 | 9/2005 | Falcon | |
| 2006/0131994 A1 | 6/2006 | D'Angelico et al. | |
| 2006/0160205 A1* | 7/2006 | Blackburn | B01F 13/0059 435/287.2 |
| 2006/0207891 A1 | 9/2006 | Althaus et al. | |
| 2006/0243591 A1 | 11/2006 | Plotkin et al. | |
| 2007/0031283 A1 | 2/2007 | Davis et al. | |
| 2007/0060815 A1 | 3/2007 | Martin et al. | |
| 2007/0154922 A1 | 7/2007 | Collier et al. | |
| 2007/0184547 A1 | 8/2007 | Handique et al. | |
| 2007/0299364 A1 | 12/2007 | Sangha | |
| 2008/0124779 A1 | 5/2008 | Oh et al. | |
| 2008/0160601 A1 | 7/2008 | Handique | |
| 2008/0160622 A1 | 7/2008 | Su et al. | |
| 2008/0160630 A1 | 7/2008 | Liu et al. | |
| 2008/0182301 A1 | 7/2008 | Handique et al. | |
| 2008/0275229 A1 | 11/2008 | Lem et al. | |
| 2008/0302193 A1 | 12/2008 | Bommarito et al. | |
| 2009/0061450 A1 | 3/2009 | Hunter | |
| 2009/0130777 A1 | 5/2009 | Arinaga et al. | |
| 2010/0180980 A1 | 7/2010 | Lee et al. | |
| 2010/0236340 A1 | 9/2010 | Lee et al. | |
| 2010/0274155 A1* | 10/2010 | Battrell | A61B 10/0096 600/572 |
| 2010/0280146 A1 | 11/2010 | Vanderlaan et al. | |
| 2010/0297708 A1 | 11/2010 | Collier et al. | |
| 2010/0331652 A1 | 12/2010 | Groll et al. | |
| 2011/0008813 A1 | 1/2011 | Dilleen et al. | |
| 2011/0059468 A1 | 3/2011 | Earhart et al. | |
| 2011/0129841 A1 | 6/2011 | Heid et al. | |
| 2011/0165562 A1 | 7/2011 | Pourahmadi et al. | |
| 2011/0171754 A1 | 7/2011 | Redmond et al. | |
| 2011/0212440 A1 | 9/2011 | Viovy et al. | |
| 2011/0233073 A1 | 9/2011 | Laczka et al. | |
| 2011/0272294 A1 | 11/2011 | Fujiwara | |
| 2012/0009588 A1 | 1/2012 | Rajagopal et al. | |
| 2012/0014836 A1 | 1/2012 | Dittmer | |
| 2012/0071342 A1 | 3/2012 | Lochhead et al. | |
| 2012/0095316 A1 | 4/2012 | Lewis et al. | |
| 2012/0164036 A1 | 6/2012 | Stern et al. | |
| 2012/0180580 A1 | 7/2012 | Immink et al. | |
| 2012/0190589 A1 | 7/2012 | Anderson et al. | |
| 2012/0255860 A1 | 10/2012 | Briman et al. | |
| 2012/0267258 A1 | 10/2012 | Uraoka et al. | |
| 2012/0271127 A1 | 10/2012 | Battrell et al. | |
| 2013/0011210 A1 | 1/2013 | Toner et al. | |
| 2013/0029324 A1 | 1/2013 | Rajagopal et al. | |
| 2013/0085680 A1 | 4/2013 | Arlen et al. | |
| 2013/0137591 A1 | 5/2013 | Clemens et al. | |
| 2013/0145591 A1 | 6/2013 | Chen | |
| 2013/0244339 A1 | 9/2013 | Ehrenkranz et al. | |
| 2013/0273528 A1 | 10/2013 | Ehrenkranz | |
| 2013/0309778 A1 | 11/2013 | Lowe et al. | |
| 2014/0027286 A1 | 1/2014 | Ikegami et al. | |
| 2014/0030717 A1 | 1/2014 | Zhong et al. | |
| 2014/0194305 A1 | 7/2014 | Kayyem et al. | |
| 2014/0242622 A1 | 8/2014 | Petrich et al. | |
| 2014/0335520 A1 | 11/2014 | Jackson et al. | |
| 2014/0336083 A1 | 11/2014 | Khattak et al. | |
| 2015/0129049 A1 | 5/2015 | Khattak et al. | |
| 2015/0140556 A1 | 5/2015 | Albert et al. | |
| 2016/0091518 A1 | 3/2016 | Khattak et al. | |
| 2016/0279635 A1 | 9/2016 | Sever et al. | |
| 2017/0043334 A1 | 2/2017 | Khattak et al. | |
| 2017/0043335 A1 | 2/2017 | Khattak et al. | |
| 2017/0043336 A1 | 2/2017 | Khattak et al. | |
| 2017/0043342 A1 | 2/2017 | Khattak et al. | |
| 2017/0045507 A1 | 2/2017 | Khattak et al. | |
| 2017/0045508 A1 | 2/2017 | Khattak et al. | |
| 2017/0080421 A1 | 3/2017 | Khattak et al. | |
| 2017/0216842 A1 | 8/2017 | Khattak et al. | |
| 2017/0241845 A1 | 8/2017 | Hwang et al. | |
| 2017/0248622 A1 | 8/2017 | Khattak et al. | |

(56) References Cited

U.S. PATENT DOCUMENTS

2017/0266657 A1    9/2017    Khattak et al.
2018/0147575 A1    5/2018    Khattak et al.

FOREIGN PATENT DOCUMENTS

| | | |
|---|---|---|
| EP | 2 050 498 A1 | 4/2009 |
| EP | 2 179 294 A2 | 4/2010 |
| GB | 2 430 032 A | 3/2007 |
| JP | 2007-505319 | 3/2007 |
| JP | 2009-531064 | 9/2009 |
| JP | 2009-226404 A | 10/2009 |
| JP | 2011-013043 A | 1/2011 |
| JP | 2012-504956 | 3/2012 |
| JP | 2012-127978 A | 7/2012 |
| JP | 2012-173181 A | 9/2012 |
| JP | 2012-521558 | 9/2012 |
| JP | 2012-528995 | 11/2012 |
| WO | WO-2005/026689 | 3/2005 |
| WO | WO 2006/121510 | 11/2006 |
| WO | WO-2007/112114 A2 | 10/2007 |
| WO | WO-2009/018473 A1 | 2/2009 |
| WO | WO-2010/003212 A1 | 1/2010 |
| WO | WO-2010/036808 A1 | 4/2010 |
| WO | WO-2010/041231 | 4/2010 |
| WO | WO-2010/109392 A1 | 9/2010 |
| WO | WO-2010/140128 | 12/2010 |
| WO | WO-2012/025729 A1 | 3/2012 |
| WO | WO-2012/032294 A1 | 3/2012 |
| WO | WO-2012/147426 | 11/2012 |
| WO | WO-2012/170703 A1 | 12/2012 |
| WO | WO-2013/136115 A1 | 9/2013 |
| WO | WO-2013/144643 A2 | 10/2013 |
| WO | WO 2016/040642 | 3/2016 |

OTHER PUBLICATIONS

U.S. Appl. No. 15/664,904, filed Jul. 31, 2017, Khattak et al.
U.S. Appl. No. 15/785,394, filed Oct. 16, 2017, Khattak et al.
U.S. Appl. No. 29/584,030, filed Nov. 10, 2016, Khattak et al.
U.S. Appl. No. 29/584,715, filed Nov. 16, 2016, Khattak et al.
U.S. Appl. No. 29/591,165, filed Jan. 17, 2017, Khattak et al.
Anderson, J.C. et al.(2008) "Thermally-Actuated Microfluidic Systems," JALA 13:65-72.
Beyor, N. et al. (2008) "Immunomagnetic bead-based cell concentration microdevice for dilute pathogen detection," Biomed Microdevices 10:909-917.
Boon, E.M. et al. (2003) "Reduction of Ferricyanide by Methylene Blue at a DNA-Modified Rotating-Disk Electrode," Langmuir 19(22):9255-9259.
Borjac-Natour, J.M. et al. (2004) "Divergence of the mRNA targets for the Ssb proteins of bacteriophages T4 and RB69," Virol. J. 1(4): 14 pages.
Brill, A.S. et al. (1967) "Reactions of Horseradish Peroxidase with Azide. Evidence for a Methionine Residue at the Active Site," Biochemistry 6(11):3528-3535.
Cecchet, F. et al. (2006) "Redox Mediation at 11-Mercaptoundecanoic Acid Self-Assembled Monolayers on Gold," J. Phys. Chem. B 110:2241-2248.
Chakrabarti, R. et al. (2001) "The enhancement of PCR amplification by low molecular weight amides," Nucleic Acids Res. 29(11):2377-2381.
Chen, Z. et al. (2005) "Thermally-actuated, phase change flow control for microfluidic systems," Lab Chip 5:1277-1285.
Cho, H. et al. (2007) "How the capillary burst microvalve works," Journal of Colloid and Interface Science 306:379-385.
Clinical IVD Products: Liat™ Analyzer; IQuum, Inc.: http://www.iquum.com/products/analyzer.shtml. Last accessed May 5, 2014.
Desplats, C. et al. (2002) "Snapshot of the Genome of the Pseudo-T-Even Bacteriophage RB49," J. Bacteriol. 184(10):2789-2804.
Dong, F. et al. (1996) "A coupled complex of T4 DNA replication helicase (gp41) and polymerase (pg43) can perform rapid and processive DNA strand-displacement synthesis," Proc. Natl. Acad. Sci. USA 93:14456-14461.

Fan, R. et al. (2008) "Integrated barcode chips for rapid, multiplexed analysis of proteins in microliter quantities of blood," Nature Biotechnology 26(12):1373-1378.
Ferguson, B.S. et al. (2009) "Integrated Microfluidic Electrochemical DNA Sensor," Anal. Chem. 81:6503-6508.
Frackman, S. et al. (1998) "Betaine and DMSA: Enhancing Agents for PCR," Promega Notes 65:27.
Fujisawa T Al. (1985) "Sequence of the T4 recombination gene, uvsX, and its comparison with that of recA gene of *Escherichia coli*," Nuclec Acid Res. 13(20):7473-7481.
Harada, K. et al. (1993) "In vitro selection of optimal DNA substrates for T4 RNA ligase," Proc. Natl. Acad. Sci. USA 90:1576-1579.
Henares, T.G. et al. (2007) "Integration of Multianalyte Sensing Functions on a Capillary-Assembled Microchip: Simultaneous Determination of Ion Concentrations and Enzymatic Activities by a "Drop-and-Sip" Technique," Anal. Chem. 79:908-915.
Jagannathan, H. et al. (2001) "Micro-Fluidic Channels with Integrated Ultrasonic Transducers," IEEE Ultrasonics Symposium:859-862.
Jarvis, T.C. et al. (1990) "'Macromolecular Crowding': Thermodynamic Consequences for Protein-Protein Interactions within the T4 DNA Replication Complex," J. Biol. Chem. 265(25):15160-15167.
Jarvis, T.C. et al. (1991) "Stimulation of the Processivity of the DNA Polymerase of Bacteriophage T4 by the Polymerase Accessory Proteins," J. Biol. Chem. 266(3):1830-1840.
Kaigala, G.V. et al. (2008) "Electrically controlled microvalves to integrate microchip polymerase chain reaction and capillary electrophoresis," Lab Chip 8:1071-1078.
Kim, D. et al. (2007) "A Bi-Polymer Micro One-Way Valve," Sensors and Actuators A 136:426-433.
Kinoshita, T. et al. (2007) "Functionalization of Magnetic Gold/Iron-Oxide Composite Nanoparticles with Oligonucleotides and Magnetic Separation of Specific Target," J. of Magnetism and Magnetic Materials 311:255-258.
Kwakye, S. et al. (2006) "Electrochemical Microfluidic Biosensor for Nucleic Acid Detection with Integrated Minipotentiostat," Biosensors and Bioelectronics 21: 2217-2223.
Laschi, S. et al. (2010) "A New Gravity-Driven Microfluidic-Based Electrochemical Assay Coupled to Magnetic Beads for Nucleic Acid Detection," Electrophoresis 31: 3727-3736.
Lavery, P.E. et al. (1992) "Enhancement of recA Protein-promoted DNA Strand Exchange Activity by Volume-occupying Agents," J. Biol. Chem. 267(13):9307-9314.
Lawi, W. et al. (2009) "A Microfluidic Cartridge System for Multiplexed Clinical Analysis," J. Assoc. Laboratory Automation 14(6):407-412.
Lee, C.S. et al. (2001) "Microelectromagnets for the Control of Magnetic Nanoparticles," Applied Physics Letters 79(20):3308-3310.
Lillehoj, P.B. et al. (2010) "A Self-Pumping Lab-on-a-Chip for Rapid Detection of Botulinum Toxin," Lab Chip 10: 2265-2270.
Liu, R.H. et al. (2004) "Self-Contained, Fully Integrated Biochip for Sample Preparation, Polymerase Chain Reaction Amplification, and DNA Microarray Detection," Analytical Chemistry 76(7):1824-1831.
Liu, R.H. et al. (2004) "Single-use, Thermally Actuated Paraffin Valves for Microfluidic Applications," Sensors and Actuators B 98:328-336.
Lomas, N. (2014) "Cue Is a Connected Lab-In-A-Box for On-Demand Health Testing At Home," TechCrunch.
Ma, X. et al. (1988) "Role of oxygen during horseradish peroxidase turnover and inactivation," Biochem Biophys Res Commun. 157(1):160-165.
Marentis, T.C. et al. (2005) "Microfluidic Sonicator for Real-Time Disruption of Eukaryotic Cells and Bacterial Spores for DNA Analysis," Ultrasound in Med. & Biol. 31(9):1265-1277.
Morrical, S.W. et al. (1991) "Amplification of Snap-back DNA Synthesis Reactions by the uvsX Recombinase of Bacteriophage T4," J. Biol. Chem. 266(21):14031-14038.

(56) References Cited

OTHER PUBLICATIONS

Mrksich, M. et al. (1997) "Using Self-Assembled Monolayers that Present Oligo(ethylene glycol) Groups to Control the Interactions of Proteins with Surfaces," American Chemical Society Symposium Series 680:361-373.
PCT International Search Report and Written Opinion (ISA/EP) for International Application No. PCT/US2015/049439, dated Dec. 7, 2015, 15 pages.
PCT International Search Report and Written Opinion (ISA/KR) for International Application No. PCT/US2014/023821, dated Jul. 7, 2014, 12 pages.
PCT International Search Report and Written Opinion, PCT/US2016/042688, Cue Inc, 16 pages (dated Jan. 10, 2017).
Prindle, D. (2014) "Sick? Need more vitamin D? Testosterone? Lick a stick and Cue fills you in," www.digitaltrends.com.
Reddy, M.K. et al. (1993) "Assembly of a functional replication complex without ATP hydrolysis: A direct interaction of bacteriophage T4 gp45 with T4 DNA polymerase," Proc. Natl. Acad. Sci. USA 90:3211-3215.
Rida, A. et al. (2004) "Manipulation of Self-Assembled Structures of Magnetic Beads for Microfluidic Mixing and Assaying," Analytical Chemistry 76(21):6239-6246.
Roderee, K. et al. (2011) "DNA Hybridization Enhancement Using Piezoelectric Microagitation through a Liquid Coupling Medium," Lab Chip, doi:10.1039/C0LC00419G.
Sharma, V. et al. (2007) "Surface Characterization of Plasma-Treated and PEG-Grafted PDMS for Micro Fluidic Applications," Vacuum 81:1094-1100.
Shin, Y.S. et al. (2010) "Chemistries for Patterning Robust DNA MicroBarcodes Enable Multiplex Assays of Cytoplasm Proteins from Single Cancer Cells," ChemPhysChem 11:3063-3069.
Simplexa™ Flu A/B & RSV Direct Kit; Focus Diagnostics, Inc.: https://www.focusdx.com/product/MOL2650. Last accessed May 5, 2014.
Sun, S. et al. (2003) "Biochemical Characterization of Interactions between DNA Polymerase and Single-stranded DNA-binding Protein in Bacteriophage RB69," J. Biol. Chem. 278(6):3876-3881.
Taylor, M.T. et al. (2001) "Lysing Bacterial Spores by Sonication through a Flexible Interface in a Microfluidic System," Analytical Chemistry 73(3):492-496.
The FilmArray System; Biofire Diagnostics, Inc.: http://filmarray.com/the-panels/. Last accessed May 5, 2014.
U.S. Office Action for U.S. Appl. No. 14/205,146 dated Sep. 26, 2014. (6 pages).
U.S. Office Action for U.S. Appl. No. 14/205,146 dated Apr. 3, 2015. (13 pages).
U.S. Office Action for U.S. Appl. No. 14/205,146 dated Oct. 22, 2015. (13 pages).
U.S. Office Action for U.S. Appl. No. 14/205,146 dated Apr. 6, 2016. (9 pages).
U.S. Office Action for U.S. Appl. No. 14/205,146 dated Dec. 21, 2016. (13 pages).
U.S. Office Action for U.S. Appl. No. 14/205,146 dated Jun. 23, 2017. (11 pages).
U.S. Office Action for U.S. Appl. No. 14/479,149 dated Jan. 13, 2015. (21 pages).
U.S. Office Action for U.S. Appl. No. 14/479,149 dated Mar. 6, 2015. (14 pages).
U.S. Office Action for U.S. Appl. No. 14/543,842 dated Feb. 12, 2015. (14 pages).
U.S. Office Action for U.S. Appl. No. 14/543,842 dated Apr. 24, 2015. (10 pages).
U.S. Office Action for U.S. Appl. No. 14/599,365 dated May 1, 2015. (13 pages).
U.S. Office Action for U.S. Appl. No. 14/599,369 dated May 7, 2015. (6 pages).
U.S. Office Action for U.S. Appl. No. 14/599,369 dated Aug. 18, 2015. (15 pages).
U.S. Office Action for U.S. Appl. No. 14/599,369 dated Jan. 4, 2016. (8 pages).
U.S. Office Action for U.S. Appl. No. 14/599,369 dated Apr. 22, 2016. (9 pages).
U.S. Office Action for U.S. Appl. No. 14/599,369 dated May 11, 2016. (4 pages).
U.S. Office Action for U.S. Appl. No. 14/599,372 dated Mar. 27, 2015, 11 pages.
U.S. Office Action for U.S. Appl. No. 14/599,372 dated Sep. 14, 2015. (17 pages).
U.S. Office Action for U.S. Appl. No. 14/599,375 dated Jun. 19, 2015. (20 pages).
U.S. Office Action for U.S. Appl. No. 14/599,375 dated Aug. 26, 2015. (13 pages).
U.S. Office Action for U.S. Appl. No. 14/954,817 dated Feb. 2, 2016. (21 pages).
U.S. Office Action for U.S. Appl. No. 14/954,817 dated May 23, 2016. (15 pages).
U.S. Office Action for U.S. Appl. No. 14/954,817 dated Sep. 19, 2016. (6 pages).
U.S. Office Action for U.S. Appl. No. 14/954,817 dated Nov. 3, 2016. (9 pages).
U.S. Office Action for U.S. Appl. No. 15/172,077 dated Feb. 10, 2017. (19 pages).
U.S. Office Action for U.S. Appl. No. 15/172,077 dated Mar. 7, 2017. (4 pages).
U.S. Office Action for U.S. Appl. No. 15/336,487 dated Jan. 30, 2017. (27 pages).
U.S. Office Action for U.S. Appl. No. 15/336,487 dated Jun. 6, 2017. (26 pages).
U.S. Office Action for U.S. Appl. No. 15/336,502 dated Jan. 27, 2017. (31 pages).
U.S. Office Action for U.S. Appl. No. 15/336,502 dated Jul. 14, 2017. (11 pages).
U.S. Office Action for U.S. Appl. No. 15/336,502 dated Feb. 21, 2018. (14 pages).
U.S. Office Action for U.S. Appl. No. 15/336,712 dated Mar. 16, 2017. (25 pages).
U.S. Office Action for U.S. Appl. No. 15/336,712 dated Jul. 12, 2017. (9 pages).
U.S. Office Action for U.S. Appl. No. 15/336,712 dated Sep. 20, 2017. (5 pages).
U.S. Office Action for U.S. Appl. No. 15/336,715 dated Feb. 9, 2017. (8 pages).
U.S. Office Action for U.S. Appl. No. 15/336,715 dated May 17, 2017. (17 pages).
U.S. Office Action for U.S. Appl. No. 15/336,715 dated Jun. 29, 2017. (3 pages).
U.S. Office Action for U.S. Appl. No. 15/336,735 dated Jan. 5, 2017. (10 pages).
U.S. Office Action for U.S. Appl. No. 15/336,735 dated Feb. 13, 2017. (5 pages).
U.S. Office Action for U.S. Appl. No. 15/336,739 dated Mar. 21, 2017. (18 pages).
U.S. Office Action for U.S. Appl. No. 15/336,739 dated Jul. 21, 2017. (7 pages).
U.S. Office Action for U.S. Appl. No. 15/336,739 dated Feb. 26, 2018. (8 pages).
U.S. Office Action for U.S. Appl. No. 29/490,660 dated Jun. 25, 2014. (6 pages).
U.S. Office Action for U.S. Appl. No. 29/490,660 dated Jun. 2, 2015. (11 pages).
U.S. Office Action for U.S. Appl. No. 29/490,660 dated Aug. 20, 2015. (9 pages).
U.S. Office Action for U.S. Appl. No. 29/545,014 dated May 10, 2016. (15 pages).
U.S. Office Action for U.S. Appl. No. 29/545,014 dated Sep. 2, 2016. (10 pages).
U.S. Office Action for U.S. Appl. No. 29/574,538 dated Feb. 17, 2017. (8 pages).
U.S. Office Action for U.S. Appl. No. 29/584,030 dated Nov. 29, 2017. (8 pages).
U.S. Office Action for U.S. Appl. No. 29/584,030 dated Feb. 22, 2018. (6 pages).

(56) References Cited

OTHER PUBLICATIONS

U.S. Office Action for U.S. Appl. No. 29/584,715 dated Feb. 20, 2018. (7 pages).
U.S. Office Action for U.S. Appl. No. 29/591,165 dated Nov. 29, 2017. (18 pages).
Wang, J. (2002) "Portable Electrochemical Systems," Trends in Analytical Chemistry 21(4):226-232.
Wang, J. et al. (2005) "Self-Actuated, Thermo-Responsive Hydrogel Valves for Lab on a Chip," Biomedical Microdevices 7(4):313-322.
Wang, J. et al. (2010) "A Self-Powered, One-Step Chip for Rapid, Quantitative and Multiplexed Detection of Proteins from Pinpricks of Whole Blood," Lab Chip 10:3157-3162.
Wu, C. et al. (2011) "Ultrasonication on a Microfluidic Chip to Lyse Single and Multiple Pseudo-Nitzschia for Marine Biotoxin Analysis," Biotechnology Journal 6:150-155.
Xpert® Flu; Cepheid: http://www.cepheid.com/us/cepheid-solutions/clinical-ivd-tests/critical-infectious-diseases/xpert-flu. Last accessed May 5, 2014.
Yoshioka, K. et al. (2010) "Suppression of Non-specific Adsorption Using Densified Tri(ethylene glycol) Alkanethiols: Monolayer Characteristics Evaluated by Electrochemical Measurements," Analytical Sciences 26:33-37.
Zhang, Z. et al. (1998) "Strand Exchange Protein 1 (Sep1) from *Saccharomyces cerevisiae* Does not Promote Branch Migration in Vitro," J. Biol. Chem. 273(9):4950-4956.
Ziegler, J. et al. (2008) "High-Performance Immunoassays Based on Through-Stencil Patterned Antibodies and Capillary Systems," Analytical Chemistry 80(5):1763-1769.
U.S. Office Action for U.S. Appl. No. 15/487,956 dated Oct. 18, 2017. (6 pages).
U.S. Office Action for U.S. Appl. No. 15/487,956 dated Jan. 31, 2018. (8 pages).
U.S. Office Action for U.S. Appl. No. 15/487,956 dated Mar. 14, 2018. (2 pages).
U.S. Appl. No. 15/945,646, filed Apr. 4, 2018, Khattak et al.
U.S. Appl. No. 29/647,395, filed May 11, 2018, Khattak et al.
U.S. Appl. No. 29/648,269, filed May 18, 2018, Sever et al.
Company Profile: Nemera (Injectbles Offering), www.ondrugdeliver.com, Issue 71, Oct. 2016, pp. 32-35, retrieved from Internet https://www.ondrugdelivery.com/publications/71/Nemera.pdf.
Nemera Safe'n'Sound Product Leaflet, 2017, http://www.nemera.net/wp-content/uploads/2017/11/Nemera-SAFENSOUND_ProductLeaflet_LD.pdf (4 pages).
PCT International Search Report and Written Opinion for Application No. PCT/US2018/015111 dated Apr. 13, 2018. (11 pages).
Syrina Data Sheet, Bespak, Oct. 28, 2015, retrieved from Internet http://www.bespak.com/wp-content/uploads/2015/10/U969_DATA-SHEET_Bespak_AW_TEMPLATE_SYRINA-ARTWORK1.pdf (2 pages).
U.S. Notice of Allowability for U.S. Appl. No. 29/584,030 dated May 18, 2018. (7 Pages).
U.S. Notice of Allowance for U.S. Appl. No. 29/591,165 dated Apr. 11, 2018. (9 pages).
U.S. Office Action for U.S. Appl. No. 15/785,394 dated Apr. 13, 2018. (6 pages).
U.S. Notice of Allowability for U.S. Appl. No. 15/368,249 dated Sep. 24, 2018. (7 pages).
U.S. Notice of Allowability for U.S. Appl. No. 29/584,715 dated May 14, 2018. (2 pages).
U.S. Notice of Allowability for U.S. Appl. No. 29/584,715 dated Mar. 30, 2018. (2 pages).
U.S. Notice of Allowability for U.S. Appl. No. 29/574,538 dated May 12, 2017. (2 pages).
U.S. Notice of Allowability for U.S. Appl. No. 29/545,014 dated Nov. 14, 2016. (2 pages).
U.S. Notice of Allowability for U.S. Appl. No. 29/591,165 dated May 21, 2018. (4 pages).

\* cited by examiner

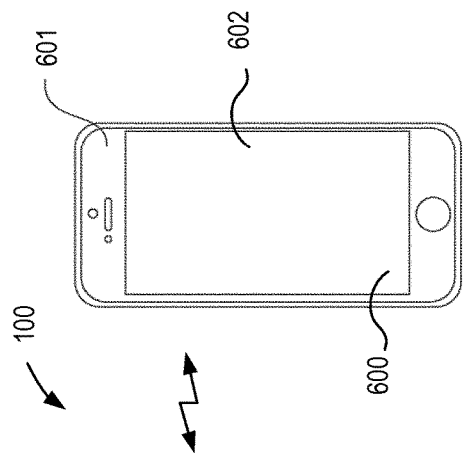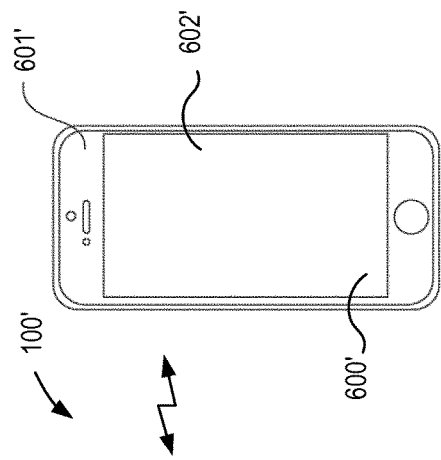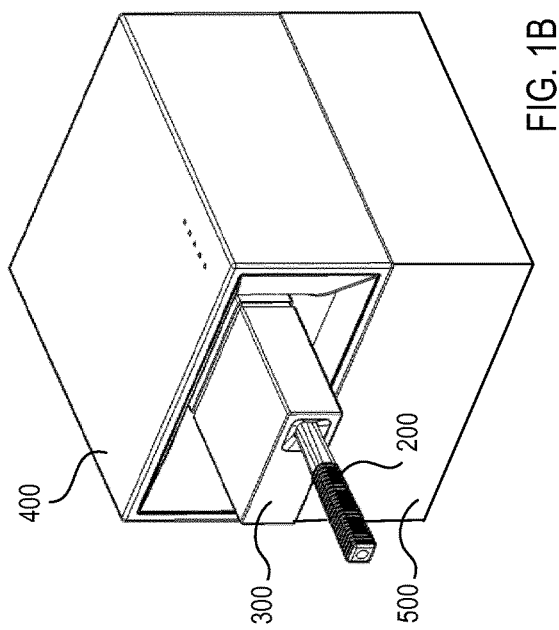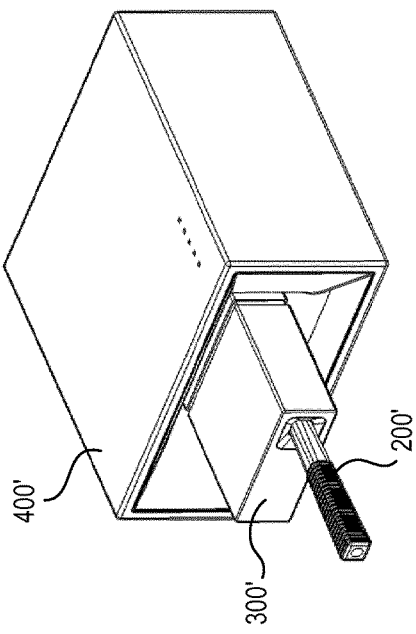
FIG. 1B
FIG. 1C

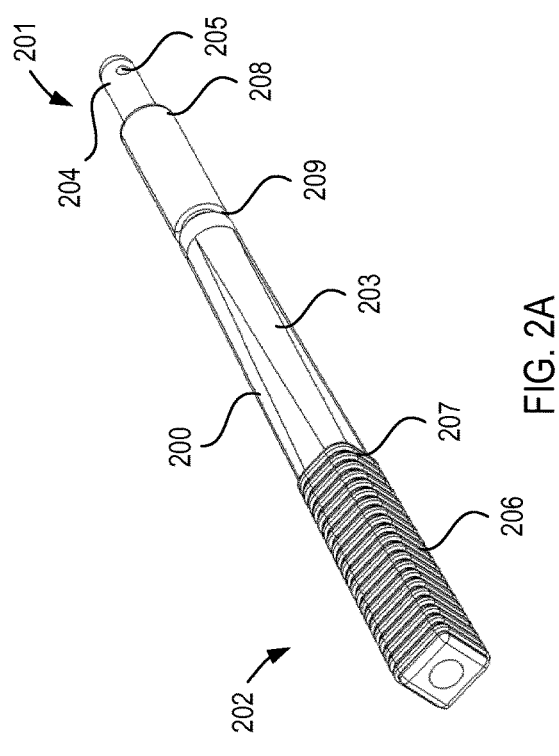
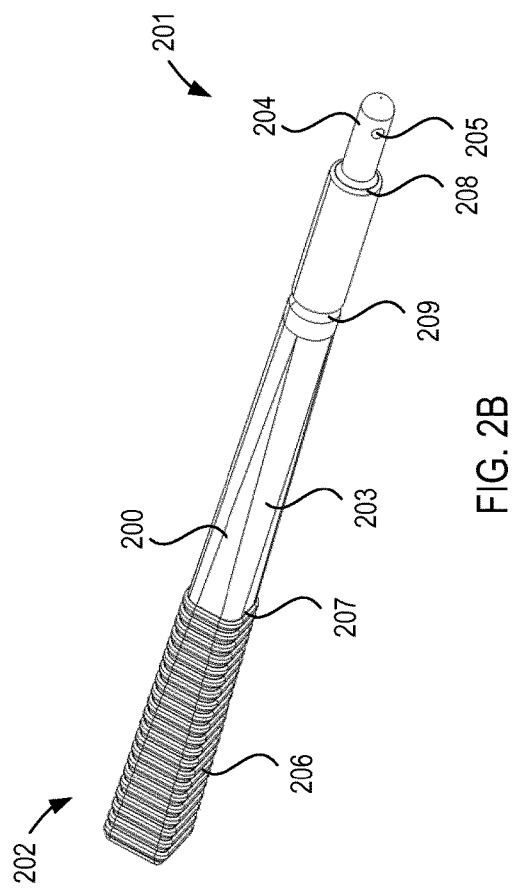
FIG. 2A
FIG. 2B

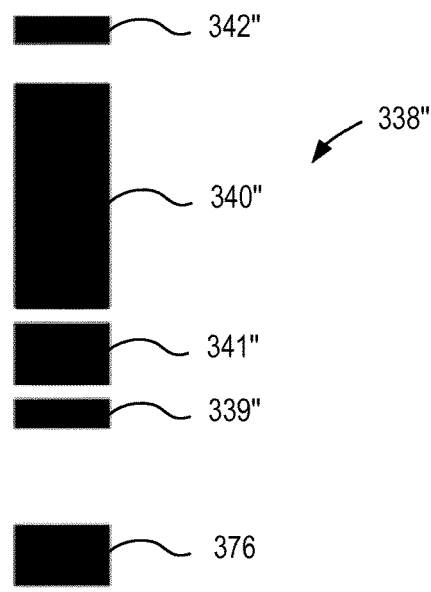
FIG. 7D
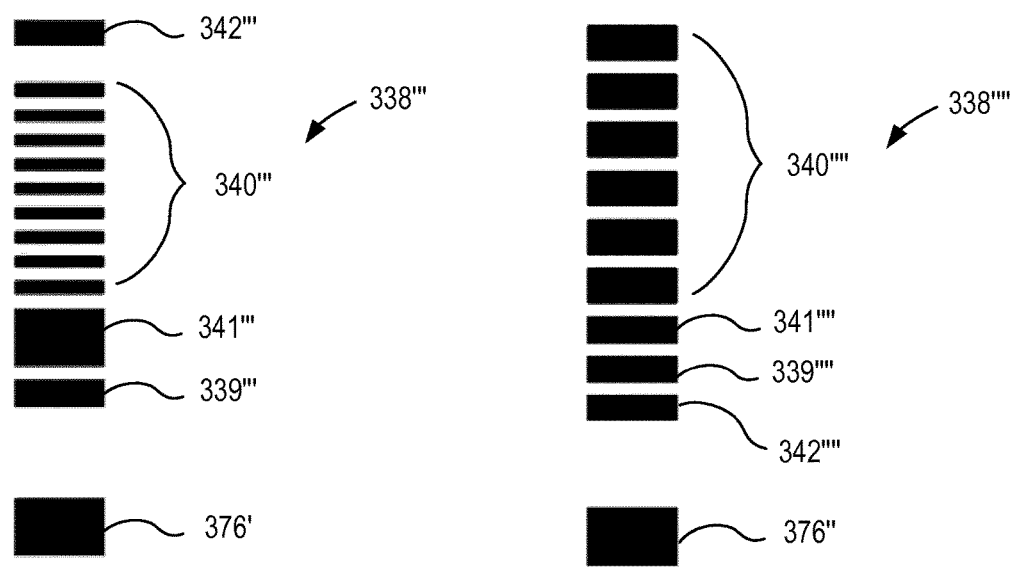
FIG. 7E
FIG. 7F

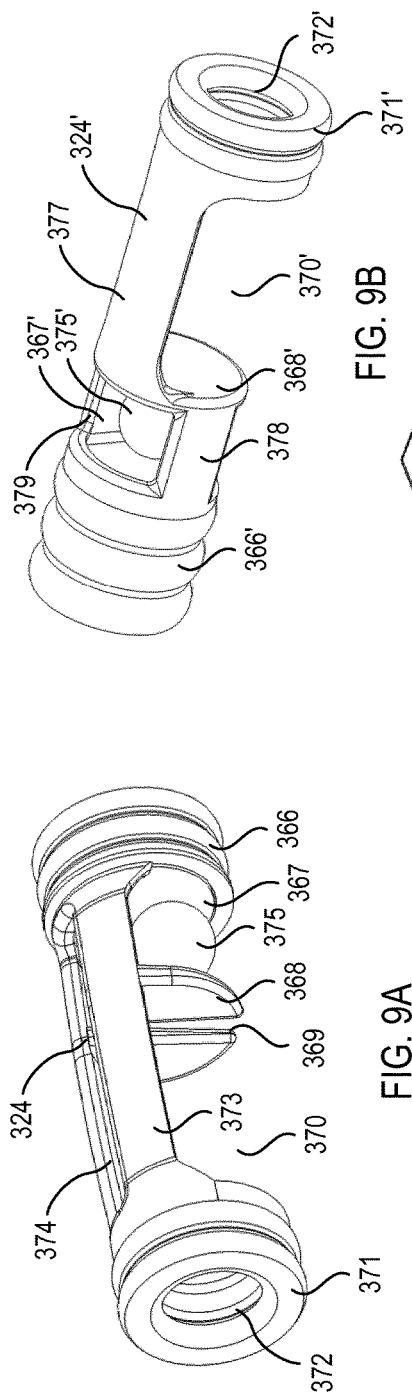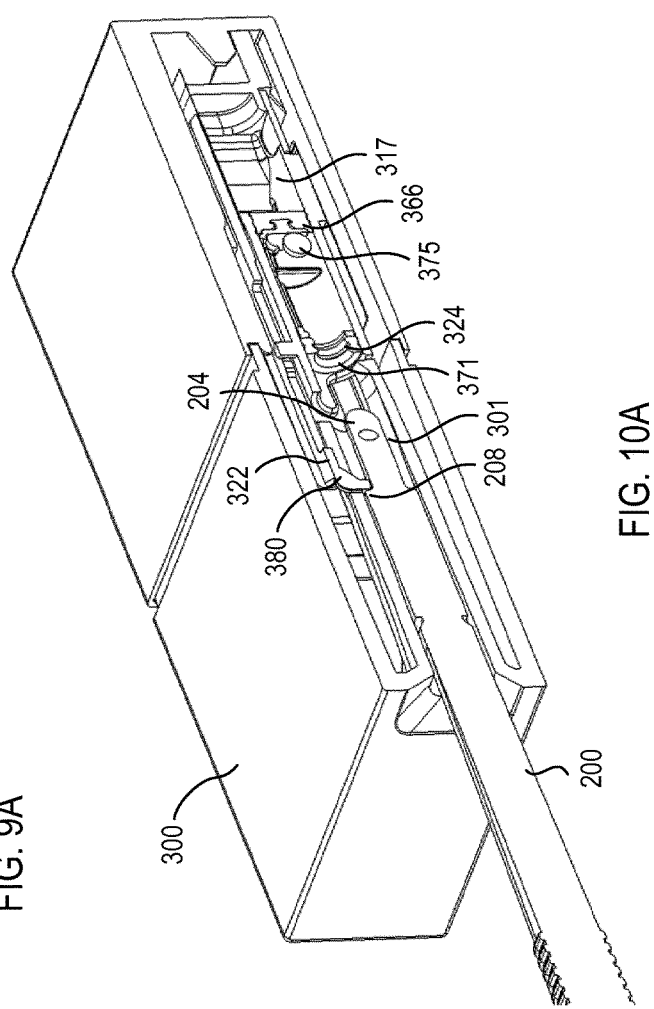

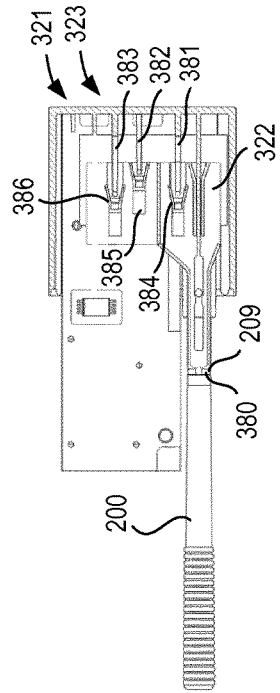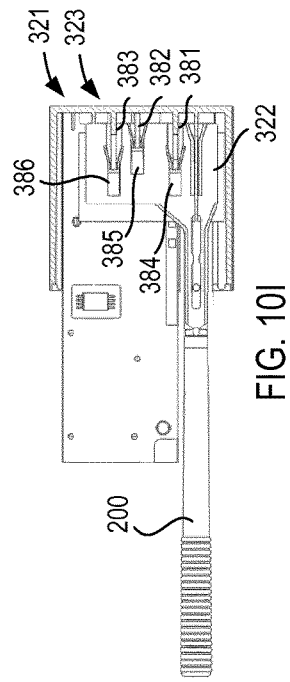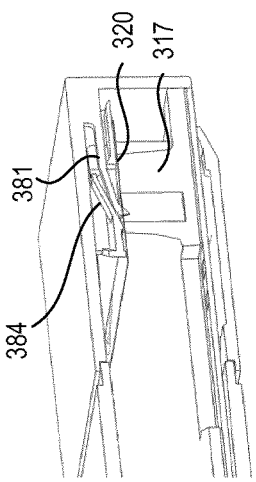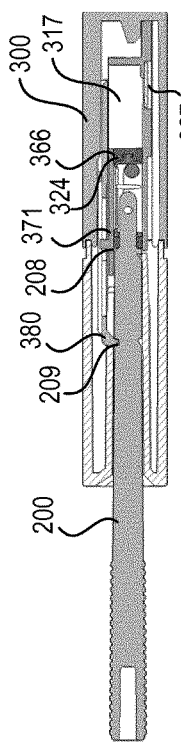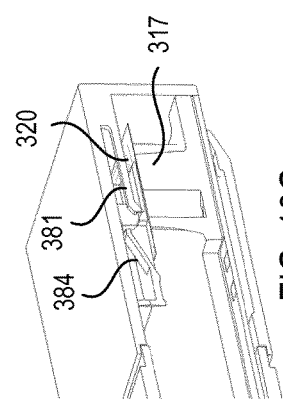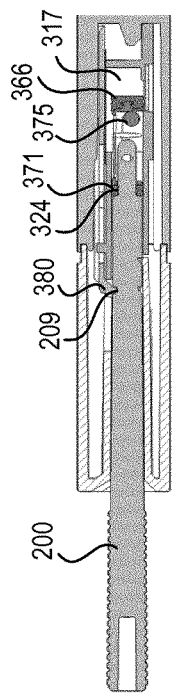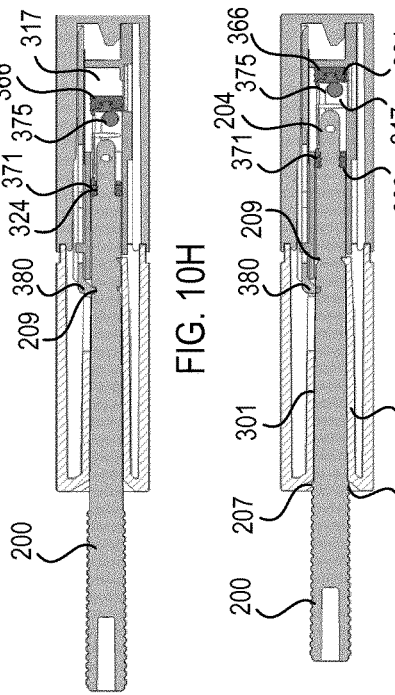

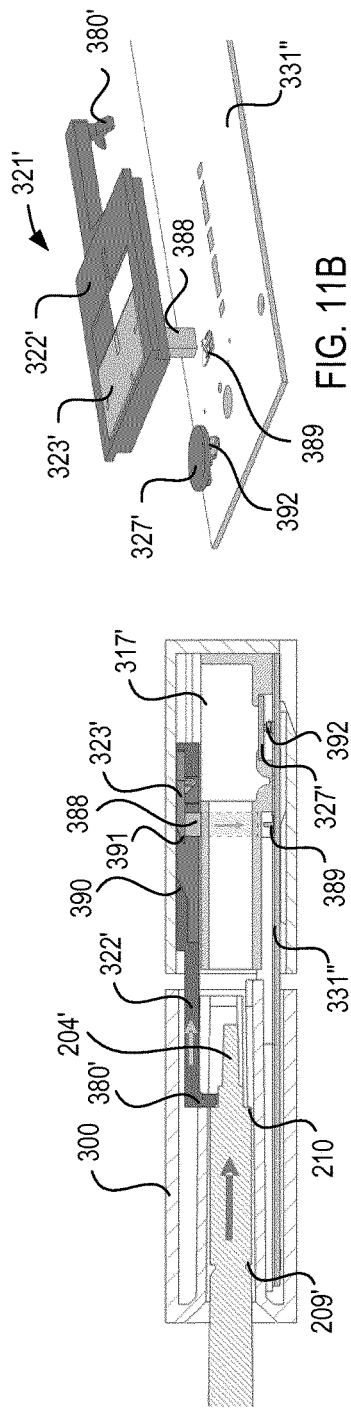
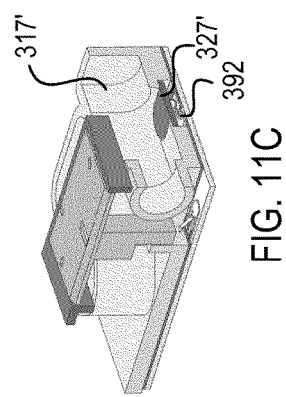
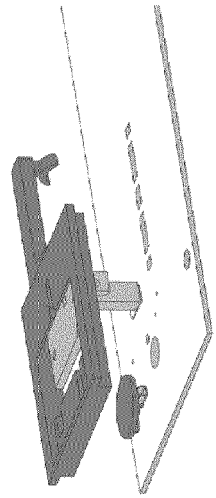
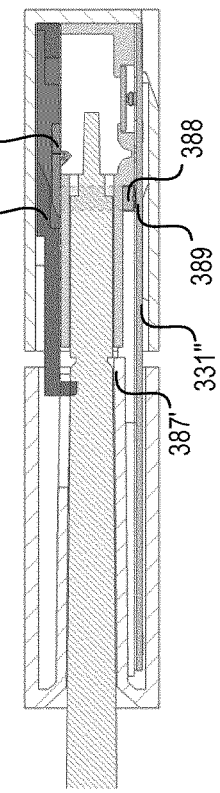
FIG. 11A
FIG. 11B
FIG. 11C
FIG. 11D
FIG. 11E

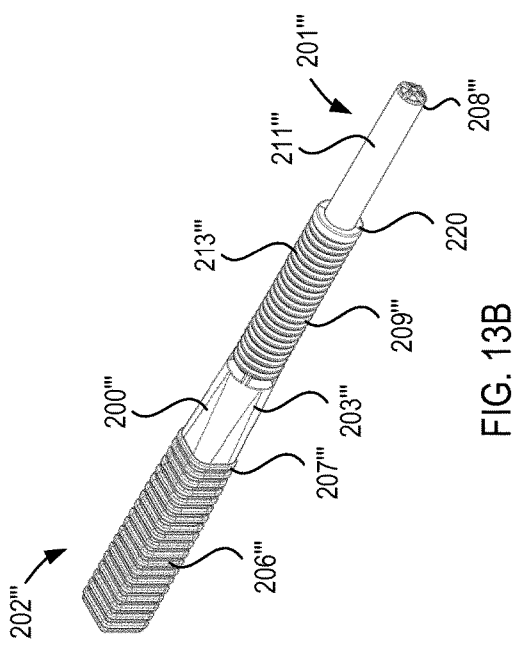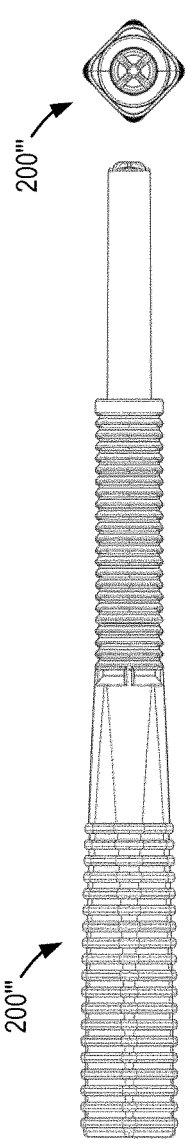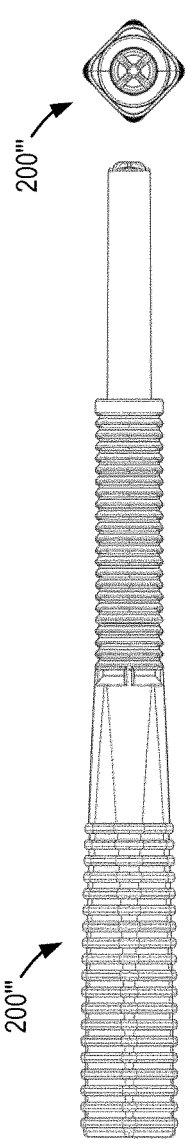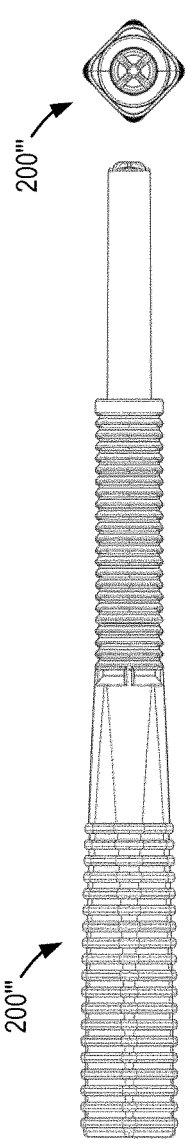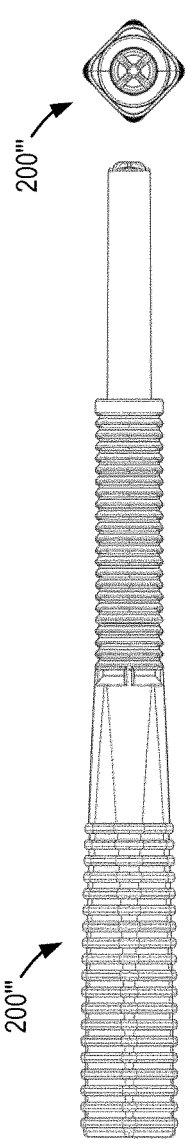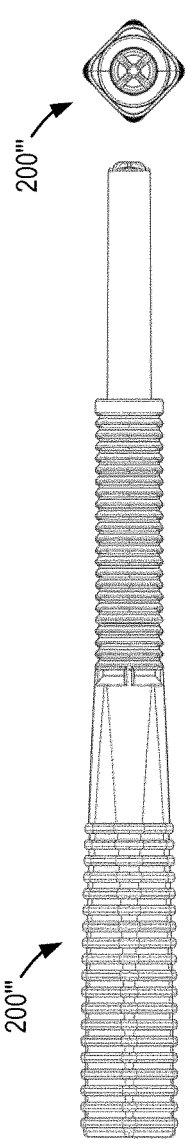

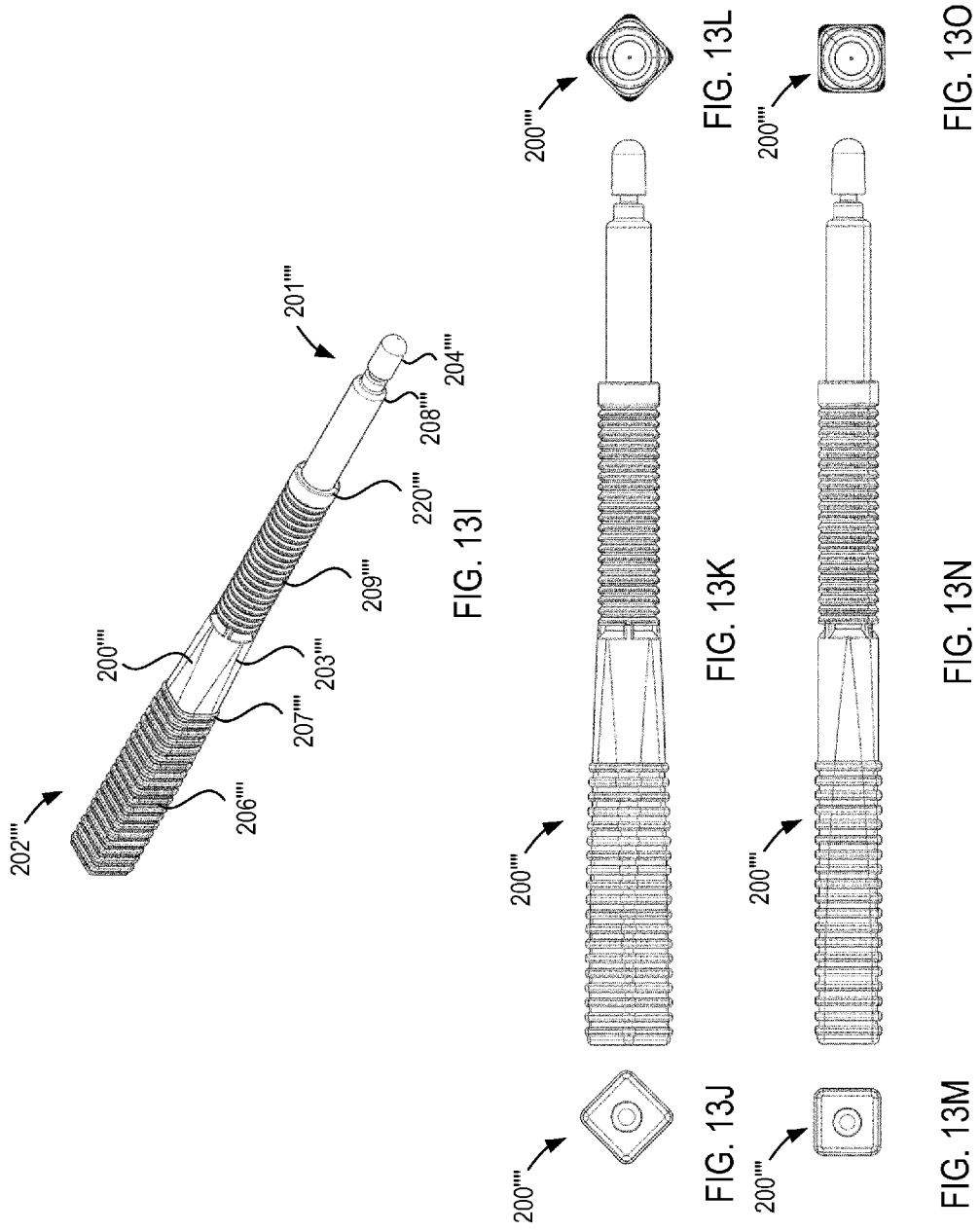

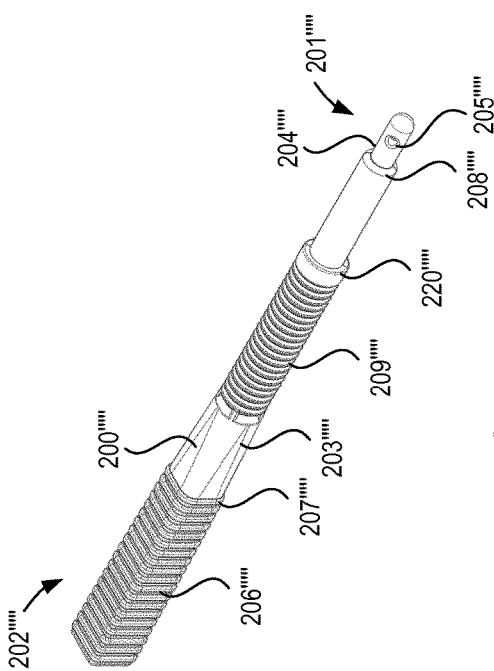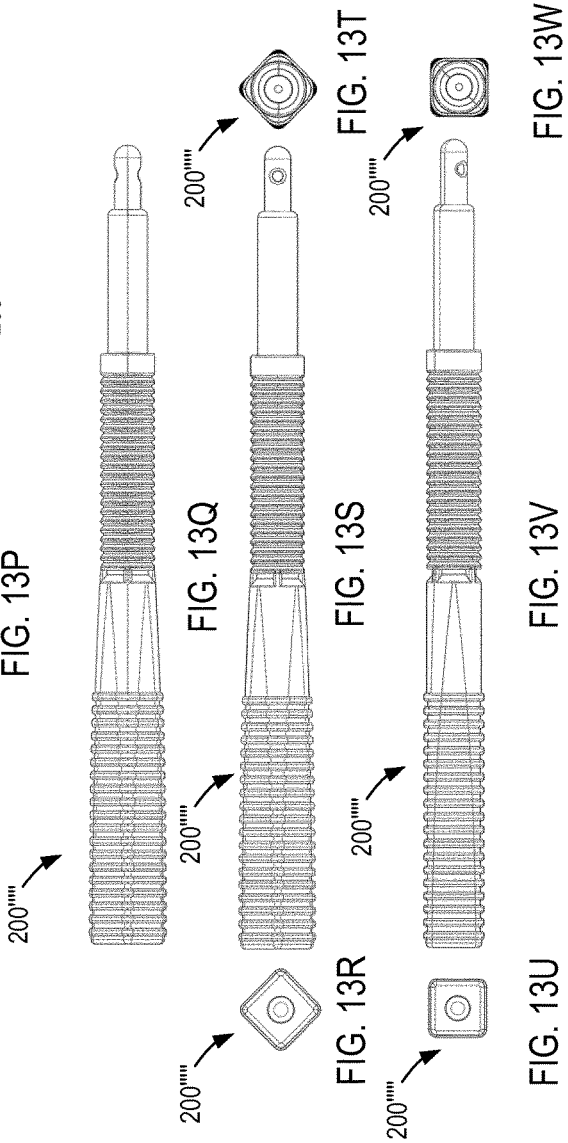

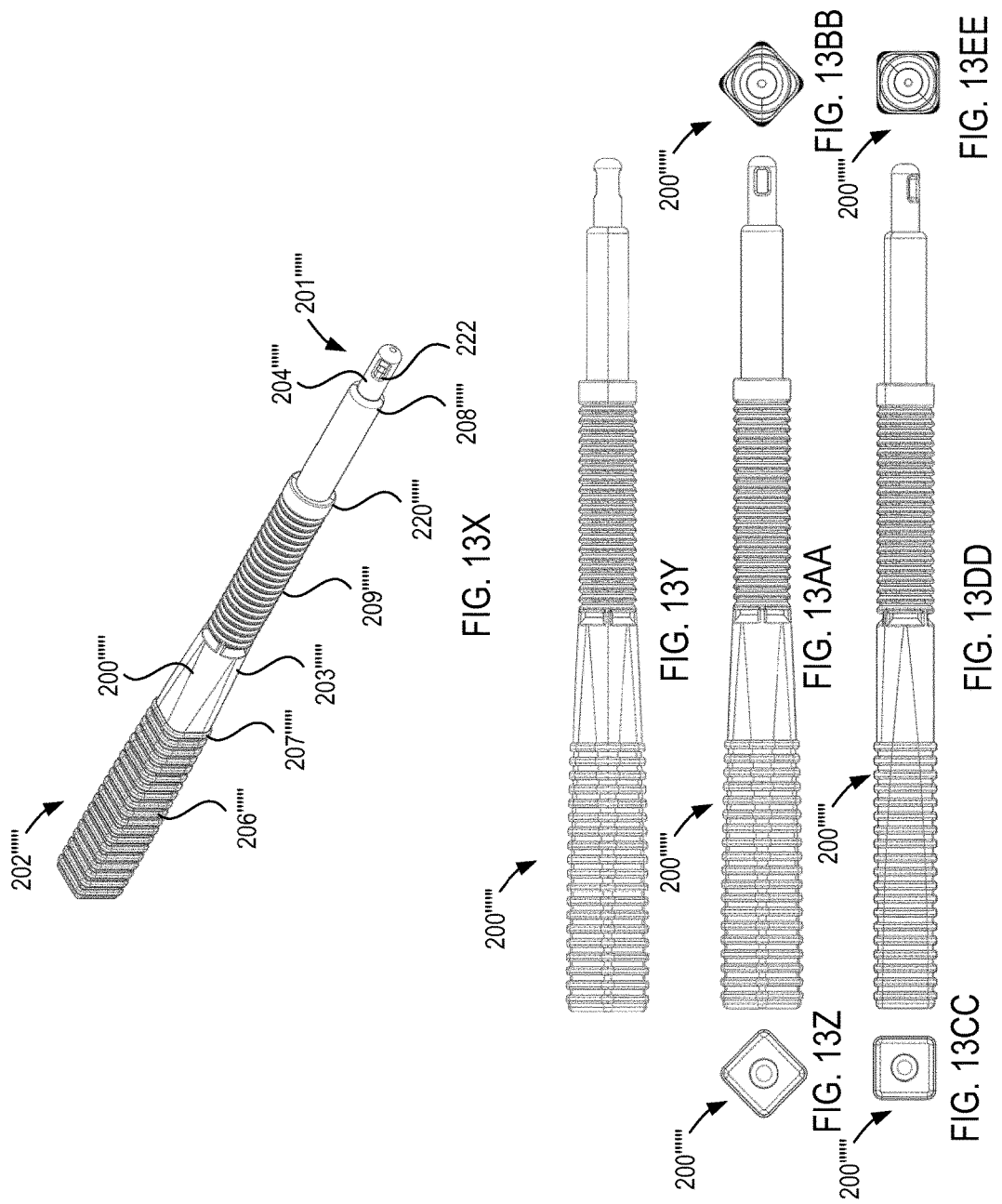

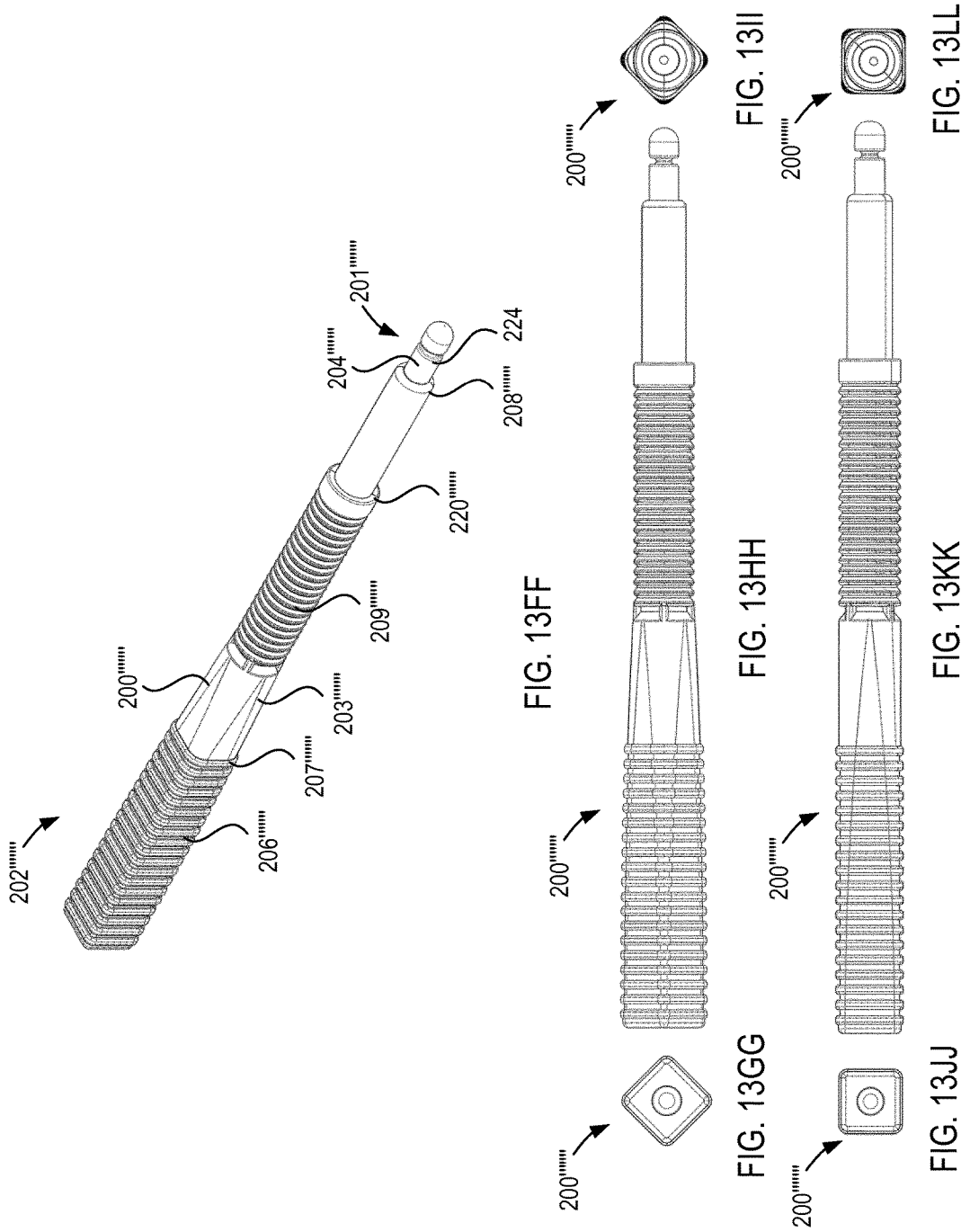

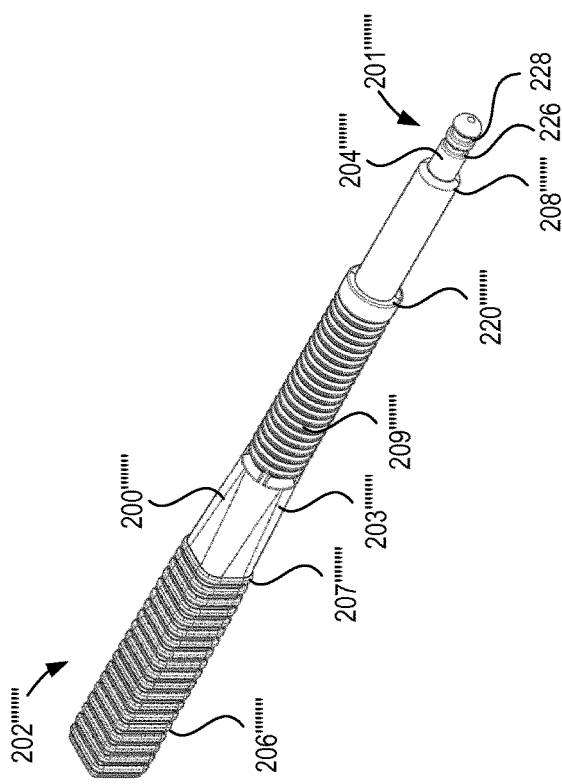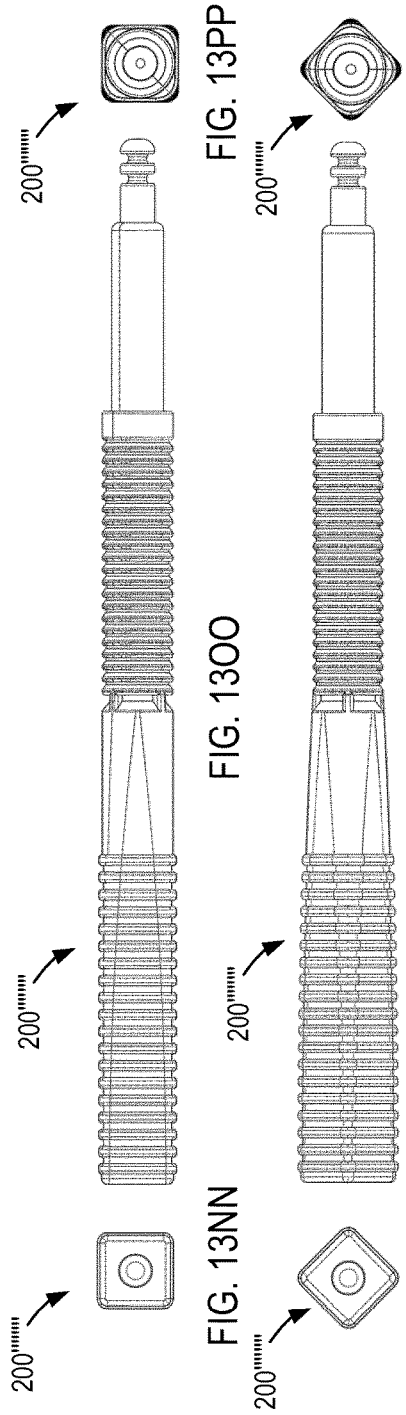

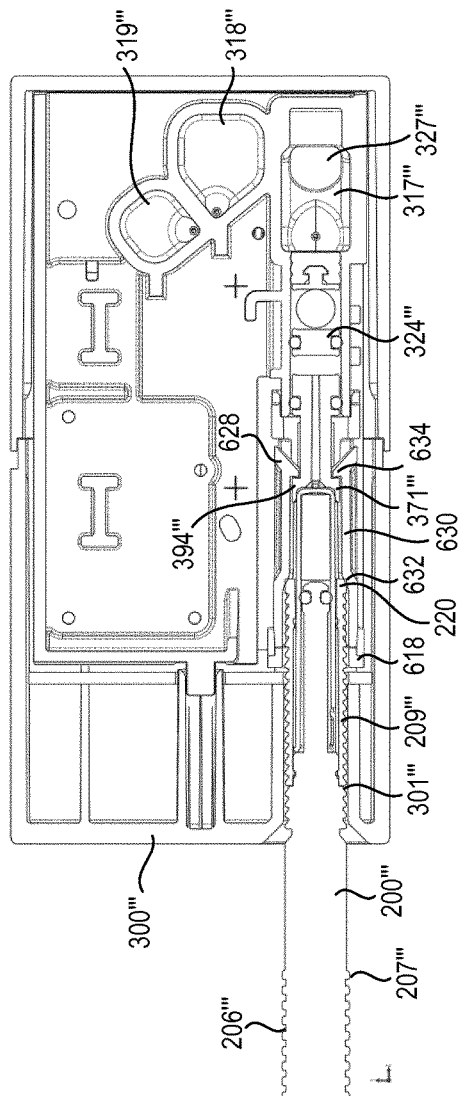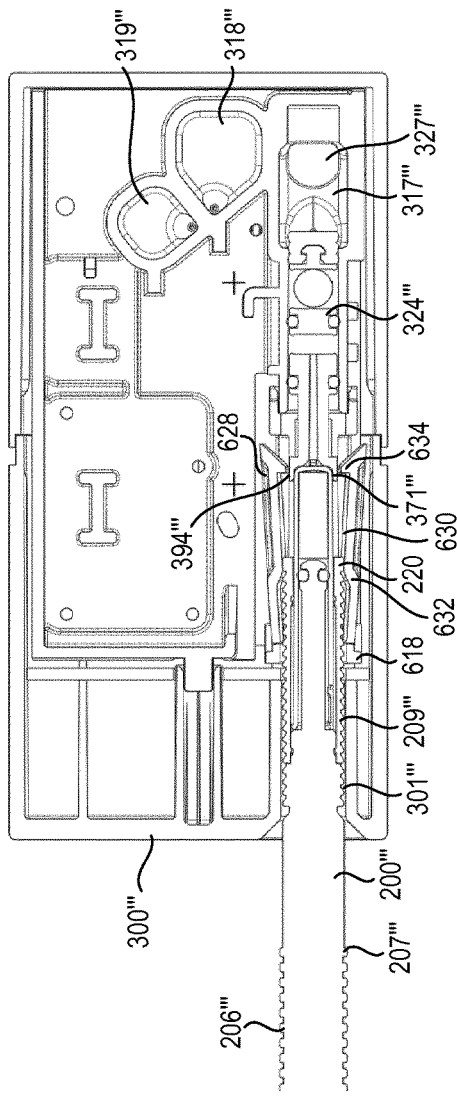
FIG. 16F
FIG. 16G

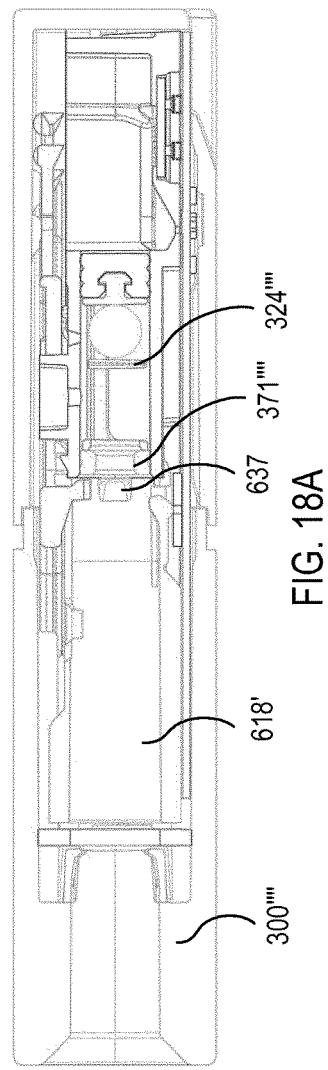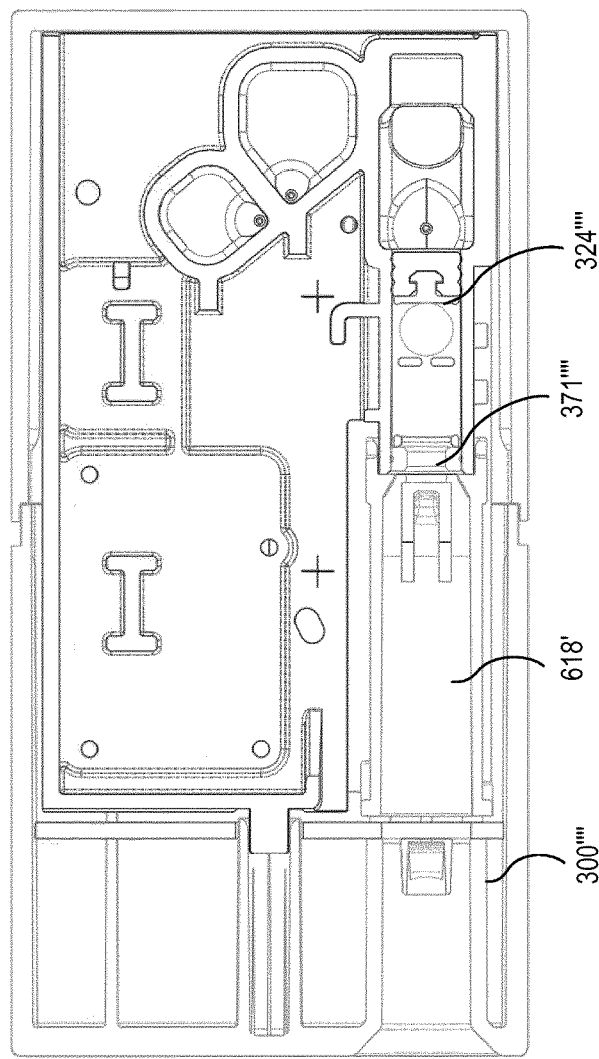
FIG. 18A
FIG. 18B

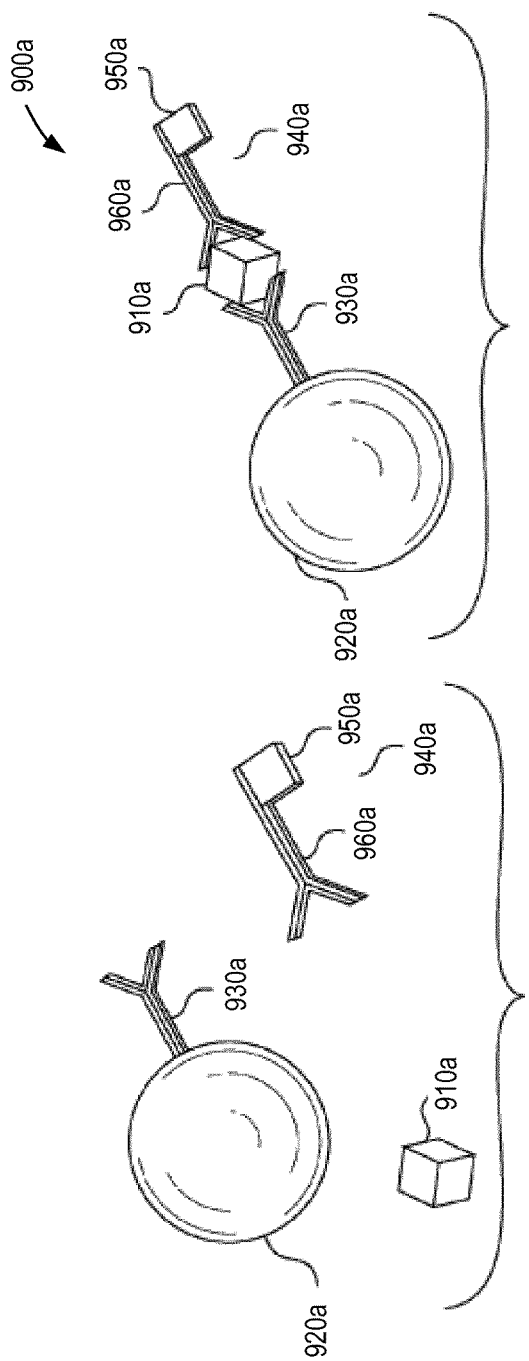
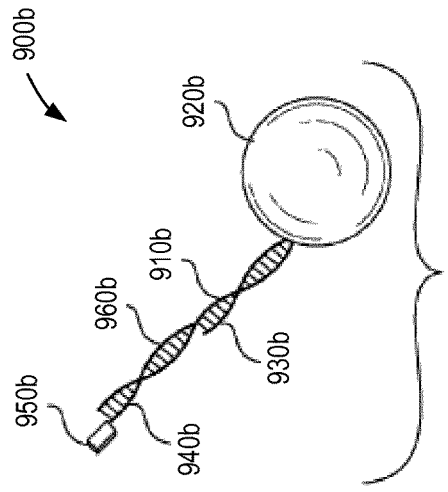
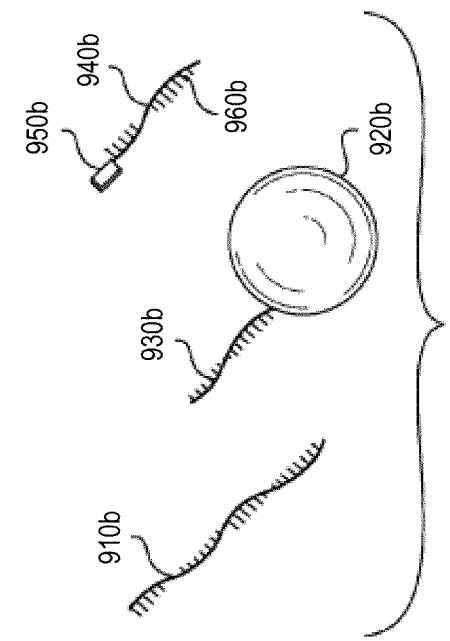
FIG. 26A FIG. 26B FIG. 26C FIG. 26D

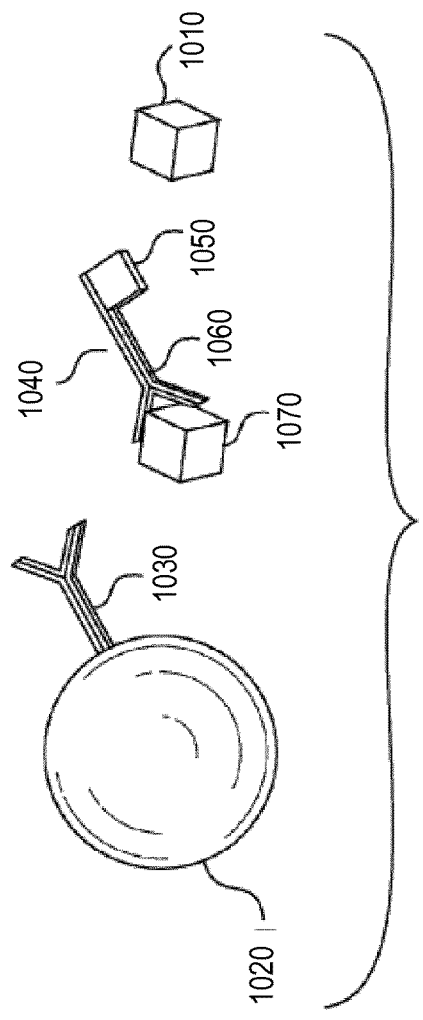
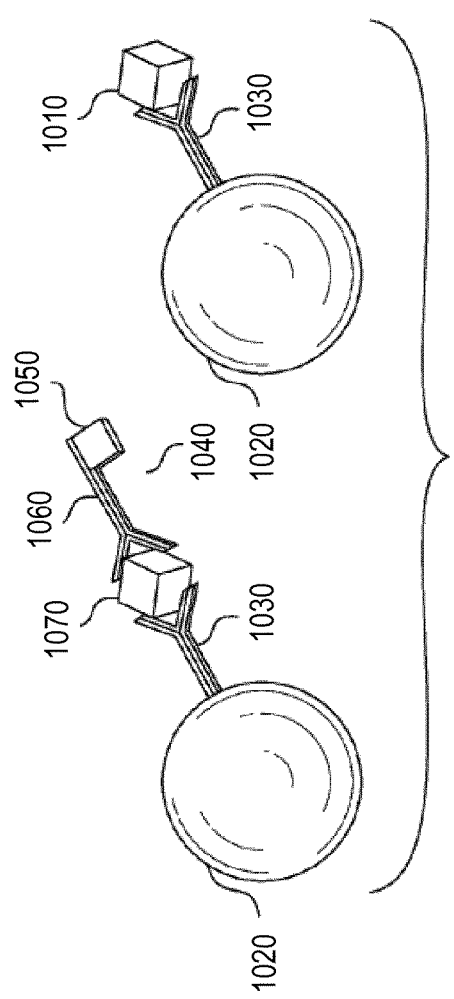
FIG. 27A
FIG. 27B

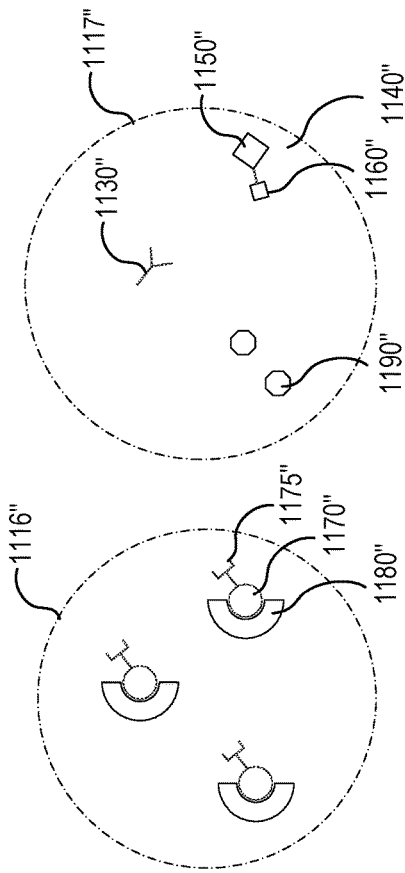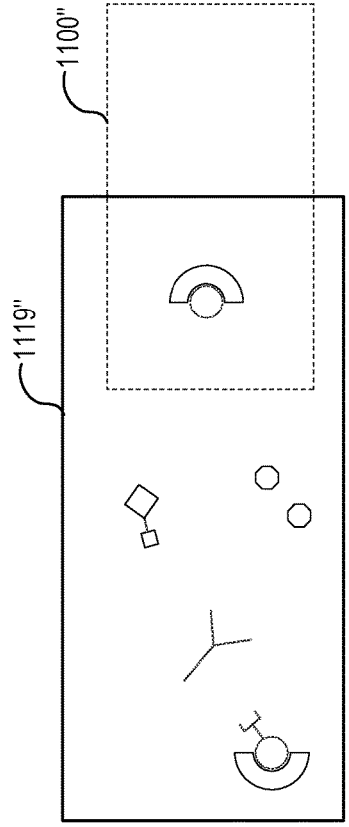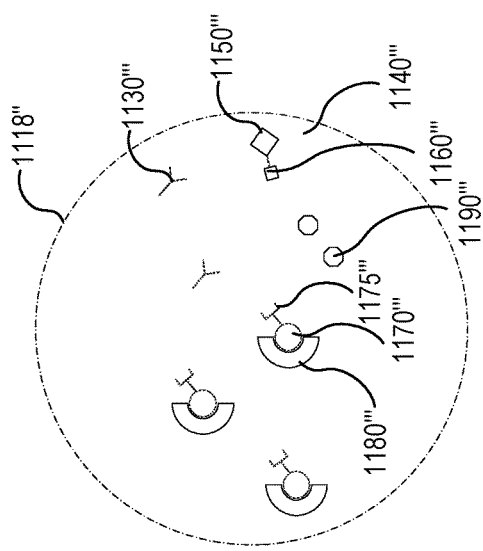

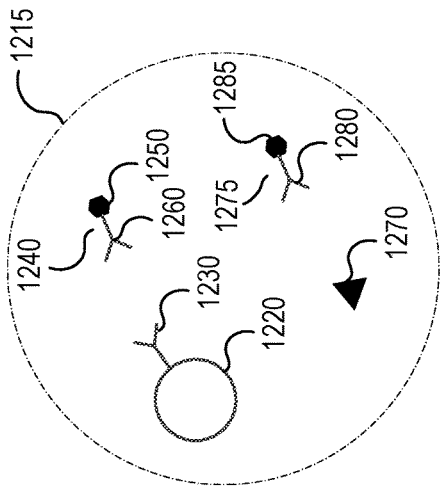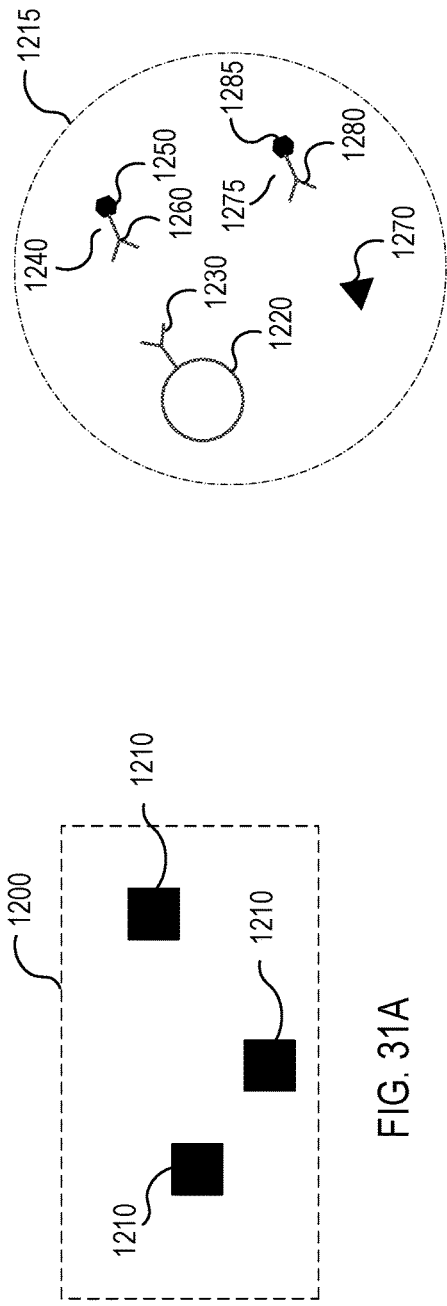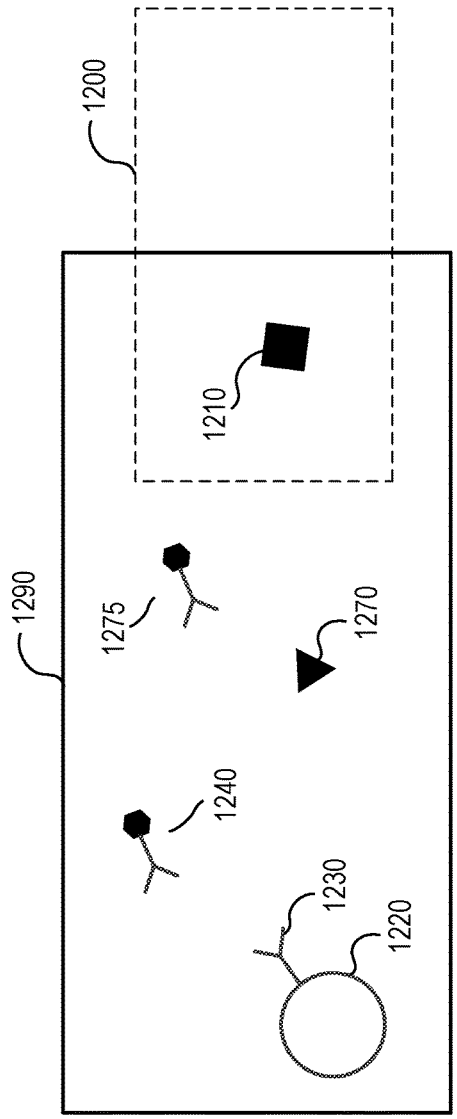
FIG. 31A
FIG. 31B
FIG. 31C

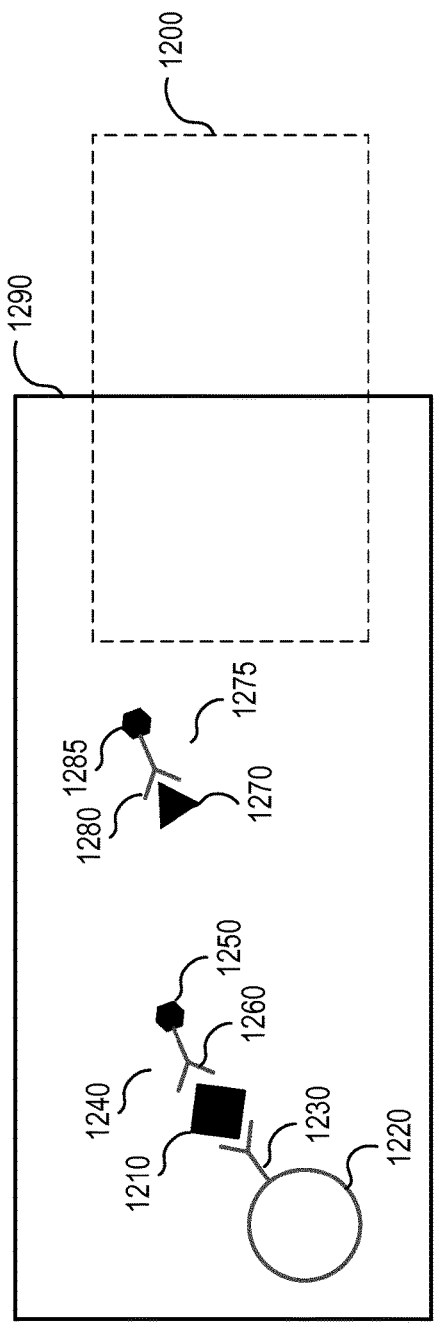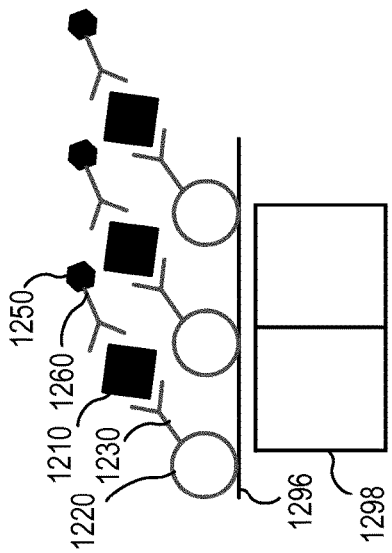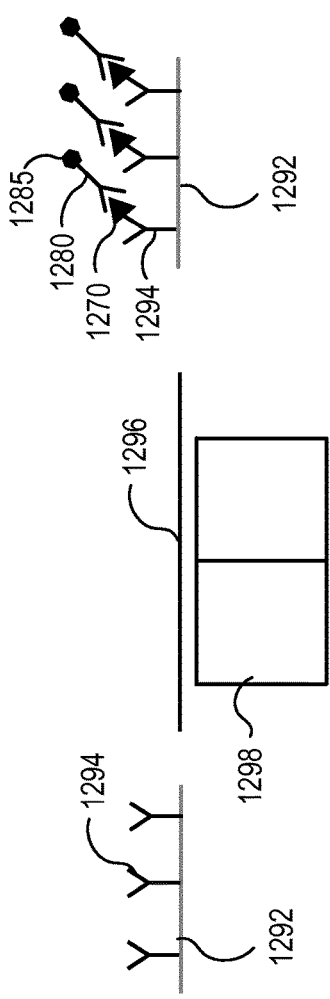

CARTRIDGES, KITS, AND METHODS FOR AMPLIFICATION AND DETECTION OF ANALYTES

CROSS-REFERENCE TO RELATED APPLICATIONS

This application is a divisional of U.S. application Ser. No. 15/487,956, filed Apr. 14, 2017, now U.S. Pat. No. 9,962,703; which is a continuation of U.S. application Ser. No. 15/336,735, filed Oct. 27, 2016, now U.S. Pat. No. 9,623,409; which is a continuation of International Application No. PCT/US2016/042688, filed Jul. 16, 2016; which claims priority to U.S. Provisional Application No. 62/194,101, filed Jul. 17, 2015, the entire contents of each of which are incorporated herein by reference.

TECHNOLOGICAL FIELD

The present technology relates generally to the field of molecule detection. In particular, the technology relates to microfluidic devices, systems, and methods for detecting the presence, absence and/or quantity of one or more particular analytes within a collected sample.

BACKGROUND

Conventional technologies for identifying the presence, absence and/or quantity of nucleic acids, proteins, and/or other molecules of interest within a sample often require expensive laboratory equipment and the expertise of highly-trained medical professionals. Consequently, such analyses are typically performed within laboratories or medical facilities. Such molecule detection can be important, for example, to detect the presence of pathogens, disease, contamination, overdoses, and poisonings within a person or other animal or within the environment. Unfortunately, today, individuals may face long waits before the proper tests can be performed and before the results can be generated and analyzed. Due to the long waits and the inconvenience of traveling to a laboratory or medical facility, illnesses and contaminations often spread and may cause substantial harm before the presence of said illness or contamination is even identified.

SUMMARY

There is a significant need for improved molecule detection and quantification technologies. Described herein are devices that may detect molecules of interest in less time and with less technical expertise than the conventional devices used today. The devices may be utilized by consumers in non-clinical settings, for example, in schools, places of employment, and in the home. In addition, the devices may be used by consumers upon entering a pharmacy or healthcare facility, and may generate results quickly so that results are available by the time the consumer talks with a pharmacist or healthcare practitioner. The devices herein also may be configured to minimize biohazard risks.

One aspect of the disclosure is directed to a system for detecting molecules. In various embodiments, the system includes a cartridge device, a reader device removably coupled to the cartridge device, and a sample collection device.

Sample preparation reagents may be used in the system and may include a plurality of magnetic particles each having surface-bound affinity molecules, a plurality of detector agents which may each include a signaling agent, a plurality of amplification reagents, and/or a plurality of agents to facilitate access to a target analyte and binding between the target analyte and the surface-bound affinity molecules and the detector agents.

In accordance with one aspect, a sample analysis cartridge is provided for detecting at least one of a presence, absence, or quantity of one or more analytes. The sample analysis cartridge may include an input tunnel, a reservoir, a reagent shuttle, and/or a sensor, each of which may be within a housing of the cartridge. The input tunnel may extend from an aperture and may be configured to permit insertion of a sample collection device having a distal portion adapted to be exposed to a sample. The reservoir may be configured to hold a fluid, which may or may not be pre-filled within the reservoir. The reagent shuttle may be disposed between the reservoir and the aperture in a first position and the reagent shuttle may have a first end and a second end. The reagent shuttle may be configured to house a reagent ball comprising reagents (e.g., sample preparation reagents) between the first and second ends. The first end may be configured to seal the reservoir from the input tunnel in the first position. The reagent shuttle may be designed to move within the input tunnel when subjected to a force greater than a threshold force to a second position such that the reagent ball and the sample move into the reservoir. The reservoir may be continuously sealed from the input tunnel proximal to the reagent shuttle during movement from the first position to the second position. The sensor may be configured to analyze the fluid mixed with the reagent ball and the sample and further configured to generate a signal indicative of at least one of the presence, absence, or quantity of the one or more analytes within the sample.

The second end of the shuttle may have an opening sized to wipe excess sample from a tip of the sample collection device such that, at most, a predetermined volume of the sample is mixed in the fluid within the reservoir. The reservoir may be sealed via the sample collection device partially inserted within the second end of the shuttle during movement from the first position to the second position. The cartridge may have one or more locking members configured to irreversibly lock the sample collection device within the input tunnel in the second position.

The shuttle may include one or more sample compartments configured to house, at most, a predetermined volume of the sample and one or more reagent ball compartments configured to house the reagent ball and, optionally, additional reagent balls. In some embodiments, the one or more sample compartments and the one or more reagent ball compartments are not exposed to the fluid within the reservoir in the first position. The one or more sample compartments and the one or more reagent ball compartments may be exposed to the fluid within the reservoir in the second position. The shuttle may have a compartment divider configured to divide at least one sample compartment from at least one reagent ball compartment. The compartment divider may have a slot configured to facilitate mixing when disposed within the sample preparation reservoir in the second position.

The reagents may include one or more of a plurality of solid particles, a plurality of affinity molecules, and/or a plurality of signaling agents. The reagents may include a plurality of magnetic particles configured to be magnetically held over a working electrode of the sensor. At least one magnetic particle of the plurality of magnetic particles may be configured to be indirectly bound to a signaling agent.

The cartridge may include an analysis channel, e.g., within the cartridge housing. At least a portion of the sensor may be disposed in the analysis channel and the fluid mixed with the reagent ball and the sample may travel to at least the portion of the sensor via the analysis channel.

The cartridge may include a contact switch, a sealing material configured to fluidicly seal the fluid within the reservoir, and/or a seal piercer and each of those components may be within the cartridge housing. Insertion of the sample collection device within the input tunnel may cause: (i) the shuttle to move from the first position to the second position, (ii) the seal piercer to pierce the sealing material to vent the fluid in the reservoir, and/or (iii) activation of the contact switch.

In accordance with another aspect, a sample analysis cartridge is provided for detecting at least one of a presence, absence, or quantity of one or more analytes. The sample analysis cartridge may include an input tunnel, a reservoir, a sealing material, and/or a seal piercer, each of which may be within a housing of the cartridge. The input tunnel may extend from an aperture and the input tunnel may be configured to permit insertion of a sample collection device having a distal portion adapted to be exposed to a sample. The reservoir may be configured to hold a fluid, which may or may not be pre-filled. The sealing material may be configured to fluidicly seal the fluid within the reservoir. The seal piercer may be disposed partially within the input tunnel and the seal piercer may be configured to be contacted by the sample collection device within the input tunnel and to move, responsive to force applied by sample collection device, to cause the sealing material to be pierced to vent the fluid in the reservoir.

The seal piercer may be configured to move in a first direction and a second direction, different from the first direction, to pierce the sealing material. The first direction may be substantially parallel to movement of the sample collection device within the input tunnel and the second direction may be substantially perpendicular to the first direction. The seal piercer may include one or more piercers. The seal piercer may include a slider configured to move in a first direction and the one or more piercers may be configured to move in a second direction, different from the first direction, to pierce the sealing material.

The reservoir may be a sample preparation reservoir and may be configured to hold sample preparation reagents which may be within the fluid and/or introduced, e.g., via introduction of a reagent ball(s). The cartridge may also include a wash reservoir and/or a substrate reservoir. The seal piercer may be configured to cause the sealing material to be pierced to vent respective fluids in the sample preparation reservoir, the wash reservoir, and the substrate reservoir. The seal piercer may include an engager disposed within the input tunnel and the engager may be configured to engage an engagement zone of the sample collection device when the sample collection device is within the input tunnel.

The cartridge may include a contact switch which may be disposed on a circuit board within the housing. The contact switch may be configured to be activated upon insertion of the sample collection device within the input tunnel. Movement of the seal piercer may cause activation of the contact switch. The seal piercer may be configured to sequentially pierce the sealing material over the sample collection reservoir, the wash reservoir, and the substrate reservoir, in any order. The seal piercer may be configured to move out of one or more holes pierced in the sealing material after piercing to vent the fluid in the reservoir.

The cartridge may include a contact switch and a shuttle disposed between the reservoir and the aperture in a first position. The shuttle may have a first end and a second end and the first end may be configured to seal the reservoir from the input tunnel in the first position. The reagent shuttle may be configured to move within the input tunnel to a second position wherein the sample is moved into the reservoir. Insertion of the sample collection device within the input tunnel may cause: (i) the shuttle to move from the first position to the second position, (ii) the seal piercer to pierce the sealing material to vent the fluid in the reservoir, and/or (iii) activation of the contact switch. The cartridge may include one or more locking members configured to irreversibly lock the sample collection device within the input tunnel in the second position. The one or more locking members may irreversibly lock the sample collection device within the input tunnel during partial and/or full insertion of the sample collection device within the input tunnel.

Insertion of the sample collection device within the input tunnel may cause the seal piercer to pierce the sealing material to vent the fluid in the reservoir before the shuttle moves from the first position to the second position. Alternatively, or additionally, insertion of the sample collection device within the input tunnel may cause the seal piercer to pierce the sealing material to vent the fluid in the reservoir during movement of the shuttle from the first position to the second position.

In accordance with yet another aspect, a sample analysis cartridge is provided for detecting at least one of a presence, absence, or quantity of one or more analytes. The sample analysis cartridge may include an input tunnel, a reservoir, an analysis channel, and/or a circuit board, each of which may be within a housing of the cartridge. The input tunnel may extend from an aperture and the input tunnel may be configured to permit insertion of a sample collection device having a distal portion adapted to be exposed to a sample. The reservoir may be configured to hold a fluid and may be configured to receive the sample on the distal portion of the sample collection device. The analysis channel may be configured to receive, from the reservoir, the fluid having the sample and reagents comprising a plurality of magnetic particles mixed therein. The circuit board may include a senor having a working electrode and the sensor may be configured to be exposed to the mixed fluid in the analysis channel and to generate a signal indicative of at least one of the presence, absence, or quantity of the one or more analytes within the sample. The working electrode may be masked with a plurality of striations configured to promote homogenous distribution of the plurality of magnetic particles over the working electrode and to promote resistance to movement of the plurality of magnetic particles off of the working electrode.

In accordance with yet another aspect, a kit is provided for detecting at least one of a presence, absence, or quantity of one or more analytes. The kit may include a sample collection device, a sample analysis cartridge, and/or a sample analysis reader. The sample collection device may have a distal portion adapted to be exposed to a sample. The sample analysis cartridge may include an input tunnel, a reservoir, an analysis channel, and/or a circuit board, each of which may be within a housing of the cartridge. The input tunnel may extend from an aperture and may be configured to permit insertion of the sample collection device. The reservoir may be configured to hold a fluid and configured to receive the sample on the distal portion of the sample collection device. The analysis channel may be configured to receive, from the reservoir, the fluid having the sample and reagents comprising a plurality of magnetic particles mixed therein. The circuit board may include a sensor configured to be exposed to the mixed fluid in the analysis channel and to generate a signal indicative of at least one of the presence, absence, or quantity of the one or more analytes within the sample. The sample analysis reader may be configured to receive the sample analysis cartridge. The sample analysis reader may have first and second magnetic generators configured to be disposed adjacent to a single working electrode of the sensor when the sample analysis cartridge is inserted in the sample analysis reader. The first and second magnetic generators may be configured to generate a magnetic field over the length of the single working electrode to promote homogenous distribution of the plurality of magnetic particles over the length of the single working electrode.

Receipt of the sample analysis cartridge by the sample analysis reader may cause electric coupling between the sample analysis cartridge and the sample analysis reader. The sample analysis cartridge may be configured to transmit the signal indicative of at least one of the presence, absence, or quantity of the one or more analytes within the sample to the sample analysis reader for processing. The sample analysis reader may be configured to transmit the processed signal indicative of at least one of the presence, absence, or quantity of the one or more analytes within the sample to a computer. The kit may include a computer readable medium with instructions that, when executed by a processor of the computer, cause a display of the computer to display information indicative of the presence, absence, and/or quantity of one or more target analytes.

A housing of the sample analysis cartridge may include a bottom surface having a magnetic generator depression. Receipt of the sample analysis cartridge in sample analysis reader may cause the first and second magnetic generators to move partially within the magnetic generator depression. The magnetic generator depression may be disposed adjacent the single working electrode.

In accordance with another aspect, a sample analysis cartridge is provided for detecting at least one of a presence, absence, or quantity of one or more analytes. The sample analysis cartridge may include an input tunnel, a reservoir, a heater, an analysis channel, and/or a sensor, each of which may be within a housing of the cartridge. The input tunnel may extend from an aperture and the input tunnel may be configured to permit insertion of a sample collection device having a distal portion adapted to be exposed to a sample. The reservoir may be configured to hold a fluid and configured to receive the sample on the distal portion of the sample collection device. The reservoir may include an outlet having a phase-changeable material therein to occlude an entire cross-section of the outlet. The heater may be configured to heat the phase-changeable material such that the phase-changeable material does not occlude the entire cross-section of the outlet. The analysis channel may be configured to receive, from the reservoir through the outlet, the fluid having the sample and reagents comprising a plurality of magnetic particles mixed therein. The sensor may be configured to be exposed to the mixed fluid in the analysis channel and to generate a signal indicative of at least one of the presence, absence, or quantity of the one or more analytes within the sample. The heater may be masked with a masking material configured to electrically isolate the heater from the sensor. The masking material may be a solder mask.

The cartridge may include a wash reservoir and a wash reservoir heater. The wash reservoir may be configured to hold a wash fluid and may include a wash reservoir outlet having a phase-changeable material therein to occlude an entire cross-section of the wash reservoir outlet. The wash reservoir heater may be configured to heat the phase-changeable material in the wash reservoir outlet such that the phase-changeable material does not occlude the entire cross-section of the wash reservoir outlet so that the wash fluid enters the analysis channel and travels to the sensor. The wash reservoir heater may be masked with a masking material configured to electrically isolate the wash reservoir heater from the sensor.

The cartridge may include a substrate reservoir and a substrate reservoir heater. The substrate reservoir may be configured to hold a substrate fluid and may include a substrate reservoir outlet having a phase-changeable material therein to occlude an entire cross-section of the substrate reservoir outlet. The substrate reservoir heater may be configured to heat the phase-changeable material in the substrate reservoir outlet such that the phase-changeable material does not occlude the entire cross-section of the substrate reservoir outlet so that the substrate fluid enters the analysis channel and travels to the sensor. The substrate reservoir heater may be masked with a masking material configured to electrically isolate the substrate reservoir heater from the sensor.

In accordance with yet another aspect, a sample analysis cartridge is provided for detecting at least one of a presence, absence, or quantity of one or more analytes. The sample analysis cartridge may include a sample preparation reservoir, a substrate reservoir, an analysis channel, a fluidic isolator, and/or one or more heaters, each of which may be within a housing of the cartridge. The sample preparation reservoir may be configured to hold a fluid and may be configured to receive a sample from a sample collection device. The sample preparation reservoir may include a sample preparation reservoir outlet having phase-changeable material therein to seal the sample preparation reservoir outlet. The substrate reservoir may be configured to hold a fluid comprising a chemical substrate. The substrate reservoir may include a substrate reservoir outlet having phase-changeable material therein to seal the substrate reservoir outlet. Each of the sample preparation and substrate reservoirs may be, at least at times, in fluid communication with the analysis channel. The fluidic isolator may be phase-changeable material. At least one of the one or more heaters may be configured to heat phase-changeable material within the sample preparation reservoir outlet such that the phase-changeable material unseals the sample preparation reservoir outlet to permit the fluid having the sample mixed therein to flow into the analysis channel. At least one of the one or more heaters may be configured to heat phase-changeable material of the fluidic isolator after unsealing the sample preparation reservoir outlet such that phase-changeable material of the fluidic isolator flows into the analysis channel to fluidically isolate the sample preparation reservoir from the substrate reservoir. At least one of the one or more heaters may be configured to heat phase-changeable material within the substrate reservoir outlet, after the fluidic isolator fluidicly isolates the sample preparation reservoir from the substrate reservoir, such that the phase-changeable material unseals the substrate reservoir outlet to permit the fluid comprising the chemical substrate to flow into the analysis channel, but not into the sample preparation reservoir.

The one or more heaters may include a sample preparation reservoir heater, a fluidic isolator heater, and/or a substrate reservoir heater. The sample preparation reservoir heater may be configured to heat the phase-changeable material within the sample preparation reservoir outlet. The fluidic isolator heater may be configured to heat the phase-changeable material of the fluidic isolator. The substrate reservoir heater may be configured to heat the phase-changeable material within the substrate reservoir outlet. The sample preparation reservoir heater, the fluidic isolator heater, and the substrate reservoir heater may each be masked with a masking material configured to electrically isolate the respective heater from a sensor in the analysis channel.

The cartridge may include a wash reservoir configured to hold a wash fluid. The wash reservoir may include a wash reservoir outlet having phase-changeable material therein to seal the wash reservoir outlet. At least one of the one or more heaters may be configured to heat phase-changeable material within the wash reservoir outlet, after the fluidic isolator fluidicly isolates the sample preparation reservoir from the substrate reservoir, but before the one or more heaters heats the phase-changeable material within the substrate reservoir outlet, such that the phase-changeable material unseals the wash reservoir outlet to permit the wash fluid to flow into the analysis channel to wash signaling agents unbound to magnetic particles from the sample preparation reservoir off a sensor in the analysis channel. The fluid having the chemical substrate may be configured to wash signaling agents unbound to magnetic particles from the sample preparation reservoir off a sensor in the analysis channel.

In accordance with another aspect, a sample analysis cartridge is provided for detecting at least one of a presence, absence, or quantity of one or more analytes. The sample analysis cartridge may include an input tunnel, a reservoir, a shuttle, and/or a sensor, each of which may be within a housing of the cartridge. The input tunnel may extend from an aperture and the input tunnel may be configured to permit insertion of a sample collection device having a distal portion adapted to be exposed to a sample fluid. The reservoir may be configured to hold a fluid, which may or may not be pre-filled. The shuttle may be disposed between the reservoir and the aperture in a first position. The shuttle may have a first end and a second end and may define a sample compartment between the first and second ends. The sample compartment may be configured to receive the sample fluid compressed from the distal portion of the sample collection device. The shuttle may be configured to move within the input tunnel when subjected to a force greater than a threshold force to a second position such that the sample compartment having the sample fluid is moved into the reservoir. The sensor may be configured to be exposed to the fluid mixed with the sample fluid and the sensor may be further configured to generate a signal indicative of at least one of the presence, absence, or quantity of the one or more analytes within the sample fluid.

The shuttle may further define a reagent ball compartment between the first and second ends. The reagent ball compartment may be configured to house one or more reagent balls comprising reagents. The reagent ball compartment may be outside the reservoir in the first position and in the reservoir in the second position. The sample compartment may be configured to receive, at most, a predetermined volume of the sample fluid compressed from the distal portion of the sample collection device. The cartridge may include an overflow compartment configured to receive a volume of the sample fluid from the sample compartment above the predetermined volume.

The reagent ball comprises reagents necessary to carry out amplification of the target analyte. The reagent ball can be of any appropriate and shape, non-limiting examples of such include a diameter of between about 1 mm to about 7 mm, or alternatively from about 2 mm to about 5 mm, or alternatively about 3 mm, or alternatively less than about 7 mm, or alternatively less than about 5 mm, or alternatively less than about 4 mm. The reagent ball can be of any appropriate shape, e.g., spherical, cylindrical, conical or ellipsoid.

The components of the reagent ball are preselected for the analyte and its method for amplification and subsequent detection and/or quantification. In one aspect, the components of the reagent ball comprise reagents for the detection or quantification of a hormone, other small molecule or a protein or fragment. In another aspect, the components of the reagent ball comprise reagents for the detection and/or quantification of a nucleic acid by a method that comprises amplifying the nucleic acid.

A kit may be provided including the sample analysis cartridge and the sample collection device. The sample collection device may include a wicking portion at the distal portion. The wicking portion may be configured to wick and absorb the sample fluid. The wicking portion may be compressed to expel the sample fluid into the sample compartment. The sample compartment may be configured to receive, at most, a predetermined volume of the sample fluid compressed from the distal portion of the sample collection device. The sample analysis cartridge may further include an overflow compartment configured to receive a volume of the sample fluid from the sample compartment above the predetermined volume. The wicking portion of the sample collection device may be configured to wick and absorb sample fluid above the predetermined volume to permit a user to meter a quantity of sample fluid compressed into the sample compartment and the overflow compartment. At least some of the wicking portion may be slidably disposed within a shroud of the sample collection device.

The sample analysis cartridge may further include one or more locking members configured to irreversibly lock the sample collection device within the input tunnel when the sample collection device is fully inserted in the input tunnel. The sample collection device may further include a sample collection indicator configured to visually alert a collector based on a volume of sample fluid that has been collected. The sample collection indicator may be a colored thread embedded in the wicking portion that becomes increasingly visually exposed as the volume of sample collected increases.

In accordance with another aspect, compositions and method are provided for detecting and/or quantifying at least one of a presence, absence, or quantity of a target analyte within a sample in a cartridge. The method may include mixing, within a fluid in a reservoir of the cartridge, a plurality of affinity molecules, a plurality of de-binding agents, a plurality of signaling agents, a plurality of competitor molecules pre-bound to competitor binding molecules, each of the plurality of competitor molecules possessing a label, and the sample having a plurality of sample target analytes pre-bound to sample binding molecules; de-binding at least one competitor molecule from the pre-bound competitor binding molecule using at least one de-binding agent of the plurality of de-binding agents; de-binding at least one sample target analyte from the pre-bound sample binding molecule using at least one de-binding agent of the plurality of de-binding agents; binding the label of the de-bound competitor molecule to a signaling agent of the plurality of signaling agents; binding the de-bound competitor molecule to an affinity molecule of the plurality of affinity molecules; and/or generating a signal indicative of at least one of a presence, absence, or quantity of the sample target analyte within the cartridge. The reagent ball can be of many sizes, non-limiting examples of such include having an diameter of between about 1 mm to about 7 mm, or alternatively from about 2 mm to about 5 mm, or alternatively about 3 mm, or alternatively less than about 7 mm, or alternatively less than about 5 mm, or alternatively less than about 4 mm. While reagent ball is illustrated as a sphere, the disclosure is not limited thereto and many shapes may be used and multiple reagent balls each containing the same or different reagents also may be used.

In accordance with another aspect, compositions and methods are provided for amplifying and detecting and/or quantifying at least one of a presence, absence, or quantity of a target analyte, e.g., a target nucleic acid (deoxyribonucleic acid (DNA) or ribonucleic acid (RNA)) within a sample in a cartridge. The method comprises or alternatively consists essentially of preparing a plurality of amplicons comprising a plurality of capture elements, by mixing within a fluid in a reservoir of the cartridge: a plurality of enzymes to facilitate an amplification reaction, e.g., polymerases; reverse transcriptases; a plurality of magnetic beads having coupled thereto an affinity molecules; and a plurality of forward and reverse primers, that may or may not be labeled.

In a further aspect, provided herein are compositions and methods for the use, wherein the reagent ball further contains a plurality of forward primers selected to amplify the target nucleic acid and having coupled to each thereto a spacer element and a capture element; a plurality of reverse primers selected to amplify the target nucleic acid and having coupled to each thereto a spacer element and a signaling agent or a signaling capture element; a plurality of nucleotides or analogs thereof (dNTPs) for the amplification reaction.

In a further aspect, the reagent ball further contains a reverse primer selected to bind a target nucleic acid, the reverse primer comprising a spacer element that is directly or indirectly conjugated to a reporter capture element. In a further aspect, the reagent ball further contains an effective amount of reverse transcriptase, effective to facilitate the amplification reaction.

In a yet further aspect, the reagent ball also contains a plurality of reporter affinity element conjugated to a reporter element.

In a further aspect, the reagent ball also contains single stranded binding proteins, e.g., from about 9 to about 18 amino acids, known to those of ordinary skill in the art such as but not limited to SSB from *E. coli* or GP 32 from phages.

In one aspect, the reagent ball further contains, a plurality of DNA template control nucleic acids. In another aspect, the reagent ball alternatively or also contains a plurality of RNA template control nucleic acids.

In a further aspect, the reagent ball may contain a plurality of reverse transcriptase-specific primers to facilitate reverse transcription of RNA to cDNA. In a yet further aspect, the reagent ball may also contain a plurality of reverse primers selected to serve as an internal control having coupled to each thereto a spacer element and a signaling agent; and a plurality of forward primers selected to serve as an internal control having coupled to each thereto a spacer element and a capture element.

In addition to the labeled primers, the reagent ball can contain an effective amount of a plurality of unlabelled primers designed to amplify at least the same target region but optionally flanking sequences to the target sequence. The presence of unlabeled primers can make amplification more efficient since labelled primers may be more sterically hindered as they bind to other elements e.g. solid particles or signaling agents.

The reagent ball can further contain an effective amount of one or lysis agents to free the target nucleic acid, templates and/or control(s) from a cell, microbe, or virus in the sample.

In a further aspect, the reagent ball contains an effective amount of a helicase to unwind dsDNA for loading primers or RecA or its analogues such as UvsX or RAD51. Further, the reagent ball may contain mutL, RecFOR enzymes, UvsY.

In one aspect the amplification reagents are selected for any one or more other amplification reactions, e.g., PCR methods or isothermal amplification. The reporter element and/or the capture element is located at the 5' termini of the nucleic acid or along the nucleic acid sequence, i.e., internal to the 5' end. The reporter and/or the capture element is covalently or non-covalently attached to the nucleic acid.

In one aspect the elements are provided in a sample reagent ball and mixed with the sample in the reservoir. Upon disintegration the reagents come in contact with the target nucleic acid and hybridization of the primers to the target nucleic acid and amplification of the target through a series of enzymatically driven melting and reconstruction of the DNA or in the case of target RNA, a complementary DNA (cDNA) molecule is first created from the RNA target nucleic acid and the double stranded cDNA containing the target sequence then serves as the template for further amplification. The reagent ball can be of many sizes, non-limiting examples of such include having an diameter of between about 1 mm to about 7 mm, or alternatively from about 2 mm to about 5 mm, or alternatively about 3 mm, or alternatively less than about 7 mm, or alternatively less than about 5 mm, or alternatively less than about 4 mm. While reagent ball is illustrated as a sphere, the disclosure is not limited thereto and many shapes may be used and multiple reagent balls each containing the same or different reagents also may be used. The spacer element separating the primer from a label comprises a polymer e.g., hexaethylene glycol or triethlyene glycol. Alternatively it can be a linear carbon polymer, e.g., hexane, pentane, containing from about 1 to about 18 carbon atoms or more.

As is apparent to the skilled artisan, combinations of the above embodiments, necessary to promote the specific amplification of a target nucleic acid, are intended within the scope of this disclosure.

The reagents and amounts thereof are pre-selected to facilitate the specific amplification of the target nucleic acids. For the purpose of illustration, non-limiting examples of reverse transcriptases are moloney murine leukemia virus (MMLV) or a derivative thereof or avian myeoblastosis virus (AMV) or a derivative thereof. The preferred reverse transcriptase will be dependent on the target and may not be the same between pellets for different targets, as it can be appreciated that the reagent ball can be used in a variety of different testing applications by modifying primers sequences and capture elements, primer concentrations, particle concentrations, affinity agents, lysis agents, polymerases, reverse transcriptases, and other enzymes to best match the optimal condition for each type of target (e.g. HIV quantification vs. influenza detection may have different reaction conditions).

Polymerases can include several different types, within the strand displacement polymerase category, options include for instance Bsu DNA polymerase or a fragment thereof such as Bsu DNA polymerase large fragment, Bst DNA polymerase, or a fragment thereof such as Bst DNA polymerase large fragment, phi29 DNA polymerase. It can be appreciated that for polymerases and reverse transcriptases it is often a desired property to have certain mutants such as polymerases lacking exonuclease activity or for the reverse transcriptase lacking RNase H activity.

Preferred reaction temperatures for an isothermal reaction can depend on the method and the reaction conditions and can include around 65 degrees Celsius as is often the case for LAMP and 55 degrees Celsius for Nicking Enzyme Amplification Reaction. A preferred but not limiting reaction temperature range is between about 37 and 42 degrees for the reverse transcriptase portion of an amplification reaction if the target nucleic acid is an RNA. Helicase Dependent Amplification, Strand Displacement Amplification, Recombinase Polymerase Amplification can all occur at about 37 degrees Celsius or between 37 degrees Celsius and 42 degrees Celsius. FIG. 20 shows the temperature profile of an isothermal reaction occurring in a reservoir at around 40 degrees Celsius.

It may be desired to include single-stranded binding proteins (SSB) to facilitate several isothermal amplification techniques as these proteins help stabilize the unwinding and strand displacement polymerization of complement strands during amplification. Examples include but are not limited to RB 49 GP 32, RB 69 GP 32, T4 GP32, E. coli's SSB protein, and others.

In some aspects, the reagent ball and the method further uses a helicase to unwind dsDNA for loading primers. Non-limiting examples include enzymes such as uvrD helicase from E. coli, T4 Gene 41 helicase, and many others. Recombinases that facilitate primer loading into dsDNA for enzymatic melting of duplex DNA for primer annealing can include RecA from E. coli, RAD51 human recombinase, DMC1 human meiotic recombinase, or analogues from phage such as T4 UvsX, RB 49 UvsX, RB 69 UvsX and many others. As is known to those of ordinary skilled in the art, combinations of helicase and SSB are helpful for facilitating isothermal amplification. Accessory factors such as MutL can be added to facilitate helicase dependent amplification. Combinations of recombinases and SSB can be helpful in RPA and sometimes accessory factors such as RecFOR from E. coli and/or UvsY from various phages are employed as well to facilitate the reaction by helping the primary enzyme (RecA) or (uvrD) within recombinase polymerase amplification and helicase dependent amplification respectively. As appreciated by the skilled artisan, the reagent ball and/or reservoir can further contain any one or more of the above reagents as necessary to facilitate the specific amplification of the target nucleic acid.

Primer concentrations for isothermal amplification reactions such as SDA, HDA, and RPA can be between 0.01 and 10 micromolar, preferably closer to 0.5 micromolar. A LAMP Primer mix can be prepared with all 4 or 6 (with Loop) primers. A 10× Primer Mix could contain: 16 µM FIP, 16 µM BIP, 2 µM F3, 2 µM BE, 4 µM LoopF, 4 µM LoopB. dNTPs can be provided in concentrations such as between 1 micromolar and 500 micromolar, preferably around 200 micromolar. SDA, HDA, RPA may require a high amount of ATP as some of the enzymes that allow for enzymatic melting and loading of primers into dsDNA require ATP to function and therefore as much as 100 micromolar to 4 millimolar of ATP can be used within a reaction.

Polymerase amounts can vary depending on the target but can be in the range of 1 unit to 1000 units per reaction. Reverse transcriptases can also be provided at such a range for a successful reaction. Magnesium is an essential co-factor for polymerase activity and can be provided in the reagent ball or in the reservoir at amounts well known in the art such as 5-50 millimolar, typically around 10 millimolar.

Methods and compositions for the non-covalent linkage of molecules that also can provide a label or signal for detection are known in the art. Non-limiting examples of such include avidin or streptavidin-biotin conjugation. Modifications to biotin are known in the art and intended within the scope of this disclosure. Non-limiting examples of such include biotin dT, biotin-TEG, dual biotin, PC biotin and desthioBiotin-TEG commercially available from Integrated DNA Technologies (see idtdna.com/pages/decoded/decoded-articles/core-concepts/decoded/2012/09/20/which-biotin-modification-to-use-, last accessed Jul. 16, 2016.) This disclosure also includes the use of additional conjugation chemistries for the linking of nucleic acids to proteins such as when a primer is conjugated directly to a signaling agent wherein in one aspect, the signaling agent is an enzyme such as HRP. Non-limiting examples of covalently joining a protein or polypeptide to another moiety include linking the moiety to a crosslinking reactive group, e.g., carbodiimides, imidoesters, and maleimides. See e.g., Bioconjugate Techniques, $3^{rd}$ Ed, Hermanson, G. T. (2013).

As is apparent to the skilled artisan, the components of the reagent ball are selected to facilitate the amplification of the target nucleic acid and/or targets, and/or controls by the appropriate method. In one aspect, the reagents are selected for rolling circle amplification (RCA), or loop-mediated isothermal amplification. In another aspect they are selected for amplification by the (LAMP) method. In another aspect they are selected for, strand displacement amplification (SDA). In another aspect they are selected for recombinase polymerase amplification (RPA). In another aspect they are selected for, helicase dependent amplification (HDA). In another aspect they are selected for, polymerase spiral reaction (PSR). In another aspect they are selected for nicking enzyme amplification reaction (NEAR). As indicated above, each particular reaction type has its own preferred combination of enzymes and components that allow efficient and selective amplification of the target and/or targets, and/or internal control nucleic acids and are known to the skilled artisan.

Each of the affinity molecules of the plurality of affinity molecules may be bound to a solid particle. The solid particle may be formed of magnetically responsive material and/or may be formed of non-magnetically responsive material. The non-magnetically responsive material may be gold nanoparticles.

The plurality of sample target analytes pre-bound to sample binding molecules may include 25-hydroxy Vitamin D2 or 25-hydroxy Vitamin D3 molecules pre-bound to vitamin D binding protein molecules. The plurality of competitor molecules pre-bound to sample binding molecules may include 25-hydroxy Vitamin D2 or 25-hydroxy Vitamin D3 molecules labeled with biotin and prebound to vitamin D binding protein molecules. At least one of the plurality of affinity molecules, the plurality of de-binding agents, the plurality of signaling agents, and the plurality of competitor molecules pre-bound to competitor binding molecules may be stored within a reagent ball.

As noted above, the primers (forward and reverse for the target nucleic acid and control templates) are designed based on the nucleotide sequence of the target nucleic acid to be amplified and detected if present. Methods to design optimal primers based on a target sequence are known in the art, see e.g., simgene.com/Primer3; quill.com; molbiol-tools.caPCR; and ncbi.nlm.nih.gov/tools/primer-blast/, each last accessed on Jul. 15, 2016, and vary with the amplification method utilized, e.g., rolling circle amplification (RCA), loop-mediated isothermal amplification (LAMP), strand displacement amplification (SDA), recombinase polymerase amplification (RPA), helicase dependent amplification (HDA), polymerase spiral reaction (PSR), and nicking enzyme amplification reaction (NEAR).

In accordance with yet another aspect, a sample analysis cartridge is provided for detecting at least one of a presence, absence, or quantity of one or more analytes. The sample analysis cartridge may include a reagent ball, a reservoir, and/or a sensor, each of which may be within a housing of the cartridge. The reagent ball may include a plurality of competitor molecules pre-bound to competitor binding molecules, each of the plurality of competitor molecules may possess a label or bound to a signaling agent. In another aspect, the reagent ball comprises, or alternatively consists essentially of, the reagents necessary for amplification and detection of a target nucleic acid. The reservoir may be configured to hold a reservoir fluid, which may or may not be pre-filled in the reservoir. The reservoir may be configured to permit mixing of, within the reservoir fluid, a plurality of affinity molecules, a plurality of de-binding agents, a plurality of signaling agents, the plurality of competitor molecules pre-bound to competitor binding molecules, and a sample from a sample collection device, the sample having a plurality of sample target analytes pre-bound to sample binding molecules. A de-binding agent of the plurality of de-binding agents may be configured to de-bind a competitor molecule from the pre-bound competitor binding molecule or a sample target analyte from the pre-bound sample binding molecule. The label of the de-bound competitor molecule may be configured to bind to a signaling agent and the de-bound competitor molecule may be configured to bind to an affinity molecule of the plurality of affinity molecules. In another aspect, the reservoir is configured to hold a reservoir fluid, which may or may not be prefilled in the reservoir. The reservoir configured to permit mixing of, within the reservoir fluid, a plurality of enzymes to facilitate an amplification reaction, e.g., polymerases, reverse transcriptases; a plurality of magnetic beads having coupled thereto an affinity molecule; a plurality of forward primers selected to amplify the target nucleic acid and having coupled to each thereto a spacer element; a plurality of reverse primers selected to amplify the target nucleic acid and having coupled to each thereto a spacer element and a signaling agent or a signaling capture element; a plurality of nucleotides or analogs thereof (dNTPs) for the amplification reaction; a plurality of DNA template control nucleic acids; a plurality of reverse primers selected to serve as an internal control having coupled to each thereto a spacer element and a signaling agent; and a plurality of forward primers selected to serve as an internal control having coupled to each thereto a spacer element and a capture element. In one aspect the amplification reagents are selected for any one or more other PCR methods or isothermal amplification.

In a further aspect, the reagent ball and/or the reservoir contains an effective amount of a lysing agent to lyse a sample comprising a cell, e.g., a bacterial sample to release intracellular DNA, RNA and/or proteins that serve as analytes. Non-limiting example of lysing agents include NP-40, CHAPS, deoxycholate, Triton X-100, NP40, and Tween 20.

In a further aspect, the reagent ball and/or the reservoir contains an RNAse inhibitor and/or DNAse inhibitor and/or protease inhibitor in an amount to inhibit RNAse, DNAse or protease activity native or endogenous to the sample being added for analysis.

Spacer elements can be advantageous because in some cases the primer can participate better in the amplification reaction if the nucleic acid portion of the primer is more distant from the label where other sterically hindering events could be occurring or have already occurred such as being bound to a particle or being bound to a signaling agent, both of which may be bulky. The spacer element separating the primer from a label comprises a polymer e.g., hexaethylene glycol, triethlyene glycol, a C3 spacer phosphoramidite, a PC spacer, hexanediol and are commercially available from Integrated DNA Technologies (see idtdna.com/site/Catalog/Modifications/Category/6, last accessed Jul. 16, 2016).

The sensor may be configured to be exposed to the mixed reservoir fluid and the sensor may be further configured to generate a signal indicative of at least one of the presence, absence, or quantity of the sample target analyte within the sample. For example, particles from the mixed reservoir fluid comprising signaling agents may localize in an analysis channel over the sensor and the localized signaling agents may react with substrates from a substrate solution to generate electrical signals sensed by the sensor. The sensor may send the signal indicative of at least one of the presence, absence, or quantity of the sample target analyte within the sample using the electrical signals from the reaction.

The reservoir may be further configured to permit mixing of a plurality of solid particles within the reservoir fluid. Each solid particle may be pre-bound to an affinity molecule of the plurality of affinity molecules. The plurality of solid particles may be formed of magnetically responsive material and/or formed of non-magnetically responsive material. The non-magnetically responsive material may be gold nanoparticles. The plurality of sample target analytes pre-bound to sample binding molecules may include 25-Hydroxy vitamin D3 and/or 25-hydroxy vitamin D2 molecules pre-bound to binding protein molecules. The magnetically responsive material may be magnetically held over the sensor.

In accordance with yet another aspect, a sample analysis cartridge is provided. The sample analysis cartridge may include an input tunnel, a reservoir, a shuttle, and/or a collet, each of which may be within a housing of the cartridge. The input tunnel may extend from an aperture and be configured to permit insertion of a sample collection device having a distal portion adapted to be exposed to a sample. The reservoir may be configured to hold a fluid. The shuttle may be disposed in the input tunnel between the reservoir and the aperture in a first position. The collet may be disposed in the input tunnel and coupled to the shuttle in the first position. The collet may decouple from the shuttle during insertion of the sample collection device in the input tunnel. The shuttle may move within the input tunnel from the first position to a second position after the collet is decoupled from the shuttle such that the shuttle is at least partially disposed within the reservoir in the second position.

The sample analysis cartridge may include a sensor configured to be exposed to the fluid mixed with the sample. The sensor may generate a signal indicative of at least one of the presence, absence, or quantity of the one or more analytes within the sample. The shuttle may have a first end and a second end disposed proximal to the first end in the input tunnel. The second end of the shuttle may be configured to be disposed within a lumen of the collet in the first position. The first end of the shuttle may form a wall of the reservoir in the first position.

The collet may have one or more locking arms configured to couple the collet to the shuttle in the first position. The one or more locking arms may be configured to be deflected to decouple the one or more locking arms from the shuttle responsive to a force applied on the one or more locking arms by the sample collection device during insertion of the sample collection device in the input tunnel.

The sample analysis cartridge may include a sealing material configured to fluidicly seal the fluid within the reservoir and a seal piercer disposed partially within the input tunnel. The seal piercer may be configured to be contacted by the sample collection device within the input tunnel and to move, responsive to force applied by the sample collection device, to pierce the sealing material to vent the fluid in the reservoir. The collet may have a slot and a portion of the seal piercer may extend through the slot into the input tunnel to permit contact between the seal piercer and the sample collection device.

The sample analysis cartridge may include a contact switch. The collet may have a deflector portion disposed adjacent the contact switch and configured to deflect to activate the contact switch responsive to a force applied on the deflector portion by the sample collection device during insertion of the sample collection device in the input tunnel. The deflector portion of the collet may include an arm configured to deflect downward to activate the contact switch. The contact switch may be positioned in the input tunnel such that activation of the contact switch indicates full insertion of the sample collection device in the input tunnel.

The shuttle may be configured to house a reagent ball comprising reagents between first and second ends of the shuttle. Preferably, the reagent ball is not exposed to the fluid in the reservoir in the first position and is exposed to the fluid in the reservoir in the second position.

In accordance with yet another aspect, a sample analysis cartridge is provided. The sample analysis cartridge may include an input tunnel, a reservoir, a collet, and/or a contact switch, each of which may be within a housing of the cartridge. The input tunnel may extend from an aperture and may permit insertion of a sample collection device having a distal portion adapted to be exposed to a sample. The reservoir may be configured to hold a fluid. The collet may be disposed in the input tunnel between the reservoir and the aperture. The collet may have a deflector portion and a lumen sized to receive the distal portion of the sample collection device therein. The contact switch may be disposed adjacent the deflector portion of the collet. The deflector portion may be configured to deflect to activate the contact switch responsive to a force applied on the deflector portion by the sample collection device during insertion of the sample collection device in the input tunnel.

The sample analysis cartridge may include a shuttle disposed within the input tunnel and configured to house a reagent ball(s) comprising reagents between first and second ends of the shuttle. The deflector portion of the collet may be an arm configured to deflect downward to activate the contact switch. The contact switch may be positioned such that activation of the contact switch indicates full insertion of the sample collection device in the input tunnel.

The sample analysis cartridge may include a sensor configured to be exposed to the fluid mixed with the sample. The sensor may generate a signal indicative of at least one of the presence, absence, or quantity of the one or more analytes within the sample.

In accordance with another aspect, a sample analysis cartridge is provided. The sample analysis cartridge may include an input tunnel, a reservoir, a shuttle, and/or a sonicator, each of which may be within a housing of the cartridge. The input tunnel may extend from an aperture and may permit insertion of a sample collection device having a distal portion adapted to be exposed to a sample. The reservoir may be configured to hold a fluid. The shuttle may define a first compartment and a second compartment. The first and second compartments may be configured to be disposed within the reservoir in a mixing position. The sonicator may be configured to emit acoustic waves to move the fluid in the reservoir in a wave pattern between the first and second compartments to mix the fluid in the reservoir.

The shuttle may include a compartment divider configured to divide the first compartment from the second compartment. The compartment divider may be a flange. Fluid flowing around the compartment divider may facilitate formation of the wave pattern. The compartment divider may have a slot configured to permit the fluid to flow through the compartment divider via the slot during mixing. The first compartment may be a reagent ball compartment configured to house a reagent ball including reagents and the second compartment may be a sample compartment configured to receive the sample from the sample collection device, e.g., expelled from the sample collection device and/or on the distal portion of the sample collection device. The reagent ball may include, as described above, reagents for the amplification of a target nucleic acid, e.g., polymerases, primers, and signaling agents. The first and second compartments are preferably not disposed within the reservoir in a pre-mixing position.

The sonicator may be a piezoelectric transducer such as a piezoceramic disc. The sonicator may form a wall of the reservoir, e.g., part of the bottom wall of the reservoir. The reservoir may be symmetric. Each of the walls of the reservoir may meet at an angle greater than a predetermined angle such as 60° to facilitate fluid emptying through an outlet of the reservoir. The sonicator may be positioned off-center of the reservoir to facilitate mixing of the fluid within the reservoir.

The sample analysis cartridge may include a printed circuit board coupled to the sonicator via one or more spring contacts. The sonicator may be electrically coupled to the printed circuit board only via the one or more spring contacts. The sonicator may be activated responsive to a signal from a processor, e.g., the processor of the reader.

The sample analysis cartridge may include a temperature sensor configured to sense temperature indicative of temperature of the fluid in the reservoir. The temperature sensor may be disposed on a printed circuit board positioned adjacent the sonicator.

The sample analysis cartridge may include a contact switch configured to indicate insertion of the sample collection device in the input tunnel. The sonicator may be configured to emit the acoustic waves after actuation of the contact switch. For example, the reader may direct the sonicator to emit the acoustic waves after the reader receives an electrical signal indicating that the contact switch has been activated.

The acoustic waves emitted by the sonicator may be configured to isothermally amplify reactions of the fluid mixed in the reservoir.

In accordance with another aspect, a method for isothermal amplification of a target nucleic acid if present in a sample analysis cartridge is provided. The method comprises or alternatively consists of contacting in the reservoir a reagent ball as described above and containing a plurality of reagents pre-selected for the amplification and detection of the target nucleic acid with the sample to produce an amplicon-signaling agent complex coupled to the solid particle. The amplicon comprises a nucleic acid duplex comprising: a reverse primer complex comprising a nucleic acid comprising the target nucleic acid coupled to a spacer element that in turn is coupled to a signaling agent and a forward primer complex comprising a nucleic acid comprising the target sequence coupled at one end to a capture element. In a further aspect, the reverse primer complex further comprises a signaling affinity element conjugated to the signaling agent and the spacer element. The amplicon-signaling agent complex in turn is conjugated to an affinity element on the solid particle that in turn, can be bound or held to the sensor surface over a magnetic field. The amplicon-signaling agent complex in turn is conjugated to an affinity element on the solid particle that in turn, can be held to the sensor surface over a magnetic field. If the analyte is present, the sensor detects and/or quantifies the signaling agent-labeled amplicon.

A sonicator may emit acoustic waves toward the reservoir to promote amplification of the target nucleic acid in the reservoir. As noted above, the amplicon-signaling agent complex may be reacted with a substrate from a substrate reservoir. For example, the reaction may occur over a sensor in an analysis channel. A signal indicative of at least one of a presence, absence or quantity of amplified nucleic acid may be generated. The signal may be transmitted from the cartridge to another device such as a reader.

A reagent ball may be held in a shuttle. The shuttle may be disposed in an input tunnel of the cartridge. The reagent ball may comprise reagents for amplification of a target nucleic acid by an isothermal reaction as noted above. The reagents may comprise a polymerase, primers for amplification of the target nucleic acid and a signaling agent for the detection of the amplification of the target nucleic acid. One or more affinity molecules may be covalently or non-covalently bound to a solid particle for detection of the target nucleic acid.

In accordance with another aspect, a kit is provided. The kit may include a reservoir, a sonicator, a temperature sensor, and/or a processor. The reservoir may be configured to hold a fluid and to receive a sample collected by a sample collection device. The sonicator may be configured to emit acoustic waves to mix the fluid and the sample in the reservoir. The temperature sensor may be configured to generate a signal indicative of temperature of the fluid in the reservoir. The processor may be configured to activate the sonicator to emit the acoustic waves and to monitor the signal from the temperature sensor. The processor further may be configured to modify emission of the acoustic waves from the sonicator if the signal indicates a temperature of the fluid in the reservoir outside a threshold. A sample analysis cartridge may include the reservoir, the sonicator, and/or the temperature sensor, each of which may be within a housing of the cartridge, and a reader may include the processor. The reader may be configured to be electrically coupled to the sample analysis cartridge.

The sample analysis cartridge may include a printed circuit board and the temperature sensor may be disposed on the printed circuit board positioned adjacent the sonicator. The sample analysis cartridge may include a contact switch configured to generate a signal to indicate insertion of the sample collection device in an input tunnel of the sample analysis cartridge. The processor of the reader may be configured to receive the signal from the contact switch and to activate the sonicator after receipt of the signal from the contact switch. The processor may modify emission of the acoustic waves from the sonicator by lowering a duty cycle of the sonicator if the signal indicates the temperature of the fluid in the reservoir is above the threshold. The processor may modify emission of the acoustic waves from the sonicator by increasing a duty cycle of the sonicator if the signal indicates the temperature of the fluid in the reservoir is below the threshold. The processor may modify emission of the acoustic waves from the sonicator by deactivating the sonicator if the signal indicates the temperature of the fluid in the reservoir is above the threshold.

The acoustic waves emitted by the sonicator may be configured to isothermally amplify reactions of the fluid mixed in the reservoir. The sample analysis cartridge may include a reagent ball disposed within the sample analysis cartridge. The sonicator may be configured to emit the acoustic waves to mix the fluid, the reagent ball, and the sample in the reservoir. The reagent ball may include polymerases, primers, and signaling agents. The sample analysis cartridge may include a shuttle configured to house the reagent ball.

In accordance with another aspect, a sensor for use in a microfluidic cartridge is provided. The sensor may include a positive control working electrode, a working electrode, and/or a negative control working electrode. The positive control working electrode may include affinity molecules pre-bound to the positive control working electrode. For example, the affinity molecules may be pre-bound to a surface of the positive control working electrode disposed within an analysis channel of the cartridge. The positive control working electrode may be configured to generate a first signal based on a reaction between signaling agents directly or indirectly bound to the affinity molecules and a chemical substrate. The signaling agents may be from a reagent ball(s). The chemical substrate may be from fluid stored in the substrate reservoir. The working electrode may be configured to generate a second signal based on a reaction between the signaling agents localized at the working electrode and the chemical substrate. The negative control working electrode may include a self-assembled monolayer. For example, the self-assembled monolayer may be at a surface of the negative control working electrode disposed within an analysis channel of the cartridge. The negative control working electrode may be configured to generate a third signal based on a reaction between the signaling agents localized at the negative working electrode and the chemical substrate. As should be understood, "first", "second", and "third" differentiate terms and do not necessarily mean order.

The second signal may be indicative of at least one of the presence, absence, or quantity of one or more analytes within a sample. The first signal may be indicative of reliability of a test. For example, the test may be determined to be reliable if the first signal indicates a quantity of the reaction within a predetermined range. The third signal is indicative of reliability of a test. For example, the test may be determined to be reliable if the third signal indicates a quantity of the reaction is below a threshold.

A cartridge may include the sensor. The cartridge may have an analysis channel and the positive control working electrode, the working electrode, and the negative control working electrode may be disposed in the analysis channel.

A kit including the cartridge is also provided. The kit may include a processor configured to process the second signal to generate information indicative of at least one of the presence, absence, or quantity of one or more analytes within a sample. The processor may process the first signal to determine if the first signal indicates a quantity of the reaction within a predetermined range. The processor may generate an alert if the quantity is outside the predetermined range. The processor may process the third signal to determine if the third signal indicates a quantity of the reaction below a threshold. The processor may generate an alert if the quantity is above the threshold. The processor may be a component of a reader.

The working electrode may be masked with a plurality of striations configured to promote homogenous distribution of a plurality of magnetic particles directly or indirectly bound to the signaling agents localized over the working electrode and to promote resistance to movement of the plurality of magnetic particles off of the working electrode.

The working electrode may include a self-assembled monolayer. For example, the self-assembled monolayer may be at a surface of the working electrode disposed within an analysis channel of the cartridge.

The working electrode may include affinity molecules pre-bound to the working electrode. For example, the affinity molecules may be pre-bound to a surface of the working electrode disposed within an analysis channel of the cartridge.

Such methods and devices may be used, for example, to determine: from which illness, among many, a person is suffering; to which drug or poison, among many, a person is adversely reacting; or which chemical, among many, has contaminated the water. Other examples include quantifying the concentrations of various agents, that include without limitation vitamins, hormones, proteins, or other analytes of interest within one's body, waterborne and foodborne pathogens, microbial growth and/or contamination of medical equipment, and other potential disease-causing contaminants from pets and livestock. Examples of contaminates include, but are not limited to viral, bacterial, and fungal pathogens, bloodstream infection (BSI), pneumonia (e.g., ventilator-associated pneumonia [VAP]), urinary tract infection (UTI), and surgical site infection (SSI), *Staphylococcus aureus*, Methicillin resistant *Staphylococcus aureus*, *Candida albicans*, *Pseudomonas aeruginosa*, *Acinetobacter baumannii*, *Stenotrophomonas maltophilia*, *Clostridium difficile*, Tuberculosis, Gastroenteritis, Vancomycin-resistant *Enterococcus*, Legionnaires' disease, Puerperal fever, MRSA, and *E. coli*. Examples of foodborne pathogens include, but are not limited to *shigella, salmonella, vibrio, Yersinia, Listeria, Escherichia coli*, and *Campylobacter*. The application of this technology is not limited to pathogens or analytes that are important to the health of human patients but also includes the health and maintenance of pets and livestock, e.g., veterinary uses.

BRIEF DESCRIPTION OF THE DRAWINGS

Exemplary embodiments are described below with reference to the accompanying drawings, wherein like numerals denote like elements. In the drawings:

FIGS. 1A-1B provide schematic depictions of an exemplary analyte detection system for analyzing the presence, absence, and/or quantity of one or more target analytes within a collected sample and for viewing analysis results, wherein FIG. 1A shows components uncoupled and FIG. 1B shows components coupled for analysis and charging.

FIG. 1C provides a schematic depiction of another exemplary analyte detection system for analyzing the presence, absence, and/or quantity of one or more target analytes within a collected sample and for viewing analysis results, wherein a charger is not provided.

FIGS. 2A and 2B illustrate perspective views of an exemplary sample collection device for use in the detection system.

FIGS. 4A and 4B illustrate perspective views of the cartridge device with the sample collection device locked therein for analysis of the collected sample, wherein FIG. 4A shows the top surface of the cartridge device and FIG. 4B shows the bottom surface of the cartridge device.

FIGS. 6A, 6B, and 6C illustrate an exemplary circuit board and an exemplary layer that may be used within the housing of the cartridge device, wherein FIG. 6A depicts the circuit board, FIG. 6B depicts the layer, and FIG. 6C depicts the layer disposed on and coupled to the circuit board.

FIGS. 7A, 7B, and 7C illustrate another exemplary circuit board and another exemplary layer that may be used within the housing of the cartridge device, wherein FIG. 7A depicts the circuit board, FIG. 7B depicts the layer, and FIG. 7C depicts the layer disposed on and coupled to the circuit board and an absorbent pad.

FIGS. 7D through 7F illustrate alternative exemplary sensors that may be used within the housing of the cartridge device.

FIGS. 9A and 9B illustrate exemplary shuttles that may be disposed in the housing of the cartridge device, wherein the shuttles are each shown housing a reagent ball.

FIG. 10A is a cross-sectional perspective view showing a sample collection device partially inserted within an input tunnel of a cartridge device.

FIG. 10E is a cross-sectional side view showing engagement between the sample collection device and the seal piercer and sealing between the sample collection device and the shuttle, wherein the sample preparation reservoir remains sealed by the shuttle.

FIG. 10F is a top view showing engagement between the sample collection device and the seal piercer in a pre-venting position.

FIG. 10G is a cross-sectional perspective view showing the piercing element and the slider of the seal piercer in a pre-venting position, wherein the sealing material over the sample preparation reservoir within the cartridge device has not yet been pierced.

FIG. 10H is a cross-sectional side view illustrating transition from the pre-mixing and pre-venting positions towards the mixing and venting positions within the input tunnel of the cartridge device.

FIG. 10I is a top view showing movement of the sample collection device causing movement of the seal piercer to the venting position.

FIG. 10J is a cross-sectional perspective view showing the piercing element piercing the sealing material over the sample preparation reservoir within the cartridge device.

FIG. 10K is a cross-sectional side view showing the sample collection device in the venting and mixing positions, wherein the sealing material over the sample preparation reservoir is vented and the collected sample and the reagent ball are mixed within the fluid in the sample preparation reservoir which has been re-sealed by the shuttle.

FIGS. 11A through 11E illustrate an alternative seal piercer wherein insertion of a sample collection device within the input tunnel of the cartridge device also activates a switch to represent proper sample collection device insertion.

FIGS. 13B through 13SS illustrate various views of exemplary sample collection devices that may be used in the detection system.

FIGS. 14A through 14D illustrate exemplary collets that may be disposed in the housing of the cartridge device, wherein FIGS. 14A and 14C show perspective views and FIGS. 14B and 14D show cross-sectional views of the collets in FIGS. 14A and 14C, respectively.

FIGS. 16F and 16G illustrate cross-sectional top views showing further distal insertion of the sample collection device in the cartridge.

FIGS. 18A and 18B are cross-sectional side and top views, respectively, of another exemplary cartridge device.

FIGS. 26A and 26B provide schematic depictions of molecules and reactions found within one embodiment of the presently disclosed analyte detection system.

FIGS. 26C and 26D provide schematic depictions of molecules and reactions found within another embodiment of the presently disclosed analyte detection system.

FIGS. 27A and 27B provide schematic depictions of molecules and reactions found within yet another embodiment of the presently disclosed analyte detection system.

FIG. 30A is another schematic depiction of molecules within a sample on a sample collection device.

FIG. 30B is another schematic depiction of molecules within two reagent balls for reacting with the molecules within the collected sample.

FIG. 30C is another schematic depiction of molecules within a single reagent ball for reacting with the molecules within the collected sample.

FIG. 30D is another schematic depiction of molecules showing the collected sample being introduced to a sample preparation reservoir.

FIGS. 31A through 32H show an exemplary process for detecting the presence, absence, and/or quantity of a target analyte(s) within a sample in a cartridge.

FIGS. 32A through 32K show an exemplary process for detecting the presence, absence, and/or quantity of a target analyte(s) within a sample in a cartridge using isothermal amplification.

DETAILED DESCRIPTION OF CERTAIN EMBODIMENTS

Figure 1A:
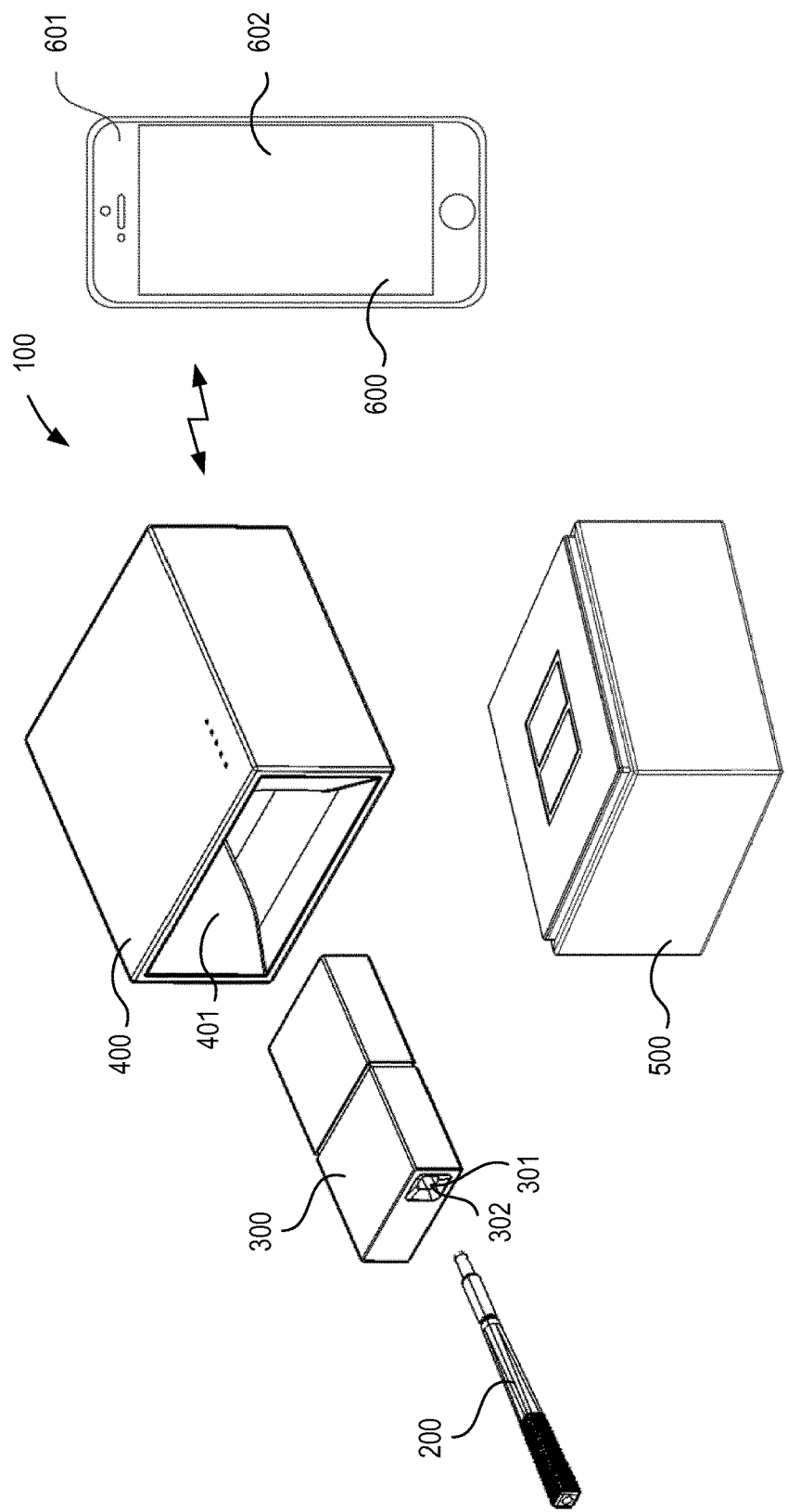

In the following detailed description, reference is made to the accompanying drawings, which form part of the present disclosure. The embodiments described in the drawings and description are intended to be exemplary and not limiting. As used herein, the term "exemplary" means "serving as an example or illustration" and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Various devices, systems, kits, and methods disclosed herein are intended to isolate, tag, and detect a target analyte within a sample taken from a specimen. In certain embodiments, chemical reactions are employed to enable such detection.

Various embodiments of systems described herein are designed to create a self-contained environment in which any of the chemical reactions occur in an automated manner entirely or substantially without human intervention, for example, as described in commonly assigned U.S. Patent Pub. No. 2014/0336083 to Khattak, U.S. Pat. No. 9,034,168 to Khattak, U.S. Pat. No. 9,052,275 to Khattak, U.S. Pat. No. 9,086,417 to Khattak, U.S. Pat. No. 9,207,244 to Khattak, U.S. Pat. No. 9,207,245 to Khattak, and U.S. Pat. No. 9,360,491 to Sever, the entire contents of each of which are incorporated herein by reference. In some designs described herein, one or more chemical reactions proceed without any need for an operator to add or remove reagents from the system. In certain embodiments, the systems are closed such that biohazard risks, such as the risk of spilling sample collected from a specimen, are minimized. In various embodiments, such systems include at least, a sample collection device, a cartridge device, and a reader device. Some exemplary embodiments of such devices are described in detail below.

FIGS. 1A and 1B illustrate an exemplary analyte detection system constructed in accordance with the principles of the present disclosure. Detection system 100 may include sample collection device 200, cartridge device 300, reader device 400, charger 500, and/or software-based detection interface system 600. Detection system 100 may be used to detect the presence, absence, and/or quantity of one or more target analytes.

Sample collection device 200 is configured to be exposed to a sample for analysis. For example, sample collection device 200 may be exposed to a biological sample, such as, but not limited to, blood, plasma, urine, saliva, mucous, cellular material and/or other biological material for determining the presence, absence, and/or quantity of one or more target analytes within the sample. In addition or alternatively, the sample collection device is exposed to a solid or other surface that is suspected of harboring a target analyte, e.g., a food-borne pathogen and the surface is a cooking or food preparation surface.

Cartridge device 300 is configured to analyze the sample collected with sample collection device 200. Cartridge device 300 may include input tunnel 301 that extends from aperture 302 into the cartridge housing. Input tunnel 301 is configured to permit insertion of sample collection device 200 as shown in FIG. 1B such that the collected sample may be analyzed within cartridge device 300. Based on the analysis, cartridge device 300 is configured to generate electric signals indicative of the presence, absence, and/or quantity of one or more target analytes within the sample.

Reader 400 is configured for electric coupling with cartridge device 300 to permit transmission of the electric signals indicative of the presence, absence, and/or quantity of one or more target analytes within the sample generated by cartridge device 300. Cartridge device 300 may be electrically coupled to reader 400 by inserting cartridge device 300 within reader opening 401 of reader 400 as shown in FIG. 1B such that respective electrical connectors of cartridge device 300 and reader 400 contact one another. Reader 400 may comprise a computer readable medium with instructions that, when executed by a processor of reader 400, cause electrical components of cartridge 300 to perform steps for analyzing the sample on sample collection device 200. Preferably, the instructions are not executed until cartridge device 300 is electrically coupled to reader 400 and sample collection device 200 is suitably disposed within cartridge device 300, for example, as shown in FIG. 1B or 4A.

In one embodiment, sample collection device 200 and cartridge device 300 are each disposable and designed for one time use while reader 400 is designed for multi-use and for receiving many different cartridge devices throughout the life of reader 400 such that many samples are analyzed by reader 400 for determining the presence, absence, and/or quantity of one or more target analytes within the respective samples. Such a configuration is expected to promote sanitary use of the system, as the components exposed to the sample are disposable, while reducing costs as the components with more expensive electronics, e.g., reader 400, may be used repeatedly.

Charger 500 is configured to charge one or more batteries within reader 400, e.g., via respective inductive coils disposed within the housings of charger 500 and reader 400. Charger 500 may be plugged into a conventional socket, e.g., via a cord or a cord with an AC to DC power converter, for charging components within charger 500 to permit charging of reader 400.

As will be readily apparent to one skilled in the art, the detection system need not require a charger. For example, referring to FIG. 1C, detection system 100' is constructed similarly to detection system 100 of FIGS. 1A and 1B, wherein like components are identified by like-primed reference numbers. Thus, for example, cartridge device 300' in FIG. 1C corresponds to cartridge device 300 of FIGS. 1A and 1B, etc. As will be observed by comparing FIGS. 1C and 1B, detection system 100' does not include charger 500. In such an embodiment, reader 400' may be plugged into a conventional socket, e.g., via a cord or a cord with an AC to DC power converter, for powering components of reader 400' and/or reader 400' may include a suitable battery such as a replaceable battery or rechargeable battery and reader 400' may include circuitry for charging the rechargeable battery, and a detachable power cord.

In FIGS. 1A and 1B, software-based detection interface system 600 is installed and runs on computing device 601 to permit a user to review analyte detection test results, e.g., on display 602 of computing device 601. Computing device 601 may be, for example, a smartphone, smartwatch, tablet, wearable device, a laptop or other computer. As shown in FIGS. 1A and 1B, reader 400 may communicate with computing device 601 wirelessly to transmit data indicative of the presence, absence, and/or quantity of one or more target analytes based on the electrical signals generated within cartridge device 300. In addition or alternatively, a removable wired connection, such as a cable connection, may be provided between reader 400 and computing device 601. Software-based detection interface system 600 may comprise a computer readable medium with instructions that, when executed by a processor of computing device 601, cause display 602 to display information indicative of the presence, absence, and/or quantity of one or more target analytes.

Sample Collection Devices and Cartridges

The sample collection device of various embodiments is configured to collect a sample from a specimen. Sample collection devices may be configured to collect cells and other biological material from any desired region or location, for example, an inner cheek, the throat, a nasal passageway, an ear, from urine, from blood, from plasma, from saliva, or from another body part. One exemplary sample collection device includes a unit that wicks a small droplet of blood or urine into a small capillary channel. In other embodiments, the sample collection device may be configured to collect biological material, particulates, or other chemicals from the environment, such as, for example, from the air or the water, or from a physical surface or other structure.

The sample collection device of various embodiments is sized and shaped to collect a sufficiently large sample from an appropriate location of a specimen such that it is possible, using the other devices described below, to detect the presence, absence, and/or quantity of one or more target analytes in and/or on the specimen. For example, for some target analytes, such as ones associated with a virus causing cold or flu-like symptoms, the sample collection device may be a nose-insertion swab; the swab is sized and shaped to collect a sufficient amount of sample from a nasal passageway of an individual to enable detection of target analytes associated with the virus causing cold or flu-like symptoms, if present in the individual. For other target analytes, such as, for example, ones associated with strep throat, the sample collection device may be a throat swab shaped to scrape sufficient cells from an individual's throat or mouth. As another example, the sample collection device appropriate for collecting a target analyte associated with HIV may comprise a blood lancet. In another example, a sample collection device configured to collect urine may be appropriate for collecting target analytes for various tests, including, for example, tests for tracking testosterone levels, drug levels, vitamin levels, and/or fertility. A sample collection device for collecting fluid, such as urine, blood, plasma, or saliva, may include features for compressing a wicking portion of the device to expel sample absorbed on the wicking portion for analyzing the expelled sample. In yet a further aspect, the sample collection devise is shaped to collect a sample from a solid surface, e.g., on a medical device, on medical equipment or from the surface of a food preparation surface such as a cutting board or flat surface.

Referring to FIGS. 2A and 2B, sample collection device 200 is illustrated. Sample collection device 200 is configured to collect a small quantity of a sample to be analyzed and configured for full or partial insertion within cartridge device 300 after sample collection. Sample collection device 200 may include distal portion 201, proximal portion 202, and shaft 203 extending therebetween. Distal portion 201 may include tip 204 having tube 205 therein. Sample collection device 200 also may include handle 206, proximal sealing zone 207, distal sealing zone 208, and/or engagement zone 209.

Distal portion 201, including tip 204, is configured to be exposed to a sample such that, at most, a predetermined volume of the sample is disposed in tube 205 for analysis. Collection of a predetermined volume of the sample is expected to promote accuracy of analyte analysis as a substantially known quantity of the sample will be analyzed. Tip 204 may be transparent to permit a collector to verify that sample is disposed in tube 205. Tip 204 may have a rounded end as illustrated although various shapes may be used including any blunt or substantially blunt tip shape. Tip 204 may be configured to collect a sample from any desired region or location, for example, an inner cheek, the throat, the mouth, a nasal passageway, an ear, from urine, from blood, from plasma, from saliva, or from another body part.

Proximal portion 202 may include handle 206 sized and shaped to be held by a collector's hand. Handle 206 may include gripping protrusions as illustrated. Handle 206 may further lock sample collection device 200 within the input tunnel of cartridge device 300. Sample collection device 200 also may include proximal sealing zone 207 configured for sealing the input tunnel of cartridge device 300 when sample collection device 200 is inserted in the input tunnel. Proximal sealing zone 207 may include a protrusion extending around shaft 203 and sized greater than the input tunnel opening so as to seal off the input tunnel. As such, the protrusion may further lock sample collection device within the input tunnel of cartridge device 300. Handle 206 may be breakable or otherwise removable from the remainder of sample collection device 200 following insertion of the remainder of sample collection device 200 into cartridge device 300.

Shaft 203 is elongated to facilitate easy and sanitary collection, with a collector's hand removed from the site of collection. For example, shaft 203 may be elongated such that tip 204 may be exposed to a sample within an inner cheek, the throat, the mouth, a nasal passageway, an ear, from urine, from blood, from plasma, from saliva, etc. to collect fluid, cells, and other biological material, while handle 206 is not exposed to the sample. Shaft 203, tip 204, and handle 206 may be formed of the same material or of different materials. Shaft 203, tip 204, and handle 206 may be formed of a plastic. Sample collection device 200 may be pre-packaged within sterile packaging and is preferably configured for one-time use.

Sample collection device 200 may have distal sealing zone 208 for facilitating the formation of a liquid-tight seal between sample collection device 200 and cartridge device 300 after insertion of sample collection device 200 into cartridge device 300. For example, distal sealing zone 208 may be sized and shaped to seal the collected sample on tip 204 and fluid within a sample preparation reservoir of cartridge device 300 within cartridge device 300. Distal sealing zone 208 may be of greater radial size than tip 204. For example, distal sealing zone 208 may include a shoulder extending further from the longitudinal axis of sample collection device 200 than tip 204 such that shoulder abuts against a portion of cartridge device 300, e.g., a shuttle, to form the liquid-tight seal. In this manner, the sample may be sealed within cartridge device 300 to reduce leakage and exposure of the sample outside the cartridge. In addition, the shoulder may be used to move a seal piercer to vent one or more reservoirs within cartridge device 300 before, during, or after formation of the liquid-tight seal.

Sample collection device 200 may include engagement zone 209 configured for engagement with one or more components of cartridge device 300. For example, engagement zone 209 may be configured to be coupled, permanently or temporarily, to a seal piercer of the cartridge device to move the seal piercer within the cartridge device responsive to movement of sample collection device 200. Engagement zone 209 also may facilitate fixed engagement between sample collection device 200 and the cartridge device such that sample collection device 200 is mated irreversibly and immovably with the cartridge when sample collection device 200 is inserted a predetermined distance in the input tunnel of the cartridge. Engagement zone 209 may be a groove around shaft 203 as illustrated or may be multiple grooves extending a shorter distance from the longitudinal axis than the regular shaft surface and/or may be one or more protrusions extending a greater distance from the longitudinal axis of sample collection device 200.

In various embodiments, a cartridge is formed of a housing, which defines an enclosed space and has various features that enable the cartridge to do one or more of the following: receive a sample with target analytes from a sample collection device, store the sample with sample preparation reagents, provide a space for mixing and binding of the target analytes with sample preparation reagents, provide an analysis zone wherein bound target analytes localize over sensors for detection, provide a fluid medium for transporting the bound target analytes to the analysis zone, store and provide a substrate that can undergo a detectable reaction when introduced to the bound target analytes, provide a fluid medium for transporting the substrate to the bound target analytes in the analysis zone, and provide a waste collection zone where waste is stored.

In various embodiments, the cartridge is a substantially closed system wherein the reactions needed to detect the presence, absence, and/or quantity of one or more target analytes occur within the cartridge. The cartridge of such embodiments is said to be "substantially closed" because the only inputs needed into the cartridge system are one or more of the following: a sample from a specimen, energy to facilitate mixing and bound, and a magnetic force to facilitate localization of bound target analytes within an analysis zone; the only outputs from the cartridge are electrical signals. In various embodiments, the cartridge is target-analyte-specific with the included sample preparation reagents selected to detect one or more specific target analytes. Different cartridge types include different reagents intended to identify different target analytes. For example, different cartridge types may include inflammation, influenza, testosterone, fertility, HIV, and Vitamin D which each include application-specific reagents intended to identify different target analytes.

Figure 3:
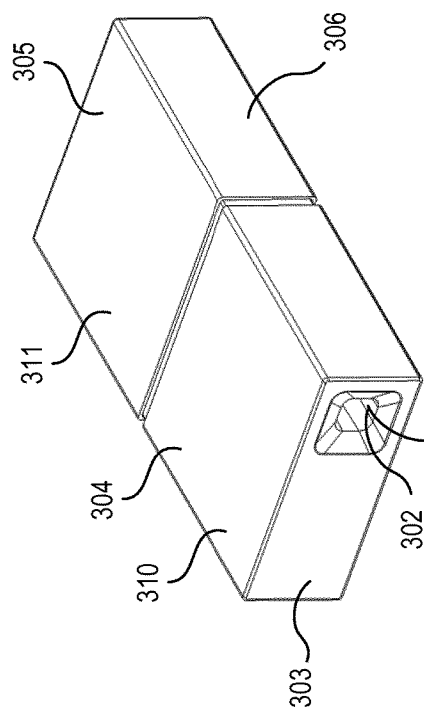
FIG. 3 illustrates a perspective view of an exemplary cartridge device for use in the detection system.

Referring now to FIG. 3, an exemplary cartridge is illustrated. Cartridge device 300 may include input tunnel 301 that extends from aperture 302 on front surface 303 into cartridge housing 304. Cartridge housing 304 may have a substantially rectangular prism shape as illustrated, although the present disclosure is not limited thereto. Cartridge housing 304 has front surface 303, top surface 305, right side surface 306, left side surface 307 (shown in FIG. 4A), bottom surface 308 (shown in FIG. 4B), and back surface 309 (shown in FIG. 4B). Cartridge housing 304 may be formed of a single component or multiple components. For example, cartridge housing 304 may include first cover component 310 configured to be laterally coupled to second cover component 311 such that the internal components of cartridge device 300 are housed therein.

Figure 4B:
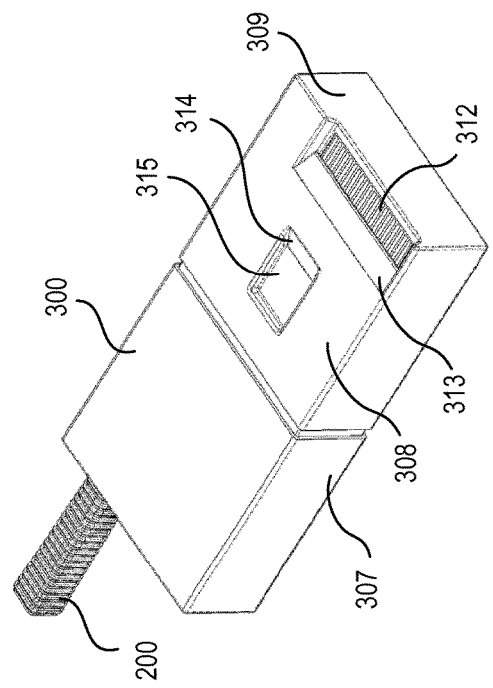
Figure 4A:
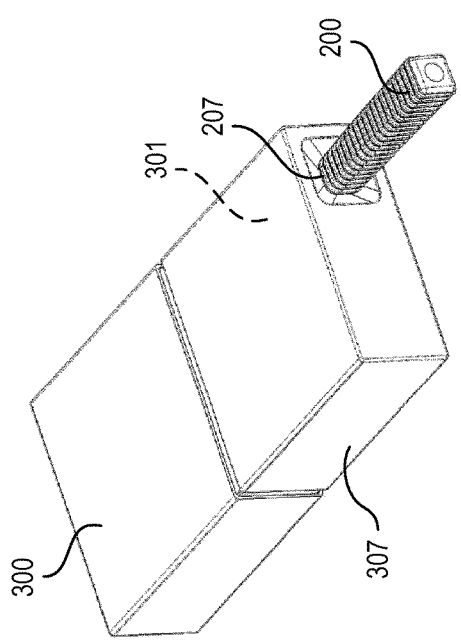

FIGS. 4A and 4B illustrate sample collection device 200 inserted within input tunnel 301 of cartridge device 300 in a mixing position. In the mixing position, proximal sealing zone 207 of sample collection device 200 may seal input tunnel 301 at aperture 302 to reduce or eliminate leakage from input tunnel 301. Input tunnel 301 may be integrally formed with housing 304 of cartridge device 300 or may be detachably coupled to cartridge housing 304. As shown in FIG. 4B, cartridge device 300 may include electrical connector 312 configured for electrical coupling with the reader, e.g., via an electrical connector of the reader. Accordingly, signals indicative of the presence, absence, and/or quantity of one or more target analytes may be transmitted from cartridge device 300 via electrical connector 312 to the reader. Electrical connector 312 may be positioned on bottom surface 308 and back surface 309 to facilitate coupling with the electrical connector within the opening of the reader.

Bottom surface 308 of cartridge device 300 may include first ramp portion 313, second ramp portion 314, and magnetic generator depression 315. First ramp portion 313 is configured to gradually depress one or more magnetic generators of the reader during insertion of cartridge device 300 within the opening of the reader. First ramp portion 313 may begin in the depression of cartridge housing 304 where electrical connector 312 is positioned and ramp down to bottom surface 308. As cartridge device 300 is inserted past first ramp portion 313, the magnetic generators remain in a depressed position until contacting the second ramp portion 314 which ramps up into magnetic generator depression 315. Second ramp portion 314 is configured to gradually guide the one or more magnetic generators of the reader into magnetic generator depression 315. Magnetic generator depression 315 is disposed beneath one or more working electrodes of cartridge device 300 such that the one or more magnetic generators of the reader move up into magnetic generator depression 315 and are disposed adjacent the one or more working electrodes when cartridge device 300 is fully inserted in the reader. Second ramp portion 314 also facilitates removal of cartridge device 300 from the reader by gradually depressing the one or more magnetic generators of the reader during cartridge removal.

Figure 5:
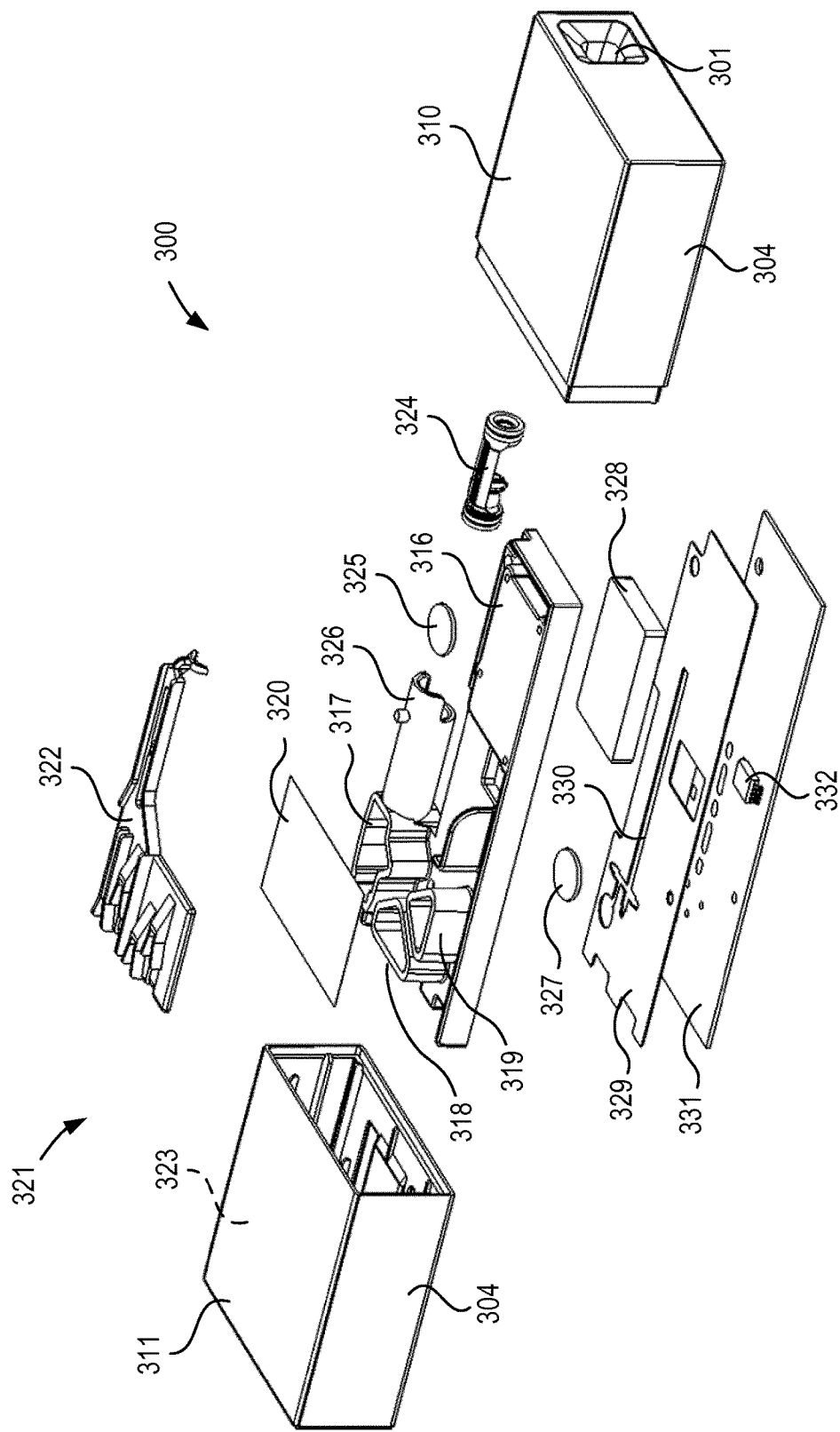
FIG. 5 illustrates an exploded view of the exemplary cartridge device showing internal components that may be within the cartridge housing.

Referring now to FIG. 5, an exploded view of cartridge device 300 is shown. Cartridge device 300 may include internal component 316—which may include sample preparation reservoir 317, wash reservoir 318, and substrate reservoir 319—sealing material 320, seal piercer 321—which may include slider 322 and piercer 323—shuttle 324, desiccant 325, input tunnel component 326, sonicator element 327, absorbent pad 328, layer 329, analysis channel 330, and circuit board 331 electrically coupled to memory 332. The internal components may be disposed within housing 304, e.g., between first and second cover components 310 and 311. Alternatively, one or more internal components may be disposed within one housing while other internal components may be disposed within another housing(s). In the case of multiple housings, such separate housing may be configured to couple to one another.

Internal component 316 is configured to define one or more reservoirs, illustratively sample preparation reservoir 317, wash reservoir 318, and substrate reservoir 319. Internal component 316 may further define a portion of analysis channel 330 such as by creating the upper boundary of analysis channel 330 when cartridge device 300 is assembled. Internal component 316 may house other internal components such as absorbent pad 328. Further, internal component 316 may be formed of a suitable material, such as plastic, and may have a base sized in a generally rectangular shape to sit over circuit board 331.

Sample preparation reservoir 317 is configured to hold a fluid, preferably a liquid having sample preparation reagents. For example, the fluid may be water, saline solution, water/saline solution mixed with one or more of magnetic particles, affinity molecules, connection molecules, signaling agents, competitor binding molecules, competitor molecules, labels, and/or signaling agents, as described in further detail below. Sample preparation reservoir 317 is positioned adjacent to the distal end of input tunnel 301 such that input tunnel 301 leads to sample preparation reservoir 317. As described further below, sample preparation reservoir 317 may be partially formed with sonicator element 327, e.g., as part or all of the bottom surface, which facilitates mixing of the fluid and additional particles in the fluid. In addition, sample preparation reservoir 317 may be partially formed with an end of shuttle 324 during the pre-mixing state and partially formed with another portion of shuttle 324 during the mixing state when one or more reagent balls and the sample are disposed in sample preparation reservoir 317. In this manner, sample preparation reservoir 317 remains fluidicly sealed in the pre-mixing state by shuttle 324 and in the mixing state by shuttle 324 and continuously fluidicly sealed throughout movement from the pre-mixing state to the mixing state such that fluid does not leak proximally past shuttle 324. Sample preparation reservoir 317 is positioned such that upon insertion of sample collection device 200 into input tunnel 301, distal portion 201 having the sample, e.g., at tip 204 and/or tube 205, enters sample preparation reservoir 317. When sample collection device 200 enters sample preparation reservoir 317, sample preparation reservoir 317 becomes further filled with sample particles, including one or more target analytes, if present in the sample. The fluid may be gently mixed, e.g., via sonicator element 327, with the one or more reagent balls and the sample to suspend and hybridize particles within sample preparation reservoir 317. The target analytes in the sample may hybridize and/or bind, at least, to the magnetic particles and/or to the affinity molecules present among the sample preparation reagents forming magnetic particle-bound complexes and/or affinity molecule-target complexes. Sample preparation reservoir 317 is configured to permit release, e.g., via an outlet, of the fluid having the sample and sample preparation reagents mixed therein into analysis channel 330 for analyzing the presence, absence, and/or quantity of one or more target analytes within the sample. The outlet of sample preparation reservoir 317 may be sealed with a heat actuated valve. When the valve opens, fluid from sample preparation reservoir 317 acts as a transport medium causing the magnetic particle-bound complexes and/or affinity molecule-target complexes and other particles to flow from sample preparation reservoir 317 into the analysis channel 330. Advantageously, the fluid serving as the mixing medium and storage medium within sample preparation reservoir 317 also acts as the flow medium to transport the contents of sample preparation reservoir 317 to an analysis zone within analysis channel 330 without the need for a pump.

Wash reservoir 318 is configured to hold a fluid, preferably a liquid configured as a wash solution. Wash reservoir 318 is further configured to permit release, e.g., via an outlet, of the wash solution into analysis channel 330 to move particles in the mixed fluid previously released from sample preparation reservoir 317 that are not bound to a magnetic particle or a pre-bound surface affinity molecule off a working electrode and/or off a positive control working electrode in the analysis channel. The outlet of wash reservoir 318 may be sealed with a heat actuated valve. When the valve opens, the wash solution flows from wash reservoir 318 into analysis channel 330, thereby removing all or substantially all unbound detector agents and/or unbound competitive binding agents from analysis channel 330. In one aspect, most or all free-floating, unbound molecules from sample preparation reservoir 317 are washed from analysis channel 330 to reduce the likelihood of having any non-specific binding of significance and/or non-specific signal generated by free floating signaling agents, e.g., HRP, of significance occur within an analysis zone of analysis channel 330.

Substrate reservoir 319 is configured to hold a fluid, preferably a substrate solution comprising a substrate such as a chemical substrate. The fluid of substrate reservoir 319 may include a substrate that undergoes a reaction in the presence of a signaling agent from sample preparation reservoir 317. For example, the substrate of substrate reservoir 319 may undergo an oxidation reaction in the presence of an oxidizing enzyme from sample preparation reservoir 317. The fluid may be a substrate solution including acceptor molecules, such as hydrogen peroxide, and the substrate which may be an enzyme substrate such as Tetramethylbenzidine (TMB) and/or o-phenylenediamine dihydrochloride (OPD) molecules. As an example, the substrate may be a commercially available enzyme-linked immunosorbent assay (ELISA) substrate. Preferably, the substrate is oxidizable and/or reducible. The acceptor molecules may be configured to receive electrons stripped from the substrate by the signaling agent (thereby oxidizing the substrate) during the reaction between the substrate and the signaling agent. For example, when the acceptor molecules are hydrogen peroxide, an oxidase reaction between the substrate, e.g., TMB, OPD, and the signaling agent, e.g., HRP, SBP, causes electrons to be stripped from the substrate and donated to the acceptor molecules (e.g., hydrogen peroxide) during the oxidase reaction such that the acceptor molecules convert to another molecule (e.g., water). In some embodiments, ferricyanide is used as the substrate (and reacted with a signaling agent, that may be an oxidation dye such as Methylene Blue, from sample preparation reservoir 317). Substrate reservoir 319 is further configured to permit release, e.g., via an outlet, of the fluid with the substrate into analysis channel 330. The outlet of substrate reservoir 319 may be sealed with a heat actuated valve. When the valve opens, fluid from substrate reservoir 319 acts as a transport medium causing the chemical substrate to flow from substrate reservoir 319 into analysis channel 330.

One skilled in the art will appreciate that while three reservoirs are depicted, in various embodiments, the plurality of reservoirs may include two reservoirs or four or more reservoirs and may adopt alternative spatial configurations. For example, wash reservoir 318 and substrate reservoir 319 could be combined into a reservoir configured to hold a fluid that acts as a wash solution and having chemical substrates. In addition, while the reservoirs are preferably pre-filled with the respective fluids described above, the disclosure is not limited thereto and one or more reservoirs may be empty in the non-use state and filled with the respective fluid during the mixing state.

Sealing material 320 is configured to fluidly seal the fluid in one or more reservoirs. For example, sealing material 320 may fluidly seal the respective fluids in sample preparation reservoir 317, wash reservoir 318, and substrate reservoir 319. Sealing material 320 may be a single piece of material configured to cover all reservoirs, as illustrated, or may be separate pieces each configured to cover one or more reservoirs within cartridge device 300. Sealing material 320 may be any material that can fluidly seal fluid, such as a foil. Preferably, sealing material 320 is a liquid-impermeable membrane.

Seal piercer 321 is configured to pierce sealing material 320 to vent the fluid in sample preparation reservoir 317, wash reservoir 318, and/or substrate reservoir 319. Seal piercer 321 may be configured to be contacted by distal portion 201, e.g., at a shoulder or engagement zone 209, of sample collection device 200 within input tunnel 301 and to move within housing 304, responsive to force applied by sample collection device 200, to cause sealing material 320 to be pierced to vent the fluid in sample preparation reservoir 317, wash reservoir 318, and/or substrate reservoir 319. Seal piercer 321 is disposed within housing 304 and may be partially disposed within input tunnel 301. In one embodiment, seal piercer 321 is configured to move in a first direction, e.g., laterally, responsive to insertion of sample collection device 200 in input tunnel 301 and in a second direction, e.g., vertically, to pierce into sealing material 320.

Seal piercer 321 may be a single piece or may include multiple pieces. Illustratively, seal piercer 321 includes slider 322 and piercer 323. Slider 322 is disposed within housing 304 and may be partially disposed within input tunnel 301. For example, slider 322 may have an engager adapted to be disposed within input tunnel 301. The engager may be configured to be temporarily or permanently coupled to sample collection device 200, e.g., at a shoulder or at engagement zone 209, to permit movement of slider 322 responsive to insertion of sample collection device 200 into input tunnel 301. The engager may be sized to fit within a groove of engagement zone 209, e.g., U-shaped as illustrated, or to receive a protrusion of engagement zone 209. Slider 322 may be configured to move within housing 304, responsive to force applied by sample collection device 200 resulting from a collector pushing sample collection device distally into input tunnel 301, to cause sealing material 320 to be pierced by piercer 323 to vent the fluid in sample preparation reservoir 317, wash reservoir 318, and/or substrate reservoir 319. Piercer 323 may be one or more piercing elements with ends sufficiently sharp to cut open sealing material 320. As described in detail below, piercer 323 may include three different piercers, each disposed within housing 304 above one of sample preparation reservoir 317, wash reservoir 318, or substrate reservoir 319. As slider 322 moves within input tunnel 301 as caused by insertion of sample collection device 200, slider 322 contacts piercer 323 and moves piercer 323 in a direction to pierce sealing material 320. In one embodiment, slider 322 is configured to move in a first direction, e.g., laterally/substantially parallel to movement of sample collection device 200, responsive to insertion of sample collection device 200 in input tunnel 301 to cause piercer 323 to move in a second direction, e.g., vertically, to pierce into sealing material 320.

Shuttle 324 is configured to be disposed within housing 304, preferably between sample preparation reservoir 317 and aperture 302. For example, shuttle 324 may be disposed within input tunnel 301 when the cartridge is in a non-use state such that a distal end of shuttle 324 forms a wall of sample preparation reservoir 317 to seal fluid therein. Shuttle 324 may define one or more compartments configured to receive the collected sample from sample collection device 200 when inserted in input tunnel 301. Shuttle 324 also may define one or more additional compartments configured to house one or more reagents balls. Shuttle 324 may be configured to move within housing 304 when subjected to a threshold force, e.g., caused by contacting sample collection device 200 to shuttle 324, to a second position such that the one or more sample compartments having the sample and/or the one or more reagent ball compartments having the one or more reagent balls therein are disposed in the fluid within sample preparation reservoir 317. The proximal end of shuttle 324 may, in conjunction within sample collection device 200, re-form the wall of sample preparation reservoir 317 to seal fluid therein when the sample and/or the one or more reagent ball are in sample preparation reservoir 317. In this manner, sample preparation reservoir 317 remains fluidicly sealed in the non-use state by shuttle 324 and in the mixing state by shuttle 324. In addition, unlike a breakable membrane housing reagents, shuttle 324 may remain intact as the sample is moved into sample preparation reservoir 317 for analysis.

Desiccant 325 may be disposed within housing 304 and in fluidic communication with one or more reagent balls housed in shuttle 324. Desiccant 325 is configured to absorb moisture that enters into housing 304 to reduce moisture exposure to the one or more reagent balls in the non-use state. Desiccant 325 may be a pad and may be at least partially disposed within input tunnel 301. Desiccant 325 may have a lumen sized to permit the sample collection device to be inserted therethrough.

Input tunnel component 326 forms a portion of input tunnel 301 and is sized and shaped to secure shuttle 324 within input tunnel 301. For example, input tunnel component 326 may have a U-shape to house a generally cylindrical shuttle.

Sonicator element 327 is disposed within housing 304 and preferably adjacent to, or integral with, sample preparation reservoir 317 to permit mixing of the fluid therein. Sonicator element 327 is configured to transmit controlled amounts of energy into sample preparation reservoir and may include piezoelectric components. Sonicator element 327 may be disposed on or form a bottom wall of sample preparation reservoir 317. Sonicator element 327 may be electrically isolated, e.g., via use of a relay, from other electrical components within housing 304 such as the components on circuit board 331, including the sensor and the heaters. Sonication energy may be controlled to achieve mixing and binding of components within sample preparation reservoir 317 while limiting damage caused to fragile DNA probes or other molecules such as antibodies and enzymes. Sonicator element 327 may include a pressure-sensitive piezoelectric disk. Sonicator element 327 also may include a high water content blister disposed between the sample preparation reservoir 317 and the piezoelectric disk. Such a high water content blister may be affixed under sample preparation reservoir 317 in the cartridge production process. The high water content blister may facilitate delivery of sonic energy from sonicator element 327 to sample preparation reservoir 317 with minimal attenuation. The blister may be replaced with another appropriately conducting sonication medium and the component serving as a sonication medium may be dry on the outside, with no liquid residue present.

Absorbent pad 328 is disposed within housing 304 at the downstream-most end of analysis channel 330. Absorbent pad 328 wicks fluid from analysis channel 330, thereby encouraging fluid to flow downstream to absorbent pad 328. Absorbent pad 328 may act as a waste receptacle, collecting all waste fluids and waste particles after they have flowed through analysis channel 330. The size and degree of absorbency of absorbent pad 328 may be selected to meter the flow of fluids and particles within the analysis channel 330. For example, the volume of fluid that absorbent pad 328 can wick must be great enough to drain all fluid from sample preparation reservoir 317 and wash reservoir 318 and draw the fluid carrying the chemical substrate from the substrate reservoir 319. Such a condition may serve as the lower limit of absorbency.

Layer 329 is disposed between internal component 316 and circuit board 331 and forms part of analysis channel 330. Layer 329 may be an adhesive layer configured to couple internal component 316 to circuit board 331. For example, layer 329 may be a double-sided adhesive tape which may be hydrophilic to support the capillary flow of fluid.

Analysis channel 330 may be defined by a wall(s) of internal component 316, a wall(s) of layer 329, and/or a wall(s) of circuit board component 331. For example, the top wall of analysis channel 330 may be defined by internal component 315, the side walls of analysis channel 330 may be defined by layer 329, and the bottom wall of analysis channel 330 may be defined by circuit board 331. Additionally, each reservoir 317, 318, 319 includes an outlet which connects the reservoir to analysis channel 330. In this manner, fluid within each of the reservoirs can flow through their respective outlets and into analysis channel 330. Analysis channel 330 may extend from the reservoirs to absorbent pad 328. Preferably, one or more sensors on circuit board 331 are at least partially positioned within analysis channel 330.

Circuit board 331 is disposed within housing 304 and may be coupled to internal component 316, e.g., via layer 329. Circuit board 331 includes electrical components, for example, one or more of: resistors, electrical leads, vias, and sensors needed for detection of target analytes. Although described separately, it is to be appreciated that electrical components of circuit board 331 need not be separate structural elements. One or more electrical components and/or circuits may perform some of or all the roles of the various components described herein.

Memory 332 is disposed within housing 304 and electrically coupled to circuit board 331. Memory 332 may be any type of memory suitable for storing data related to cartridge device 300 such as an EPROM, EEPROM, flash memory, or the like. Memory 332 may store data such as information on cartridge type (e.g., inflammation, influenza, testosterone, fertility, Vitamin D), cartridge identification information (e.g., serial number), and/or calibration information. When cartridge device 300 is electrically coupled to reader device 400, reader device 400 may receive data transmitted from memory 332 to facilitate determination of the presence, absence, and/or quantity of one more target analytes using such data. In one embodiment, one or more cartridge devices of a select group of cartridges (e.g., common lot of production cartridges) may be tested using a known quantity of target analytes to determine electrical properties associated with one or more target analytes sensed by the sensor of the tested devices. Calibration information based on the test results may be stored in memory 332 in the select group of cartridges to precisely and consistently determine the presence, absence, and/or quantity of one more target analytes using the electrical signals generated by the sensor of the cartridge and the calibration information. Memory 332 also may store test result reliability information such as a predetermined range(s) of parameter(s), e.g., voltage, current, that may be compared to electrical signals generated by a positive control working electrode to determine whether the parameter(s) are within the predetermined range(s), as described below.

Figure 6A:
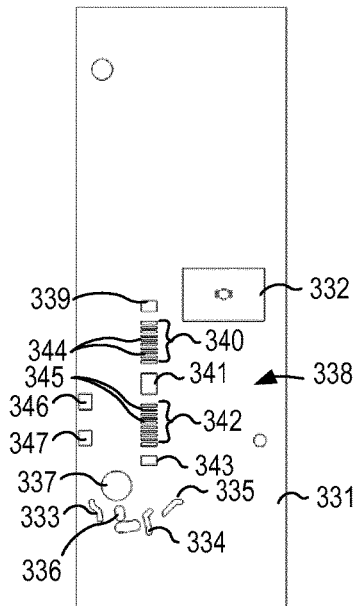
Figure 6B:
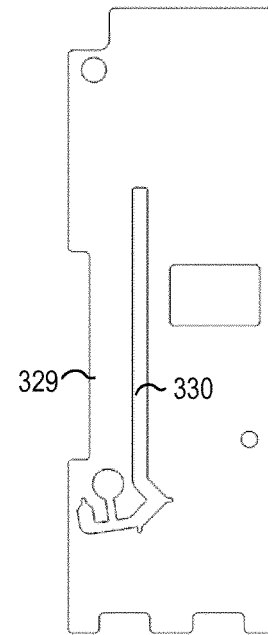
Figure 6C:
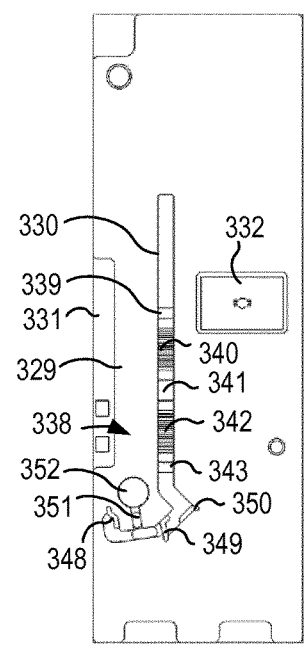

Referring now to FIGS. 6A, 6B, and 6C, exemplary circuit board and layer are illustrated, wherein FIG. 6A depicts circuit board 331, FIG. 6B depicts layer 329, and FIG. 6C depicts layer 329 disposed on and coupled to circuit board 331.

As shown in FIG. 6A, circuit board 331 may include heating elements 333, 334, 335, 336, and/or 337, and sensor 338 which may include reference electrode 339, working electrode 340, counter electrode 341, background working electrode 342, and/or reference electrode 343. Working electrode 340 may be masked with one or more striations 344 and background working electrode 342 may be masked with one or more striations 345. Circuit board 331 may further include contacts 346 and 347 for electrically coupling circuit board 331 to sonicator element 327 via wires, although sonicator element 327 also may be electrically coupled to circuit board 331 with a spring contact as described below.

Heating elements 333, 334, 335, 336, and 337 are configured to generate heat within housing 304, e.g., based on electric signals transmitted from reader 400 at times specified in a protocol stored within the memory of reader 400. Each of heating elements 333, 334, 335, 336, and 337 may form part of circuit board 331. For example, heating elements 333, 334, 335, 336, and 337 may be a resistive heating element appearing as a serpentine trace located on the bottom side of circuit board 331, surrounding a via. In other embodiments, the heating element is located external to the cartridge, for example, on the reader. In various embodiments in which a resistive heating element is used, in order to generate heat, current is allowed to flow through the resistive heating element, for example, through actuation of a transistor. Current passing through the resistive heating element generates heat through Joule heating. The heat is conducted to the via due to physical contact between the resistive heating element and the via. Heating elements 333, 334, 335, 336, and 337 may be masked, e.g., with a solder mask, to maintain heat transfer while promoting electrical isolation from sensor 338 to minimize interference with electrical signals sensed by sensor 338.

Heating element 333 may be positioned adjacent to an outlet of sample preparation reservoir 317. The outlet may have a phase-changeable material therein to occlude the entire cross-section of the outlet, thereby fluidically sealing the outlet. Heating element 333 may be configured to heat the phase-changeable material within the outlet of sample preparation reservoir 317 such that the phase-changeable material unseals the outlet of sample preparation reservoir 317 to permit the fluid having the sample mixed therein held in sample preparation reservoir 317 to flow into analysis channel 330. Heating element 333 may be caused to heat the phase-changeable material at a time specified by a protocol stored in the memory of reader 400, e.g., after reader 400 detects cartridge device 300 electrically coupled thereto and after reader 400 detects proper insertion of sample collection device 200 into cartridge device 300.

Heating element 334 may be positioned adjacent to an outlet of wash reservoir 318. The outlet may have a phase-changeable material therein to occlude the entire cross-section of the outlet, thereby fluidically sealing the outlet. Heating element 334 may be configured to heat the phase-changeable material within the outlet of wash reservoir 318 such that the phase-changeable material unseals the outlet of wash reservoir 318 to permit the wash solution held in wash reservoir 318 to flow into analysis channel 330. Heating element 334 may be caused to heat the phase-changeable material at a time specified by the protocol stored in the memory of reader 400, e.g., a predetermined time after reader 400 causes heating element 333 to be heated and/or a predetermined time after reader 400 causes heating element 336 to be heated.

Heating element 335 may be positioned adjacent to an outlet of substrate reservoir 319. The outlet may have a phase-changeable material therein to occlude the entire cross-section of the outlet, thereby fluidically sealing the outlet. Heating element 335 may be configured to heat the phase-changeable material within the outlet of substrate reservoir 319 such that the phase-changeable material unseals the outlet of substrate reservoir 319 to permit the fluid with the substrates held in substrate reservoir 319 to flow into analysis channel 330. Heating element 335 may be caused to heat the phase-changeable material at a time specified by the protocol stored in the memory of reader 400, e.g., a predetermined time after reader 400 causes heating element 334 to be heated.

Heating element 336 may be positioned adjacent to a fluidic isolator which may comprise a phase-changeable material. Heating element 336 may be configured to heat the phase-changeable material of the fluidic isolator after the outlet of sample preparation reservoir 317 is unsealed such that the phase-changeable material of the fluidic isolator flows into analysis channel 330 to fluidicly isolate sample preparation reservoir 317 from substrate reservoir 319. Heating element 336 may be caused to heat the phase-changeable material at a time specified by the protocol stored in the memory of reader 400, e.g., a predetermined time after reader 400 causes heating element 333 to be heated.

Heating element 337 may be positioned adjacent to a pocket of gas, e.g., air, within analysis channel 330. Heating element 337 may be configured to heat the pocket of air to cause the air to expand and put pressure on the phase-changeable material, thereby facilitating movement of the phase-changeable material in analysis channel 330. Heating element 336 may be caused to heat the phase-changeable material at a time specified by the protocol stored in the memory of reader 400, e.g., a predetermined time after reader 400 causes heating element 333 to be heated. Placement of heating element 337 in the downstream direction of heating elements 333, 334, and 335 is expected to reduce bubble formation in analysis channel 330.

Electrical leads (shown in FIG. 8) of circuit board 331 may be provided to establish electrical connections and continuity with a reader device. The electrical leads may be electrically coupled to heating elements 333, 334, 335, 336, 337, sensor 338 including each of reference electrode 339, working electrode 340, counter electrode 341, background working electrode 342, and reference electrode 343, contacts 346, 347, and to memory 332. In this manner, such components may receive electrical current when activated by the reader device. Advantageously, while the electrical leads are exposed at the electrical connector portion on the bottom surface of circuit board 331 (shown in FIG. 4B), the electrical leads electrically coupling the connectors to the components may be traceless on the top surface of circuit board 331 as shown in FIG. 6A. The traceless configuration of circuit board 331 between the electrical connector portion and these components creates a smooth top surface of circuit board 331 to reduce bonding interferences, thereby promoting secure adhesion, with layer 329. The bonding interferences may cause leakage when fluid enters analysis channel 330 due to malformation of layer 329 caused by such interferences.

Heating elements 333, 334, 335, 336, 337 may be formed of a conductor and each may include a via. A via is a standard product on printed circuit boards and is typically used to enable signal traces on one layer of a circuit board to continue electrically with another layer. The vias provide electrical continuity through multiple layers. Such vias are excellent conductors of heat; they are able to transfer heat to a very precise location without affecting the surrounding areas, because the surrounding material that comprises most circuit boards is an excellent insulator of heat. Thus, in various embodiments, a plurality of vias are provided in circuit board 331 as heating elements, and each via is disposed under, over, or adjacent to a phase-changeable, heat-actuated valve disposed in a reservoir outlet to create a valve actuating element. The precision of heat transfer associated with the vias allows for minimal crosstalk between valves located close to each other; thus, the timing of valve actuation can be carefully controlled for each valve. The valves may be formed of a phase-changeable material such as wax, for example, a hydrophilic wax, and the vias act as conductors of heat to melt wax at precise points of time, as controlled by a reader device. Upon phase transition, e.g., melting, of a wax valve disposed in the outlet of a reservoir, the outlet is no longer occluded and the reservoir has an opening through which its fluid contents can drain into the analysis channel. The holes in the vias may be filled with a filling material, e.g., solder, and the vias may be masked, e.g., with a solder mask, to maintain heat transfer while promoting electrical isolation from sensor 338 to minimize interference with electrical signals sensed by sensor 338.

In order to ensure full melting of the wax with precise timing, in various embodiments, the wax valves are carefully constructed within the outlets of the reservoirs. For example, in some embodiments, it is preferable for the wax valves to have the minimum height necessary to occlude the outlet of the reservoir; the minimal height minimizes the distance heat must travel to melt the wax. One example method for realizing a wax barrier having such characteristics involves applying melted wax to a pre-heated via. Advantageously, when the via is pre-heated, it takes longer for the wax valve to solidify relative to a room-temperature via; thus the wax has more time to flatten and expand outward before hardening. "Pancaking" of the wax is desirable to minimize the height, which will maximize the chance of proper melting actuation of the valve. Additionally, the heating of the via facilitates a greater level of contact area between the wax and the via such that a greater proportion of the wax experiences the heat, also maximizing the chance of proper valve actuation. The method of heating the via prior to deposition of wax is further enhanced with the following method: the opening of the reservoir is aligned over the via such that when the melted wax is applied to the pre-heated via, the opening at the bottom of the reservoir is spatially close to the via such that when the wax hardens, the wax adheres simultaneously to multiple inner walls of the reservoir and the via itself. This is advantageous for enhancing the manufacturing yield of intact valves that fully occlude the opening to the analysis channel such that no inadvertent flow of fluid from the reservoir occurs.

Sensor 338 may be configured to be exposed to the fluid in analysis channel 330 and to generate a signal indicative of the presence, absence, and/or quantity of one or more analytes within the sample. Sensor 338 may detect electrical signals resulting from chemical reactions over sensor 338. For example, the mixed fluid from sample preparation reservoir 317 may be introduced into analysis channel 330 and signaling agents in the mixed fluid may localize over sensor 338 (e.g., responsive to magnetic fields holding magnetic particles (if present) directly or indirectly bound to the signaling agents). The chemical reactions may occur when fluid from substrate reservoir 319 reacts with the particles from mixed fluid from sample preparation reservoir 317 localized over sensor 338. For example, a substrate solution having a substrate may be introduced from substrate reservoir 319 and sensor 338 may detect electrical signals resulting from the reactions between the substrate (e.g., TMB, OPD) and the signaling agents (e.g., HRP, SBP) localized over sensor 338. The reactions may cause electrons to be stripped from the substrate by the signaling agents (which electrons may be donated to acceptor molecules from the substrate solution) thereby generating electrical signals detectable by sensor 338. Such detected electrical signals may be used to generate the signal indicative of the presence, absence, and/or quantity of one or more analytes within the sample. The signal may be transmitted to reader device 400, e.g., via respective electrical connectors of cartridge device 300 and reader device 400.

Sensor 338 may include reference electrode 339, working electrode 340, counter electrode 341, background working electrode 342, and/or reference electrode 343. Sensor 338 is disposed in analysis channel 330 and the area of analysis channel 330 above sensor 338 may be referred to as the "analysis zone." Sensor 338 is strategically located such that, when circuit board 331 is included within the assembled cartridge 300 with a surface of circuit board 331 forming one wall of analysis channel 330, sensor 338 is at least partially disposed within analysis channel 330. While one sensor is illustrated, a plurality of sensors may be provided, each spaced relative to the others, and preferably all aligned within analysis channel 330. In addition, working electrode 340 and background working electrode 342 may be disposed upstream and downstream of one another, or vice versa, and sensor 338 may include additional working electrodes beyond working electrode 340 and background working electrode 342.

Sensor 338 may be an electrochemical sensor that forms an electrochemical cell within analysis channel 330. Reference electrode 339 may be configured to create a voltage differential between itself and working electrode 340. Counter electrode 341 may provide electrons (e.g., from the substrate stripped by the signaling agents) which gather on working electrode 340 when the electrical environment created by reference electrode 339 and working electrode 340 results in a positive charge over working electrode 340. As is explained above, an oxidation reaction may occur at sensor 338 if an oxidizing enzyme (e.g., a signaling agent described herein such as HRP, SBP which may be introduced into analysis channel 330 from sample preparation reservoir 317) bound indirectly to a particle (e.g., a magnetic particle which may be introduced into analysis channel 330 from sample preparation reservoir 317) is present at sensor 338 and an appropriate chemical substrate (e.g., TMB, OPD) is introduced into analysis channel 330 (e.g., from substrate reservoir 319). In such embodiments, working electrode 340 releases electrons to replenish electrons stripped from the substrate by the oxidizing enzyme in a quantity proportional to the amount of oxidizing enzyme present. The release of electrons from working electrode 340 (e.g., from the substrate reacting with the signaling agent over working electrode 340) is a current which may be detectable as a signal within a circuit connected to sensor 338. Sensor 338 can thereby indirectly detect the presence, absence, and/or quantity of oxidizing enzymes localized in the analysis zone. A processor, for example, within the reader device described below, can then correlate the presence, absence, and/or quantity of one or more target analytes to the presence, absence, and/or quantity of oxidizing enzymes. The functions of such a processor are described in more detail below. One or more magnetic fields may be used to facilitate localization of the enzymes or other signaling agents within the analysis zone. Advantageously, in such embodiments, no affinity molecules need to be pre-bound to sensor 338 to achieve localization, which would otherwise significantly slow the analyte quantification process due to the limits of diffusion-based hybridization kinetics. Details of the magnetic fields are also provided below.

Sensor 338 may include gold surfaces made through an ENIG process. In other embodiments, gold or gold-plated sensors are used that have not been made through an ENIG process. A person skilled in the art can appreciate that there are many plating processes for catalytic and autocatalytic deposition of gold utilized to create electrically active pads within the printed circuit board industry. Working electrode 340 may have a surface chemistry formed of a self-assembled monolayer such as thiolated ethylene glycol and/or a dithiol such as hexaethylene glycol dithiol for added stability. The hydrophilic nature of the head groups of such surface chemistry facilitates flow and protein resistance. Additionally or alternatively, the surface of one or more of the electrodes may be backfilled with mercaptoundecanoic acid, mercaptohexanol, or other suitable backfiller. The surface of one or more of the electrodes within sensor 338 may be formed through sequential addition and incubation of the ethylene glycol dithiol and the backfiller at unelevated temperatures.

Background working electrode 342 may be ambient electrochemical noise sensors spaced within analysis channel 330 away from the site of magnetic particle localization. Background working electrode 342 may be used to quantify background noise downstream or upstream of working electrode 340, depending on the selected order of working electrode 340 and background working electrode 342 within analysis channel 330. Such noise may be due to, for example, the presence of non-specifically bound enzyme. During processing of the detection results, a processor at reader 400 may apply an algorithm to remove the background working electrode signal(s) (from background working electrode 342) from the detection sensor signal (from working electrode 340) to account for and/or eliminate system noise and to thereby allow for proper quantification or detection of the one or more target analytes. The signal from background working electrode 342 may be used for error detection and diagnosis of an improperly functioning cartridge, e.g., as evidenced by the signal from background working electrode 342 having electrical value(s) outside a predetermined range(s).

Reference electrode 343 may be configured to create a voltage differential between itself and background working electrode 342. Counter electrode 341 also may provide electrons which gather on background working electrode 342 when the electrical environment created by reference electrode 343 and background working electrode 342 results in a positive charge over background working electrode 342.

In some embodiments, the detection is carried out using a standard electrochemical circuit that utilizes a bias potential generated at background working electrode 342 for the oxidation/reduction reaction to proceed. The potential is held at the reduction potential of the chemical substrate (low enough that there is little nonspecific reduction of reducible species in the solution) so that the flow of electrons to the oxidized molecules can be quantified using an operational amplifier based current-to-voltage (op amp) circuit topology in reader device 400 electrically connected to working electrode 340.

A common substrate molecule, tetramethylbenzidine, may be used for HRP. When present, HRP oxidizes TMB molecules, and these molecules are in turn reduced by working electrode 340. Since this event occurs in proportion to the amount of HRP present which in turn is proportional to the amount of target analyte present, a change in the current-to-voltage op amp measurement results. Using an analog-to-digital converter, the actual signal can be delivered to a processor for processing. As described in more detail below, in various embodiments, the processor and signal processing components are provided within the reader device.

Working electrode 340 may be masked, e.g., solder masked, with a plurality of striations 344 configured to promote homogenous distribution and retention of the plurality of magnetic particles released from sample preparation reservoir 317 over working electrode 340. Accuracy of analyte detection may be adversely impacted by premature wash away of magnetic particles during analysis due, for example, force on the particles in the analysis channel flow direction caused by release of the wash solution from wash reservoir 318 and/or the fluid having the chemical substrates from substrate reservoir 319 being greater than the magnetic force toward the magnetic generators of reader 400 disposed beneath working electrode 340 during analysis. Such striations 344 promote resistance to movement of the plurality of magnetic particles off working electrode 340. In addition, background working electrode 342 may be masked, e.g., solder masked, with a plurality of striations 345, although such striations are not necessary on background working electrode 342 and are merely exemplary of an alternate embodiment.

In alternative embodiments, sensor 338 may be configured to analyze the fluid in analysis channel 330 and to generate a signal indicative of the presence, absence, and/or quantity of one or more analytes within the sample, wherein the signal is visible. For example, the housing of the cartridge device may include a window that permits a user to view, e.g., with a camera, fluorescence and quantify that fluorescence to determine the presence, absence, and/or quantity of one or more analytes within the sample.

Referring now to FIG. 6C, layer 329 is disposed on the top surface of circuit board 331 such that sensor 338 is disposed at least partially in analysis channel 330. Heating elements 333, 334, 335, 336, and 337 may be covered, partially or fully, with masks 348, 349, 350, 351, and 352, respectively. Masks 348, 349, 350, 351, and 352 may be solder masks. Mask 348 is configured to maintain heat transfer from heating element 333 to the phase-changeable material within the outlet of sample preparation reservoir 317 at an energy level sufficient to cause a phase change of the material while promoting electrical isolation between heating element 333 and sensor 338 to minimize interference by heating element 333 with the electrical signals sensed by sensor 338. Mask 349 is configured to maintain heat transfer from heating element 334 to the phase-changeable material within the outlet of wash reservoir 318 at an energy level sufficient to cause a phase change of the material while promoting electrical isolation between heating element 334 and sensor 338 to minimize interference by heating element 334 with the electrical signals sensed by sensor 338. Mask 350 is configured to maintain heat transfer from heating element 335 to the phase-changeable material within the outlet of substrate reservoir 319 at an energy level sufficient to cause a phase change of the material while promoting electrical isolation between heating element 335 and sensor 338 to minimize interference by heating element 335 with the electrical signals sensed by sensor 338. Mask 351 is configured to maintain heat transfer from heating element 336 to the phase-changeable material of the fluidic isolator at an energy level sufficient to cause a phase change of the material while promoting electrical isolation between heating element 336 and sensor 338 to minimize interference by heating element 336 with the electrical signals sensed by sensor 338. Mask 352 is configured to maintain heat transfer from heating element 337 to the pocket of gas in analysis channel 330 above heating element 337 at an energy level sufficient to cause movement downstream in analysis channel 330 of phase-changeable material while promoting electrical isolation between heating element 337 and sensor 338 to minimize interference by heating element 337 with the electrical signals sensed by sensor 338.

Figure 7A:
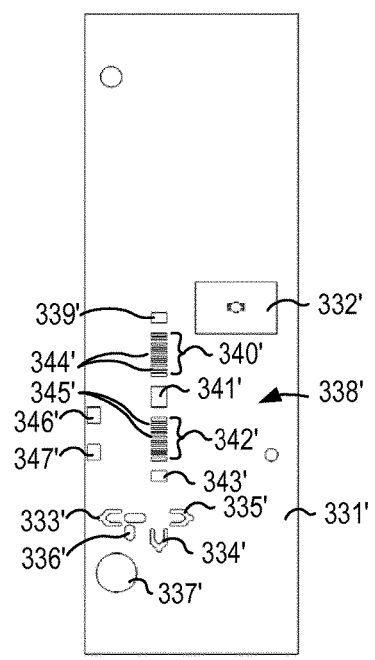
Figure 7B:
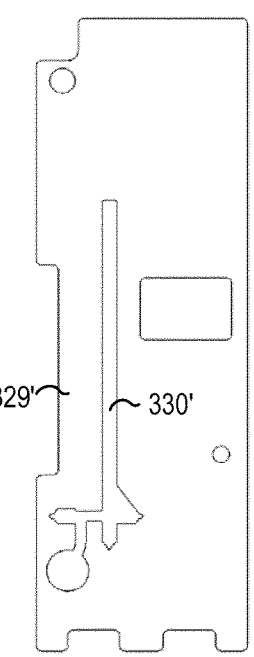
Figure 7C:
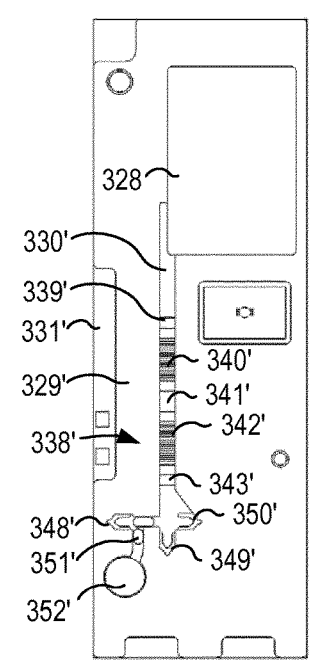

Referring now to FIGS. 7A, 7B, and 7C, circuit board 331' and layer 329' are constructed similarly to circuit board 331 and layer 329 of FIGS. 6A, 6B, and 6C except that heating elements 333', 334', 335', 336', and 337' are positioned in a different configuration on circuit board 331' and analysis channel 330' is re-shaped accordingly. In addition, FIG. 7C depicts absorbent pad 328 coupled to layer 329' at the downstream end of analysis channel 330'.

Referring now to FIGS. 7D and 7E, alternative exemplary sensors that may be used in the cartridges described herein are provided. Sensor 338" may include reference electrode 339", working electrode 340", counter electrode 341", negative control working electrode 342" (also referred to herein as a background working electrode), and/or positive control working electrode 376. Sensor 338" may detect electrical signals generated by chemical reactions at sensor 338" as described above for sensor 338. Sensor 338" is disposed in the analysis channel in the same manner as sensor 338 described above. While one sensor is illustrated, a plurality of sensors may be provided, each spaced relative to the others, and preferably all aligned within the analysis channel. Preferably, fluid flows from the reservoirs in the analysis channel and travels over the electrodes in the following order: positive control working electrode 376, reference electrode 339", counter electrode 341", working electrode 340", and negative control working electrode 342".

Sensor 338" may be an electrochemical sensor that forms an electrochemical cell within the analysis channel. Positive control working electrode 376 may have affinity molecules pre-bound to the surface of positive control working electrode 376 to achieve localization of oxidizing enzymes, or other signaling agents, over positive control working electrode 376. The affinity molecules may be surface bound antibodies. Positive control working electrode 376 may be configured to detect current generated by reactions between an oxidizing enzyme, or other signaling agents, indirectly bound to the affinity molecules and an appropriate chemical substrate introduced into the analysis channel, e.g., from the substrate reservoir. In such embodiments, positive control working electrode 376 releases electrons to replenish electrons stripped from the substrate by the oxidizing enzyme in a quantity proportional to the amount of oxidizing enzyme present. The release of electrons from positive control working electrode 376 is a current which may be detectable as a signal within a circuit connected to sensor 338". A processor, for example, within the reader device described below, may process the signal to determine if the signal indicates a quantity of oxidizing enzyme, or other signaling agent, within a predetermined range which may be stored in memory of the cartridge and/or reader device. If the detected quantity is within the range, the processor may verify the cartridge and continue processing signals to determine the presence, absence, and/or quantity of one or more target analytes within the sample. The signal from positive control working electrode 376 may be used for error detection and diagnosis of an improperly functioning cartridge, e.g., as evidenced by the signal from positive control working electrode 376 having electrical value(s) outside a predetermined range(s). For example, the processor of the reader may generate an error alert if the signal from the positive working control electrode 376 is outside a predetermined range and/or may consider a reading from working electrode 340" acceptable if within the predetermined range.

Reference electrode 339" may be configured to create a voltage differential between itself and working electrode 340". Counter electrode 341" may provide electrons which gather on working electrode 340" when the electrical environment created by reference electrode 339" and working electrode 340" results in a positive charge over working electrode 340". Reference electrode 339 and/or counter electrode 341" may have a surface chemistry formed of a self-assembled monolayer such as thiolated ethylene glycol and/or a dithiol such as hexaethylene glycol dithiol for added stability. The hydrophilic nature of the head groups of such surface chemistry facilitates flow and protein resistance. Additionally or alternatively, the surface of reference electrode 339 and/or counter electrode 341" may be backfilled with mercaptoundecanoic acid, mercaptohexanol, or other suitable backfiller.

Sensor 338" may be used when magnetic particles are not present in the cartridge. For example, working electrode 340" may have affinity molecules pre-bound to the surface of working electrode 340" to achieve localization of oxidizing enzymes, or other signaling agents, over working electrode 340". The affinity molecules may be surface bound antibodies. Working electrode 340" may be configured to detect current generated by reactions between an oxidizing enzyme, or other signaling agents, indirectly bound to the affinity molecules and an appropriate chemical substrate introduced into the analysis channel, e.g., from the substrate reservoir. In such embodiments, working electrode 340" releases electrons to replenish electrons stripped from the substrate by the oxidizing enzyme in a quantity proportional to the amount of oxidizing enzyme present. The release of electrons from working electrode 340" is a current which may be detectable as a signal within a circuit connected to sensor 338". Sensor 338 can thereby indirectly detect the presence, absence, and/or quantity of oxidizing enzymes localized in the analysis zone. A processor, for example, within the reader device described below, can then correlate the presence, absence, and/or quantity of one or more target analytes to the presence, absence, and/or quantity of oxidizing enzymes. The functions of such a processor are described in more detail below.

Working electrode 340" illustratively does not include a plurality of striations as sensor 338" may be used to detect the presence, absence, and/or quantity of one or more target analytes without the use of magnetic particles.

Negative control working electrode 342" may be ambient electrochemical noise sensors spaced within the analysis channel away from the site of localization. Negative control working electrode 342" may be used to quantify background noise downstream of working electrode 340". Such noise may be due to, for example, the presence of non-specifically bound enzyme. During processing of the detection results, a processor at reader 400 may apply an algorithm to remove the negative control working electrode signal(s) (from negative control working electrode 342") from the detection sensor signal (from working electrode 340") to account for and/or eliminate system noise and to thereby allow for proper quantification or detection of the one or more target analytes. The signal from negative control working electrode 342" may be used for error detection and diagnosis of an improperly functioning cartridge, e.g., as evidenced by the signal from negative control working electrode 342" having electrical value(s) outside a predetermined range(s). For example, the processor of the reader may generate an error alert if the signal from the negative working control electrode 342" is above a threshold and/or may consider a reading from working electrode 340" acceptable if below the threshold.

Negative control working electrode 342" may have a surface chemistry formed of a self-assembled monolayer such as thiolated ethylene glycol and/or a dithiol such as hexaethylene glycol dithiol for added stability. The hydrophilic nature of the head groups of such surface chemistry facilitates flow and protein resistance. Additionally or alternatively, the surface of Negative control working electrode 342" may be backfilled with mercaptoundecanoic acid, mercaptohexanol, or other suitable backfiller.

Referring now to FIG. 7E, sensor 338''' may be used when magnetic particles are present in the cartridge. Like sensor 338", sensor 338''' includes positive control working electrode 376', reference electrode 339''', counter electrode 341''', and negative control working electrode 342''' structured similarly to the like-primed components of FIG. 7D described above. Working electrode 340''' may be structurally similar to working electrode 340 described above with respect to FIG. 6A. In this manner, sensor 338''' is particularly well suited for target analyte detection using one or more magnetic fields to facilitate localization of the enzymes or other signaling agents within the analysis zone.

Referring now to FIG. 7F, an alternative exemplary sensor that may be used in the cartridges described herein is provided. Sensor 338" may be structured the same manner as sensor 338'" except that negative control working electrode 342" may be positioned between positive control working electrode 376" and reference electrode 339". Preferably, fluid flows from the reservoirs in the analysis channel and travels over the electrodes in the following order: positive control working electrode 376", negative control working electrode 342", reference electrode 339", counter electrode 341"", and working electrode 340"".

Figure 8B:
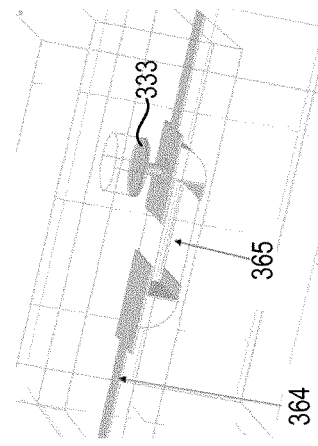
FIGS. 8B and 8C show a close-up views of certain components of the circuit board and a valve for use in the housing of the cartridge device.
Figure 8C:
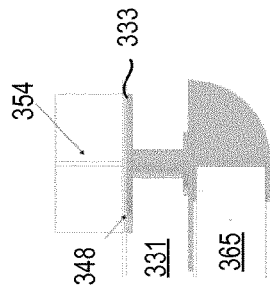
Figure 8D:
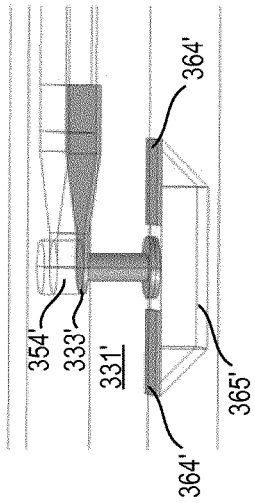
FIG. 8D shows a close-up views of alternative components of the circuit board and a valve for use in the housing of the cartridge device.
Figure 8A:
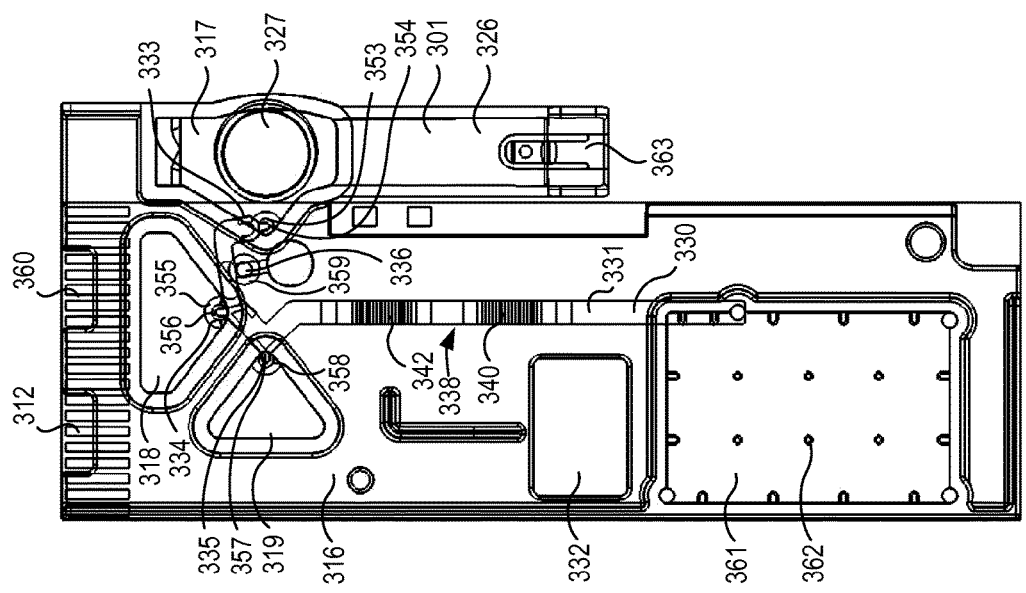
FIG. 8A illustrates an exemplary internal component coupled to an exemplary circuit board via a layer positioned therebetween, all of which may be disposed within the housing of the cartridge device.

Referring to FIG. 8A, internal component 316 is coupled to circuit board 331, e.g., via layer 329 positioned therebetween. Internal component 316 may include sample preparation reservoir 317 having outlet 353 with valve 354 positioned adjacent to heating element 333, wash reservoir 318 having outlet 355 with valve 356 positioned adjacent to heating element 334, and substrate reservoir 319 having outlet 357 with valve 358 positioned adjacent to heating element 335. Each of reservoirs 317, 318, and 319 is, at least at times, in fluid communication with analysis channel 330 such that fluid exiting the reservoirs, e.g., via their respective outlets when the respective valves are opened, flows into analysis channel 330. In addition, fluidic isolator 359 may be positioned adjacent to heating element 336 and in fluidic communication with analysis channel 330.

Valves 354, 356, and 358 may be located within outlets 353, 355, and 357, respectively, at the bottom of reservoirs 317, 318, and 319, respectively, of cartridge 300. Outlets 353, 355, and 357 may each be formed of a hole within a bottom wall of internal component 316 above analysis channel 330. Valves 354, 356, and 358 may each be formed of a heat-sensitive, phase-changeable material, such as, for example, a hydrophilic wax. Prior to actuation, the wax or other heat-sensitive material of the valve is in a solid or semi-solid state and is sized and shaped to fill an entire cross-section of the outlet such that no fluid can escape from the respective reservoir into analysis channel 330. Valves 354, 356, and 358 may be aligned directly above one or more heating elements (with a solder mask therebetween) or other localized heat-conductive element. Such alignment allows for the localized application of heat to induce a phase change in the valve without causing a phase change of any neighboring valves. In various embodiments, the phase change melts or otherwise transforms the heat-sensitive material such that it no longer causes full occlusion of the outlet, but instead permits fluid in the respective reservoir to flow into analysis channel 330.

In addition, fluidic isolator 359 may be formed of a heat-sensitive, phase-changeable material, such as, for example, a hydrophilic wax. Prior to actuation, the wax or other heat-sensitive material is in a solid or semi-solid state and is disposed out of the flow path between the outlets of the respective reservoirs and sensor 338 within analysis channel 330. Fluidic isolator 359 may be sized and shaped to block the flow path on analysis channel 330 between an outlet of one reservoir, e.g., sample preparation reservoir 317, and the outlet of another reservoir, e.g., substrate reservoir 319, when fluidic isolator is activated, e.g., by heating heating element 336. Fluidic isolator 359 may be aligned directly above heating element 336 (with a solder mask therebetween) or other localized heat-conductive element. Such alignment allows for the localized application of heat to induce a phase change in fluidic isolator 359 without causing a phase change of any neighboring valves. In various embodiments, the phase change melts or otherwise transforms the heat-sensitive material such that it flows into analysis channel to block outlet 353 of sample preparation reservoir 317 from analysis channel 330. In this manner, fluid from substrate reservoir 319, when released into analysis channel 330, cannot enter into sample preparation reservoir 317 and cannot interact with leftover signaling agents from sample preparation reservoir 317.

The wax material disposed upon the via or a solder mask over via, and which occludes the opening of the respective reservoir or isolates the analysis channel, may be a hydrophilic material such as hexadecanol or octodecanol. This advantageously promotes, rather than obstructs the flow of fluid past any wax bits that harden within any area of the analysis channel after actuation. These materials also preferably have a melting temperature between 50 and 100 degrees Celsius, which allows for actuation with reasonable power-consumption for a battery-operated device, yet remains unactuated in general handling and storage environments and/or during a sonication protocol. The amount of wax per valve may be below 1 microliter in its liquid state, the amount may be less than or equal to 0.5 microliters, and the amount may be greater than 2 nanoliters. Using minimal amount of wax in the valves is one way to reduce any occlusion of the analysis channel and maximize full valve actuation when heat is applied. The valve also may have a feedback-and-control system that allows for a consistent thermal profile to be achieved at the via for consistent valve actuation. Furthermore, this feedback-and-control system may incorporate sensing elements to enable the system to confirm that each valve has properly actuated.

As shown in FIG. 8A, circuit board 331 may have exposed leads 360 at electrical connector 312. In one embodiment, leads 360 are exposed only on the bottom surface of circuit board 331 although leads 360 may be exposed on the top surface of circuit board 331 but are preferably traceless as shown. As described above, electrical connector 312 permits electrical connection with a corresponding electrical connector of reader device 400 such that cartridge device 300 may transmit signals indicative of the presence, absence, and/or quantity of one or more target analytes within a collected sample sensed by the sensor of cartridge device 300.

Internal component 316 may include absorber pad housing 361 sized and shaped to hold absorber pad 328. Absorber pad housing 361 may include a plurality of vent holes 362 to permit exposure of absorber pad 328 within absorber pad housing 361 to the environment within housing 304 of cartridge device 300.

Input tunnel 301 of cartridge device 300 may include slot 363 configured to permit seal piercer 321 to be at least partially disposed within input tunnel 301. Slot 363 may be at the proximal end of input tunnel component 326 as illustrated. Slot 363 may be sized and shaped to permit engager 324 of slider 321 to be disposed within input tunnel 301. In addition, slot 363 may have a length sufficient to permit slider 322 to slide, when engager 324 contacts the sample collection device within input tunnel 301, distally from a pre-venting position to a venting position.

Referring now to FIGS. 8B and 8C, a close-up view of certain components of circuit board 331 and a valve are shown. FIG. 8B depicts conductor 364 coupled to resistor 365, e.g., an aluminum resistor, which is coupled to heating element 333 and FIG. 8C further shows mask 348 disposed between heating element 333 and valve 354. As will be clear to one skilled in the art, while the details of heating element 333, mask 348, and valve 354 are illustrated, such a configuration may be utilized with respect to heating elements 334, 335, 336, and 337 with their respective masks and valves, fluidic isolators, or air pockets. Current from reader device 400 may pass from conductor 364 through resistor 365 to generate heat through Joule heating. The heat is conducted to heating element 333 due to physical contact between resistor 365 and heating element 333. Heating element 333 generates heat through mask 348 to cause a phase change of the phase-changeable material of valve 354 while promoting electrical isolation from sensor 338 to minimize interference by heating element 333 with electrical signals sensed by sensor 338.

Referring now to FIG. 8D, a close-up view of alternative components of circuit board 331' and a valve are shown. FIG. 8D depicts conductors 364', e.g., solder pads, coupled to resistor 365', e.g., an aluminum resistor. Unlike the configuration shown in FIGS. 8B and 8C, conductor 364' is not coupled to heating element 333' (which includes a via in circuit board 331') such that a mask disposed between heating element 333' and valve 354' is not needed. As will be clear to one skilled in the art, while the details of heating element 333' and valve 354' are illustrated, such a configuration may be utilized with respect to heating elements 334, 335, 336, and 337 with their respective valves, fluidic isolators, or air pockets. Current from reader device 400 may pass from conductor 364' through resistor 365' to generate heat through Joule heating. The via of heating element 333' is disposed between, and electrically isolated from, conductors 364' coupled to resistor 365'. The heat is conducted to heating element 333' through indirect contact between resistor 365' and heating element 333'. Heating element 333' generates heat to cause a phase change of the phase-changeable material of valve 354' while promoting electrical isolation from the sensor to minimize interference by heating element 333' with electrical signals sensed by the sensor.

FIGS. 9A and 9B illustrate various shuttles that may be disposed within the input tunnel of the cartridge device. Referring to FIG. 9A, shuttle 324 may include first end 366, reagent ball compartment 367, compartment divider 368 having slot 369, sample compartment 370, second end 371 having opening 372 therethrough, and/or beams 373, 374.

Shuttle 324 is configured to be disposed within the cartridge housing, preferably within the input tunnel between the sample preparation reservoir and the aperture defining the opening of the input tunnel in a pre-mixing state. In such a pre-mixing state, first end 366 may form a wall of the sample preparation reservoir to seal fluid within the reservoir. First end 366 may include one or more sealing members, e.g., O-rings, to enhance a liquid tight seal that may be comprised in part of chlorobutyl. The area between first end 366 and compartment divider 368 may be referred to as reagent ball compartment 367. Reagent ball compartment 367 is configured to house one or more reagent balls, e.g., reagent ball 375. In the pre-mixing state, reagent ball compartment 367 is preferably sealed off from the fluid in the sample preparation reservoir. Compartment divider 368 may be used to divide compartments in shuttle 324, e.g., reagent ball compartment 367 and sample compartment 370. Compartment divider 368 may include slot 369 which permits fluid to flow through compartment divider 368 when compartment divider 368 is disposed within the fluid of the sample preparation reservoir in an mixing state. Permitting fluid to flow through slot 369 may enhance mixing of the sample, the reagent ball, and the fluid in the sample preparation reservoir. In addition, slot 369 permits enhanced fluidic communication between reagent ball 375 and desiccant 325 disposed within the cartridge housing in the pre-mixing state. It should be understood without being explicitly stated that the compartment may contain reagent balls that are the same or different from each other, and can be preselected for detection and/or quantification of the target analyte.

In the pre-mixing state, second end 371 may be disposed between first end 366 and the aperture defining the opening of the input tunnel. Second end 371 may include opening 372 which is configured to permit the collected sample to be inserted therethrough and into sample compartment 370. For example, opening 372 may be sized slightly larger than the tip of the sample collection device such that the tip can travel through opening 372 while opening 372 wipes excess sample from the tip. In this manner, at most a predetermined volume of sample is inserted in sample compartment 370. The area between second end 371 and compartment divider 368 may be referred to as sample compartment 370. Shuttle 324 may include one or more beams 373, 374 configured to couple first end 366 to second end 371 and to be coupled to compartment divider 368. Beams 373, 374 are preferably positioned closer to the top surface of the cartridge housing when in the input tunnel to avoid interference with fluid mixing in the mixing state.

Shuttle 324 may move from a first position in a pre-mixing state to a second position in a mixing state, e.g., responsive to application of a force beyond a threshold force exerted on shuttle 324 by the sample collection device. In the mixing state, first end 366, reagent ball compartment 367, and sample compartment 370 may be disposed within the sample preparation reservoir. Accordingly, the sample and the reagent ball(s) may be mixed within fluid in the sample preparation reservoir. Second end 371 of shuttle 324 may re-form the wall of the sample preparation reservoir to seal fluid therein when the sample and/or the one or more reagent ball are in the sample preparation reservoir. Preferably, the distal portion of the sample collection device fluidically seals opening 372 such that fluid cannot escape the sample preparation reservoir into the input tunnel in the mixing state. Second end 371 may include one or more sealing members, e.g., O-rings, to enhance a liquid tight seal. In this manner, the sample preparation reservoir remains fluidically sealed in the pre-mixing state by first end 366 and in the mixing state by second end 371 and the sample collection device and during movement from the pre-mixing state to the mixing state. In addition, unlike a breakable membrane housing reagents, shuttle 324 may remain intact as the sample is moved into sample preparation reservoir 317 for analysis.

Reagent ball 375 may include one or more of magnetic particles, affinity molecules, connection molecules, signaling agents, competitor binding molecules, competitor molecules, labels, signaling agents, primers, nucleic acid probes, and/or polymerases, and other enzymes or components as described in further detail herein and the components, encapsulation material and dimensions may be the same or different from each other. In one aspect, reagent ball 375 is formed by the freezing (i.e. lowering the temperature of a volume of liquid (such as between 5 microliters and 30 microliters)) to a temperature to induce a phase change in the liquid. The temperature may vary depending on the components of the liquid. In a further aspect, the liquid additionally comprises excipients known to those of ordinary skill in the art of lyophilization such as lyoprotectants for the functional preservation of the reagents that may be temperature sensitive, e.g., nucleic acids and/or protein components, within the liquid volume as it undergoes the process of freezing and drying to become reagent ball 375. Stabilizers such as dissacharides like sucrose and trehalose or other lyoprotectants such as polethylene glycol of various molecular weights and bulking or caking agents such as mannitol, glycine, povidone, and others known in the art can comprise some of the final constituents of reagent ball 375 in addition to the reagents noted herein. The (w/v) percentage of the excipients within the volume of liquid to be freeze dried to form reagent ball 375 can vary widely from about 0.1% to about 30% and be combined in various ways, often with a combination of a dissacharide as a lyoprotectant and a caking agent or bulking agent to add structure. Reagent ball 375 can be of many sizes, non-limiting examples of such include having an diameter of between about 1 mm to about 7 mm, or alternatively from about 2 mm to about 5 mm, or alternatively about 3 mm, or alternatively less than about 7 mm, or alternatively less than about 5 mm, or alternatively less than about 4 mm. While reagent ball 375 is illustrated as a sphere, the disclosure is not limited thereto and many shapes may be used and multiple reagent balls each containing the same or different reagents also may be used. As is ordinary in the art, such liquid when formed containing the components and excipients can be frozen through flash freezing in liquid nitrogen or through shelf freezing within a lyophilizer machine. After freezing, said frozen volume is subjected potentially to annealing treatments for crystallization of caking agents, primary drying and secondary drying wherein water is removed until a sufficiently small percentage (e.g. <8%, preferably <5% and preferably around 1%) remains in the final freeze dried product, which is reagent ball 375.

Referring now to FIG. 9B, shuttle 324' is constructed similarly to shuttle 324 of FIG. 9A except compartment divider 368' is solid without a slot and beams 377, 378, and 379 are positioned in different orientations on shuttle 324'.

As will be readily apparent to one skilled in the art, while FIGS. 9A and 9B illustrate shuttles having one sample compartment and one reagent ball compartment, the disclosure is not limited thereto and the shuttles may define one or more compartments configured to receive the collected sample from the sample collection device when inserted in the input tunnel 301 and one or more additional compartments configured to house one or more reagents balls.

Figure 10B:
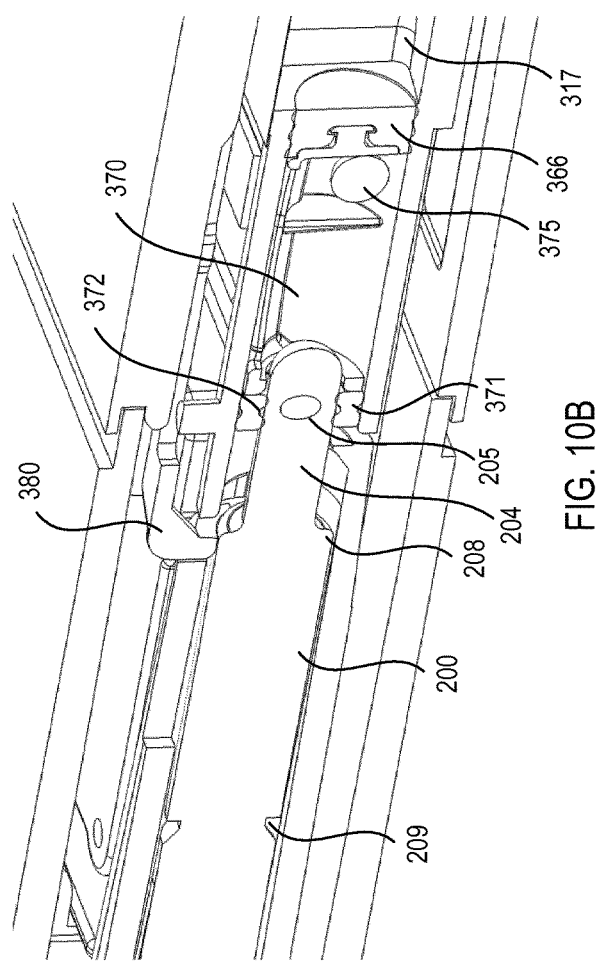
FIG. 10B is a cross-sectional perspective view showing a tip of the sample collection device entering a shuttle disposed within the input tunnel of the cartridge device.
Figure 10D:
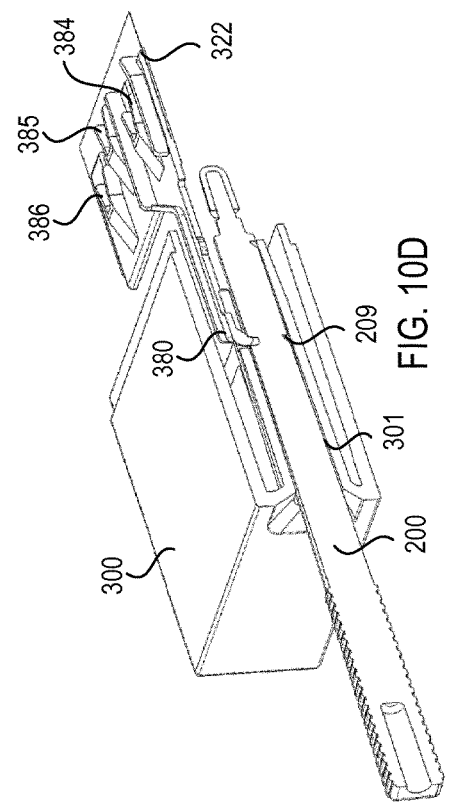
FIG. 10D is a cross-sectional perspective view showing engagement between the sample collection device and a slider of a seal piercer within the input tunnel of the cartridge device, wherein part of the cartridge device is removed.
Figure 10C:
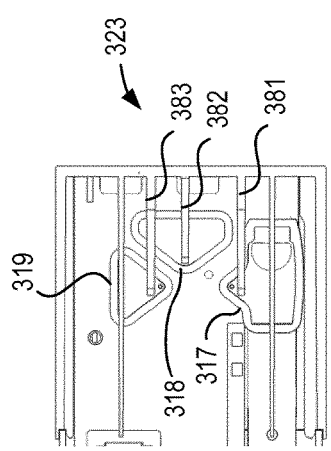
FIG. 10C is a top view showing an exemplary orientation of piercing elements over reservoirs within the housing of the cartridge device.
Figure 10M:
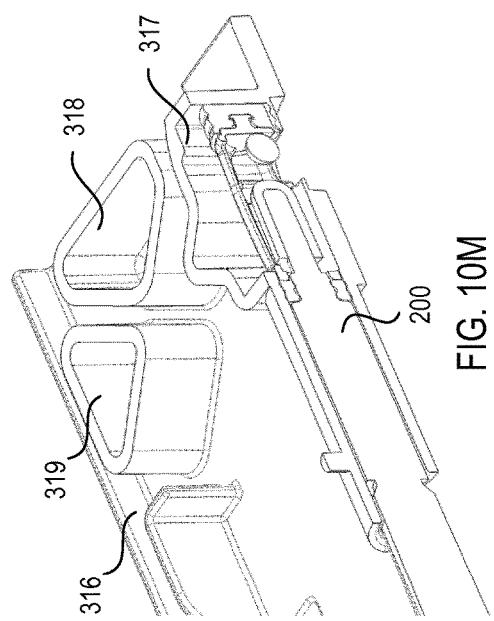
FIG. 10M is a cross-sectional perspective view showing the sample collection device in the venting and mixing positions within the sample preparation reservoir of the internal component of the cartridge device.
Figure 10O:
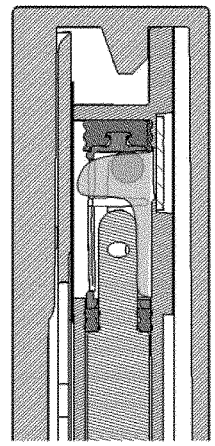
FIGS. 10N, 10O, and 10P are cross-sectional side views showing enhanced mixing of the fluid in the sample preparation reservoir with the collected sample and the reagent ball via a sonicator element.
Figure 10P:
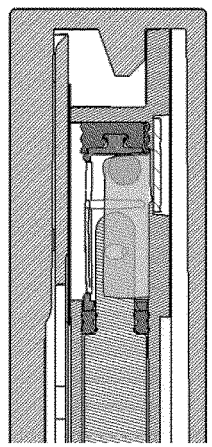

Referring now to FIGS. 10A through 10P, insertion of a sample collected by a sample collection device into a cartridge device is described. Prior to insertion within input tunnel 301 of cartridge device 300, sample collection device 200 is exposed to a sample, e.g., within an inner cheek, the throat, the mouth, a nasal passageway, an ear, from urine, from blood, from plasma, from saliva, etc. Tip 204 of sample collection device 200 is designed to retain some of the sample to permit analysis of the presence, absence, and/or quantity of one or more target analytes within the sample using cartridge device 300 and reader device 400. Cartridge device 300 may be electrically coupled to reader device 400 before or after sample collection device 200 is inserted in cartridge device 300.

Referring to FIG. 10A, the distal end of sample collection device 200 is first inserted into the aperture defining the opening of input tunnel 301. Shuttle 324 is disposed within input tunnel 301 in a pre-mixing position wherein first end 366 of shuttle 324 forms a wall of sample preparation reservoir 317 to fluidically seal fluid within sample preparation reservoir 317. In this pre-mixing position, reagent ball 375 housed by shuttle 324 is within input tunnel 301 and not exposed to fluid within sample preparation reservoir 317. As the distal end of sample collection device 200 moves distally into input tunnel 301, sample collection device 200 may contact engager 380 of slider 322. For example, distal sealing zone 208 may contact engager 380 as illustrated. Distal sealing zone 208 may be angled to facilitate movement of engager 380 past distal sealing zone 208 as sample collection device 200 is moved more distally or distal sealing zone 208 may be a shoulder sized to cause movement of slider 322.

As shown in FIG. 10B, tip 204 (having sample thereon and/or within tube 205) enters sample compartment 370 of shuttle 324 through opening 372 of second end 371. Preferably, as tip 204 enters sample compartment 370, shuttle 324 remains substantially in position within input tunnel 301 and first end 366 of shuttle 324 continues to form a wall of sample preparation reservoir 317 to seal fluid within sample preparation reservoir 317. In addition, first end 366 of shuttle 324 may continue to form a wall of sample preparation reservoir 317 to seal fluid within sample preparation reservoir 317 (and shuttle 324 may remain substantially in pre-mixing position) until distal sealing portion 208 contacts second end 371 to fluidicly seal opening 372. Application of a force greater than a threshold force on shuttle 324 (e.g., at second end 371) by sample collection device 200 (at distal sealing portion 208) may move shuttle 324 from the pre-mixing position to the mixing position wherein the sample on sample collection device 200 and reagent ball 375 are mixed within fluid of sample preparation reservoir 317.

In addition, as sample collection device 200 (e.g., tip 204) is inserted into shuttle 324 (e.g., via opening 372), shuttle 324 may wipe excess sample from sample collection device 200, thereby preventing the wiped sample from entering shuttle 324. For example, the walls of second end 371 that define opening 372 may wipe excess sample from tip 204 as tip 204 is inserted through opening 372. All or substantially all of the sample on the outer surface of tip 204 may be wiped away leaving only sample disposed within tube 205. Tube 205 may hold, at most, a predetermined volume of sample, e.g., about 2 µl. Wiping excess sample from sample collection device 200 may enhance precision, accuracy, and/or consistency of analysis as, at most, a predetermined volume of sample is inserted in sample preparation reservoir 317 in the mixing position.

Referring now to FIGS. 10C through 10K, an exemplary process is described for piercing the sealing material disposed over one or more reservoirs in the cartridge device via interaction between the sample collection device and the seal piercer within the cartridge device. As described above, seal piercer 321 may include slider 322 and piercer 323.

FIG. 10C is a top view of a portion of cartridge device 300 illustrating a possible orientation of piercing elements over the reservoirs. Piercer 323 may have first piercing element 381 having a piercing end disposed over sample preparation reservoir 317, second piercing element 382 having a piercing end disposed over wash reservoir 318, and/or third piercing element 383 having a piercing end disposed over substrate reservoir 319. In the pre-mixing state, piercing elements 381, 382, and 383 are disposed over their respective reservoirs and have not pierced the sealing material sealing fluid within the respective reservoirs. Piercing elements 381, 382, and 383 may be coupled (e.g., at an end opposite the piercing end) to the housing of the cartridge device.

FIG. 10D is a perspective view of sample collection device 200 within the input tunnel of cartridge device 300, with half the cartridge housing removed to show slider 322 for clarity. Slider 322 may include first track 384 configured to engage and move first piercer 381 into a piercing position, second track 385 configured to engage and move second piercer 382 into a piercing position, and/or third track 386 configured to engage and move third piercer 383 into a piercing position. As sample collection device 200 is moved distally through input tunnel 301, preferably slider 322 does not move within the cartridge housing, and remains in a pre-vent position, until sample collection device 200 securely engages slider 322. Slider 322 may securely engage sample collection device 200 by temporarily or permanently coupling engager 380 of slider 322 to engagement zone 209 of sample collection device 200. Engager 380 is disposed in input tunnel 301 (e.g., hanging below, at least at times, slot 363 of FIG. 8A). Engager 380 may be sized to fit within a groove of engagement zone 209, e.g., protrusions and/or U-shaped, or to receive a protrusion of engagement zone 209.

FIG. 10E is a cross-sectional side view depicting the seal piercer in the pre-piercing position and the shuttle in the pre-mixing position. As shown, sample collection device 200 has been moved distally in input tunnel 301 such that engager 380 of the slider has engaged engagement zone 209 of sample collection device 200 and distal sealing zone 208 of sample collection device 200 has fluidicly sealed the opening of second end 371 of shuttle 324. Preferably, first end 366 continues to fluidicly seal fluid within sample preparation reservoir 317 at least until sample collection device 200 fluidicly seals second end 371 of shuttle 324. As such, the one or more reagent balls housed by shuttle 324 and the collected sample within shuttle 324 remain out of fluidic contact with the fluid in sample preparation reservoir 317. Slider 322 and shuttle 324 may be positioned within the cartridge housing such that engager 380 of slider 322 engages engagement zone 209 of sample collection device 200 at the same time, or approximately the same time, that distal sealing zone 208 of sample collection device contacts and fluidicly seals second end 371 of shuttle 324. In such an embodiment, slider 322 and/or shuttle 324 may not yet have been caused to move within cartridge device 300 at this time.

FIGS. 10F and 10G further illustrate positioning of the slider and the piercer in the pre-venting position shown in FIG. 10E. As shown in FIG. 10F, when engager 380 of slider 322 engages engagement zone 209 of sample collection device 200 in the pre-venting position, piercing elements 381, 382, and 383 have not yet been deflected downwardly toward their respective reservoirs by slider 322. In such a pre-venting position, tracks 384, 385, and 386 may not yet contact piercing elements 381, 382, and 383, respectively. As shown in FIG. 10G, in the pre-venting position, piercing element 381 is disposed above, but has not yet pierced, sealing material 320 which seals fluid within sample preparation reservoir 317. In FIG. 10G, track 384 of slider 322 has not yet contacted piercing element 381 of piercer 323.

Referring now to FIG. 10H, sample collection device 200 is moved further distally within input tunnel 301 from the pre-mixing and pre-venting positions towards the mixing and venting positions. As collector pushes sample collection device 200 distally, shuttle 324 is partially moved within sample preparation reservoir 317. Shuttle 324 may be caused to move within the cartridge by, for example, application of a force greater than a threshold force by sample collection device 200 (e.g., at distal sealing zone 208) on shuttle 324 (e.g., at second end 371). As shuttle 324 moves distally, first end 366 may unseal such that one or more reagent balls within shuttle 324 and the collected sample within shuttle 324 are exposed to fluid within sample preparation reservoir 317. Advantageously, before first end 366 of shuttle 324 is unsealed, second end 371 of shuttle 324 is fluidicly sealed by sample collection device 200 such that fluid from sample preparation reservoir 317 does not leak into input tunnel 301 beyond second end 371. In addition, as distal movement of sample collection reservoir 200 causes the transition from the pre-mixing position to the mixing position, second end 371 of shuttle continuously fluidicly seals the fluid in sample preparation reservoir 317 from input tunnel 301.

As collector pushes sample collection device 200 distally, seal piercer 321 also may be moved from the pre-venting position towards the venting position. Seal piercer 321 may be caused to move within the cartridge by, for example, application of a force greater than a threshold force by sample collection device 200 (e.g., at engagement zone 209) on seal piercer 321 (e.g., at engager 380 of slider 322). As sample collection device 200 is moved distally, seal piercer 321 causes the sealing material over sample preparation reservoir 317, wash reservoir 318, and/or substrate reservoir 319 to be pierced to vent the fluid within the reservoir(s). Seal piercer 321 may be caused to move in a first direction, e.g., generally laterally in a direction generally parallel with movement of sample collection device 200 within input tunnel 301, responsive to insertion of sample collection device 200 in input tunnel 301 and in a second (different) direction, e.g., downwardly in a generally vertical manner toward the respective reservoir, to pierce into sealing material 320. For example, slider 322 may move in the first direction and piercer 323 may move in the second direction.

As shown in FIG. 10I, as sample collection device 200 causes slider 322 to move distally in a direction generally parallel to movement of sample collection device 200, slider 322 may contact piercer 323 to cause piercer 323 to move in a different direction, e.g., generally perpendicular to movement of slider 322. As slider 322 moves distally, tracks 384, 385, and 386 of slider 322 may contact piercing elements 381, 382, and 383, respectively, of piercer 323. Distal movement of slider 322 may cause piercer 323 to pierce the sealing material to vent the reservoir(s).

FIG. 10J illustrates piercing element 381 piercing sealing material 320 over sample preparation reservoir 317 to vent sample preparation reservoir 317. As shown, track 384 contacts and moves piercing element 381 downwardly into the piercing position.

FIG. 10K shows shuttle 324 in the mixing position and the seal piercer in the venting position. In the mixing position, first end 366 of shuttle 324, the one or more reagent ball compartments of shuttle housing one or more reagent balls, and/or the one or more sample compartments housing the sample(s) to be analyzed may be disposed within sample preparation reservoir 317. As explained above, shuttle 324 (e.g., at second end 371) and sample collection device 200 (e.g., via tip 204 inserted in opening 372 and distal sealing zone 208) also may fluidicly seal sample preparation reservoir 317 in the mixing position such that the collected sample(s), the reagent ball(s), and the fluid within sample preparation reservoir 317 are sealed within the reservoir. In this manner, the collected sample(s), the reagent ball(s), and the fluid may be mixed within sample preparation reservoir 317.

Advantageously, a configuration where insertion of sample collection device 200 causes sample preparation reservoir 317, wash reservoir 318, and/or substrate reservoir 319 to be vented ensures that the reservoir(s) remain fluidicly sealed prior to sample collection device 200 insertion and facilitates drainage of the reservoir(s) into the analysis channel when the outlet of the respective reservoir permits fluid flow therethrough.

In the mixing position, seal piercer 321 may move out of the pierced holes to open the pierced holes and facilitate venting. As shown in FIG. 10K, engagement zone 209 of sample collection device 200 may be moved distally past engager 380 such that engager 380 disengages engagement zone 209 of sample collection device 200 in the venting position. In addition, in the mixing position, proximal sealing zone 207 of sample collection device 200 is configured to seal input tunnel 301 at aperture 302. In this manner, proximal sealing zone 207 provides additional structure to minimize or eliminate liquid leakage from cartridge device 300, e.g., at aperture 302.

Cartridge device 300 may further include locking member 387 configured to irreversibly lock sample collection device 200 within cartridge device 300. Locking member 387 may be biased inwardly in input tunnel 301 such that a locking end of locking member 387 engages sample collection device 200 in the mixing position. The locking end may lock to engagement zone 209. The locking end may be a protrusion sized to fit within a groove of engagement zone 209, as illustrated. Locking member 387 also may define a portion of input channel 301, as illustrated, and may be coupled to the cartridge housing at the end opposite its locking end. Advantageously, locking sample collection device 200 (e.g., longitudinally and/or axially) within input tunnel 301 promotes sealing of sample preparation reservoir 317 over time as sample collection device 200 cannot be retracted once locked to facilitate safe disposability and consistency of testing because a user cannot pull out sample collection device 200 from cartridge device 300 inadvertently once the test has started.

Figure 10L:
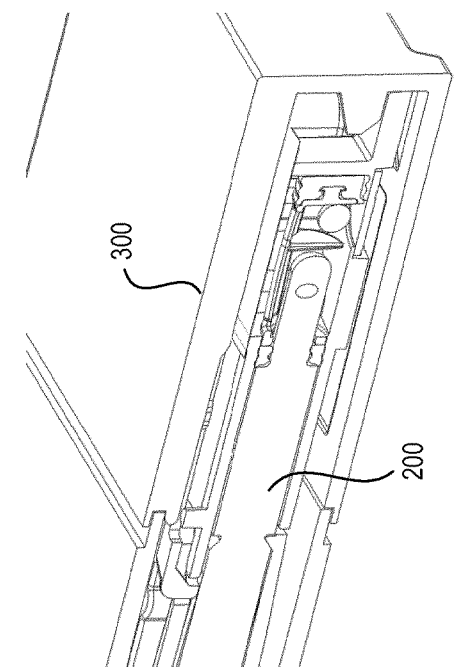
FIG. 10L is a cross-sectional perspective view showing the sample collection device in the venting and mixing positions within the cartridge device.

FIGS. 10L and 10M further depict sample collection device 200 in the mixing position within cartridge device 300 (FIG. 10L) and internal component 316 (FIG. 10M) for clarity.

Figure 10N:
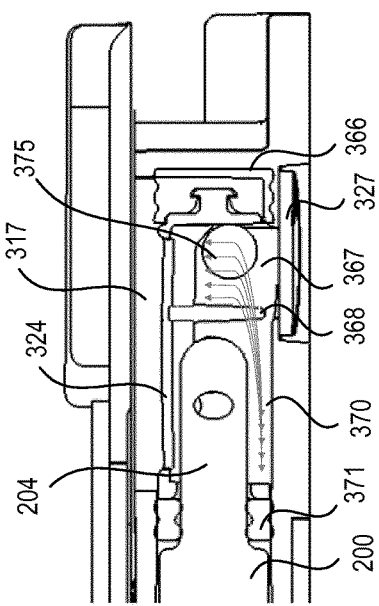

Referring now to FIGS. 10N, 10O, and 10P, a process for enhanced mixing of the contents within sample preparation reservoir 317 is described. In the mixing position, the fluid within sample preparation reservoir 317 is mixed with the collected sample and one or more reagent balls (if provided). Mixing may be enhanced via sonicator element 327 which may be a piezoelectric transducer such as a piezoceramic disc. Sonicator element 327 is configured to vibrate responsive to electrical signals (e.g., transmitted from the reader device) to further mix the contents within sample preparation reservoir 317. For example, sonicator element 327 may facilitate mixing of fluid held in sample preparation reservoir 317, which may be pre-filled and/or filled during the mixing process, with reagent ball 375 and the collected sample. Sonicator element 327 may cause the fluid to flow in a wave pattern as shown in FIGS. 10O and 10P. Such a wave pattern may be between compartments defined by the shuttle, e.g., between reagent ball compartment 367 and sample compartment 370. For example, sonicator element 327 may cause the fluid to flow in one or more directions (e.g., generally up and down as shown in FIG. 10O) within reagent ball compartment 367 during portions of the wave cycle. Such flow is expected to speed up, and enhance, mixing within sample preparation reservoir 317. The wave motion of fluid within sample preparation reservoir 317 also may facilitate removal of sample from the distal portion of sample collection device 200 to enhance mixing and homogenization.

Sonicator element 327 may be configured to emit acoustic waves to move the fluid in sample preparation reservoir 317 in the wave pattern between reagent ball compartment 367 and sample compartment 370 to mix the fluid in sample preparation reservoir 317. Such mixing may create a fluid mix of the sample, fluid from the reservoir, and the dissolved reagent ball(s). The acoustic emissions from sonicator element 327 may both heat fluid within sample preparation reservoir 317 and mix the contents of sample preparation reservoir 317 at the macro and the micro level for amplification such as isothermal amplification. The reagent ball(s) may include, for example, polymerases, primers, and signaling agents for isothermal amplification. Shuttle 324 may have compartment divider 368, which may be a flange, configured to divide reagent ball compartment 367 and sample compartment 370. The fluid flowing around compartment divider 368 may facilitate formation of the wave pattern. Compartment divider 368 may have a slot configured to permit the fluid to flow through compartment divider 368 via the slot during mixing. Sonicator element 327 may form a wall, e.g., part of the bottom wall, of sample preparation reservoir 317 and may be positioned off-center of sample preparation reservoir 317 to facilitate mixing of the fluid within sample preparation reservoir 317. For example, sonicator element 327 may be positioned off-center relative to a center axis of sample preparation reservoir 317 running perpendicular to a longitudinal axis running through the center of the input tunnel of the cartridge. Such off-center positioning of sonicator element 327 also facilitates enhanced mixing. Sonicator element 327 may be electrically coupled to a printed circuit board via one or more spring contacts as described in detail below.

Referring now to FIGS. 11A through 11E, an alternative seal piercer is shown. FIGS. 11A and 11B show seal piercer 321' in a pre-venting and pre-contact position. Seal piercer 321' includes slider 322' slidably coupled to piercer 323' throughout the piercing process. Seal piercer 321' may further include post 388 configured to press contact switch 389 of circuit board 331'. Depression of contact switch 389 may complete a circuit such that electrical signals may be transmitted, e.g., to the reader device and/or the computing device running the software-based user interface system. In this manner, proper insertion of sample collection device 200' within the input tunnel generates an electrical signal that may be transmitted to the reader device and/or computing device to notify the reader device and/or computing device of such proper insertion. Post 388 may be coupled to piercer 323' or may be integral with piercer 323'. As sample collection device 200' causes slider 322' to move distally in a direction generally parallel to movement of sample collection device 200' (e.g., by force applied by engagement zone 209' and/or engagement zone 210 to engager 380'), slider 322' may cause piercer 323/post 388 to move in a different direction, e.g., generally perpendicular to movement of slider 322'. Slider 322' may have angled face 390 configured to contact angled face 391 of piercer 323' as distal movement of sample collection device 200' causes distal movement of slider 322'. Continuing distal movement of sample collection device 200', and thereby distal movement of slider 322', causes piercer 323' and post 388 to be moved downwardly such that piercer 323' pierces the sealing material on the respective reservoir(s) and post 388 activates contact switch 389 as shown in FIGS. 11D and 11E in the contact position.

After contact with contact switch 389 and piercing of the sealing material, seal piercer 321' may move such that post 388 no longer depresses contact switch 389 and piercer 323' moves out of the hole(s) pierced in the sealing material to vent the respective reservoir(s). Insertion of the sample collection device within the input tunnel may cause the seal piercer to pierce the sealing material before a shuttle begins movement from the pre-mixing position to the mixing position or during movement from the pre-mixing position to the mixing position.

FIGS. 11A to 11E illustrate sonicator element 327' coupled to spring contact 392. Spring contact 392 is coupled to circuit board 331' and is a conductor such that sonicator element 327' is electrically coupled to circuit board 331' via spring contact 392. Beneficially, spring contact 392 absorbs movement of sonicator element 327' such that circuit board 331' vibrates minimally in a suitable manner when sonicator element 327' is activated, e.g., responsive to signals transmitted by the reader device, and spring contact 392 permits ease of assembly and reproducibility compared to soldering which may adversely impact sonicator element 327'.

As will be readily understood to one skilled in the art, while FIGS. 11A and 11D do not depict a shuttle and/or reagent balls within the input tunnel, such features may be included in these embodiments.

Referring now to FIGS. 12A through 12E, an alternative configuration for collecting and analyzing a fluid sample is described. Cartridge device 300" may be constructed similarly to cartridge device 300 described above except cartridge device 300" may be modified for enhanced collection of relatively large amounts of fluid. In addition, sample collection device 200" may be constructed similarly to sample collection device 200 described above except sample collection device 200" may have a modified collection area for enhanced collection of relatively large amounts of fluid. For example, sample collection device 200" and cartridge device 300" may be particularly useful for collecting and analyzing saliva, blood, plasma, urine, or the like.

Sample collection device 200" may include modified distal portion 201" for enhanced collection of relatively large amounts of fluid (e.g., about 10-100 microliters) that may include distal sealing zone 208", wicking portion 211, intermediate sealing zone 212, and shroud 213. Distal portion 201" of sample collection device 200" is adapted to be exposed to a sample, preferably a liquid sample, to absorb at least a portion of the sample, and to be compressed to expel the collected sample from distal portion 201" into cartridge device 300" for analysis of the expelled sample. Wicking portion 211 is configured to wick and absorb a sample and may be formed from a wicking material. Wicking portion 211 may be coupled to intermediate sealing zone 212. Intermediate sealing zone 212 may be slidably disposed within shroud 213 and may include one or more sealing members, e.g., O-rings, configured to create a liquid tight seal that reduces or prevents fluid absorbed on wicking portion 211 from moving proximally within shroud 213 beyond intermediate sealing zone 212. Wicking portion 211 is at least partially disposed within shroud 213 and may slide within a lumen of shroud 213. Wicking portion 211 may be configured to become transparent when exposed to fluid such that increasing amounts of wicking portion 211 become transparent as increasing amounts of sample fluid are collected. Sample collection device 200" may include sample collection indicator 214 configured to visually alert a collector based on a volume of sample fluid that has been collected. In one embodiment, sample collection indicator 214 visually alerts a collector as the volume of sample collected increases and, optionally, that at least a predetermined volume of sample fluid has been collected. For example, sample collection indicator 214 may change color when the predetermined volume of sample, or more, has been collected. As another example, an increasing amount of sample collection indicator 214 may become visible as the volume of sample collected increases. For example, sample collection indicator 214 may be a colored thread embedded in wicking portion 211 that becomes increasingly visually exposed as increasing volumes of collected fluid sample cause the surrounding wicking material to turn more transparent such that a collector may monitor progress of fluid collection and determine when a sufficient volume of sample has been collected. In one embodiment, sample collection indicator 214 includes a transparent area on shroud 213. In addition, or alternatively, sample collection indicator 214 may change color as the volume of sample collected increases.

Shuttle 324" may include first end 366", reagent ball compartment 367", compartment divider 368", and sample compartment 370" constructed similarly to those respective components described above. Preferably, compartment divider 368" does not have a slot, similar to compartment divider 368', such that compartment divider 368" fluidically seals reagent ball compartment 367" from sample compartment 370" in the pre-mixing position. Second end 371" of shuttle 324" may be modified to include distal flange 393 and proximal flange 394 having cavity 395. In addition, unlike opening 372 of shuttle 324, opening 372" is configured to permit flow of expelled sample compressed from sample collection device 200" to sample compartment 370", but not a portion of sample collection device 200". Second end 371" (e.g., at distal flange 393) may be configured to fluidicly seal sample compartment 370" in both the pre-mixing position and the mixing position and continuously during the transition therebetween. Distal flange 393 may include one or more sealing members, e.g., O-rings, configured to create a liquid tight seal that reduces or prevents fluid from flowing proximally out of sample compartment 370". In addition, compartment divider 368" may be configured to fluidically seal sample compartment 370" in the pre-mixing position. Compartment divider 368" may include one or more sealing members, e.g., O-rings, configured to create a liquid tight seal that reduces or prevents fluid from flowing distally out of sample compartment 370".

Prior to insertion within input tunnel 301" of cartridge device 300", sample collection device 200" is exposed to a sample, e.g., within an inner cheek, the throat, the mouth, a nasal passageway, an ear, from urine, from blood, from plasma, from saliva, etc. Wicking portion 211 of sample collection device 200" is designed to retain some of the sample to permit analysis of the presence, absence, and/or quantity of one or more target analytes within the sample using cartridge device 300" and the reader device. Cartridge device 300" may be electrically coupled to the reader device before or after sample collection device 200" is inserted in cartridge device 300".

Figure 12A:
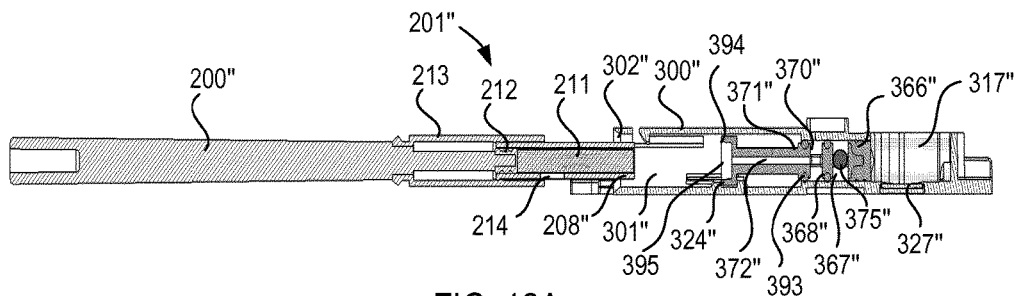
FIGS. 12A through 12E illustrate cross-sectional side views of an alternative sample collection device and an alternative cartridge device for collecting and analyzing a fluid sample.

Referring to FIG. 12A, the distal end of sample collection device 200" is first inserted into aperture 302" defining the opening of input tunnel 301". Shuttle 324" is disposed within input tunnel 301" in a pre-mixing position wherein first end 366" of shuttle 324" forms a wall of sample preparation reservoir 317" to fluidicly seal fluid within sample preparation reservoir 317". In this pre-mixing position, reagent ball 375" housed by shuttle 324" is within input tunnel 301" and not exposed to fluid within sample preparation reservoir 317".

Figure 12B:
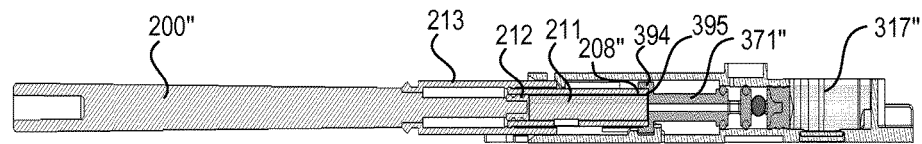

Referring to FIG. 12B, as sample collection device 200" moves distally in input tunnel 301", sample collection device 200" may contact shuttle 324". For example, the distal end and/or distal sealing zone 208" may contact second end 371" (e.g., at cavity 395 and/or proximal flange 394) as illustrated. Cavity 395 may be sized slightly larger than the outer surface of wicking portion 211 such that the distal end of wicking portion 211 fits snuggly within cavity 395. Distal sealing zone 208" may be configured to fluidicly seal sample collection device 200" to shuttle 324" such that fluid expelled from sample collection device 200" travels into sample compartment 370". In this pre-mixing position, sample compartment 370" is within input tunnel 301" and not exposed to fluid within sample preparation reservoir 317".

Figure 12C:
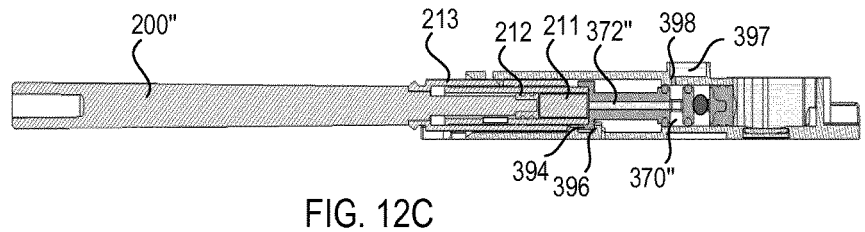

As shown in FIG. 12C, as sample collection device 200" moves further distally in input tunnel 301", sample collection device 200" may expel collected fluid sample into sample compartment 370" of shuttle 324", e.g., through opening 372" of second end 371". As sample collection device 200" is moved distally, wicking portion 211 may be compressed to expel collected sample and the distal end of wicking portion 211 may remain substantially in position during compression. Intermediate sealing zone 212 and/or shroud 213 may move distally in proportion to movement of the handle of sample collection device 200" during such compression. Preferably, as wicking portion 211 is compressed and sample is expelled therefrom, the expelled sample travels through opening 372" into sample compartment 370". During compression, shuttle 324" may remain substantially in position within input tunnel 301" and first end 366" of shuttle 324" may continue to form a wall of sample preparation reservoir 317" to seal fluid within sample preparation reservoir 317". Cartridge device 300" may include proximal ledge 396 configured to hold shuttle 324" in the pre-mixing position during compression of wicking portion 211. Proximal ledge 396 may engage proximal flange 394 to hold shuttle 324" in position.

A predetermined volume of sample, at most, may be configured to be held in sample compartment 370". Cartridge device 300" may include overflow compartment 397 and overflow lumen 398. Overflow compartment 397 and overflow lumen 398 may be part of the cartridge housing or the internal component within the cartridge. If the amount of sample introduced into sample compartment 370" exceeds the predetermined volume, e.g., exceeds about 20 µl, the excess sample may travel to overflow compartment 397 fluidicly connected to sample compartment 370", e.g., via overflow lumen 398. Limiting the volume of sample within sample compartment 370" may enhance precision, accuracy, and/or consistency of analysis as, at most, a predetermined volume of sample is inserted in sample preparation reservoir 317 in the mixing position. Overflow compartment 397 may be otherwise sealed to prevent or reduce leakage of excess sample within overflow compartment 397.

Figure 12D:
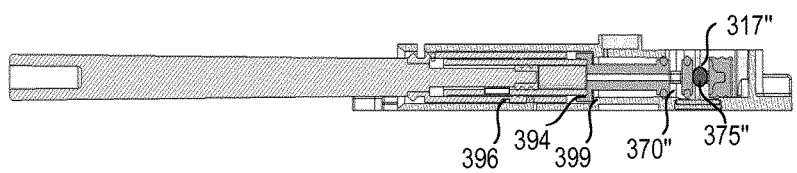
Figure 12E:
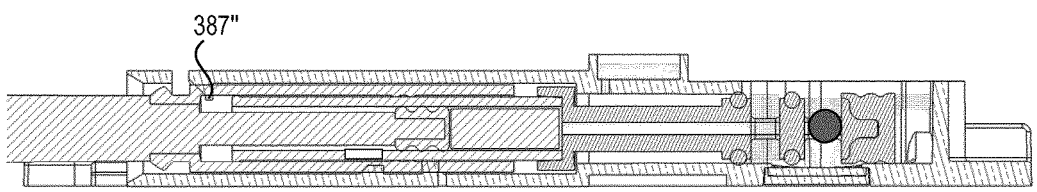

FIG. 12D shows sample collection device 200" and cartridge device 300" in the mixing position and FIG. 12E shows a close up view of a portion of FIG. 12D for clarity. As collector pushes sample collection device 200" distally from the pre-mixing position to the mixing position, shuttle 324" is partially moved within sample preparation reservoir 317". Application of a force greater than a threshold force on shuttle 324" (e.g., at second end 371" and preferably within cavity 395) by sample collection device 200" (at distal sealing portion 208" and/or the distal end of wicking material 211) may cause shuttle 324" to move from the pre-mixing position to the mixing position wherein the expelled sample in sample compartment 370" and reagent ball 375" are mixed within fluid of sample preparation reservoir 317". For example, the threshold force may be the force required to push shuttle 324" distally past proximal ledge 396. As shuttle 324" moves distally, first end 366" may unseal such that one or more reagent balls within shuttle 324" and the collected sample within shuttle 324" are exposed to fluid within sample preparation reservoir 317". Advantageously, before first end 366" of shuttle 324" is unsealed, second end 371" of shuttle 324" is fluidicly sealed by sample collection device 200" such that fluid from sample preparation reservoir 317" does not leak into input tunnel 301" beyond second end 371" and/or intermediate sealing zone 212. In addition, as distal movement of sample collection device 200" causes the transition from the pre-mixing position to the mixing position, distal flange 393 of shuttle 324" continuously fluidicly seals the fluid in sample preparation reservoir 317" from input tunnel 301". Cartridge device 300" may include distal ledge 399 configured to hold shuttle 324" in the mixing position and to prevent further distal movement. Distal ledge 399 may engage proximal flange 394 to hold shuttle 324" in position.

In the mixing position, first end 366" of shuttle 324", the one or more reagent ball compartments of shuttle housing one or more reagent balls, and/or the one or more sample compartments housing the sample(s) to be analyzed may be disposed within sample preparation reservoir 317". As explained above, shuttle 324" (e.g., at second end 371") and sample collection device 200" (e.g., via distal sealing zone 208" inserted in cavity 395) also may fluidicly seal sample preparation reservoir 317" in the mixing position such that the collected sample(s), the reagent ball(s), and the fluid within sample preparation reservoir 317" are sealed within the reservoir. In this manner, the collected sample(s), the reagent ball(s), and the fluid may be mixed within sample preparation reservoir 317".

Cartridge device 300" may further include locking member 387" configured to irreversibly lock sample collection device 200" within cartridge device 300". Locking member 387" may be biased inwardly in input tunnel 301" such that a locking end of locking member 387" engages sample collection device 200" in the mixing position. The locking end may lock to an engagement zone of sample collection device 200". The locking end may be a protrusion sized to fit within a groove on the shaft of sample collection device 200" or within a groove on shroud 213, as illustrated. Locking member 387" also may define a portion of input channel 301", as illustrated, and may be coupled to the cartridge housing at the end opposite its locking end. Advantageously, locking sample collection device 200" (e.g., longitudinally and/or axially) within input tunnel 301" promotes sealing of sample preparation reservoir 317" over time as sample collection device 200" cannot be retracted once locked to facilitate safe disposability and consistency of testing because a user cannot pull out sample collection device 200" from cartridge device 300" inadvertently once the test has started.

As will be readily understood to one skilled in the art, while FIGS. 12A through 12E do not depict a seal piercer in the cartridge device, a seal piercer may be included in these embodiments. For example, sample collection device 200" (e.g., at distal sealing zone 208") may contact the seal piercer to move the seal piercer from the pre-venting position to the venting position in a manner described above with respect to FIGS. 10A to 10J and/or FIGS. 11A to 11E. Sample collection device 200" may contact and move the seal piercer from the pre-venting to the venting position before, during, and/or after contacting shuttle 324" and moving shuttle 324" from the pre-mixing to the mixing position. In addition, insertion of sample collection device 200" may cause activation of a contact switch as described above with respect to FIGS. 11A to 11E. For example, sample collection device 200''' may cause movement of a seal piercer which in turn causes activation of the contact switch.

Figure 13A:
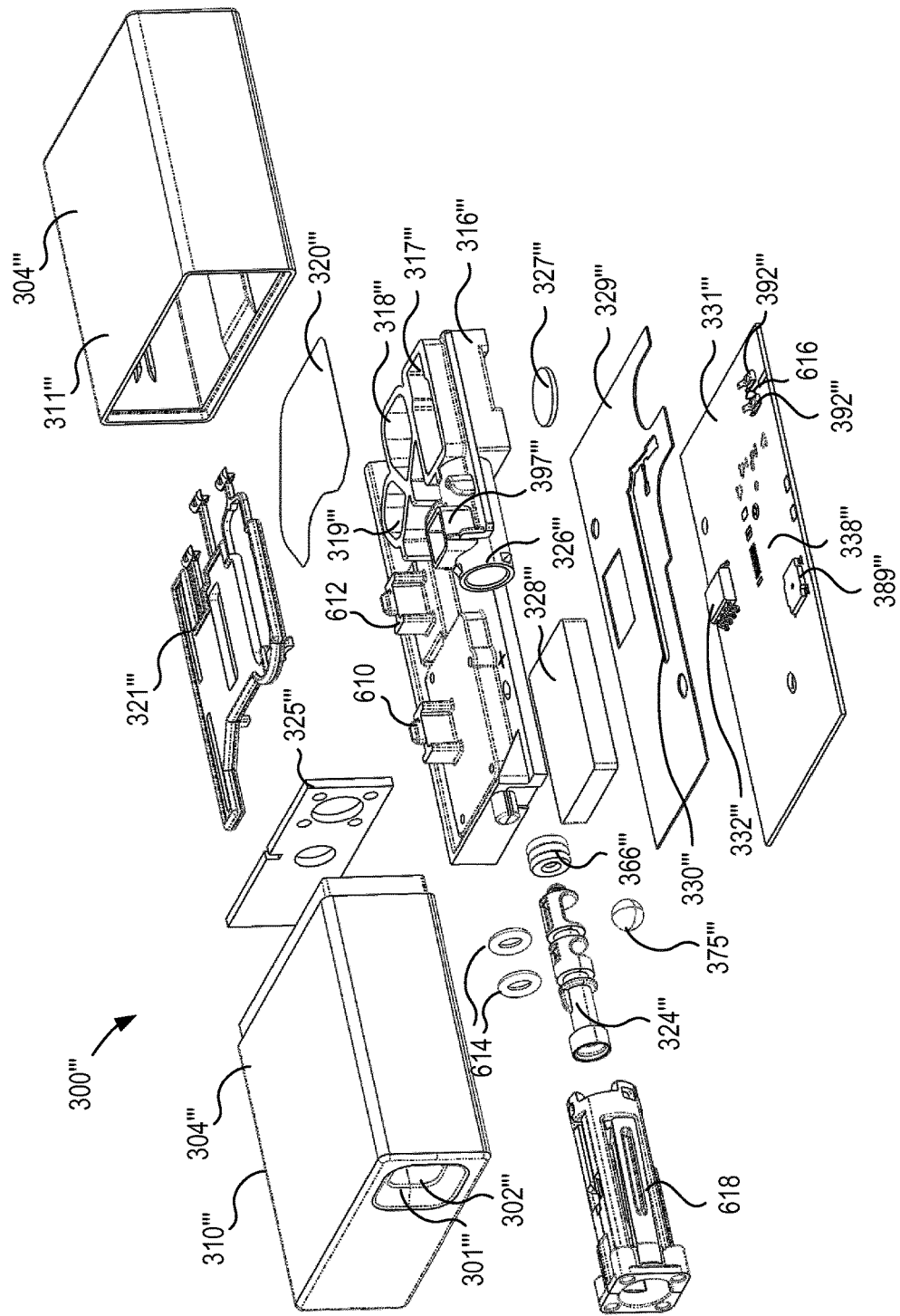
FIG. 13A illustrates an exploded view of another exemplary cartridge device showing internal components that may be within the cartridge housing.

Referring now to FIG. 13A, an alternative cartridge for analyzing a sample is described. Cartridge device 300''' may be constructed similarly to cartridge device 300 and/or cartridge device 300'' described above wherein like components are identified by like-primed reference numbers. Cartridge device 300''' is a universal configuration that includes components that may be used for different types of samples. For example, many components within cartridge device 300''' may be used for various types of samples without modification and, in some embodiments, only the shuttle, collet, and reagent ball(s) may be varied for analysis of different indications. In this manner, cartridge device 300''' may be universal and the shuttle, collet, and/or reagent ball(s) may be selected for use in cartridge device 300''' based on the target analyte(s) to be analyzed. For example, cartridge device 300''' may be fitted with a shuttle designed for relatively small sample collection, e.g., a nasal passageway, an ear, blood, such as shuttle 324 or 324' described above with respect to FIGS. 9A and 9B, and a collet also designed for relatively small sample collection or cartridge device 300''' may be fitted with a shuttle designed for relatively large fluid sample collection, e.g., saliva, blood, plasma, urine, such as shuttle 324'' described above with respect to FIGS. 12A through 12E and a collet also designed for relatively large fluid sample collection. Cartridge device 300''' may be further fitted with a reagent ball(s) intended to identify different target analytes that may be indicative of, for example, inflammation, influenza, testosterone, fertility, HIV, or Vitamin D. Accordingly, cartridge device 300''' is highly interchangeably for different types of samples and indications which reduces costs and manufacturing burdens.

In FIG. 13A, an exploded view of cartridge device 300''' is shown. Cartridge device 300''' may include internal component 316'''—which may include sample preparation reservoir 317''', wash reservoir 318''', substrate reservoir 319''', input tunnel component 326'', overflow compartment 397', and/or posts 610 and 612—sealing material 320''', seal piercer 321''', shuttle 324''' having first end 366''' and sealing members 614, desiccant 325''', sonicator element 327', absorbent pad 328'', layer 329'', analysis channel 330''', circuit board 331''', memory 332'', sensor 338'', heating elements, contact switch 389'', spring contacts 392'', reagent ball 375''', temperature sensor 616, and/or collet 618. The internal components may be disposed within housing 304''', e.g., between first and second cover components 310''' and 311'''. Alternatively, one or more internal components may be disposed within one housing while other internal components may be disposed within another housing(s). In the case of multiple housings, such separate housing may be configured to couple to one another.

In FIG. 13A, shuttle 324''' is illustrated as being substantially similar to shuttle 324'' of FIGS. 12A through 12E although a shuttle like that of shuttle 324 in FIG. 9A or shuttle 324' in FIG. 9B may be used depending on the type of sample to be collected. Collet 618 also may be substituted for collet 618' described below based on the type of sample to be collected. Various reagent ball(s) 375''' may be substituted in cartridge device 300''' as well.

Posts 610 and 612 are configured to be coupled to seal piercer 321''' and to permit seal piercer 321''' to be moved from the pre-venting position to the venting position. Posts 610 and 612 may be integrally formed with internal component 316''' or may be separate pieces.

Temperature sensor 616 may be configured to sense temperature indicative of temperature of fluid in a reservoir, e.g., sample preparation reservoir 317'''. For example, temperature sensor 616 may sense temperature changes adjacent the reservoir that are indicative of temperature in the reservoir. Temperature sensor 616 may be a thermistor and may be disposed on circuit board 331''' to permit electrical coupling with the reader device via one or more leads in circuit board 331'''. Preferably, temperature sensor 616 is positioned adjacent sonicator element 327''' on circuit board 331''' such that temperature sensor 616 senses temperature during mixing within sample preparation reservoir 317''' via sonicator element 327''. Advantageously, temperature indicative of temperature in sample preparation reservoir 317''' may be monitored during mixing of the fluid in the reservoir with reagents from reagent ball(s) and the sample, to ensure that temperature within sample preparation reservoir 317''' is within a predetermined range. If outside the predetermined range, emission of acoustic waves into sample preparation reservoir 317''' via sonicator element 327''' may be modified, e.g., responsive to electrical signals sent by the reader to the sonicator element 327'. Temperature sensor 616 may generate a signal indicative of temperature of the fluid in the reservoir which may be transmitted to the reader for processing via leads in circuit board 331'''. Temperature sensor 616 may be positioned beneath sonicator element 327''' on circuit board 331''' and adjacent to one or more spring contacts, e.g., between first and second spring contacts 392''.

Collet 618 is preferably disposed in input tunnel 301''' between aperture 302''' and sample preparation reservoir 317'''. Collet 618 also may be disposed at least partially proximal to shuttle 324''' in input tunnel 301'''. For example, in the pre-mixing position, an end, e.g., the second end, of the shuttle may be disposed within collet 618. Collet 618 also may be configured to hold shuttle 324''' in the pre-mixing position and to decouple from shuttle 324''' during insertion of the sample collection device in input tunnel 301'''. In this manner, collet 618 may hold shuttle 324''' in the pre-mixing state until force applied from the sample collection device decouples collet 618 from shuttle 324''' such that shuttle 324''' moves from the pre-mixing position to the mixing position while collet 618 remains in place within input tunnel 301'''. Collet 618 has a lumen therethrough sized to permit insertion of the distal portion of the sample collection device. Collet 618 may have a generally tubular shape as illustrated in FIG. 13A. Collet 618 also may be configured to activate contact switch 389''. For example, collet 618 may activate contact switch 389''' responsive to a force applied on collet 618 by the sample collection device during insertion of the sample collection device in input tunnel 301'''.

Referring now to FIGS. 13B through 13SS, various exemplary sample collection devices are illustrated that may be used in detection system 100.

Referring to FIG. 13B, sample collection device 200''' may be constructed similarly to sample collection device 200'' described above except sample collection device 200''' may have a modified shaft for locking sample collection device 200''' within a cartridge during partial and full insertion of sample collection device 200'''. For example, sample collection device 200''' illustratively includes engagement zone 209''' having a plurality of grooves and protrusions distal to, and spaced apart from, proximal sealing zone 207'''. The plurality of grooves and protrusions are configured for engagement with one or more components of the cartridge device for irretractability of sample collection device 200''' during partial and full insertion of sample collection device 200''' within the cartridge. For example, the cartridge may sequentially engage grooves of the multiplicity of grooves in engagement zone 209''' in a distal to proximal direction as sample collection device 200''' is moved distally in the input tunnel. Engagement zone 209''' may be configured to be coupled, permanently or temporarily, to the seal piercer of the cartridge device to move the seal piercer within the cartridge device responsive to movement of sample collection device 200'''. In addition or alternatively, engagement zone 209''' may be configured to activate a contact switch during sample collection device insertion. For example, shoulder 220 at the distal end of engagement zone 209''' may be configured to be coupled to the seal piercer and/or to activate the contact switch.

Like sample collection device 200'', sample collection device 200''' may include modified distal portion 201''' for enhanced collection of relatively large amounts of fluid (e.g., about 10-100 microliters, preferably about 20 microliters) that may include distal sealing zone 208''', wicking portion 211''', intermediate sealing zone, and/or shroud 213'''. Sample collection device 200''' also may include proximal portion 202''', shaft 203''' extending between distal portion 201''' and proximal portion 202''', handle 206''', proximal sealing zone 207''', and/or engagement zone 209''' having shoulder 220 similar to the like primed references described above. Sample collection device 200''' is configured for full or partial insertion within cartridge device 300''' after sample collection. Sample collection device 200''' and cartridge device 300''' may be particularly useful for collecting and analyzing saliva, blood, plasma, urine, or the like. Shoulder 220 of engagement zone 209''' preferably extends further from the longitudinal axis of sample collection device 200''' than a shoulder of distal sealing zone 208''' such that shoulder 220 contacts and moves the seal piercer to vent one or more reservoirs within cartridge device 300''' and/or contacts the collet to activate the contact switch while the shoulder of distal sealing zone 208''' may be sized to move distally through the input tunnel without moving the seal piercer and/or without activating the contact switch.

FIGS. 13C, 13D, 13E, 13F, 13G, and 13H are back, side, front, back, side, and front views, respectively, of sample collection device 200'''.

Referring to FIG. 13I, sample collection device 200'''' may be constructed similarly to sample collection device 200 described above except sample collection device 200'''' may have engagement zone 209'''' similar to engagement zone 209''' of FIG. 13B and tip 204'''' does not include a tube. Tip 204'''' may have a rounded end as illustrated and may be configured to collect a sample from any desired region or location, although tip 204'''' may be particularly useful when collecting a sample from a nasal area. FIGS. 13J, 13K, 13L, 13M, 13N, and 13O are back, side, front, back, side, and front views, respectively, of sample collection device 200''''.

Referring to FIG. 13P, sample collection device 200''''' may be constructed similarly to sample collection device 200'''' shown in FIG. 13I except tip 204''''' of sample collection device 200''''' includes tube 205''''' (like the tube shown in FIGS. 2A and 2B). Distal portion 201''''', including tip 204''''', is configured to be exposed to a sample such that, at most, a predetermined volume of the sample (e.g., less than 10 microliters, preferably about 2 microliters) is disposed in tube 205''''' for analysis. Collection of a predetermined volume of the sample is expected to promote accuracy of analyte analysis as a substantially known quantity of the sample will be analyzed. Tip 204''''' may have a rounded end as illustrated and may be configured to collect a sample from any desired region or location, although tip 204''''' may be particularly useful when collecting a sample of blood. FIGS. 13Q, 13R, 13S, 13T, 13U, 13V, and 13W are side, back, side, front, back, side, and front views, respectively, of sample collection device 200'''''.

Referring to FIG. 13X, sample collection device 200'''''' may be constructed similarly to sample collection device 200''''' shown in FIG. 13P except tip 204'''''' of sample collection device 200'''''' includes slot 222 rather than a tube. Distal portion 201'''''', including tip 204'''''', is configured to be exposed to a sample such that, at most, a predetermined volume of the sample (e.g., less than 10 microliters, preferably about 5 microliters) is disposed in slot 222 for analysis. Collection of a predetermined volume of the sample is expected to promote accuracy of analyte analysis as a substantially known quantity of the sample will be analyzed. Tip 204'''''' may have a rounded end as illustrated and may be configured to collect a sample from any desired region or location, although tip 204'''''' may be particularly useful when collecting a sample of blood. FIGS. 13Y, 13Z, 13AA, 13BB, 13CC, 13DD, and 13EE are side, back, side, front, back, side, and front views, respectively, of sample collection device 200''''''.

Referring to FIG. 13FF, sample collection device 200''''''' may be constructed similarly to sample collection device 200''''' shown in FIG. 13P except tip 204''''''' of sample collection device 200''''''' includes ring 224 rather than a tube. Distal portion 201''''''', including tip 204''''''', is configured to be exposed to a sample such that, at most, a predetermined volume of the sample (e.g., less than 10 microliters, preferably about 2 microliters) is disposed in a groove formed by ring 224 for analysis. Collection of a predetermined volume of the sample is expected to promote accuracy of analyte analysis as a substantially known quantity of the sample will be analyzed. Tip 204''''''' may have a rounded end as illustrated and may be configured to collect a sample from any desired region or location, although tip 204''''''' may be particularly useful when collecting a sample of blood. FIGS. 13GG, 13HH, 13II, 13JJ, 13KK, and 13LL are back, side, front, back, side, and front views, respectively, of sample collection device 200'''''''.

Referring to FIG. 13MM, sample collection device 200'''''''' may be constructed similarly to sample collection device 200''''' shown in FIG. 13P except tip 204'''''''' of sample collection device 200'''''''' includes first ring 226 and second ring 228 rather than a tube. Distal portion 201'''''''', including tip 204'''''''', is configured to be exposed to a sample such that, at most, a predetermined volume of the sample (e.g., less than 10 microliters, preferably about 5 microliters) is disposed in a groove formed by first ring 226 and a groove formed by second ring 228 for analysis. Collection of a predetermined volume of the sample is expected to promote accuracy of analyte analysis as a substantially known quantity of the sample will be analyzed. Tip 204'''''''' may have a rounded end as illustrated and may be configured to collect a sample from any desired region or location, although tip 204'''''''' may be particularly useful when collecting a sample of blood. FIGS. 13NN, 13OO, 13PP, 13QQ, 13RR, and 13SS are back, side, front, back, side, and front views, respectively, of sample collection device 200''''''''.

Figure 14B:
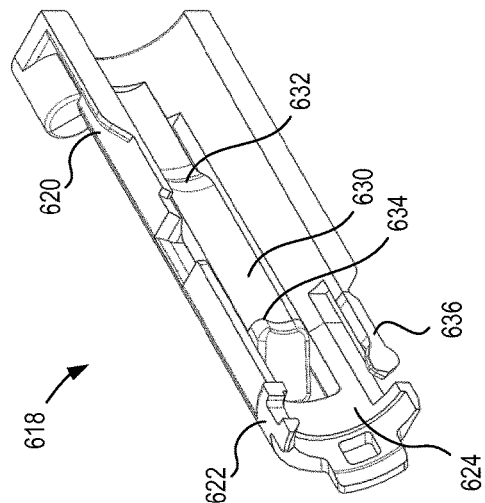
Figure 14D:
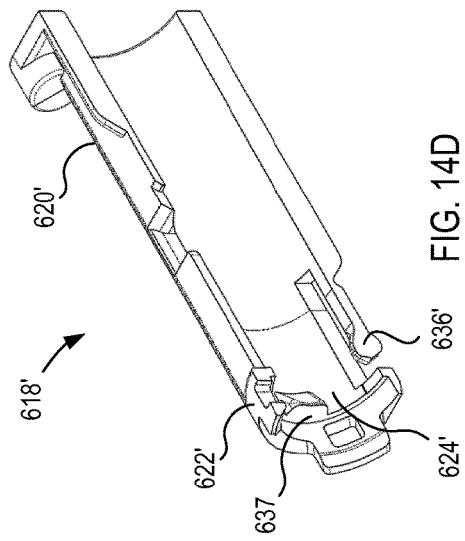
Figure 14A:
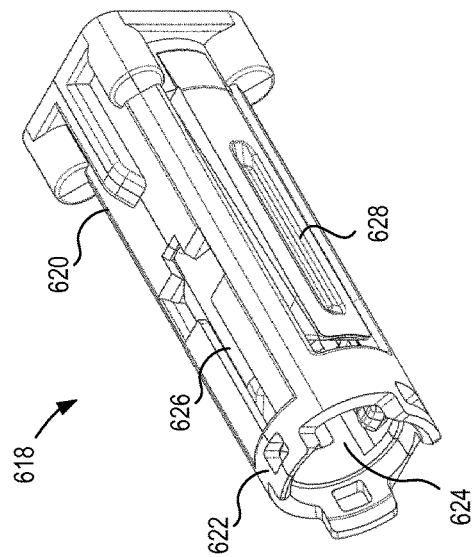

Referring now to FIGS. 14A and 14B, an exemplary collet for use in a cartridge is described. Collet 618 may be specifically designed for relatively large fluid sample collection, e.g., saliva, blood, plasma, urine, such as when the sample is compressed from the distal portion of the sample collection device as described above with respect to FIGS. 12A through 12E, FIG. 13B, and below. Collet 618 may include proximal end 620, distal end 622, and lumen 624 extending between ends 620 and 622. Lumen 624 may be sized to permit insertion of the distal portion of a sample collection device into lumen 624. Collet 618 is positioned in the input tunnel such that the distal portion of the sample collection device first enters lumen 624 at proximal end 620. Collet 618 also may include slot 626, e.g., at upper surface of collet 618. Slot 626 is sized to receive a portion of the seal piercer therethrough. For example, the engager of the seal piercer may extend through the slot into the input tunnel to permit contact between the seal piercer and the sample collection device.

Lumen 624 of collet 618 also may be sized to receive a portion of the shuttle therein. For example, the proximal end of the shuttle may be disposed in lumen 624 through distal end 622 of collet 618. Collet 618 also may be configured to hold the shuttle in the input tunnel in the pre-mixing position. For example, collet 618 may include one or more locking arms configured to couple collet 618 to the shuttle in the pre-mixing position. Illustratively, collet 618 includes first locking arm 628 and second locking arm 630 at opposing lateral sides of collet 618. Advantageously, when using a sample collection device having a compressible distal portion for collecting a fluid sample, collet 618 may hold the shuttle in place in the input tunnel during compression of the distal portion to expel sample fluid into the shuttle. Each locking arm may include a ramp and a protrusion, shown as ramp 632 and protrusion 634 for locking arm 630 in FIG. 14B. Protrusion 634 may be coupled to the shuttle to hold the shuttle in place in the pre-mixing position. For example, the protrusions may hold the proximal flange of the shuttle during compression of the distal portion of the sample collection device. First and second locking arms 628 and 630 also may decouple from the shuttle during insertion of the sample collection device in the input tunnel 301. First and second locking arms 628 and 630 may be deflected to decouple first and second locking arms 628 and 630 from the shuttle responsive to a force applied on first and second locking arms 628 and 630 by the sample collection device during insertion of the sample collection device in the input tunnel. For example, the shoulder of the sample collection device may contact the ramp(s) of the locking arm(s) and cause the protrusion(s) to deflect outwardly as the sample collection device moves distally along the ramp(s) and in the input tunnel. The ramp(s) are shaped such that the protrusion(s) decouple from the proximal flange of the shuttle to unlock the shuttle and permit the shuttle to move from the pre-mixing position to the mixing position where the shuttle is partially disposed within the sample preparation reservoir.

Collet 618 may include deflector portion 636 configured to deflect to activate a contact switch within the cartridge. Preferably, deflector portion 636 is disposed on a bottom face of collet 618 and positioned above the contact switch in the input tunnel. Deflector portion 636 may deflect to activate the contact switch responsive to a force applied on deflector portion 636 by the sample collection device during insertion of the sample collection device in the input tunnel. For example, the shoulder of the sample collection device may contact deflector portion 636 and force deflector portion 636 downwardly as the sample collection device moves distally in the input tunnel to activate the contact switch. Illustratively, deflector portion 636 is an arm configured to deflect downwardly.

Figure 14C:
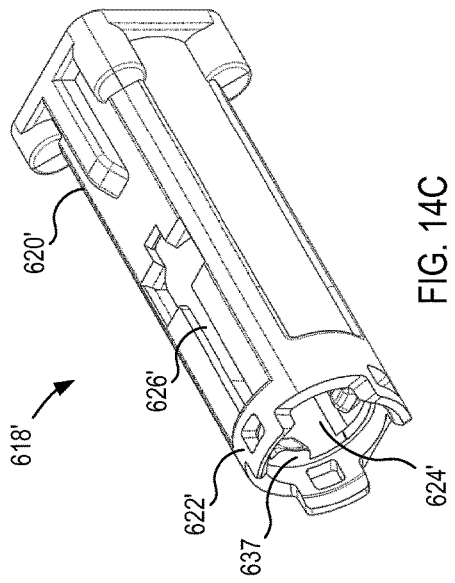

Referring now to FIGS. 14C and 14D, an alternative collet for use in a cartridge is described. Collet 618' may be specifically designed for relatively small sample collection, e.g., a nasal passageway, an ear, blood, such as when the sample need not be compressed from the distal portion of the sample collection device. As will be appreciated when comparing FIGS. 14C and 14D to FIGS. 14A and 14B, collet 618' is similar to collet 618 expect collet 618' does not have locking arms. Collet 618' has one or more protrusions 637 disposed at distal end 622' and configured to contact the proximal end of the shuttle in the pre-mixing position. For example, the one or more protrusions 637 may contact a sealing member, e.g., O-ring, at second end 371, 371' of shuttle 324, 324' to retain the sealing member in position. The one or more protrusions may have lead-in angles configured to guide the distal portion of the sample collection device into the opening at the second end of the shuttle.

Figure 15A:
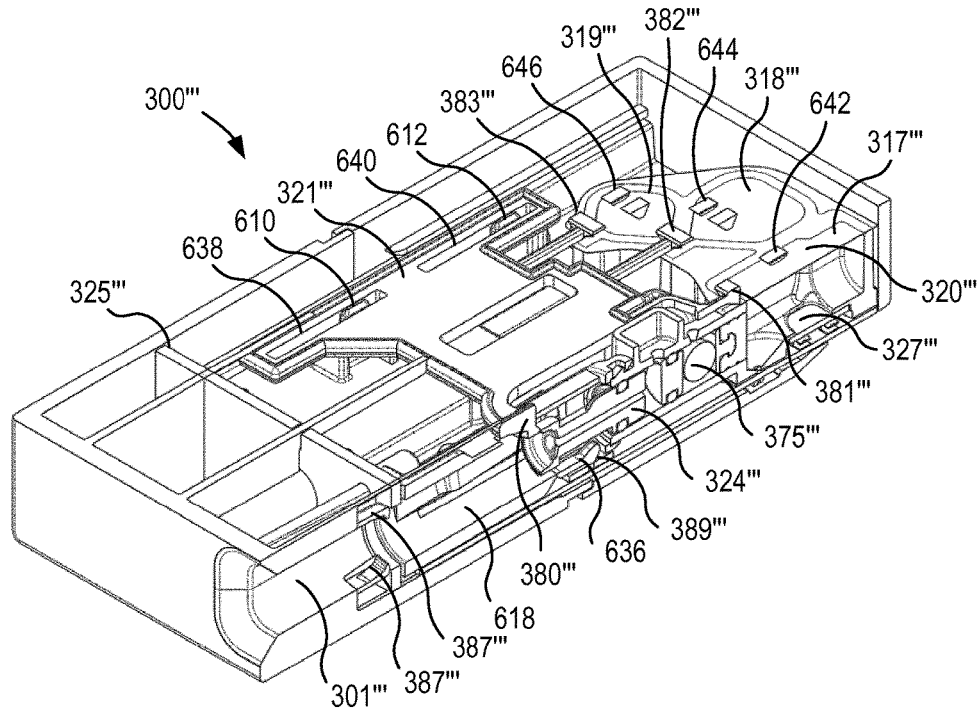
FIG. 15A illustrates a cross-sectional view through the center of the input tunnel of an exemplary cartridge in the pre-mixing, pre-venting, storage position.
Figure 15B:
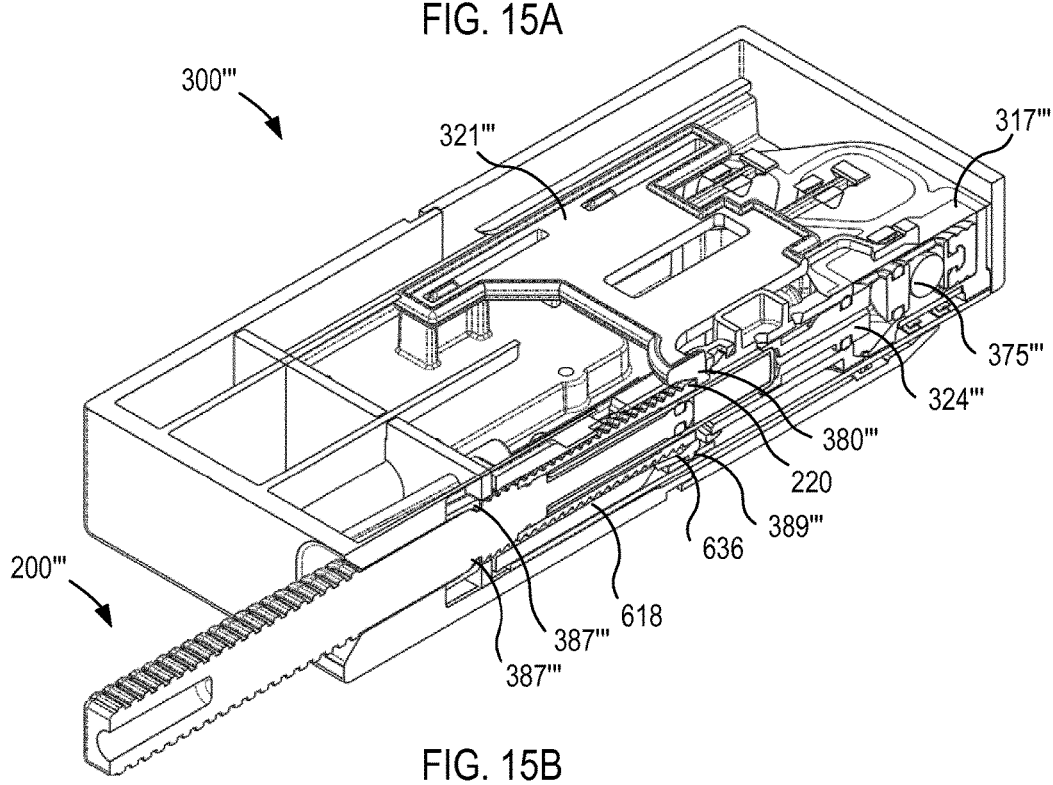
FIG. 15B illustrates a cross-sectional view of the exemplary cartridge and an exemplary sample collection device fully inserted in the input tunnel in the mixing, venting, analysis position.
Figure 15C:
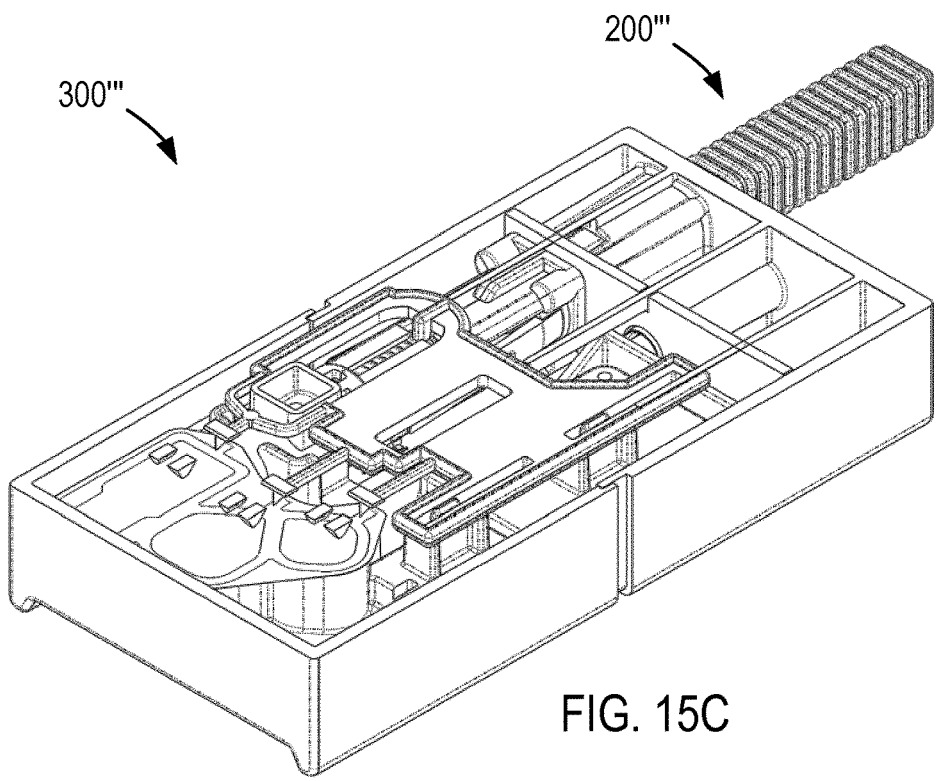
FIGS. 15C and 15D illustrate perspective views of the exemplary cartridge having the exemplary sample collection device inserted therein in the pre-venting position (FIG. 15C) and in the venting position (FIG. 15D).
Figure 15D:
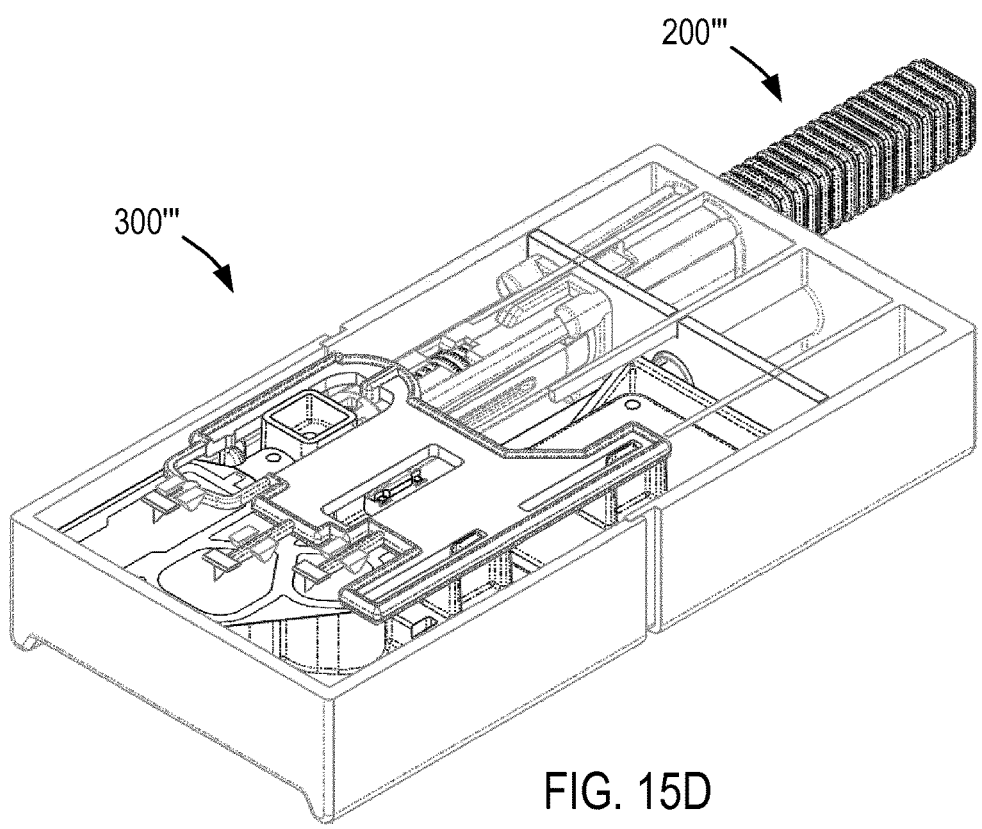

Referring now to FIGS. 15A through 15D, cartridge 300''' is shown in various positions with the upper surface of the housing removed for clarity. FIGS. 15A and 15B are cross-sectional views through the center of the input tunnel for additional clarity. In FIG. 15A, cartridge 300''' is shown in the pre-mixing, pre-venting, storage position where a sample collection device has not yet been inserted in input tunnel 301'''. As shown, seal piercer 321''' is in the pre-venting position and has not yet pierced seal material 320''' over the reservoirs, the proximal end of shuttle 324''' is disposed within the distal end of collet 618 while the distal end of shuttle 324''' forms a wall of sample preparation reservoir 317''', and deflector portion 636 of collet 618 is in the pre-deflection position where deflector portion 636 does not activate contact switch 389". In FIG. 15B, cartridge 300''' is shown in the mixing, venting, analysis position where the sample collection device is fully inserted in input tunnel 301'''. As shown, seal piercer 321''' is in the venting position and has pierced seal material 320''' over each of the reservoirs, shuttle 324''' has moved distally from collet 618 such that the sample and reagent ball 375''' are mixing with the fluid in sample preparation reservoir 317''', deflector portion 636 of collet 618 is in the deflection position where deflector portion 636 has activated contact switch 389", and locking members 387''' have locked the sample collection device in input tunnel 301'''. In FIG. 15C, cartridge 300''' is still in the pre-mixing, pre-venting position as the sample collection device has only been partially inserted in input tunnel 301'''. FIG. 15D shows cartridge 300''' in the venting position.

Referring back to FIG. 15A, an exemplary process is described for piercing the sealing material disposed over one or more reservoirs in the cartridge device via interaction between the sample collection device and the seal piercer within the cartridge device.

Seal piercer 321''' is configured to pierce sealing material 320''' to vent the fluid in sample preparation reservoir 317''', wash reservoir 318''', and/or substrate reservoir 319'''. Preferably, seal piercer 321''' is configured to pierce sealing material 320''' over the reservoirs sequentially to reduce resistance on the sample collection device during piercing. Seal piercer 321''' may be configured to be contacted by the distal portion, e.g., at a shoulder, of a sample collection device within input tunnel 301''' and to move within housing 304''', responsive to force applied by the sample collection device, to cause sealing material 320''' to be pierced to vent the fluid in sample preparation reservoir 317''', wash reservoir 318''', and/or substrate reservoir 319'''. Illustratively, seal piercer 321''' is a single piece. Seal piercer 321''' is disposed within housing 304''' and may be partially disposed within input tunnel 301'''. For example, engager 380''' of seal piercer 321''' may be disposed within input tunnel 301''', e.g., through slot 626 of collet 618. Seal piercer 321''' has one or more piercing elements with ends sufficiently sharp to cut open sealing material 320'''. Illustratively, seal piercer 321''' has first piercing element 381''' having a piercing end disposed adjacent sample preparation reservoir 317''', second piercing element 382''' having a piercing end disposed adjacent wash reservoir 318''', and third piercing element 383''' having a piercing end disposed adjacent substrate reservoir 319'''.

Seal piercer 321''' also may include slots 638 and 640 configured to receive a portion of posts 610 and 612 respectively. Accordingly, seal piercer 321''' may move within housing 304''' while the portions of posts 610 and 612 remain in slots 638 and 640. Cartridge 300''' also may include one or more ramps configured to deflect the one or more piercing elements toward sealing material 320''' to pierce sealing material 320'''. The one or more ramps may be directly coupled to housing 304''' of cartridge 300'''. The peak(s) of the one or more ramps may be positioned such that the one or more piercing elements travel past the peak(s) when the sample collection device is fully inserted in input tunnel 301''' to facilitate venting of the reservoirs. Illustratively, cartridge 300''' has first ramp 642 disposed adjacent sample preparation reservoir 317''', second ramp 644 disposed adjacent wash reservoir 318''', and third ramp 646 disposed adjacent substrate reservoir 319'''. The distance between each ramp and each piercing element in the preventing position may be different such that the reservoirs are pierced sequentially. Each ramp may have a break in the middle to fit the portion of seal piercer 321''' adjacent the piercing elements in the venting and mixing positions, as shown in FIG. 15B.

As sample collection device 200''' is moved distally through input tunnel 301''', preferably seal piercer 321''' does not move within the cartridge housing, and remains in a pre-vent position, until sample collection device 200''' securely engages seal piercer 321'''. Seal piercer 321''' may securely engage sample collection device 200''' by temporarily or permanently coupling engager 380''' of seal piercer 321''' to sample collection device 200''', e.g., at shoulder 220, once sample collection device 200''' is sufficiently inserted in input tunnel 301'''.

As collector pushes sample collection device 200''' distally, seal piercer 321''' is moved from the pre-venting position towards the venting position. Seal piercer 321''' may move within the cartridge by, for example, application of a force greater than a threshold force by sample collection device 200''' (e.g., at shoulder 220 which may be at the distal end of shroud 213''' and/or at the distal end of engagement zone 209''') on seal piercer 321''' (e.g., at engager 380'''). As sample collection device 200''' is moved distally, the piercing element the shortest distance from its ramp first pierces the sealing material above that reservoir. For example, as sample collection device 200''' is moved distally, seal piercer 321''' moves generally parallel to movement of sample collection device 200''' until second piercing element 382''' contacts second ramp 644 and second ramp 644 deflects second piercing element 382''' downwardly to pierce sealing material 320''' over wash reservoir 318'''. As seal piercer 321''' continues to move distally second piercing element 382''' moves past the peak of second ramp 644 and moves upward out of the hole pierced above wash reservoir 318''' and third piercing element 383''' contacts third ramp 646 and third ramp 646 deflects third piercing element 383''' downwardly to pierce sealing material 320''' over substrate reservoir 319'''. As seal piercer 321''' continues to move distally third piercing element 383''' moves past the peak of third ramp 646 and moves upward out of the hole pierced above substrate reservoir 319''' and first piercing element 381''' contacts first ramp 642 and first ramp 642 deflects first piercing element 381''' downwardly to pierce sealing material 320''' over sample preparation reservoir 317'''. As seal piercer 321''' continues to move distally first piercing element 381''' moves past the peak of first ramp 642 and moves upward out of the hole pierced above sample preparation reservoir 317'''. As will be understood to one skilled in the art, the order of piercing may be varied for sequential piercing.

Advantageously, a configuration where insertion of sample collection device 200''' causes sample preparation reservoir 317''', wash reservoir 318''', and/or substrate reservoir 319''' to be vented sequentially ensures that the reservoir(s) remain fluidically sealed prior to sample collection device 200 insertion, eases resistive forces during insertion of the sample collection device, and facilitates drainage of the reservoir(s) into the analysis channel when the outlet of the respective reservoir permits fluid flow therethrough.

Referring now to FIGS. 16A through 16J, a configuration for collecting and analyzing a sample using cartridge 300''' is described. Illustratively, sample collection device 200''' is inserted in cartridge 300''', although it should be understood that any sample collection device described herein may be used as cartridge 300''' is designed for universal application for different types of sample and different types of indications, although certain internal components may be substituted such as the shuttle, reagent ball(s), and/or collet based on the application. Sample collection device 200''' is described above with respect to FIG. 13B. Sample collection device 200''' illustratively includes engagement zone 209''' having a plurality of grooves and protrusions distal to, and spaced apart from, the sealing zone at the proximal portion of sample collection device 200'''. The plurality of grooves and protrusions are configured for engagement with one or more components of cartridge device 300''' for irretractability of sample collection device 200''' during partial and full insertion of sample collection device 200''' within cartridge 300'''. Engagement zone 209''' may facilitate fixed engagement between sample collection device 200''' and the cartridge device, e.g., via locking members 387', such that sample collection device 200''' is mated irreversibly with the cartridge when sample collection device 200''' is partially inserted a predetermined distance in the input tunnel of the cartridge, e.g., when the distal-most groove of engagement zone 209''' engages locking members 387'. Sample collection device 200''' continues to be mated irreversibly with the cartridge as insertion continues toward the full insertion position. For example, locking members 387''' may sequentially engage grooves of the multiplicity of grooves in engagement zone 209''' in a distal to proximal direction as sample collection device 200''' is moved distally in input tunnel 301'''. Locking members 387''' may engage the proximal-most groove of the multiplicity of grooves in engagement zone 209''' when sample collection device 200''' is fully inserted in input tunnel 301'''. Preferably, sample collection device 200''' cannot be retracted after both partial and full insertion, thereby reducing the risk of contamination. Engagement zone 209''' may be configured to be coupled, permanently or temporarily, to the seal piercer of the cartridge device to move the seal piercer within the cartridge device responsive to movement of sample collection device 200'''. In addition or alternatively, engagement zone 209''' may be configured to activate a contact switch during sample collection device insertion. For example, shoulder 220 at the distal end of engagement zone 209''' may be configured to be coupled to the seal piercer and/or to activate the contact switch.

Prior to insertion within input tunnel 301''' of cartridge device 300''', sample collection device 200''' is exposed to a sample, e.g., within an inner cheek, the throat, the mouth, a nasal passageway, an ear, from urine, from blood, from plasma, from saliva, etc. Wicking portion 211''' of sample collection device 200''' is designed to retain some of the sample to permit analysis of the presence, absence, and/or quantity of one or more target analytes within the sample using cartridge device 300''' and the reader device. Cartridge device 300''' may be electrically coupled to the reader device before or after sample collection device 200''' is inserted in cartridge device 300'''.

Figure 16A:
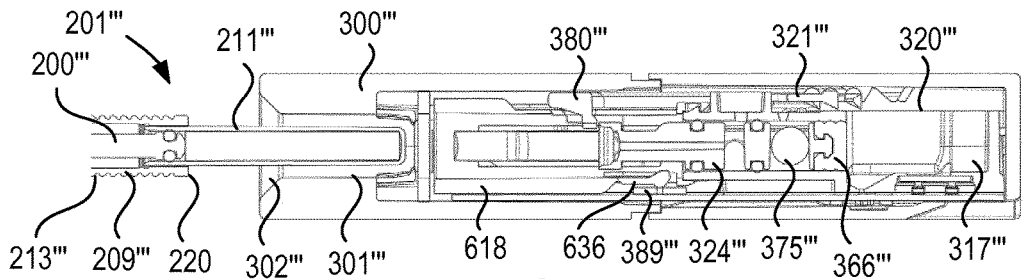
FIGS. 16A through 16E illustrate cross-sectional side views showing insertion of the sample collection device in the cartridge.

Referring to FIG. 16A, the distal end of sample collection device 200''' is first inserted into aperture 302''' defining the opening of input tunnel 301'''. As shown, seal piercer 321''' is in the pre-venting position and has not yet pierced seal material 320''' over the reservoirs, the proximal end of shuttle 324''' is disposed within the distal end of collet 618 while the distal end of shuttle 324''' forms a wall of sample preparation reservoir 317''', and deflector portion 636 of collet 618 is in the pre-deflection position where deflector portion 636 does not activate contact switch 389''. In this pre-mixing position, reagent ball 375''' housed by shuttle 324''' is within input tunnel 301''' and not exposed to fluid within sample preparation reservoir 317'''.

Figure 16B:
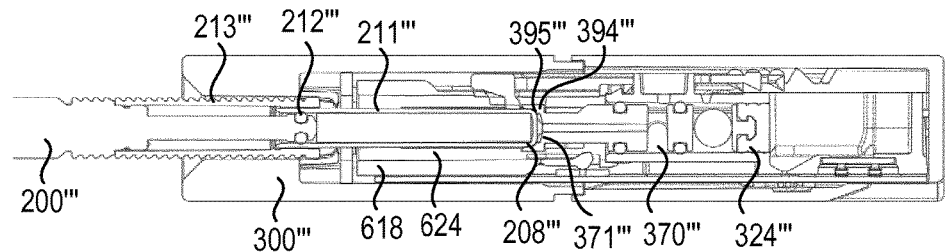

Referring to FIG. 16B, as sample collection device 200''' moves distally in input tunnel 301''', the distal end of sample collection device 200''' travels through lumen 624 of collet 618 and contacts shuttle 324''. For example, the distal end and/or distal sealing zone 208''' may contact second end 371''' (e.g., at cavity 395''' and/or proximal flange 394'') as illustrated. As explained above with respect to FIGS. 12A through 12E, cavity 395''' may be sized slightly larger than the outer surface of wicking portion 211''' such that the distal end of wicking portion 211''' fits snuggly within cavity 395''' and distal sealing zone 208''' may be configured to fluidicly seal sample collection device 200''' to shuttle 324''' such that fluid expelled from sample collection device 200''' travels into sample compartment 370'''. In this pre-mixing position, sample compartment 370''' is within input tunnel 301''' and not exposed to fluid within sample preparation reservoir 317'''.

Figure 16C:
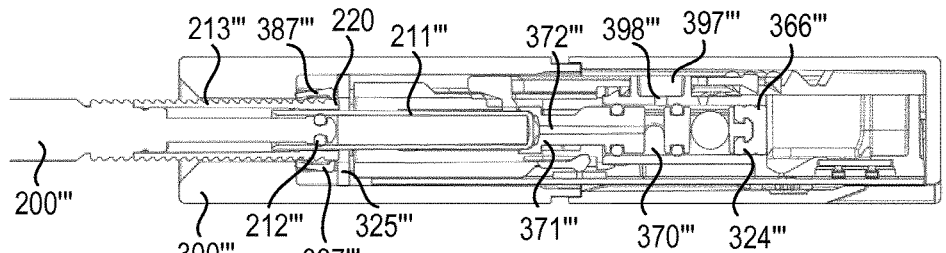

As shown in FIG. 16C, as sample collection device 200''' moves further distally in input tunnel 301''', sample collection device 200''' may deflect one or more locking members 387''' of cartridge device 300''', e.g., via shoulder 220, and sample collection device 200''' may expel collected fluid sample into sample compartment 370''' of shuttle 324'', e.g., through opening 372''' of second end 371'''. As is explained above, as sample collection device 200''' is moved distally, wicking portion 211''' may be compressed to expel collected sample and the distal end of wicking portion 211''' may remain substantially in position during compression. Intermediate sealing zone 212''' and/or shroud 213''' may move distally in proportion to movement of the handle of sample collection device 200''' during such compression. Preferably, as wicking portion 211''' is compressed and sample is expelled therefrom, the expelled sample travels through opening 372''' into sample compartment 370'''. During compression, shuttle 324''' may remain substantially in position within input tunnel 301''' and first end 366''' of shuttle 324''' may continue to form a wall of sample preparation reservoir 317''' to seal fluid within sample preparation reservoir 317'''. Collet 618 may hold shuttle 324''' in the pre-mixing position during compression of wicking portion 211'''. For example, first and second locking arms of collet 618 may hold shuttle 324''' in the pre-mixing position.

Cartridge device 300''' may include overflow compartment 397''' and overflow lumen 398''' configured to receive excess sample if the amount of sample introduced into sample compartment 370''' exceeds a predetermined volume, e.g., exceeds about 20 µl, as explained above. Overflow compartment 397''' is illustratively formed as part of the internal component and is sealed on the top surface by the cartridge housing.

Figure 16D:
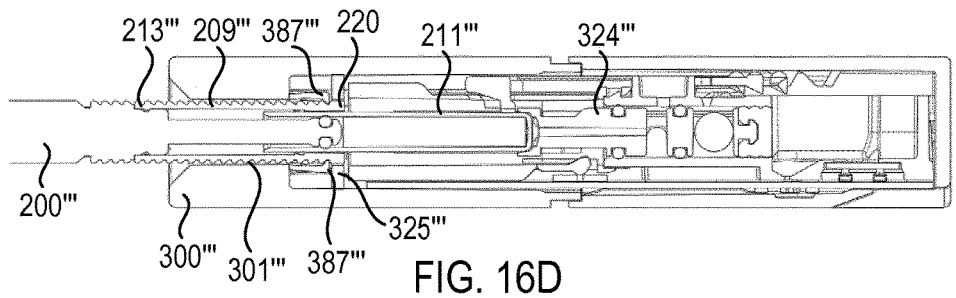

As shown in FIG. 16D, as sample collection device 200''' moves further distally in input tunnel 301''', sample collection device 200''' may deflect one or more locking members 387''' of cartridge device 300''' past shoulder 220 such that one or more locking members 387''' lock to engagement zone 209''' during partial sample collection device 200''' insertion. Illustratively, locking members 387''' engage the distal-most groove of engagement zone 209''' to accomplish the first lock during insertion. As the distal end of shroud 213''', e.g., at shoulder 220, passes desiccant 325''', a liquid safety barrier is formed in input tunnel 301''' by shroud 213''' and desiccant 325'''. During wicking portion 211''' compression shown in FIG. 16D, like FIG. 16C, sealing zone 212''' and/or shroud 213''' may move distally to further expel sample into sample compartment 370''' while shuttle 324''' may remain substantially in position within input tunnel 301'''.

Figure 16E:
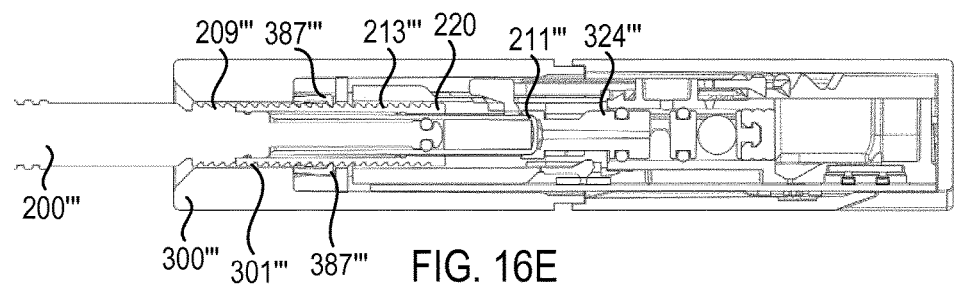

Referring to FIG. 16E, as sample collection device 200''' moves further distally in input tunnel 301''', sample collection device 200''' continues to deflect one or more locking members 387''' of cartridge device 300''' past protrusions and into grooves of engagement zone 209''' in a distal to proximal direction such that one or more locking members 387''' continue to lock to engagement zone 209''' throughout partial sample collection device 200''' insertion. During wicking portion 211''' compression shown in FIG. 16E, like FIGS. 16C and 16D, sealing zone 212''' and/or shroud 213''' may move distally to further expel sample into sample compartment 370''' while shuttle 324''' may remain substantially in position within input tunnel 301'''. Once sample collection device 200''' causes collet 618 to decouple from shuttle 324'', shuttle 324''' may move within input tunnel 301''' from the pre-mixing position to the mixing position. For example, sample collection device 200''' may apply a force on collet 618 during insertion of sample collection device 200''' in input tunnel 301''' to decouple collet 618 from shuttle 324''. In FIG. 16E, engagement zone 209''', e.g., at shoulder 220, contacts collet 618, e.g., at first and second locking arms.

FIG. 16F is a top view of FIG. 16E showing partial insertion of sample collection device 200''' in cartridge 300'''. Collet 618 is disposed in input tunnel 301''' and configured to be coupled to shuttle 324''' in the pre-mixing position. Collet 618 also may be configured to be coupled to shuttle 324''' during compression of sample collection device 200''' to allow the distal portion of sample collection device 200''' to compress while shuttle 324''' remains in place. Illustratively, second end 371''' of shuttle 324''' is disposed in the lumen of collet 618. In this example, collet 618 includes first locking arm 628 and second locking arm 630 at opposing lateral sides of collet 618. The protrusion of first locking arm 628 and protrusion 634 of second locking arm 630 hold proximal flange 394''' of shuttle 324''' during compression of the distal portion of sample collection device 200'''. First and second locking arms 628 and 630 also may decouple from shuttle 324''' during insertion of sample collection device 200''' in input tunnel 301'''. First and second locking arms 628 and 630 may be deflected to decouple first and second locking arms 628 and 630 from shuttle 324''' responsive to a force applied on first and second locking arms 628 and 630 by sample collection device 200''' during insertion of sample collection device 200''' in input tunnel 301'''. In FIG. 16F, shoulder 220 of sample collection device 200''' contacts the ramp of first locking arm 628 and ramp 632 of second locking arm 630 during partial sample collection device 200''' insertion.

Referring to FIG. 16G, as sample collection device 200''' moves further distally in input tunnel 301''', sample collection device 200''', e.g., at shoulder 220, applies a force on the ramps of first and second locking arms 628 and 630 to cause the protrusions of first locking arm 628 and protrusion 634 of second locking arm 630 to deflect outwardly. The ramps are shaped such that the protrusions decouple from proximal flange 394''' of shuttle 324''' to unlock shuttle 324''' from collet 618 and permit shuttle 324''' to move from the pre-mixing position towards the mixing position.

As depicted in FIGS. 16F and 16G, sample preparation reservoir 317''', wash reservoir 318''', and/or substrate reservoir 319''' may each have symmetric shapes. For example, each of the walls of sample preparation reservoir 317''' may form a symmetric shape wherein each of the walls of sample preparation reservoir 317''' meet at an angle greater than a predetermined angle, e.g., 60°, 90°, to facilitate fluid emptying through the outlet of sample preparation reservoir 317'''. Sonicator element 327''' may be positioned off-center as illustrated of sample preparation reservoir 317''' to facilitate mixing of the fluid within sample preparation reservoir 317'''. Similarly, each of the walls of wash reservoir 318''' and/or substrate reservoir 319''' may form a symmetric shape wherein each of the walls of wash reservoir 318''' and/or substrate reservoir 319''' meet at an angle greater than a predetermined angle, e.g., 60°, 90°, to facilitate fluid emptying through the respective outlets of wash reservoir 318''' and/or substrate reservoir 319'''.

Figure 16H:
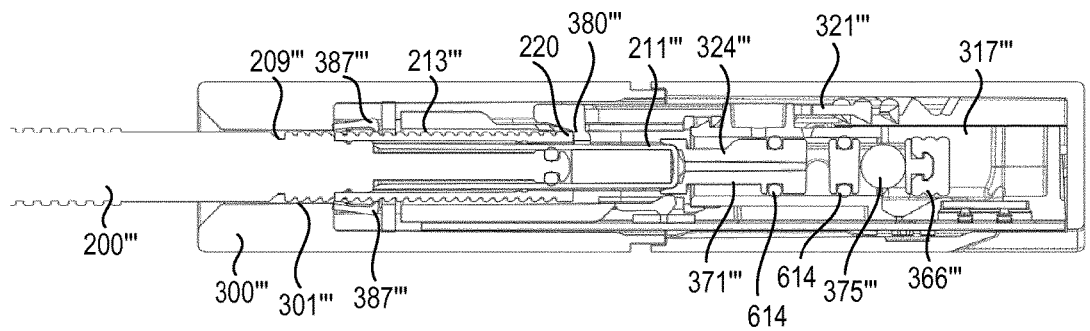
FIGS. 16H through 16J illustrate cross-sectional side views showing further distal insertion of the sample collection device in the cartridge, wherein the sample collection device is fully inserted in the input tunnel in the mixing, venting, analysis position in FIG. 16J.

Referring to FIG. 16H, as sample collection device 200''' moves further distally in input tunnel 301''', sample collection device 200''' contacts seal piercer 321'''. For example, shoulder 220 of sample collection device 200''' may contact engager 380''' of seal piercer 321''' within input tunnel 301'''. As collector pushes sample collection device 200''' distally from the pre-mixing position towards the mixing position, shuttle 324''' may be partially moved within sample preparation reservoir 317''' as shown in FIG. 16H. As shuttle 324''' moves distally, first end 366''' may unseal such that one or more reagent balls 375''' within shuttle 324''' and the collected sample within shuttle 324''' are exposed to fluid within sample preparation reservoir 317'''. Advantageously, before first end 366''' of shuttle 324''' is unsealed, second end 371''' of shuttle 324''' is fluidicly sealed by sample collection device 200''' such that fluid from sample preparation reservoir 317''' does not leak into input tunnel 301''' beyond second end 371''' and/or intermediate sealing zone 212'''. In addition, as distal movement of sample collection device 200''' causes the transition from the pre-mixing position toward the mixing position, sealing members 614 of shuttle 324'' continuously fluidicly seal the fluid in sample preparation reservoir 317''' from input tunnel 301'''.

Figure 16I:
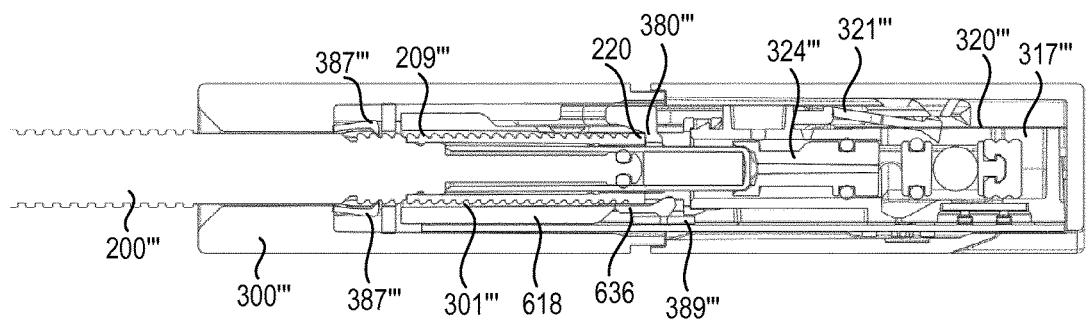

Referring to FIG. 16I, as sample collection device 200''' moves further distally in input tunnel 301''', sample collection device 200''' moves seal piercer from the pre-venting position towards the venting position. As collector pushes sample collection device 200''' distally, sample collection device 200''' applies a force to seal piercer 321''' (e.g., via contact between shoulder 220 and engager 380''') to cause the piercing elements to move to sequentially pierce sealing material 320''' over the reservoirs as described above with respect to FIGS. 15A through 15D. In addition, as collector pushes sample collection device 200''' more distally from the pre-mixing position toward the mixing position, shuttle 324'' moves more distally within sample preparation reservoir 317'''. Sample collection device 200''' also may contact collet 618 to facilitate activation of contact switch 389'. For example, shoulder 220 of sample collection device 200''' may contact deflection portion 636 of collet 618.

Figure 16J:
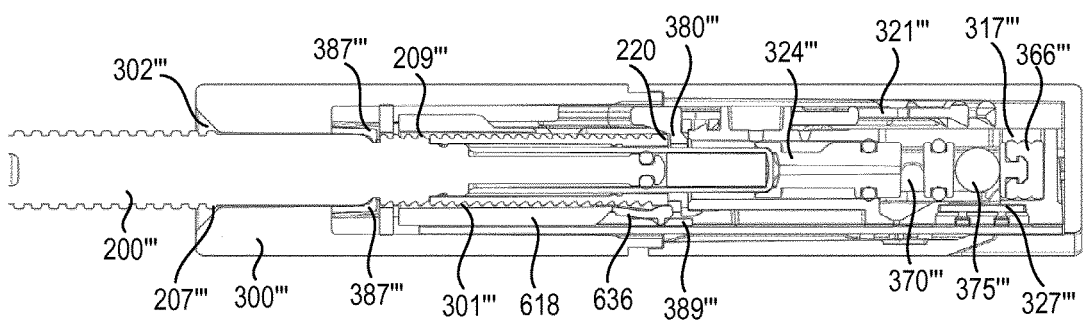
Figure 17B:
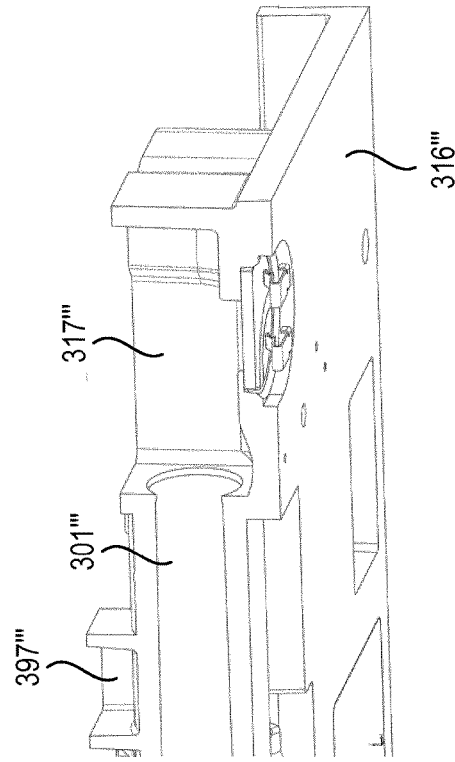
FIGS. 17A through 17D illustrate various views of an exemplary sonicator electrically coupled to a circuit board via spring contacts for use within an exemplary cartridge housing.
Figure 17D:
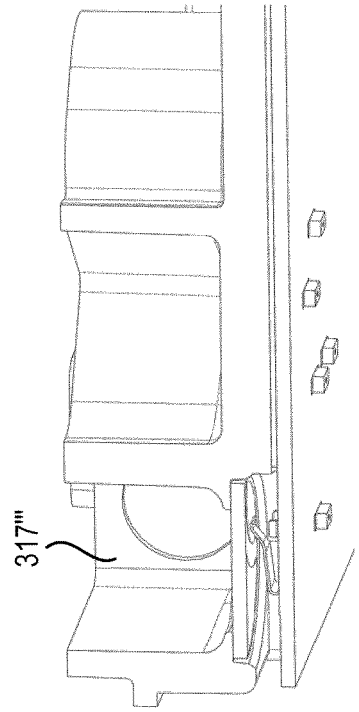
Figure 17A:
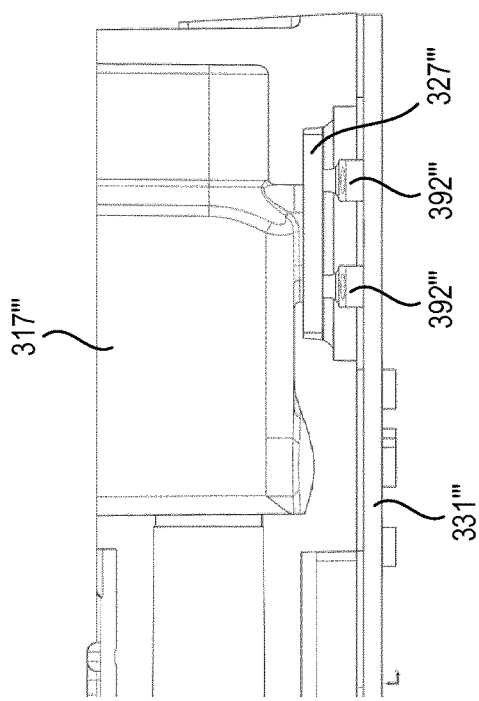
Figure 17C:
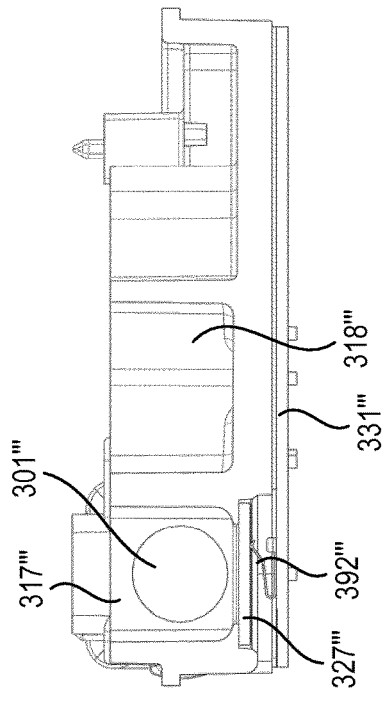

As sample collection device 200''' moves further distally in input tunnel 301''', sample collection device 200''' and cartridge device 300''' are moved into the mixing, venting, analysis positions shown in FIG. 16J wherein the expelled sample in sample compartment 370''' and reagent ball 375''' are mixed within fluid of sample preparation reservoir 317'''. In FIG. 16J, sample collection device 200''' is fully inserted in input tunnel 301'''. As shown, seal piercer 321''' is in the venting position and has pierced seal material 320''' over each of the reservoirs, shuttle 324'' has moved distally from collet 618 such that the sample and reagent ball 375''' are mixing with the fluid in sample preparation reservoir 317''', deflector portion 636 of collet 618 is in the deflection position where deflector portion 636 has activated contact switch 389', and locking members 387' have locked sample collection device 200' in input tunnel 301'''.

In this mixing position, first end 366'' of shuttle 324', the one or more reagent ball compartments of shuttle housing one or more reagent balls, and/or the one or more sample compartments housing the sample(s) to be analyzed may be disposed within sample preparation reservoir 317'''. As explained above, the components fluidicly seal sample preparation reservoir 317''' in the mixing position such that the collected sample(s), the reagent ball(s), and the fluid within sample preparation reservoir 317''' are sealed within the reservoir and may be mixed within sample preparation reservoir 317'''.

Sample collection device 200''' may be configured to activate contact switch 389''' of circuit board 331'''. For example, insertion of sample collection device 200''' may cause collet 618 to activate contact switch 389''. Illustratively, deflector portion 636 of collet 618 deflects to activate contact switch 389''' responsive to a force applied on deflector portion 636 by sample collection device 200''' during insertion of sample collection device 200''' in input tunnel 301'''. Shoulder 220 of sample collection device 200''' may contact deflector portion 636 and force deflector portion 636 downwardly as sample collection device 200''' moves distally in input tunnel 301''' to activate contact switch 389''. Depression of contact switch 389''' may complete a circuit such that electrical signals may be transmitted, e.g., to the reader device and/or the computing device running the software-based user interface system. In this manner, proper insertion of sample collection device 200''' within the input tunnel generates an electrical signal that may be transmitted to the reader device and/or computing device to notify the reader device and/or computing device of such proper insertion. While contact switch 389''' is positioned within input tunnel 301''' such that depression of contact switch 389''' indicates full insertion of sample collection device 200''' at the mixing position, contact switch 389''' also could be positioned within input tunnel 301''' to indicate partial insertion of sample collection device 200'''. In addition, or alternatively, more than one contact switch may be disposed in the input tunnel such that insertion of the sample collection device within the tunnel may be tracked by sequential depression of the contact switches aligned along the input tunnel.

In the mixing position, locking members 387''' are configured to irreversibly lock sample collection device 200''' within cartridge device 300'''. Locking members 387''' may engage the proximal-most groove of the multiplicity of grooves in engagement zone 209''' when sample collection device 200''' is fully inserted in input tunnel 301''' as shown in FIG. 16J. Locking members 387''' may be biased inwardly in input tunnel 301''' such that a locking end of locking member 387''' engages sample collection device 200''' in the mixing position. Advantageously, locking sample collection device 200''' (e.g., longitudinally and/or axially) within input tunnel 301''' during partial insertion and full insertion promotes sealing of sample preparation reservoir 317''' over time as sample collection device 200''' cannot be retracted once locked to facilitate safe disposability and consistency of testing because a user cannot pull out sample collection device 200''' from cartridge device 300''' inadvertently after partial or full insertion. In addition, in the mixing position, proximal sealing zone 207''' of sample collection device 200''' is configured to seal input tunnel 301''' at aperture 302'''. In this manner, proximal sealing zone 207''' provides additional structure to minimize or eliminate fluid leakage from cartridge device 300''', e.g., at aperture 302'''. Proximal sealing zone 207''' of sample collection device 200''' is also configured to contact the cartridge housing to resist insertion force by collector once sample collection device 200''' and cartridge device 300''' are properly in the mixing position.

In the mixing position, sonicator element 327' may be used to enhance mixing the fluid in sample preparation reservoir 317''' with the sample and reagent ball(s) as described above with respect to FIGS. 10N through 10P.

Referring now to FIGS. 17A through 17D, sonicator element 327' may be electrically coupled to circuit board 331''' via first spring contact 392" and second spring contact 392" as shown. Preferably, sonicator element 327' is electrically coupled to circuit board 331" only via first and second spring contacts 392', e.g., without a wired connection between sonicator element 327' and circuit board 331'''. Beneficially, spring contacts 392" absorb movement of sonicator element 327' such that circuit board 331''' vibrates minimally in a suitable manner when sonicator element 327' is activated, e.g., responsive to signals transmitted by the reader device, and spring contact 392" permits ease of assembly and reproducibility compared to soldering which may adversely impact sonicator element 327'. Sonicator element 327' may form a wall, e.g., part of the bottom wall, of sample preparation reservoir 317'''. Sonicator element 327' may be adhered to internal component 316''' to form the wall. For example, an annulus of adhesive, e.g., epoxy, may be applied on the top surface of sonicator element 327' and UV cured to internal component 316' at the bottom of sample preparation reservoir 327'. Such an annulus of adhesive permits fluidic sealing between sonicator element 327' and sample preparation reservoir 317''' while permitting sonicator element 327' to vibrate during activation. As is explained above, sonicator element 327' may be positioned off-center of sample preparation reservoir 317''' to facilitate mixing of the fluid with the sample and reagent ball(s) within sample preparation reservoir 317'''.

Referring now to FIGS. 18A and 18B, an alternative cartridge for analyzing a sample is described. Cartridge device 300'''' may be constructed similarly to cartridge device 300''', wherein like components are identified by like-primed reference numbers, except cartridge device 300'''' includes collet 618' and shuttle 324" which may be constructed similarly to shuttle 324 of FIG. 9A. In this embodiment, cartridge device 300'''' is designed for relatively small sample collection, e.g., less than 10 microliters, preferably 2-5 microliters, of a sample, e.g., from a nasal passageway, from an ear, from blood. Cartridge device 300'''' may be further fitted with a reagent ball(s) intended to identify different target analytes that may be indicative of, for example, inflammation, influenza, testosterone, fertility, HIV, or Vitamin D. FIGS. 18A and 18B illustrate the ease of interchangeability between cartridge device 300''' and cartridge device 300''''.

As shown in FIG. 18A, collet 618' has one or more protrusions 637 disposed the distal end of collet 618' configured to contact second end 371'''' of shuttle 324'''' in the pre-mixing position. The one or more protrusions 637 may contact a sealing member, e.g., O-ring, at second end 371'''' of shuttle 324'''' to retain the sealing member in position. The one or more protrusions may have lead-in angles configured to guide the distal portion of the sample collection device into the opening at second end 371'''' of shuttle 324''''. Similar to that described above, collet 618' is configured to decouple from shuttle 324'''' responsive to a force applied by the sample collection device on shuttle 324'''', e.g., via the shoulder of the distal sealing zone on second end 371'''' of shuttle 324'''', during sample collection device insertion in the input tunnel. In this manner, shuttle 324'''' moves from the pre-mixing position to the mixing position as described above.

Figure 19:
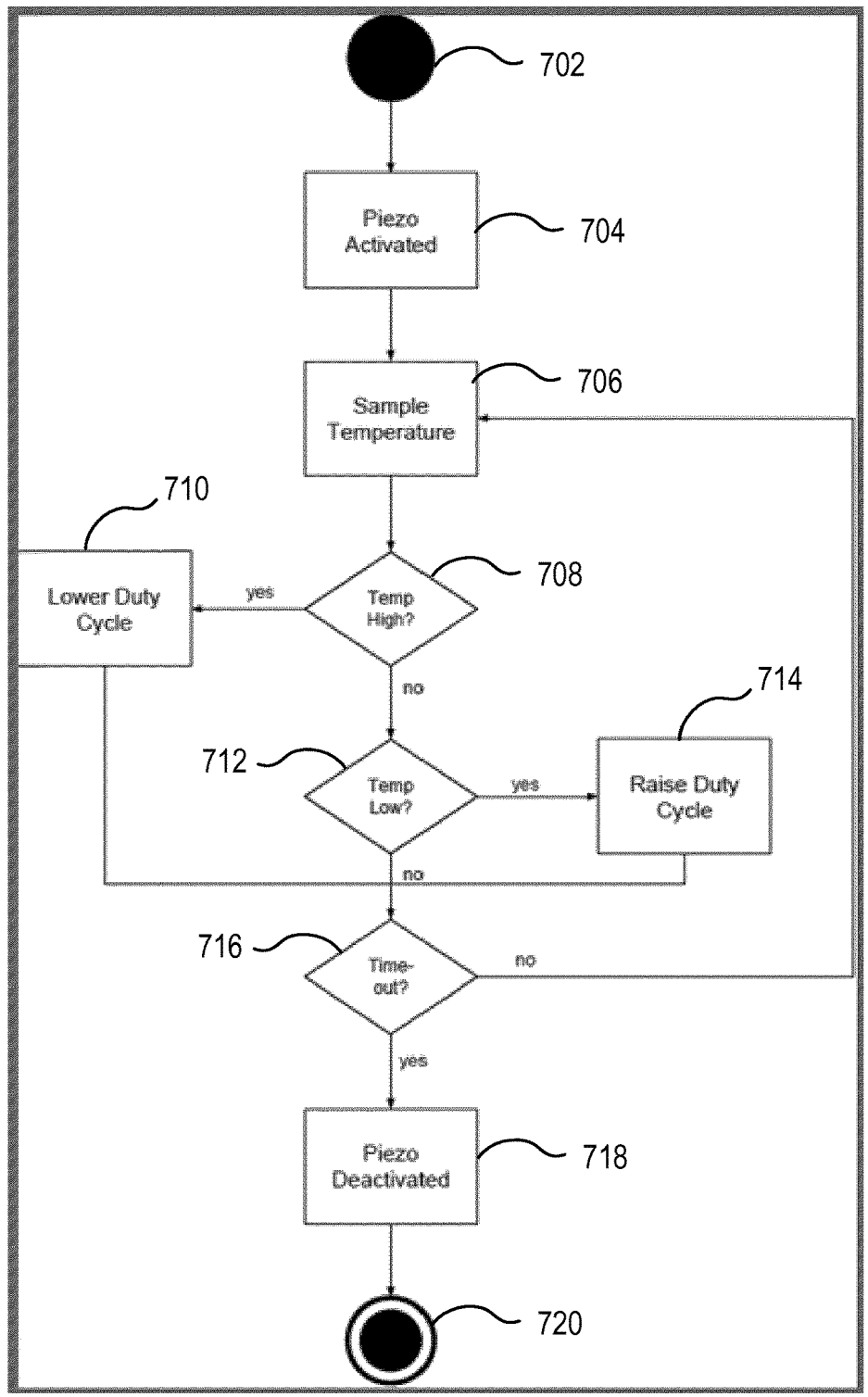
FIG. 19 illustrates an exemplary process for monitoring temperature during enhanced mixing via the sonicator.

Referring now to FIG. 19, a process for monitoring temperature during enhanced mixing via the sonication element is described. As is described below, the computerized reader may largely control the operations of the detection system. The reader includes a processor with memory, the memory having instructions stored thereon for implementing various methods needed to successfully detect the presence, absence, and/or quantity of one or more target analytes within a collected sample. For example, the computerized reader may cause the process of FIG. 19 to be performed in an automated manner.

As is described above, a sonicator element (e.g., sonicator element 327, 327', etc.) of the cartridge may be activated for enhanced mixing of the contents in the sample preparation reservoir when the sample collection device and the cartridge are in the mixing position. At 702, the process begins. The process may begin responsive to an event. For example, the process may begin when the processor of the reader device receives a signal indicating that a contact switch has been activated in the cartridge device responsive to full insertion of the sample collection device in the cartridge device.

At 704, the sonicator element, e.g., a piezoelectric transducer, is activated. Upon activation, the sonicator element emits acoustic waves toward the sample preparation reservoir to move fluid within the reservoir. The sonicator element may emit acoustic waves at a predetermined frequency, e.g., 4 MHz, which may be modified by the reader. As is described above, the acoustic waves may cause fluid within the reservoir to move in a wave pattern to mix the fluid in the reservoir. The processor of the reader device may activate the sonicator element by causing transmission of electrical signals to the sonicator element, e.g., via one or more electrical leads of the printed circuit board in the cartridge.

At 706, a temperature is sampled. The temperature may be indicative of temperature of the fluid within the sample preparation reservoir. For example, the cartridge may include a temperature sensor, e.g., temperature sensor 616 disposed on the circuit board, configured to generate a signal indicative of temperature of the fluid in the sample preparation reservoir. The signal may be transmitted from the cartridge to the reader, e.g., via one or more electrical leads on the printed circuit board of the cartridge, when the cartridge and reader are electrically coupled. The signal may be processed by the processor of the reader device to determine whether the signal indicates a temperature of the fluid in the reservoir outside a threshold.

At 708, it is determined whether the sampled temperature is too high. For example, the processor of the reader device may compare the temperature information from the signal generated by the temperature sensor to temperature thresholds stored in memory of the reader device. For example, the memory may store a threshold high temperature, e.g., above 42° C., and/or a look-up table with threshold high temperatures based on cartridge specific parameters such that the processor may compare the sensed temperature to the stored information to determine whether a sensed temperature is too high. If the temperature is determined to be outside a threshold, e.g., too high, too low, not within a range, emission of acoustic waves from the sonicator element may be modified.

At 710, if the temperature is determined to be too high, emission of acoustic waves from the sonicator element may be modified by lowering the duty cycle of the sonicator element. For example, the processor of the reader device may modify emission of the acoustic waves from the sonicator element by transmitting electrical signals to the sonicator element to cause the sonicator element to lower the duty cycle. The processor may modify emission of the acoustic waves from the sonicator by deactivating the sonicator if the signal indicates the temperature of the fluid in the reservoir is above the threshold.

At 712, it is determined whether the sampled temperature is too low. For example, the processor of the reader device may compare the temperature information from the signal generated by the temperature sensor to temperature thresholds stored in memory of the reader device. For example, the memory may store a threshold low temperature, e.g., below 37° C., and/or a look-up table with threshold low temperatures based on cartridge specific parameters such that the processor may compare the sensed temperature to the stored information to determine whether a sensed temperature is too low.

At 714, if the temperature is determined to be too low, emission of acoustic waves from the sonicator element may be modified by raising the duty cycle of the sonicator element. For example, the processor of the reader device may modify emission of the acoustic waves from the sonicator element by transmitting electrical signals to the sonicator element to cause the sonicator element to increase the duty cycle.

At 716, it is determined whether the temperature indicative of temperature of the fluid within the sample preparation reservoir is within a threshold range, e.g., below the threshold high temperature and above the threshold low temperature, for a predetermined amount of time (e.g., between 3 minutes to 15 minutes, between 3 minutes to 10 minutes, between 3 minutes to 5 minutes, about 10 minutes), which may be cumulative or consecutive, such that the sonicator element may be timed-out. For example, the memory of the reader may store the predetermined amount of time that the temperature indicative of fluid temperature within the sample preparation reservoir should be within the threshold temperature range. The predetermined amount of time may be the time required for suitable mixing of the fluid within the sample preparation reservoir with the sample and the reagent ball(s) for isothermal amplification for analysis. The acoustic emissions from the sonicator element may both heat fluid within the sample preparation reservoir and mix the contents of the sample preparation reservoir at the macro and the micro level for isothermal amplification. For example, the sonicator element may pass energy into the sample preparation reservoir sufficient to increase the temperature in the sample preparation reservoir such that an amplification reaction may occur such as isothermal DNA or RNA amplification, thereby generating nucleic acid amplicons for downstream detection. Such downstream detection may be partially based on the binding of nucleic acids or detectable moieties thereon or therein to affinity molecules on magnetic particles (which could be in a combination of anitbodies, DNA probes, detectable moieties, and/or enzymes) or it could be based on specific binding to surface bound affinity molecules on one or more working electrodes each with their own population of affinity molecules. Alternatively, or additionally, such a reaction may take place in the sample preparation reservoir and be observed there. If the processor of the reader determines that the sampled temperature has not been within the threshold range for the predetermined amount of time, the process returns to 706.

At 718, the sonicator element is deactivated. For example, the sonicator element may be deactivated if the sampled temperature has been within the threshold range for the predetermined amount of time. The processor of the reader may determine that the sampled temperature has been within the threshold range for the predetermined amount of time.

At 720, the process ends after the sonicator element is deactivated.

Figure 20:
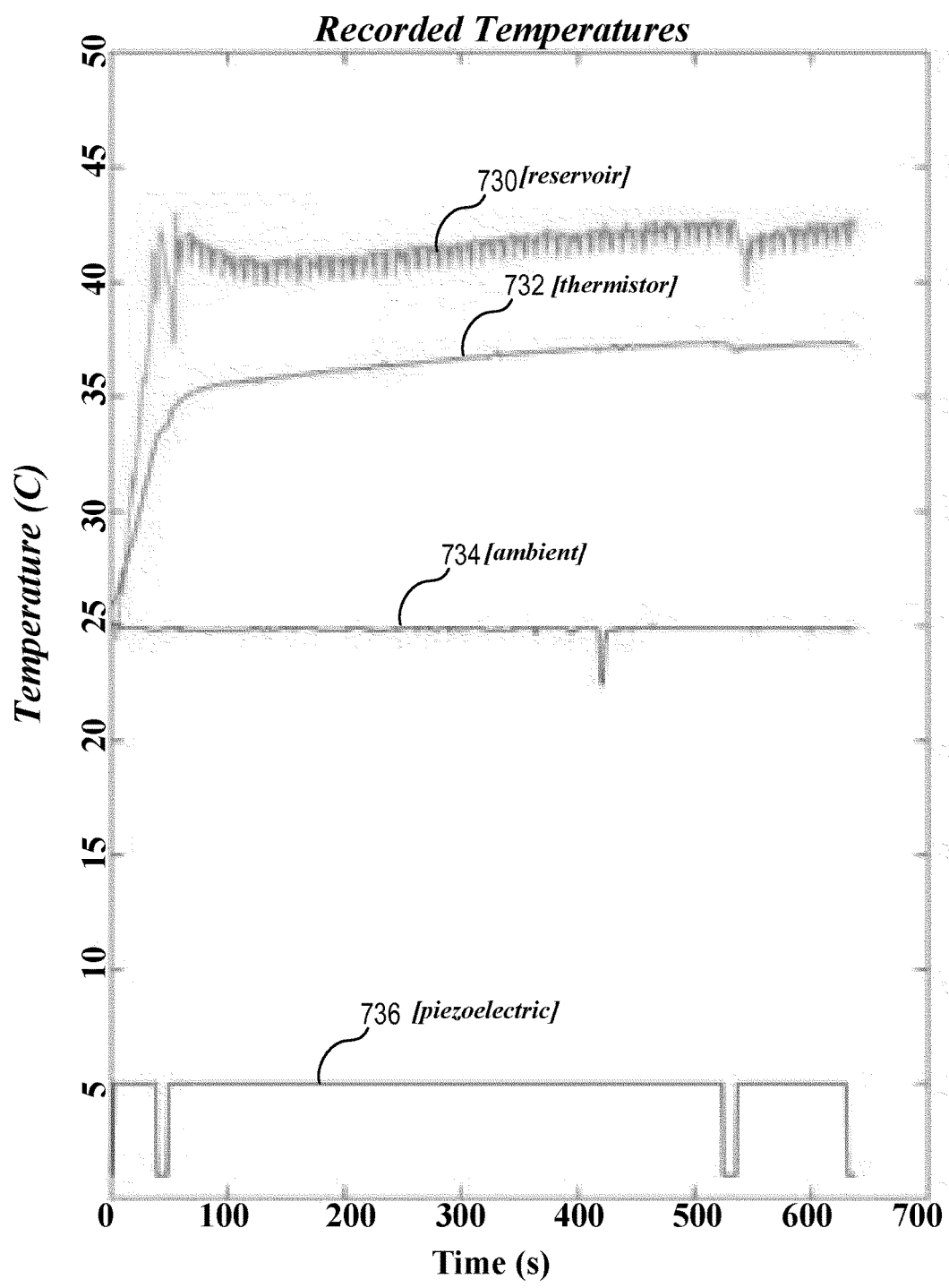
FIG. 20 is a graph showing measured temperature over time during enhanced mixing via the sonicator.

Referring now to FIG. 20, a graph showing temperature in Celsius versus time in seconds is shown. The graph shows the measured temperature of the fluid mixing in the sample preparation reservoir at line 730, the measured temperature at the thermistor, e.g., temperature sensor 616, at line 732, the measured ambient temperature at line 734, and the measured temperature at the piezoelectric transducer, e.g., sonicator element 327, 327', etc., at line 736. As will be observed, the duty cycle of the sonicator is reduced at about the 40 second mark on the graph, causing the temperature of the fluid mixed in the sample preparation reservoir to decrease. The duty cycle of the sonicator is again reduced around the 520 second mark on the graph, again causing the temperature of the fluid mixed in the sample preparation reservoir to decrease.

The Reader Device

The reader device, or reader, of various embodiments is, comprises, or is comprised of, a specialized computer. The computer includes a processor with memory having instructions stored thereon for executing one or more methods for detecting the presence, absence, and/or quantity of one or more target analytes in a sample. In various embodiments, the reader's computer controls the operations of the detection system, controlling when and how various functions of the system occur, such as, for example: mixing of the fluids in the sample preparation reservoir of the cartridge, opening of valves, and/or localization of magnetic particles over the sensors. To control such operations, the computerized reader is configured to receive information from, and send information to, physical components present within the reader or cartridge.

Figure 21A:
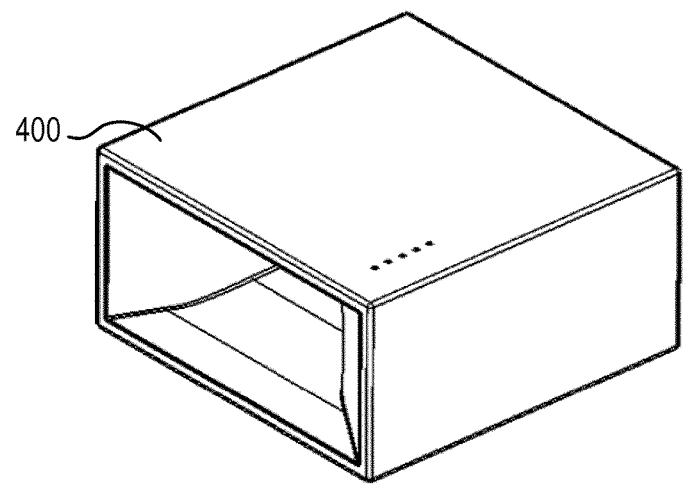
FIG. 21A illustrates a perspective view of an exemplary reader device for use in the detection system.
Figure 21B:
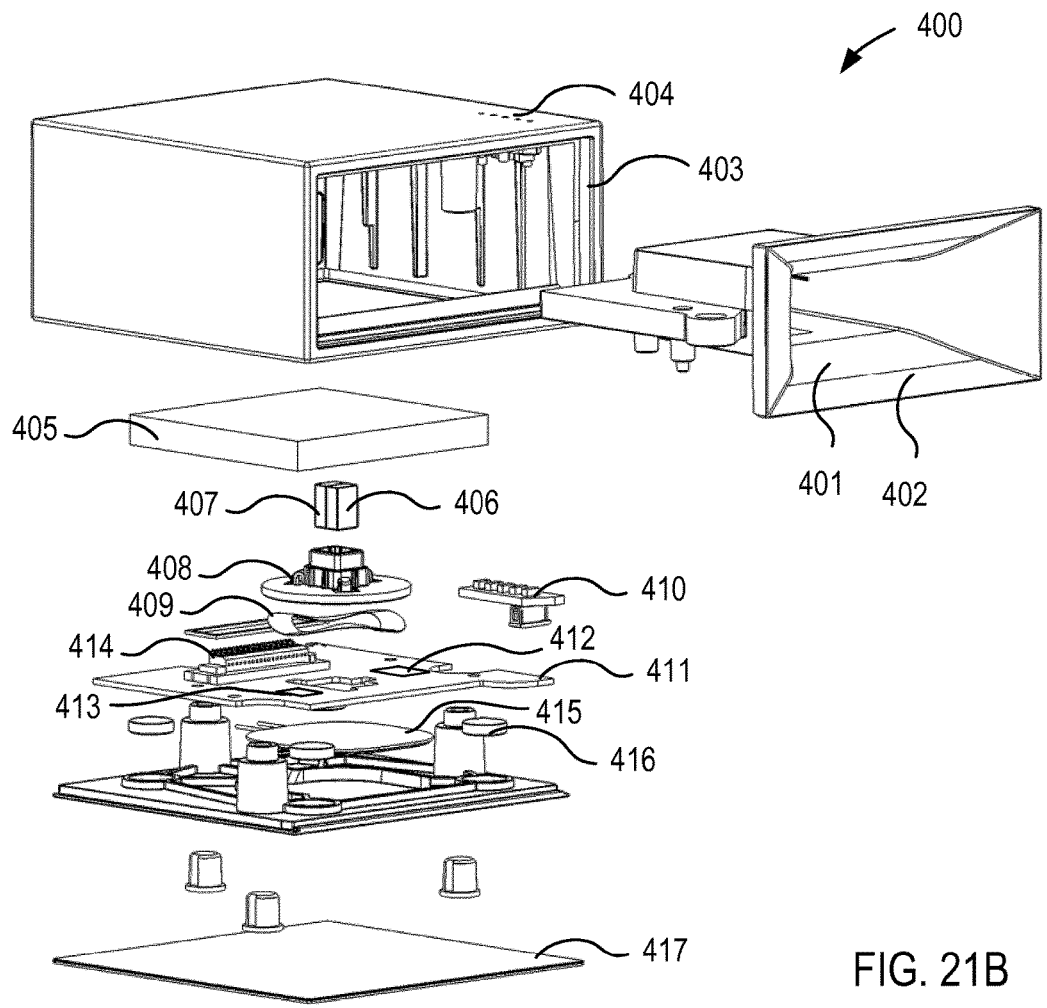
FIG. 21B illustrates an exploded view of the exemplary reader device of FIG. 21A showing internal components that may be within the reader housing.

FIG. 21A illustrates a perspective view of an exemplary reader device and FIG. 21B is an exploded view illustrating the internal components of the reader device of FIG. 21A.

Reader device 400 may include opening 401 in cartridge dock 402, housing 403, user interface 404, power supply 405, first magnetic generator 406, second magnetic generator 407, magnetic generator housing 408, elastic member 409, light pipe 410, circuit board 411, processor 412, communication circuit 413, electrical connector 414, inductive coil 415, alignment magnets 416, and/or base 417.

Opening 401 of reader device 400 permits the cartridge device to be docked within cartridge dock 402. The cartridge, when received by reader device 400, may be disposed on or in, partially or fully, or otherwise coupled to, reader device 400. Several of the reader components may be strategically positioned in particular locations relative to cartridge dock 402 to achieve desired interactions with the cartridge. For example, electrical connector 414 may be positioned relative to cartridge dock 402 such that the electrical connector of the cartridge device is electrically coupled to electrical connector 414 when the cartridge device is inserted in cartridge dock 402. In addition, magnetic field generators 406 and 407 may be positioned relative to cartridge dock 402 such that magnetic field generators 406 and 407 are disposed under the working electrode of the cartridge device when the cartridge device is inserted in cartridge dock 402.

Housing 403 is configured to house the internal components of reader device 400 and may cooperate with cartridge dock 402 and base 417 to house the internal components.

User interface 404 may be used to receive inputs from, and provide outputs to, a user. Illustratively, user interface 404 includes LEDs configured to notify a user when a cartridge device is properly inserted into reader device 400 and/or when a sample collection device is properly inserted in the cartridge device. User interface 404 may be coupled to processor 412.

User interface 404 may include a touchscreen, LED matrix, other LED indicators, or other input/output devices for receiving inputs from, and providing outputs to, a user. In other embodiments, user interface 404 is not present on reader 400, but is instead provided on a remote computing device communicatively connected to reader 400 via the communication circuit 413. User interface also may be a combination of elements on the reader and a remote computing device.

Power supply 405 may be a suitable battery such as a replaceable battery or rechargeable battery and apparatus may include circuitry for charging the rechargeable battery, and a detachable power cord. Power supply 405 may be charged by charger 500 via an inductive coil within the charger and inductive coil 415. Alternatively, the power supply may be a port to allow reader device 400 to be plugged into a conventional wall socket, e.g., via a cord with an AC to DC power converter, for powering components within the housing.

Magnetic field generators 406 and 407 may be inductors or other electromagnetic components movably affixed within reader 400. Magnetic field generators 406 and 407 may be permanent magnets. Magnetic field generators 406 and 407 are positioned such that, when a cartridge is electrically coupled to reader device 400, the working electrode is disposed directly within a magnetic field created by magnetic field generators 406 and 407. In various embodiments, the magnetic field(s) are the cause of localization; the magnetic field(s) are what induce magnetic particles and accompanying hybridized molecules to localize within the analysis zone. First and second magnetic generators 406 and 407 may be configured to generate a magnetic field over the length of a single working electrode to promote homogeneous distribution of a plurality of magnetic particles over the length of the single working electrode.

Magnetic field generators 406 and 407 emit a magnetic field sufficiently strong to cause the magnetic particles released into the analysis channel from the sample preparation reservoir to remain localized over magnetic field generators 406 and 407, and thereby over the working electrode, as the wash solution and/or the fluid carrying chemical substrates flows over the magnetic particles in the analysis channel in the cartridge.

Magnetic generator housing 408 is configured to house magnetic field generators 406 and 407. Magnetic generator housing 408 may be coupled to elastic member 409 that permits movement of magnetic field generators 406 and 407, e.g., upon insertion and removal of a cartridge device from cartridge dock 402.

Reader device 400 may include light pipe 410 designed to guide light from LEDs within reader device 400 to user interface 404.

Circuit board 411 includes electrical components and permits electrically coupling between processor 412, communication circuit 413, and/or electrical connector 414. One or more electrical components and/or circuits may perform some of or all the roles of the various components described herein. Although described separately, it is to be appreciated that electrical components need not be separate structural elements. For example, processor 412 and communication circuit 413 may be embodied in a single chip. In addition, while processor 412 is described as having memory, a memory chip(s) may be separately provided.

Processor 412 may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

Processor 412 may contain memory and/or be coupled, via one or more buses, to read information from, or write information to, memory. The memory may include processor cache, including a multi-level hierarchical cache in which different levels have different capacities and access speeds. The memory may also include random access memory (RAM), other volatile storage devices, or non-volatile storage devices. The storage devices can include, for example, hard drives, optical discs, flash memory, and Zip drives.

Processor 412, in conjunction with firmware/software stored in the memory may execute an operating system, such as, for example, Windows, Mac OS, Unix or Solaris 5.10. Processor 412 also executes software applications stored in the memory. In one non-limiting embodiment, the software comprises, for example, Unix Korn shell scripts. In other embodiments, the software may be programs in any suitable programming language known to those skilled in the art, including, for example, C++, PHP, or Java.

Communication circuit 413 is configured to transmit information, such as signals indicative of the presence, absence, and/or quantity of one or more target analytes within a sample, locally and/or to a remote location such as a server. Communication circuit 413 is configured for wired and/or wireless communication over a network such as the Internet, a telephone network, a Bluetooth network, and/or a WiFi network using techniques known in the art. Communication circuit 413 may be a communication chip known in the art such as a Bluetooth chip and/or a WiFi chip. Communication circuit 413 may include a receiver and a transmitter, or a transceiver, for wirelessly receiving data from, and transmitting data to a remote computing device. In some such embodiments, the remote computing device may be a mobile computing device that provides the system with a user interface; additionally or alternatively, the remote computing device is a server. In embodiments configured for wireless communication with other devices, communication circuit 413 may prepare data generated by processor 412 for transmission over a communication network according to one or more network standards and/or demodulates data received over a communication network according to one or more network standards.

Processor 412 is also coupled to electrical connector 414, which may include an EDGE card or other electrical connector, to send electrical signals to, and receive electrical signals from, the circuit board component of the cartridge (e.g., via electrical connector 312). Electrical connector 414 may be located on, under, within, or adjacent to cartridge dock 402 and is positioned such that the pins of electrical connector 414 make contact with, and establish electrical connectivity with, the electrical leads of a docked cartridge device. Electrical connector 414 thereby establishes electrical continuity between the sensors on the circuit board of the cartridge and electrochemical circuitry within the reader. Electrical connector 414 of the reader also may establish electrical continuity with one or more heating elements, if present on the circuit board of the cartridge. Reader device 400 may include a portion of an electrochemical circuit, which is completed with the addition of the cartridge based on electrical continuity between electrical connector 414 and the electrical leads of the cartridge. The addition of the cartridge may complete or close the circuit. Coupling the cartridge to reader 400 may activate reader device 400, causing it to "wake up." Once awoken, electrical connector 414 may identify signals being received from a portion of the cartridge to identify what type of cartridge is coupled to its dock. Electrical connector 414 may receive signals indicative of information on cartridge type (e.g., inflammation, influenza, testosterone, fertility, Vitamin D), cartridge identification information (e.g., serial number), and/or calibration information from memory within the cartridge and transmit such information to processor 412 for processing.

Once awoken, reader device 400 also may determine what test protocol to run for the identified cartridge and/or searches for, and connects to, nearby mobile computing devices.

Reader device 400 may include one or more magnets 416 configured to align with one or more magnets in the charger to facilitate efficient energy transfer between inductive coil 415 and an inductive coil within the charger. Illustratively, four magnets are used. Magnets 416 may be keyed to align with a corresponding keyed magnet in the charger.

Figure 22A:
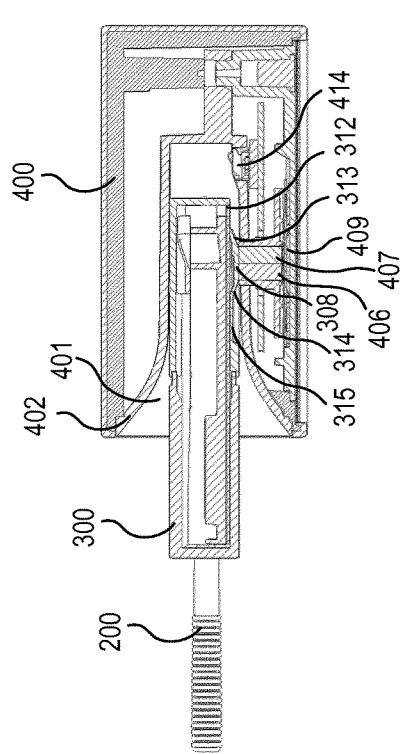
FIG. 22A shows a cross-sectional perspective view of the exemplary reader device.

Referring now to FIGS. 22A through 22D, insertion of a cartridge device within a reader device is described. As shown in the cutaway view of reader device 400 in FIG. 22A, first and second magnetic generators 406 and 407 may extend partially into opening 401 through cartridge dock 402. In FIG. 22A, first and second magnetic generators 406 and 407 are shown in a raised position. Elastic member 409 may be biased to cause first and second magnetic generators 406 and 407 to rest in the raised position.

Figure 22B:
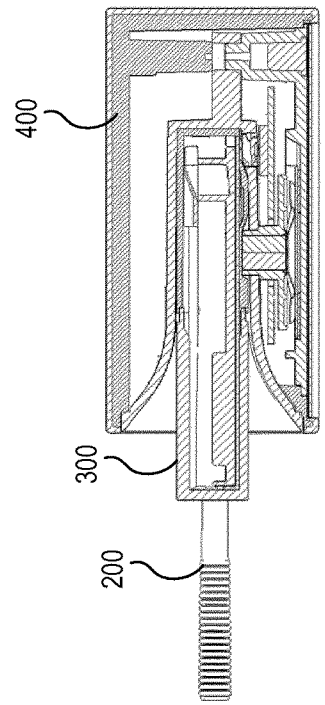
FIG. 22B is a cross-sectional side view showing a cartridge device (having a sample collection device partially inserted therein) partially inserted within the exemplary reader device.

FIG. 22B shows cartridge device 300, having sample collection device 200 partially inserted therein, being inserted into reader device 400. Specifically, cartridge device 300 is inserted in opening 401 at cartridge dock 402. As cartridge device 300 moves distally into cartridge dock 402, the top surfaces of first and second magnetic generators 406 and 407 preferably do not contact electrical connector 312 and first contact first ramp portion 313. First ramp portion 313 causes first and second magnetic generators 406 and 407 to gradually depress during further distal insertion, e.g., by causing a downward force on first and/or second magnetic generators 406, 407 that depresses elastic member 409. As cartridge device 300 is inserted past first ramp portion 313, first and/or second magnetic generators 406, 407 contact bottom surface 308 of cartridge device 300 and move to a depressed position as shown in FIG. 22B.

Figure 22C:
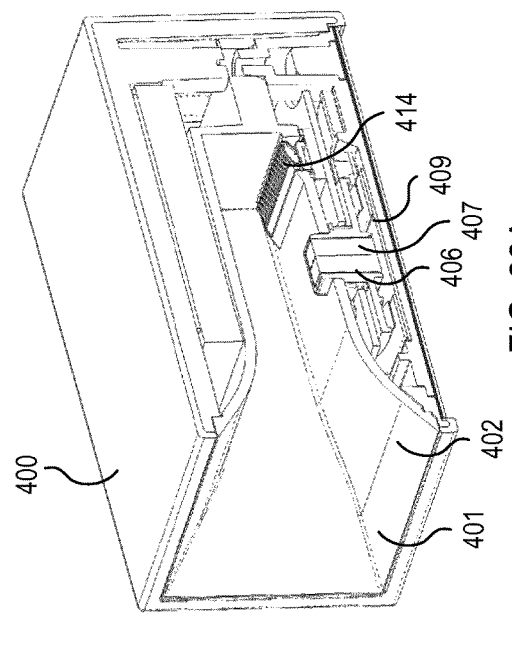
FIGS. 22C and 22D are cross-sectional perspective and side views, respectively, showing the cartridge device inserted within the exemplary reader device in the analysis position.
Figure 22D:
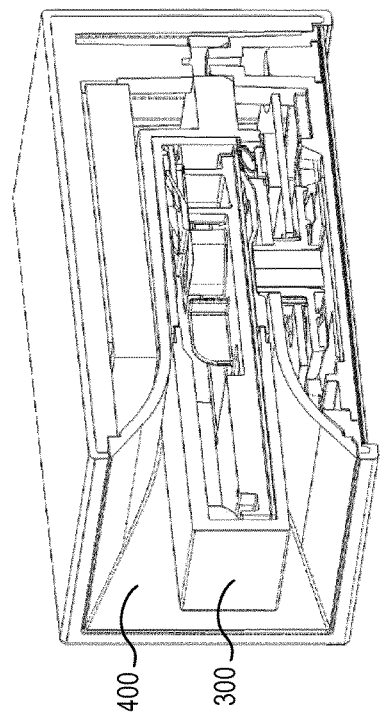

As cartridge device 300 moves further distally into cartridge dock 402, first and/or second magnetic generators 406, 407 contact second ramp portion 314 which ramps up into magnetic generator depression 315. Second ramp portion 314 gradually guides first and/or second magnetic generators 406, 407 into magnetic generator depression 315 as shown in FIGS. 22C and 22D. FIGS. 22C and 22D depict cartridge device 300 inserted in reader device 400 in the analysis position where first and second magnetic generators 406 and 407 are disposed in magnetic generator depression 315 and electrical connector 312 of cartridge device 300 is electrically coupled to electrical connector 414 of reader device 400. Magnetic generator depression 315 is disposed beneath one or more working electrodes of cartridge device 300 such that first and second magnetic generators 406 and 407 move up into magnetic generator depression 315 into a raised position and are disposed adjacent the one or more working electrodes when cartridge device 300 is fully inserted in the reader. The bias of elastic member 409 may cause first and second magnetic generators 406 and 407 to move up into magnetic generator depression 315. Second ramp portion 314 also facilitates removal of cartridge device 300 from reader device 400 by gradually depressing first and second magnetic generators 406 and 407 during removal of cartridge device 300.

The interaction of the bias of elastic member 409 and magnetic generator depression 315 may allow for first and second magnetic generators 406 and 407 to be positioned as close to the working electrode as possible. The closer first and second magnetic generators 406 and 407 are to the working electrode, the more force the magnet field is able to exert, meaning that smaller magnets or inductors are capable of exerting equivalent magnetic field strengths as larger, more costly magnets or inductors. The use of small magnets or inductors is particularly advantageous in embodiments having multiple magnetic fields and multiple analysis zones (for example, in embodiments configured to detect a plurality of different target analytes), because the smaller the magnet or inductor, the less the magnetic fields overlap. Smaller magnetic fields can limit the amount of cross talk between the magnets or inductors under the different detection sensors.

Figure 23B:
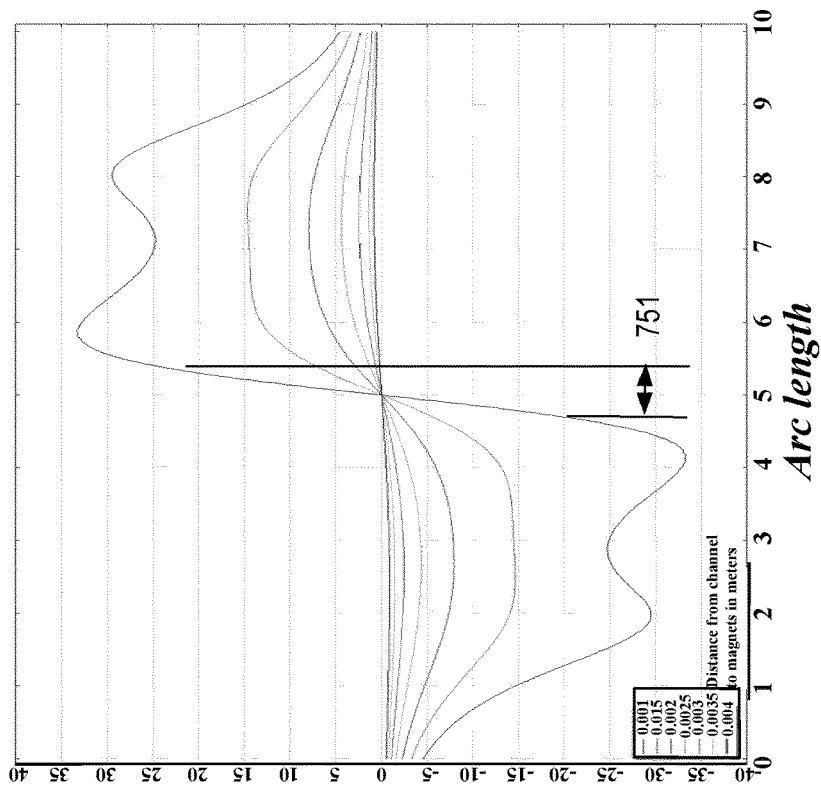
FIGS. 23A and 23B are graphs showing magnetic field strengths over the length of a single working electrode for a single magnet (FIG. 23A) versus a dual magnet (FIG. 23B) design.
Figure 23A:
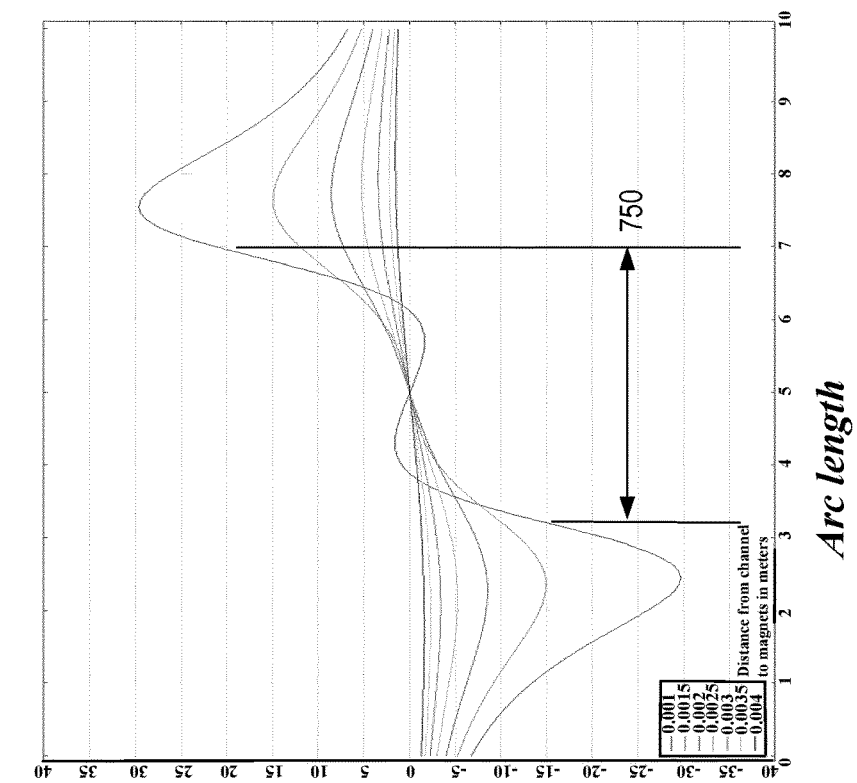

Referring to FIGS. 23A and 23B, graphs are shown depicting the measured strengths of magnetic fields at varying distances from the analysis channel for designs where one magnetic generator generates a magnetic field for one working electrode (FIG. 23A) and where two magnetic generators generates a magnetic field for one working electrode (FIG. 23B). It has been discovered that magnetic fields at or near the absolute peak strength will retain suitable magnetic particles in the analysis channel over the working electrode, but magnetic particles tend to wash off the working electrode as the magnetic field strength decreases from the peaks toward zero, creating dead zones 750 and 751. Use of two magnetic field generators creates a much more uniform absolute magnetic field over the working electrode as compared to use of one magnetic field generator. Accordingly, dead zone 751 for a dual magnet design is significantly smaller than dead zone 750 for a single magnet design. Accordingly, as described above, first and second magnetic generators 406 and 407 may be used in reader device 400 to generate a magnetic field over the length of a single working electrode to promote homogenous distribution of a plurality of magnetic particles over the length of the single working electrode.

The Computerized Methods of Detection

The timing of heat delivery and valve opening within the cartridge device may be precisely timed and controlled by the reader device. For example, the reader may control when heat-generating current flows through the heating elements. Current may flow from the reader to the cartridge to cause actuation in the following sequence: (1) valve actuation for sample preparation reservoir, (2) fluidic isolator actuation, if present, (3) valve actuation for wash reservoir, if present, then (4) valve actuation for chemical substrate reservoir. Actuation of each valve may be timed such that: the respective valve fully actuates, the associated reservoir has time to empty its contents into the analysis channel, and at least some of the contents of the reservoir have time to travel to the absorbent pad positioned downstream of the sensors before the contents of the next reservoir is released. In some embodiments, the time between valve actuations is selected to be great enough for the absorbent pad to entirely or substantially absorb fluid present within the analysis channel. Advantageously, in such embodiments, very little mixing occurs between the contents of successive reservoirs. In addition, or alternatively, actuation of each valve may be based on a feedback control system wherein the cartridge and/or reader recognizes when flow has initiated and/or stopped from the respective reservoirs, e.g., using a flow sensor disposed in the analysis channel adjacent to the respective reservoir and electrically coupled to the memory of the cartridge and/or the processor of the reader, such that the valves may be turned on and off with respect to the "state" of the progression of events, e.g., based on signals sensed by the flow sensors disposed adjacent each reservoir.

Figure 24:
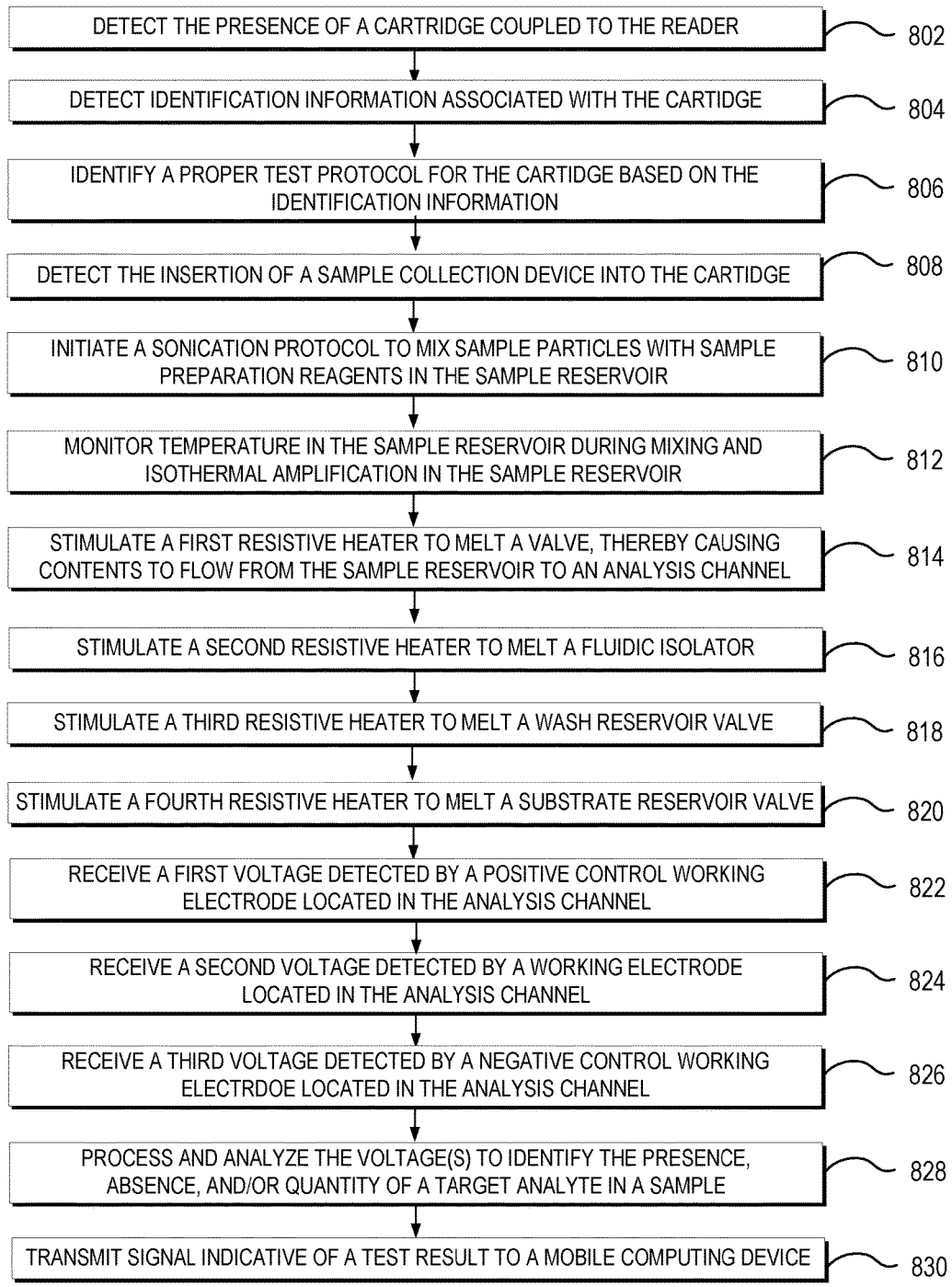
FIG. 24 provides a flowchart of one embodiment of a method for detecting the presence, absence, and/or quantity of one or more target analytes in a sample.

As mentioned above, the computerized reader largely controls the operations of the detection system. The reader includes a processor with memory, the memory having instructions stored thereon for implementing various methods needed to successfully detect the presence, absence, and/or quantity of one or more target analytes within a collected sample. For example, an embodiment of one method performed by the computerized reader in an automated manner is provided in FIG. 24.

At block 802, the computerized reader detects the presence of a cartridge loaded into or onto the reader. For example, a cartridge may be coupled to the reader such that electrical leads on the cartridge come into physical contact with electrical pins on the reader, completing a circuit that turns on the reader and signals the reader to the presence of a cartridge.

At block 804, the reader detects identification information associated with the cartridge. For example, the cartridge may include cartridge type information stored within its memory, which generates signals unique to the particular type of the cartridge, allowing the reader to distinguish between cartridges and types. The cartridge also may include calibration information stored within its memory.

The reader's processor receives the cartridge type information signals, and as shown at block 806, may identify a proper test protocol for the cartridge based on the cartridge type information. The reader's processor may compare cartridge type information signals to a database of protocols based on the cartridge type stored in memory. If the processor does not recognize the cartridge type information, the processor may communicate with a remote computing device such as a mobile computing device and/or a server to signal that an unidentifiable cartridge has been detected. In some embodiments, the reader downloads updates directly from a server or indirectly with the mobile computing device acting as an intermediary. In some embodiments, when an unknown cartridge type is detected, a user is prompted via the user interface of the mobile computing device, to download updates; in other embodiments, the updates are downloaded automatically. In various embodiments, the updates include newly developed cartridge types and test protocols. Once the new types and test protocols are downloaded, they will be added to the reader's database of supported tests so that future tests with this cartridge type will automatically be recognized and implemented without the need for communicating with remote computing devices. The reader's processor also may receive calibration information signals and may account for the calibration information during the test protocol.

As shown at block 808, the computerized reader detects insertion of a sample collection device into the cartridge. For example, the reader may receive electrical signals indicating that the contact switch in the cartridge device has be activated responsive to insertion of the sample collection device into the input tunnel, which may also substantially correspond to the sample entering the sample preparation reservoir. The sample (and reagent ball(s), if present) is then mixed within the fluid of the sample preparation reservoir by introducing the sample (and reagent ball(s), if present) into the sample preparation reservoir.

At block 810, the reader's processor sends signals to the sonicator element to instruct it to initiate a sonication protocol to mix a plurality of reagents, affinity molecules, and sample particles within a fluid disposed within the sample preparation reservoir. In various embodiments, the resulting mixture includes magnetic particles bound to: target analytes, target analytes and detector agents, and/or competitive binding agents. As used herein, sandwich complexes refer to magnetic particles bound directly or indirectly to target analytes and detector agents; competitive binding complexes refer to magnetic particles bound to competitive binding agents. Each sandwich complex and competitive binding complex may include a detector agent bound within the complex. In one embodiment described here, the detector agent is an oxidizing enzyme. The sonicator also may pass energy into the sample preparation reservoir sufficient to increase the temperature in the sample preparation reservoir such that an amplification reaction may occur such as isothermal DNA or RNA amplification, thereby generating nucleic acid amplicons for downstream detection. Such downstream detection may be partially based on the binding of nucleic acids or detectable moieties thereon or therein to affinity molecules on magnetic particles (which could be in a combination of anitbodies, DNA probes, detectable moieties, and/or enzymes) or it could be based on specific binding to surface bound affinity molecules on one or more working electrodes each with their own population of affinity molecules. Alternatively, or additionally, such a reaction may take place in the sample preparation reservoir and be observed there.

As shown at block 812, the reader may monitor temperature of the fluid in the sample preparation reservoir during mixing by the sonicator element and isothermal amplification. For example, a temperature sensor in the cartridge may transmit signals indicative of temperature of the fluid in the sample preparation reservoir, as described above with respect to FIG. 19.

As shown at block 814, the reader may generate a current, which heats or otherwise stimulates a first heating element, thereby causing heat to transfer to a heat-actuated valve sealing the outlet of the sample preparation reservoir within the cartridge. Such heating may cause the valve to melt or undergo another phase change, which allows fluid to flow out of the sample preparation reservoir into an analysis channel via capillary action. As the fluid flows, it transports the mixture with it, and the magnetic particles within the mixture, including magnetic particles within sandwich complexes and/or competitive binding complexes, localize over one or more magnetic fields within the analysis channel, forming one or more localized samples.

Optionally, at block 816, the reader generates a current, which heats or otherwise stimulates a second heating element that causes a fluidic isolator to block the outlet of the sample preparation reservoir from the rest of the analysis channel. In this manner, fluid released from other reservoirs cannot flow into the sample preparation reservoir and/or cause undesirable reactions with leftover reagents.

Optionally, at block 818, the reader generates a current, which heats or otherwise stimulates a third heating element such that a second valve within the cartridge undergoes a phase change and a wash solution flows out of a wash reservoir into the analysis channel. In various embodiments, the wash solution removes, from the one or more localized samples, oxidizing enzymes (or other detector agents) that are not indirectly bound to magnetic particles.

At block 820, the reader generates a current, which heats or otherwise stimulates a fourth heating element such that a third valve within the cartridge undergoes a phase change and a solution of substrates flows out of a substrate reservoir into the analysis channel. In various embodiments, when the detector agent is an oxidizing enzyme, the oxidizing enzymes within the sandwich complexes and/or competitive binding complexes of each localized sample oxidize the substrate molecules present in the aqueous media used to transport said substrate molecules. In embodiments in which sandwich complexes are present, oxidation occurs at an electrochemical cell formed by an electrochemical sensor and the volume of fluid substantially over it and electrons flow from the working electrode of the electrochemical sensor to the volume substantially above the sensor in a quantity proportional to a quantity of target analyte present within the localized sample (e.g., magnetic particle bound complexes and/or surface bound complexes). In embodiments in which competitive binding complexes are present, oxidation occurs at an electrochemical cell formed by an electrochemical sensor and the volume of fluid substantially over the sensor and electrons flow from working electrode of the electrochemical sensor in a quantity inversely proportional to a quantity of target analyte present within the localized sample.

At block 822, the reader's processor receives from the reader's electric connector a first signal detected at the positive control working electrode within the analysis channel in the cartridge. In various embodiments, the signal is a voltage or current or resistivity signal. At least a portion of the signal may be caused by the oxidation of the substrate bound to surface bound antibodies at the positive control working electrode. At block 824, the reader's processor receives from the reader's electric connector a second signal detected at the working electrode within the analysis channel in the cartridge. In various embodiments, the signal is a voltage or current or resistivity signal. At least a portion of the signal is caused by the oxidation of the substrate over the working electrode, e.g., substrates magnetically bound to magnetic particles magnetically held over the working electrode. At block 826, the reader's processor receives from the reader's electric connector a third signal detected by a negative control working electrode within the analysis channel in the cartridge. At block 828, the reader's processor processes and analyzes the signal from the working electrode (and, optionally, the signal from the positive control working electrode and/or the signal from the negative control working electrode) to identify the presence and/or quantity of one or more target analytes. The reader's processor may determine whether the parameter(s), e.g., current, voltage, of the first signal are within a predetermined range stored in the reader's memory, e.g., in a lookup table. Alternatively, the predetermined range may be stored in the memory of the cartridge, stored in the memory for the device running the software application, or stored in a server in the system's network. The first signal may be used for error detection and diagnostic of faulty cartridges.

The third signal may be indicative of noise present within the system. The reader's processor may subtract or apply another algorithm to remove the third signal from the second signal to account for and/or eliminate noise that may be present within the system. Alternatively, the third signal may be used for error detection and diagnostic of faulty cartridges. Optionally, as shown at block 830, the reader may transmit signals indicative of a test result to a mobile computing device for further processing, storage, transmission to a server, and/or display of results to a user.

The Charger

Figure 25A:
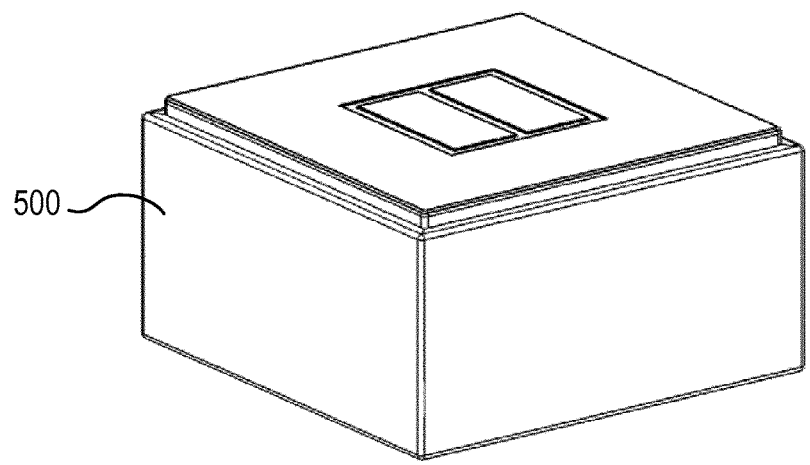
FIG. 25A illustrates a perspective view of an exemplary charger that may be used in the detection system.
Figure 25B:
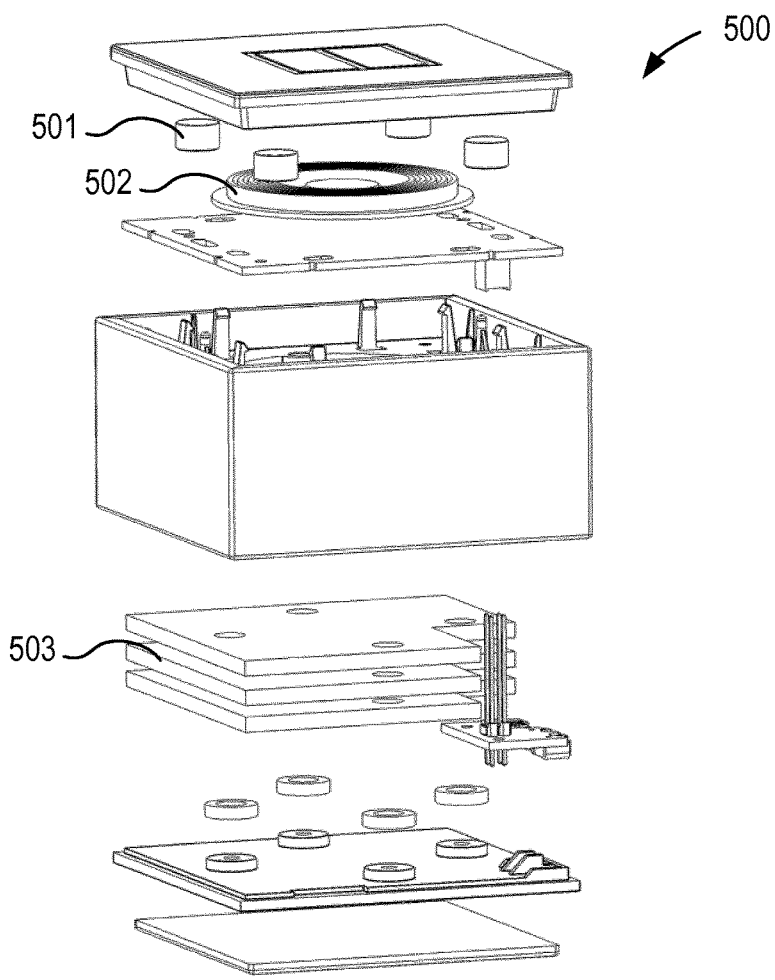
FIG. 25B illustrates an exploded view of the exemplary charger of FIG. 25A showing internal components that may be within the charger housing.

FIG. 25A illustrates a perspective view of an exemplary charger and FIG. 25B is an exploded view illustrating the internal components of the charger of FIG. 25A. Charger 500 is an optional feature that may be used to charge reader device 400. Charger 500 may include alignment magnets 501, inductive coil 502, and batteries 503. Charger 500 may include one or more alignment magnets 501 configured to align with one or more alignment magnets in the reader device to facilitate efficient energy transfer between inductive coil 502 and the inductive coil within the reader. Illustratively, four magnets are used. Magnets 501 may be keyed to align with a corresponding keyed magnets in the reader. Charger 500 may be plugged into a conventional socket, e.g., via a cord or a cord with an AC to DC power converter, for charging components within charger 500 such as batteries 503 to permit charging of reader 400.

The Reactants and the Reactions

Various devices, systems, kits, and methods disclosed herein are intended to isolate, tag, and detect one or more target analytes within a sample taken from a specimen. Chemical reactions may be employed to enable such detection. Chemical reactions may take place in a reservoir such as the sample preparation reservoir described above. For example, the sample preparation reservoir may hold a fluid such as water, saline solution, water/saline solution mixed with one or more of magnetic particles, affinity molecules, connection molecules, signaling agents, competitor binding molecules, competitor molecules, labels, and/or signaling agents. One or more reagent balls also may hold one or more of magnetic particles, affinity molecules, connection molecules, signaling agents, competitor binding molecules, competitor molecules, labels, and/or signaling agents outside of the fluid in the sample preparation reservoir. A reaction may begin when a sample potentially having one or more target analytes (and, optionally, one or more reagent balls) is (are) mixed with fluid in the sample preparation reservoir, e.g., by introducing a sample collected on a distal portion of a sample collection device into the sample preparation reservoir when the sample collection device is fully inserted into an input tunnel of a cartridge. Exemplary chemical reactions are discussed below and depicted in FIGS. 26A-28H.

Referring to FIGS. 26A and 26C, target analyte $910a$, $910b$ is added to a solution of sample preparation reagents, e.g., in the sample preparation reservoir. Target analyte $910a$, $910b$ may be any molecule such as a nucleic acid, protein, small molecule, or heavy metal or in the case of a biologic or large molecule, the target analyte is a fragment thereof associated with a particular condition or possible contamination or presence of a particular cell type, e.g., to detect a target biomarker present on the surface of cell. Non-limiting examples include specific pathogens, e.g. bacteria, viruses, parasites; toxins; hormones; immune regulatory molecules; or detectable fragments thereof.

Target analyte $910a$, $910b$ may be detected using the systems and methods described herein to for studying a condition such as molecular levels indicative of inflammation, influenza, testosterone, fertility, and/or Vitamin D. The sample preparation reagents may include magnetic microbeads or nanoparticles $920a$, $920b$ (referred to herein as "magnetic particles"). Magnetic particles $920a$, $920b$ are magnetically responsive such that they will be attracted to a magnetic field emitted from one or more magnetic generators. In this manner, magnetic particles $920a$, $920b$ released from the sample preparation reservoir travel downstream in the analysis channel until they are localized over the one or more working electrodes of the sensor within the analysis channel of the cartridge responsive to magnetic fields generated by one or more magnetic generators of the reader. Each magnetic particle $920a$, $920b$ may have affinity molecule $930a$, $930b$ bound to its surface. The magnetic particles may be different sizes and may have a diameter between 50 nanometers to 5000 nanometers, between 100 nanometers to 4000 nanometers, between 100 nanometers to 3000 nanometers, between 100 nanometers to 2000 nanometers, between 100 nanometers to 1000 nanometers, between 500 nanometers to 4000 nanometers, between 1000 nanometers to 4000 nanometers, or between 1500 nanometers to 3000 nanometers.

The affinity molecule may be any suitable molecule or moiety that can bind to or capture a target molecule. Non-limiting examples of affinity molecules include antibodies (including single chain, multi-chain antibodies, diabodies, humanized antibodies, etc.), antibody fragments with affinity, ligands, polypeptide or protein molecules and moieties with binding affinity for substrates, nucleic acid molecules (e.g., aptamers), other molecules with binding affinity, and the like. The affinity molecules include chemically modified naturally occurring molecules. Affinity molecules for a particular target analyte may be selected according to generally understood methods. For example, methods of generating antibodies and fragments thereof are well known in the literature and are exemplified by Antibodies: A Laboratory Manual (1988) Eds. Harlow and Lane, Cold Spring Harbor Laboratories Press, and U.S. Pat. Nos. 4,381,292, 4,451,570, and 4,618,577. Further, affinity molecules are commercially available for specific target analytes. A listing of such sources may be found in Linscott's Directory of Immunological and Biological Reagents.

As used herein the terms "hybridize" and "hybridization" intend the specific interaction between two entities, such as an antigen and antibody or two complementary nucleic acids, such that specific binding (covalent or non-covalent) can occur.

FIGS. 26A and 26B depict antibody $930a$ and FIGS. 26C and 26D depict nucleic acid probe $930b$, although any suitable affinity molecule could be used, including a nucleic acid aptamer or other binding protein or molecule. The sample preparation reagents also may include detector agent $940a$, $940b$, such as, for example, an antibody $960a$ conjugated to signaling agent $950a$ (FIG. 26A) or labeled nucleic acid probe $960b$ bound to signaling agent $950b$ (FIG. 26C). Detector agents $940$ may each include signaling agent $950$, such as, for example, an oxidizing enzyme or other signaling enzyme, alkaline phosphatase (AP), methylene blue or other electrochemically responsive tag, or a fluorescent tag such as ethidium bromide, fluorescein, green fluorescent protein, or other fluorophore.

In embodiments that include detector agents $940$, the various reagents listed above may hybridize together to form sandwich complexes. Exemplary sandwich complexes $900a$, $900b$ are illustrated in FIGS. 26B and 26D. Each sandwich complex may be formed of: (1) magnetic particle $920a$, $920b$ having surface-bound affinity molecule $930a$, $930b$, (2) target analyte $910a$, $910b$, and (3) detector agent $940a$, $940b$. As such, sandwich complex $900a$, $900b$ held over the working electrode of the sensor within the analysis channel of the cartridge due to the magnetic attraction between magnetic particle $920a$, $920b$ and the magnetic field generators of the reader will include target analyte $910a$, $910b$ and detector agent $940a$, $940b$. The exemplary sandwich complex $900a$ of FIG. 26B uses antibodies as affinity molecules, and the target analyte is a protein or small molecule of interest. The exemplary sandwich complex $900b$ of FIG. 26D uses nucleic acid probes designed to capture a particular sequence of nucleic acids. Also, competitor molecules may be used where the competitor molecules are each pre-bound to HRP, such as testosterone-HRP.

In various embodiments, signaling agent $950a$, $950b$ is an oxidizing enzyme such as, for example, horseradish peroxidase (HRP) or soybean peroxidase (SBP). In such embodiments, the enzyme induces an oxidation reaction to occur at an electrochemical cell when in the presence of a particular chemical substrate, e.g., released from the substrate reservoir, such as TMB and/or OPD which may be in a substrate solution including acceptor molecules such as hydrogen peroxide. Thus, if the particular substrate flows over, or otherwise encounters, the oxidizing enzyme bound to a target analyte and magnetic particle at an electrochemical cell, an oxidation reaction occurs. In such embodiments, electrons are accordingly released from a working electrode of the electrochemical cell to replenish electrons stripped from the substrate by the oxidizing enzyme in a quantity proportional to the amount of target analyte present. The release or flow of electrons results in a current, which is detectable by the sensor in the analysis channel (e.g., at the working electrode), for example, as a change in current or a change in voltage. Advantageously, signaling agents that are not bound to magnetic particles are not magnetically held over the working electrode and instead wash further downstream (e.g., caused by release of fluid from the sample preparation, wash, and/or substrate reservoirs) so as to not interfere with sensor readings. Accordingly, a signal indicative of the presence, absence, and/or quantity of one or more target analytes within a sample may be generated at the sensor in the cartridge and transmitted to the reader for further processing. In addition, or alternatively, surface bound target analytes with HRP may also produce signal that may be sensed by the sensor and transmitted to the reader for further processing.

Referring now to FIGS. 27A and 27B, the sample preparation reagents may include a population of magnetic particles 1020, each having affinity molecule 1030 bound to its surface. Competitive binding agent 1040 and a sample containing target analyte 1010 may be added to the sample preparation reagents, e.g., by mixing the collected sample (and, optionally, one or more reagent balls) with fluid in the sample preparation reservoir. Competitive binding agent 1040 may include pre-bound target analyte 1070, which comes pre-bound to signaling agent 1050, for example, any of the signaling agents described above. The pre-bound target analyte 1070 may be indirectly bound to the signaling agent 1050, for example, via an antibody, a nucleic acid probe, a nucleic acid aptamer, or other affinity molecule 1060. Unbound target analyte 1010 from a sample and competitive binding agent 1040 may compete with each other to bind to affinity molecules 1030 on magnetic particles 1020. The amount of competitive binding agent 1040 and signaling agent 1050 that successfully binds to magnetic particles 1020 is inversely proportional to the amount of target analyte 1010 present in a sample. In embodiments where signaling agent 1050 of competitive binding agent 1040 is an oxidizing enzyme, an oxidation reaction occurs if a particular substrate (e.g., from the substrate reservoir) flows over, or otherwise encounters, magnetic particles 1020 bound to competitive binding agents 1040 at the sensor within the analysis channel of the cartridge. Electrons are accordingly released from a working electrode of the sensor to replenish electrons stripped from the substrate by the oxidizing enzyme in a quantity inversely proportional to the amount of target analyte present in the sample. The release or flow of electrons results in a current, which is detectable by an electrode coupled to electrical circuitry with a current-to-voltage topology. Accordingly, a signal indicative of the presence, absence, and/or quantity of one or more target analytes within a sample may be generated at the sensor in the cartridge and transmitted to the reader for further processing.

Figure 28B:
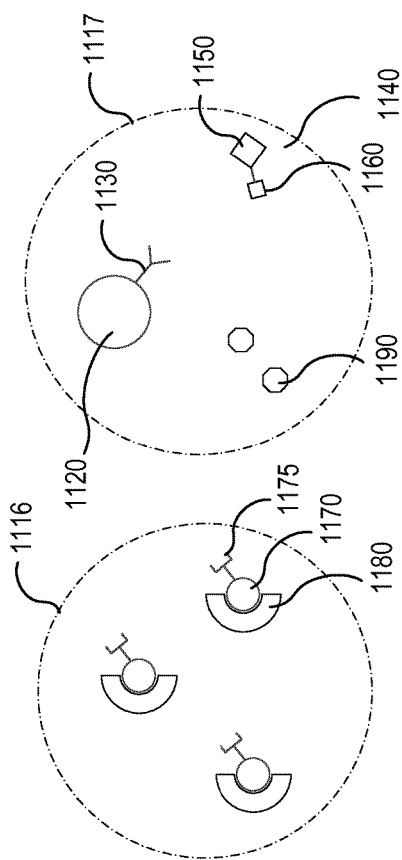
FIG. 28B is a schematic depiction of molecules within two reagent balls for reacting with the molecules within the collected sample.
Figure 28A:
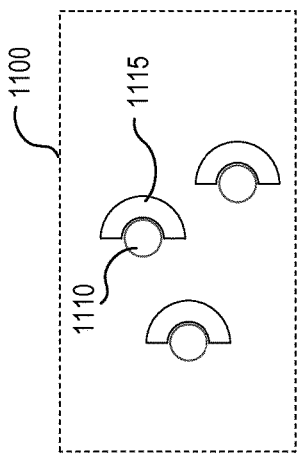
FIG. 28A is a schematic depiction of molecules within a sample on a sample collection device.

Referring now to FIGS. 28A through 28H, a process for detecting the presence, absence, and/or quantity of a target analyte(s) within a sample in a cartridge is described. As shown in FIG. 28A, a sample having a plurality of sample target analytes 1110 may be collected with sample collection device 1100. Sample collection device 1100 may be constructed in the manner described above with respect to any of the sample collection devices. Each sample target analyte 1110 may be bound to sample binding molecule 1115. Sample target analyte 1110 may be any type of analyte described herein such as 25-hydroxy vitamin D3 or 25-hydroxy vitamin D2 or 1α,25-dihydroxyvitamin D2 or 1α,25-dihydroxyvitamin D. Sample binding molecule 1115 of the plurality of sample binding molecules may be any type of binding molecule such as the naturally occurring vitamin D binding protein also known as gc-component (group-specific component).

One or more reagent balls may be provided for mixing with the collected sample. The reagent ball(s) may be stored within the cartridge, e.g., within a shuttle stored in the cartridge as described above. Referring to FIG. 28B, reagent ball 1116 may include a plurality of competitor molecules 1170, a plurality of labels 1175, and a plurality of competitor binding molecules 1180. Each competitor molecule 1170 may be pre-bound to competitor binding molecule 1180 of the plurality of competitor binding molecules. Each competitor molecule 1170 may possess label 1175 of the plurality of labels. Competitor molecule 1170 may be any type of competitor molecule such as a 25-hydroxy vitamin D2 or 25-hydroxy vitamin D3 possessing a label. Label 1175 may be any type of label such as biotin, and competitor binding molecule 1180 may be any type of competitor binding molecule such as vitamin D binding protein. Each label 1175 is configured to bind to signaling agent 1150, e.g., via attachment or affinity molecule 1160. In addition, or alternatively, label 1175 acts as signaling agent 1150. Reagent ball 1117 may include a plurality of solid particles 1120, a plurality of affinity molecules 1130, a plurality of detector agents 1140 which may each have signaling agent 1150 and other affinity molecule 1160, and a plurality of de-binding agents 1190. Reagent balls 1116, 1117 may be constructed in the manner, and used in a cartridge as, described above with respect to any reagent ball described herein including reagent balls 375, 375', 375", 375'".

The plurality of solid particles 1120 may comprise magnetically responsive material such as the magnetic particles, as described herein, or non-magnetically responsive material such as gold nanoparticles. Preferably, each solid particle 1120 is bound to affinity molecule 1130, as described herein. Affinity molecule 1130 may be any affinity molecule described herein and preferably has an affinity to bind to sample target analyte 1110 and/or competitor molecule 1170. Detector agent 1140 having signaling agent 1150 and affinity molecule 1160 may be similar to the respective agent/molecule described herein. For example, signaling agent 1150 may be HRP and affinity molecule 1160 may be streptavidin. Each de-binding agent 1190 of the plurality of depending agents is configured to de-bind competitor molecule 1170 from competitor binding molecule 1180 and, in some embodiments, to then bind to competitor binding molecule 1180, and/or to de-bind sample target analyte 1110 from sample binding molecule 1115 and, in some embodiments, to then bind the sample binding molecule 1115.

The molecules may be lyophilized in multiple reagent balls configured to be used with a single cartridge or one reagent ball configured to be used with a single cartridge. The types of molecules may be distributed amongst the reagent balls in a desired manner, for example as shown in FIG. 28B, or randomly. In addition, certain types of molecules may be stored in the fluid within the sample preparation reservoir while other types are stored within a reagent ball(s).

Figure 28C:
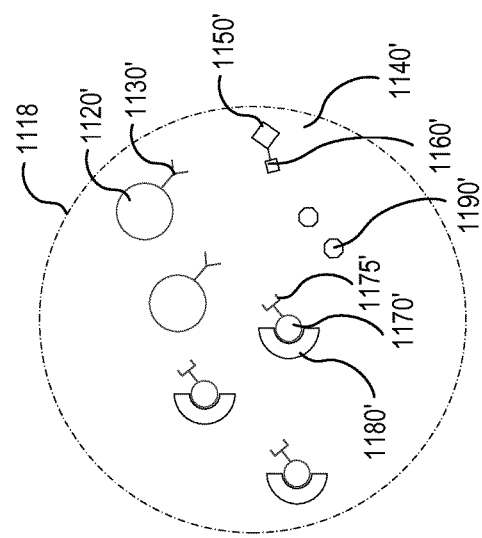
FIG. 28C is a schematic depiction of molecules within a single reagent ball for reacting with the molecules within the collected sample.

As shown in FIG. 28C, all the molecules of reagent ball 1116 and reagent ball 1117 of FIG. 28B may be lyophilized in a single reagent ball. Reagent ball 1118 may include a plurality of solid particles 1120', a plurality of affinity molecules 1130', a plurality of detector agents 1140' (having a plurality of signaling agents 1150' and a plurality of affinity molecules 1160'), a plurality of competitor molecules 1170', a plurality of labels 1175', a plurality of competitor binding molecules 1180', and/or a plurality of de-binding agents 1190'. Reagent ball 1118 may be constructed in the manner, and used in a cartridge as, described above with respect to any reagent ball described herein including reagent balls 375, 375', 375", 375'".

Figure 28D:
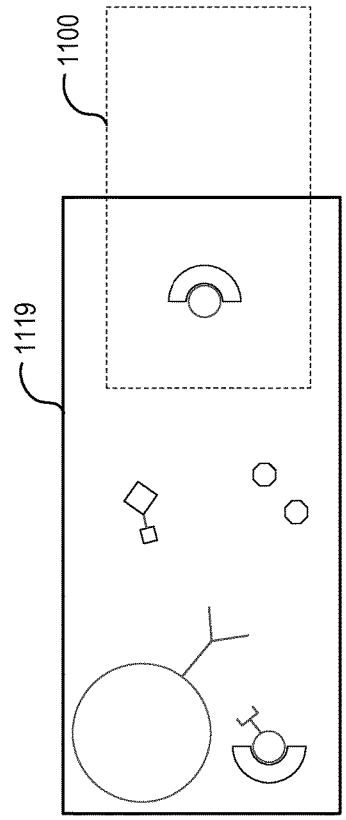
FIG. 28D is a schematic depiction of molecules showing the collected sample being introduced to a sample preparation reservoir.

Referring now to FIG. 28D, a plurality of solid particles, a plurality of affinity molecules, a plurality of detector agents (having a plurality of signaling agents and a plurality of affinity molecules), a plurality of competitor molecules, a plurality of labels, a plurality of competitor binding molecules, and/or a plurality of de-binding agents may be mixed in fluid held in sample preparation reservoir 1119 with a sample collected with sample collection device 1100. The sample may be introduced into sample preparation reservoir 1119 while on the distal portion of sample collection device 1100 or after being released from the distal portion of sample collection device 1100, both of which are described above. The sample may have a plurality of sample target analytes that may each be pre-bound to sample binding molecules. The plurality of solid particles, plurality of affinity molecules, plurality of detector agents (having the plurality of signaling agents and the plurality of affinity molecules), plurality of competitor molecules, plurality of labels, plurality of competitor binding molecules, and/or plurality of de-binding agents may be pre-stored in the fluid within sample preparation reservoir 1119 or some or all of those molecules may be introduced into the fluid from a reagent ball(s), such as reagent balls 1116, 1117, 1118. Sample preparation reservoir 1119 may be constructed in the same manner as any sample preparation reservoir described herein including sample preparation reservoirs 317, 317', 317", 317'''.

Figure 28E:
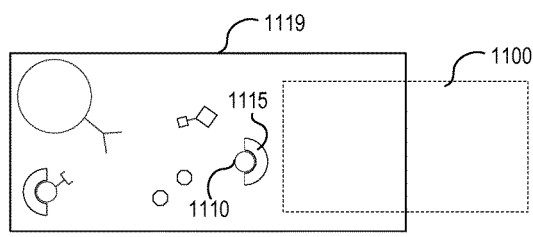
FIG. 28E is a schematic depiction of molecules showing mixing of the molecules of the collected sample with sample preparation reagent molecules within the fluid of the sample preparation reservoir.

Referring now to FIG. 28E, sample target analyte 1110 having sample binding molecule 1115 pre-bound thereto may further mix within sample preparation reservoir 1119. While not necessary, mixing within sample preparation reservoir 1119 may be enhanced by actuation of a sonicator element disposed adjacent sample preparation reservoir 1119, as described above.

Figure 28F:
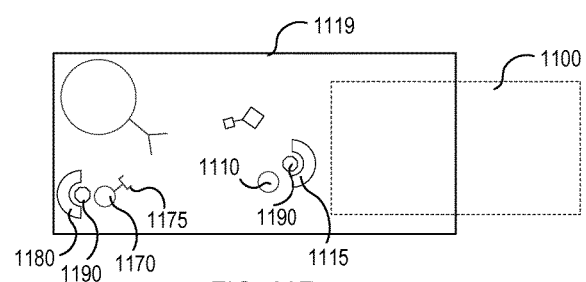
FIGS. 28F, 28G, and 28H are schematic depictions of molecules showing reactions between the molecules of the collected sample and the sample preparation reagent molecules within the fluid of the sample preparation reservoir.

As shown in FIG. 28F, de-binding agent 1190 may de-bind competitor molecule 1170 from pre-bound competitor binding molecule 1180 and then de-binding agent 1190 may bind to competitor binding molecule 1180 leaving competitor molecule 1170 having label 1175 unbound. Another de-binding agent 1190 may de-bind sample target analyte 1110 from sample binding molecule 1115 and then the other de-binding agent 1190 may bind to sample binding molecule 1190 leaving sample target analyte 1110 unbound.

Figure 28G:
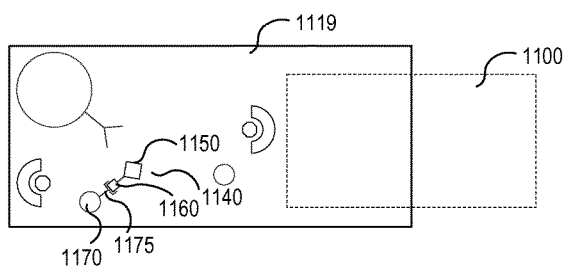

Referring to FIG. 28G, label 1175 of de-bound competitor molecule 1170 may be configured to bind to signaling agent 1150 (e.g., via bonding with affinity molecule 1160).

Figure 28H:
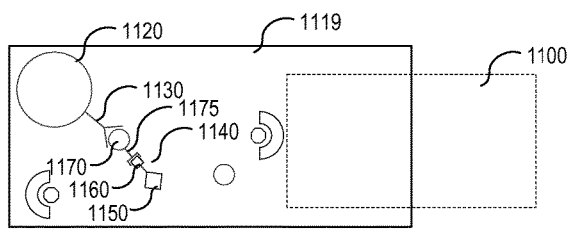

De-bound competitor molecule 1170 may be configured to bind to affinity molecule 1130 of the plurality of affinity molecules which may be pre-bound to solid particle 1120 as shown in FIG. 28H. In this manner, solid particle 1120 may be indirectly bound to competitor molecule 1170 indirectly bound to signaling agent 1150. A sandwich complex may be formed of solid particle 1120, affinity molecule 1130, competitor molecule 1170, label 1175, affinity molecule 1160, and/or signaling agent 1150. Illustratively, solid particle 1120 is bound to affinity molecule 1130 which is bound to competitor molecule 1170 which is bound to label 1175 which is bound to affinity molecule 1160 which is bound to signaling agent 1150.

Figure 29A:
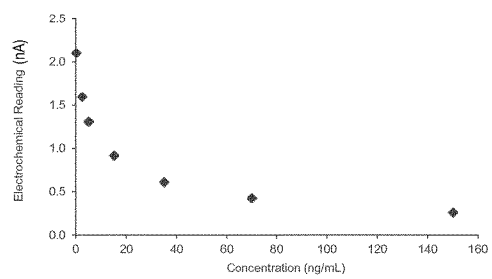
FIG. 29A is a graph showing electrochemical sensor readings versus concentration of a target analyte using pre-bound competitor binding molecules and FIG. 29B shows a graph comparing electrochemical sensor readings versus concentration when a competitor binding molecule is not pre-bound.
Figure 29B:
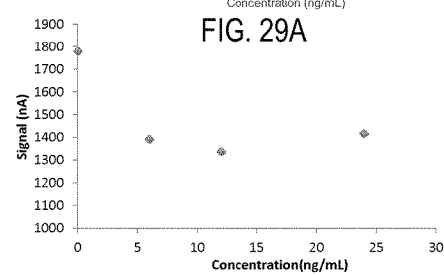
Figure 30F:
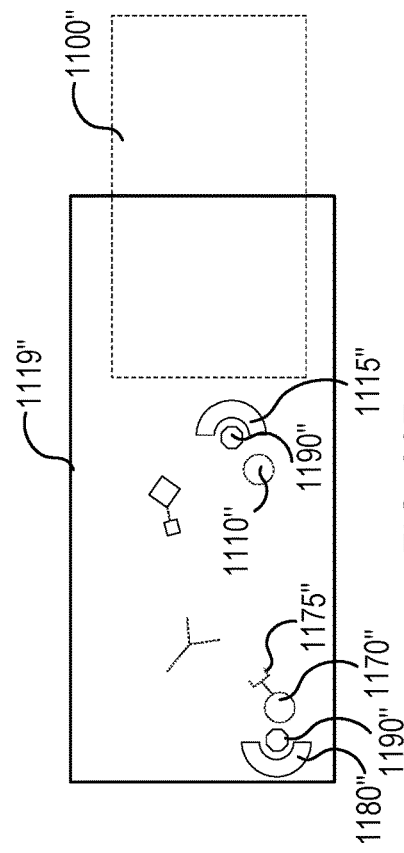
FIGS. 30F, 30G, and 30H are schematic depictions of molecules showing reactions between the molecules of the collected sample and the sample preparation reagent molecules within the fluid of the sample preparation reservoir.
Figure 30H:
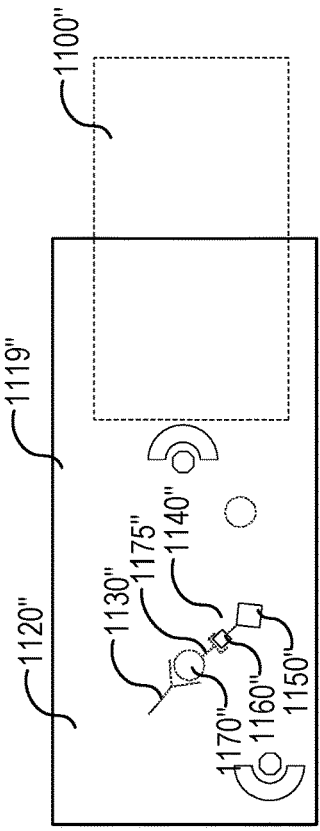
Figure 30E:
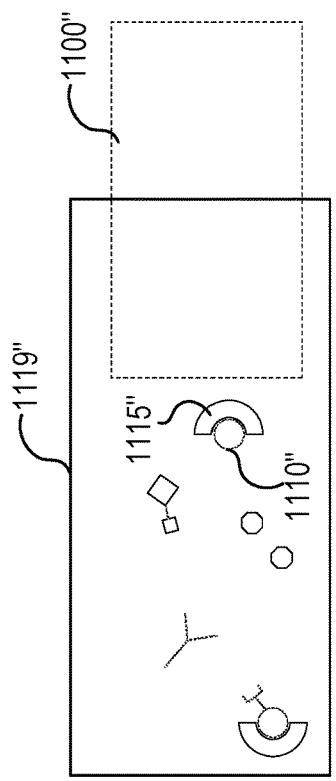
FIG. 30E is another schematic depiction of molecules showing mixing of the molecules of the collected sample with sample preparation reagent molecules within the fluid of the sample preparation reservoir.
Figure 30G:
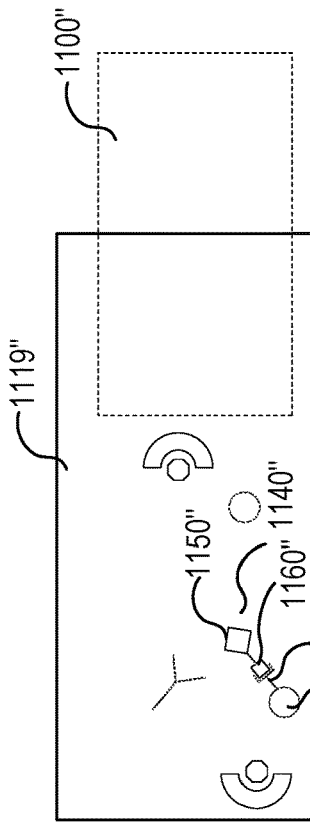

Sample target analyte 1110 and competitor molecule 1170 may compete with each other to bind to affinity molecules 1130 on solid particles 1120. The amount of competitor molecule 1170 and signaling agent 1150 that successfully binds to solid particles 1120 is inversely proportional to the amount of unbound target analyte 1110 present in a sample. In embodiments where signaling agent 1150 of competitive binding agent 1140 is an oxidizing enzyme, an oxidation reaction occurs if a particular substrate (e.g., from the substrate reservoir) flows over, or otherwise encounters, solid particles 1120 bound to competitor molecules 1140 at the sensor within the analysis channel of the cartridge. Electrons are accordingly released from a working electrode of the sensor to replenish electrons stripped from the substrate by the oxidizing enzyme in a quantity inversely proportional to the amount of target analyte present in the sample. For example, as shown in the graph of FIG. 29A comparing electrochemical reading (microamps) versus concentration (ng/mL), the higher the electrochemical reading, the lower the concentration of sample target analytes. The release or flow of electrons results in a current, which is detectable by an electrode coupled to circuitry, for example, as a change in current or a change in voltage. Accordingly, a signal indicative of the presence, absence, and/or quantity of one or more target analytes within a sample may be generated at the sensor in the cartridge and transmitted to the reader for further processing. FIG. 29B shows a graph comparing electrochemical reading (microamps) versus concentration (ng/mL) when competitor binding molecule is not pre-bound for vitamin D quantification analysis. As FIG. 29B illustrates, the electrochemical reading does not show a relationship with the concentration of vitamin D.

As will be readily apparent to one skilled in the art, while one type of molecule may be shown as present in an illustrated reaction, for example, one sample target analyte 1110 in FIGS. 28D through 28H, a plurality of the types of molecules may be present. In addition, all the types of molecules shown in FIGS. 28A through 28H need not be included in a reaction. For example, referring to FIGS. 30A through 30H, the reactions are similar to FIGS. 28A through 28H except affinity molecule 1130" is not bound to a solid particle and the plurality of solid particles are not needed.

Referring now to FIGS. 31A through 31H, a process for detecting the presence, absence, and/or quantity of a target analyte(s) within a sample in a cartridge is described. As shown in FIG. 31A, a sample having a plurality of sample target analytes 1210 may be collected with sample collection device 1200. Sample collection device 1200 may be constructed in the manner described above with respect to any of the sample collection devices. Sample target analyte 1210 may be any type of analyte described herein.

One or more reagent balls may be provided for mixing with the collected sample. The reagent ball(s) may be stored within the cartridge, e.g., within a shuttle stored in the cartridge as described above. Referring to FIG. 31B, reagent ball 1215 may include a plurality of solid particles 1120, a plurality of affinity molecules 1230, a plurality of detector agents 1240 which may each include signaling agent 1250 and affinity molecule 1260, a plurality of control targets 1270, and/or a plurality of control detector agents 1275 which may each include control signaling agent 1285 and control affinity molecule 1280. Reagent ball 1215 may be constructed in the manner, and used in a cartridge as, described above with respect to any reagent ball described herein including reagent balls 375, 375', 375", 375'''.

The plurality of solid particles 1220 may comprise magnetically responsive material such as the magnetic particles, as described herein, or non-magnetically responsive material such as gold nanoparticles. The plurality of solid particles 1220 may be similar to the magnetic particles described above. Preferably, each solid particle 1220 is pre-bound to affinity molecule 1230, as described herein. Affinity molecule 1230 may be any affinity molecule described herein and preferably has an affinity to bind to sample target analyte 1210. Detector agent 1240 having signaling agent 1250 and affinity molecule 1260 may be similar to the respective agent/molecule described herein. For example, signaling agent 1250 may be HRP and affinity molecule 1260 may be streptavidin. The plurality of control targets 1270 may be configured to bind to affinity molecules pre-bound to the surface of the sensor of the cartridge, for example, affinity molecules pre-bound to the positive control working electrode of the sensor (e.g., see FIGS. 7D, 7E, 7F) and/or the working electrode of the sensor (e.g., see FIG. 7D). Control targets 1270 may be a protein. Control affinity molecule 1280 may be any affinity molecule described herein and preferably has an affinity to bind to control target 1270. Control signaling agent 1285 may be similar to the signaling agents described herein, including signal agent 1250.

The molecules may be lyophilized in multiple reagent balls configured to be used with a single cartridge or one reagent ball configured to be used with a single cartridge. The types of molecules may be distributed amongst the reagent balls in a desired manner or randomly. In addition, certain types of molecules may be stored in the fluid within the sample preparation reservoir while other types are stored within a reagent ball(s).

Methods encapsulate materials are known in the art but have not, to the best of Applicants' knowledge, been utilized to encapsulate reaction reagents for use in a device, cartridge or system as described herein. As noted above, the reagent ball(s) may include one or more of magnetic particles, affinity molecules, connection molecules, signaling agents, competitor binding molecules, competitor molecules, labels, signaling agents, primers, nucleic acid probes, and/or polymerases, and other enzymes or components as described in further detail herein and the components, encapsulation material and dimensions may be the same or different from each other.

Referring now to FIG. 31C, a plurality of solid particles, a plurality of affinity molecules, a plurality of detector agents (having a plurality of signaling agents and a plurality of affinity molecules), a plurality of control targets, and/or a plurality of control detector agents (having a plurality of control signaling agents and a plurality of control affinity molecules) may be mixed in fluid held in sample preparation reservoir 1290 with a sample collected with sample collection device 1200. The sample may be introduced into sample preparation reservoir 1290 while on the distal portion of sample collection device 1200 or after being released from the distal portion of sample collection device 1200, both of which are described above. The sample may have a plurality of sample target analytes. The plurality of solid particles, the plurality of affinity molecules, the plurality of detector agents (having the plurality of signaling agents and the plurality of affinity molecules), the plurality of control targets, and/or the plurality of control detector agents (having the plurality of control signaling agents and the plurality of control affinity molecules) may be pre-stored in the fluid within sample preparation reservoir 1290 or some or all of those molecules may be introduced into the fluid from a reagent ball(s), such as reagent ball 1215. Sample preparation reservoir 1290 may be constructed in the same manner as any sample preparation reservoir described herein including sample preparation reservoirs 317, 317', 317", 317'''.

Referring now to FIG. 31D, sample target analyte 1210 may further mix within sample preparation reservoir 1290. While not necessary, mixing within sample preparation reservoir 1290 may be enhanced by actuation of a sonicator element disposed adjacent sample preparation reservoir 1290, as described above. Affinity molecule 1230 (pre-bound to solid particle 1220) may bind with sample target analyte 1210 and detector agent 1240 may bind to sample target analyte 1210. For example, affinity molecule 1260 (pre-bound to signaling agent 1250) may bind to sample target analyte 1210. A sandwich complex may be formed of solid particle 1220, affinity molecule 1230, target analyte 1210, affinity molecule 1260, and/or signaling agent 1250. Illustratively, solid particle 1220 is bound to affinity molecule 1230 which is bound to target analyte 1210 which is bound to affinity molecule 1260 which is bound to signaling agent 1250. Control detector agent 1275 may bind to control target 1270. For example, control affinity molecule 1280 (pre-bound to signaling agent 1285) may bind to control target 1270. A partial sandwich complex may be formed of target control 1270, control affinity molecule 1280, and/or control signaling agent 1285. Illustratively, control target 1270 is bound to control affinity molecule 1280 which is bound to control signaling agent 1285.

Referring now to FIG. 31E, a surface of a sensor for use in a cartridge device described herein is shown. Sensor surface 1292 may include a plurality of affinity molecules 1294 pre-bound to sensor surface 1292 within the cartridge. Surface affinity molecule 1294 may be any affinity molecule described herein and preferably has an affinity to bind to control target 1270. Sensor surface 1292 is preferably positioned within the analysis channel of the cartridge for exposure to fluid released from the sample preparation reservoir and/or fluid released from the substrate reservoir. FIG. 31E shows sensor surface 1292 prior to exposure to fluid from the reservoir(s). Sensor surface 1292 may be used on any of the sensors described above including sensors 338, 338', 338", 338''', 338''''. Sensor surface 1292 may be used for a working electrode of the sensor such as working electrode 340" and/or may be used for a positive control working electrode of the sensor such as positive control working electrodes 376, 376', 376".

Referring now to FIG. 31F, another surface of a sensor for use in a cartridge device described herein is shown. Sensor surface 1296 may have a self-assembled monolayer such as thiolated ethylene glycol and/or a dithiol such as hexaethylene glycol dithiol for added stability. Sensor surface 1296 is preferably positioned within the analysis channel of the cartridge for exposure to fluid released from the sample preparation reservoir and/or fluid released from the substrate reservoir. FIG. 31F shows sensor surface 1296 prior to exposure of fluid from the reservoir(s). Sensor surface 1296 may be used on any of the sensors described above including sensors 338, 338', 338", 338''', 338''''. Sensor surface 1296 may be used for a working electrode of the sensor such as working electrodes 340, 340', 340''', 340''''. Sensor surface 1296 is configured to be exposed to magnetic fields from magnetic field generator 1298, e.g., when the cartridge is inserted in the reader. For example, magnetic field generator 1298 may be similar to first magnetic generator 406 and second magnetic generator 407 of reader 400 described above.

Referring now to FIG. 31G, sensor surface 1292 is shown after exposure to reagents, e.g., from fluid flowing into the analysis channel from the sample preparation reservoir. As shown in FIG. 31G, partial sandwich complexes of control molecules may bind to surface affinity molecules 1294 to complete the sandwich complexes. For example, surface affinity molecule 1294 may bind to control target 1270 which is bound to control affinity molecule 1280 which is bound to control signaling agent 1285. A chemical reaction may occur when the sandwich complexes are exposed to a substrate, e.g., from substrate reservoir, such that the sensor may detect electrical signals resulting from chemical reactions over the sensor. For example, the mixed fluid from the sample preparation reservoir may be introduced into the analysis channel such that control signaling agents 1285 directly or indirectly bound to control targets 1270 from the mixed fluid from the sample preparation reservoir localize over sensor surface 1292 by binding with pre-bound surface affinity molecules 1294. The chemical reactions may occur when fluid from the substrate reservoir reacts with particles from the mixed fluid from the sample preparation reservoir localized over the sensor. For example, substrate solution having a substrate may be introduced from the substrate reservoir and the sensor having sensor surface 1292 may detect electrical signals resulting from the reactions between the substrate (e.g., TMB, OPD) and the signaling agents (e.g., HRP, SBP) localized over the sensor. The reactions may cause electrons to be stripped from the substrate by the signaling agents (which electrons may be donated to acceptor molecules of the substrate solution) thereby generating electrical signals detectable by the sensor. If sensor surface 1292 is on a working electrode, such detected electrical signals may be used to generate the signal indicative of the presence, absence, and/or quantity of one or more analytes within the sample. If sensor surface 1292 is on a positive control working electrode, such detected electrical signals may be used for error detection. For example, if a parameter(s), e.g., voltage, current, of the detected electrical signals is not within a predetermined range(s), there may be an error and the test may be rejected. If the parameter(s) is within the predetermined range, electrical signals detected by the working electrode of the sensor may be used to generate the signal indicative of the presence, absence, and/or quantity of one or more analytes within the sample. The signals from the positive control working electrode and/or the working electrode may be transmitted to reader device 400, e.g., via respective electrical connectors of cartridge device 300 and reader device 400.

Referring now to FIG. 31H, sensor surface 1296 is shown after exposure to reagents, e.g., from fluid flowing into the analysis channel from the sample preparation reservoir. It should be understood that sensor surface 1296 and sensor surface 1292 may be exposed to the sample preparation reservoir fluid at substantially the same time, e.g., when sensor surface 1296 corresponds to working electrode 340''' or working electrode 340'''' and sensor surface 1292 corresponds to positive control working electrode 376' of sensor 338''' or positive control working electrode 376'' of sensor 338''''. Similarly, sensor surface 1296 and sensor surface 1292 may be exposed to the substrate reservoir fluid at substantially the same time, thereby causing reactions to occur between the substrate and reagents (e.g., signaling agents) at substantially the same time. A chemical reaction may occur when the sandwich complexes are exposed to a substrate, e.g., from substrate reservoir, such that the sensor may detect electrical signals resulting from chemical reactions over the sensor. For example, the mixed fluid from the sample preparation reservoir may be introduced into the analysis channel such that signaling agents directly or indirectly bound to target analytes from the mixed fluid from the sample preparation reservoir localize over sensor surface 1296 responsive to magnetic fields from magnetic field generator 1298 holding solid particles 1220 directly or indirectly bound to signaling agents 1250. The chemical reactions may occur when fluid from the substrate reservoir reacts with particles from the mixed fluid from the sample preparation reservoir localized over the sensor. For example, a substrate solution having a substrate may be introduced from the substrate reservoir and the sensor having sensor surface 1296 may detect electrical signals resulting from the reactions between the substrate (e.g., TMB, OPD) and the signaling agents (e.g., HRP, SBP) localized over the sensor. The reactions may cause electrons to be stripped from the substrate by the signaling agents (which electrons may be donated to acceptor molecules in the substrate solution) thereby generating electrical signals detectable by the sensor. If sensor surface 1296 is on a working electrode, such detected electrical signals may be used to generate the signal indicative of the presence, absence, and/or quantity of one or more analytes within the sample. The signal from the working electrode may be transmitted to reader device 400, e.g., via respective electrical connectors of cartridge device 300 and reader device 400.

As will be readily apparent to one skilled in the art, while one type of molecule may be shown as present in an illustrated reaction, for example, one sample target analyte 1210 in FIGS. 31C and 31D, a plurality of the types of molecules may be present. In addition, all the types of molecules shown in FIGS. 31A through 31H need not be included in a reaction.

Referring now to FIGS. 32A through 32I, a process for detecting the presence, absence, and/or quantity of a target analyte(s) within a sample in a cartridge is generally described. The process may involve amplification such as isothermal amplification as shown in general in FIG. 32D. As used herein, the term "isothermal amplification" refers to a method of amplifying a nucleic acid, e.g. DNA or RNA, wherein the temperature remains constant. In one aspect, the reaction system is in contact with an outside source having a temperature differential but the temperature change, if any, occurs slowly enough to allow the system to continuously adjust the temperature. Non-limiting exemplary of isothermal amplification include rolling circle amplification (RCA), loop-mediated isothermal amplification (LAMP), strand displacement amplification (SDA), recombinase polymerase amplification (RPA), helicase dependent amplification (HDA), polymerase spiral reaction (PSR), and nicking enzyme amplification reaction (NEAR). These and further non-limiting exemplary methods are disclosed in Zhao et al. (2015) Chem. Rev. 115(22):12491-12545; and Dong et al. (2015) Scientific Reports 5:12723; Yan et al. (2014) Mol. BioSyst. 10:970-1003.

Depending on the isothermal amplification method selected, the reagent ball(s) may include one or more amplification enzymes, e.g., reverse transcriptases, endonucleases (e.g. a nicking endonuclease, restriction endonuclease, flap endonuclease, or endonuclease III), polymerases (e.g. a strand displacing polymerase), method specific primers or probes (e.g. a padlock probe, linked probe, or LAMP primers), helicases, recombinases, and/or single-stranded DNA binding proteins. The requisite combination of reagents required to carry out each method of isothermal amplification is appreciated by an ordinary skilled artisan. Non-limiting exemplary combinations of reagents required to perform the various methods of isothermal amplification are described in Chinese Patent Application No. 104232622; U.S. Pat. No. 5,223,414; U.S. Pat. No. 6,410,278; U.S. Pat. No. 5,455,166; U.S. Pat. No. 5,470,723; U.S. Pat. No. 5,714,320; U.S. Pat. No. 6,235,502; and U.S. Pat. No. 7,282,328.

As used herein, the term "dNTPs" intend the nucleotides that are the building blocks for DNA. They principally include (d)ATP, (d)GTP, (d)CTP, (d)TTP and (d)UTP and are necessary for nucleic acid amplification reactions.

RT specific primers intends a primer, typically unlabelled, that is designed to hybridize with an RNA molecule containing the target region and allowing for a reverse transcriptase to polymerize a cDNA strand from the 3' end of the primer. The cDNA strand will is then used as a template for isothermal amplification. The RT specific primer may have design characteristics that differ from the primers that are optimized for amplification of DNA within the isothermal amplification reaction that proceeds subsequently to the reverse transcription of the target RNA. Applicant has determined that use of RT specific primers will increase amplification efficiency.

Figure 32A:
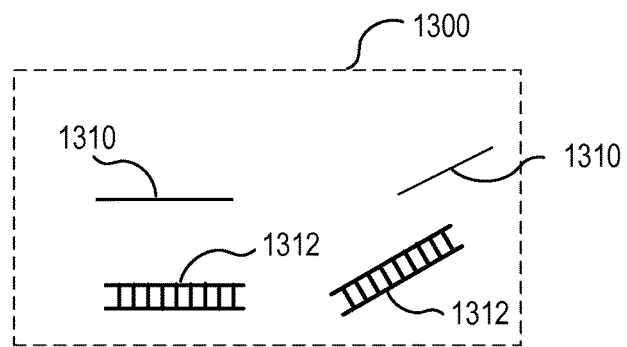

As shown in FIG. 32A, a sample having a plurality of sample target analytes 1310 and/or 1312 may be collected with sample collection device 1300. Sample collection device 1300 may be constructed in the manner described above with respect to any of the sample collection devices. Sample target analyte 1310 may be any type of analyte described herein and illustratively is RNA. Sample target analyte 1312 may be any type of analyte described herein and illustratively is DNA. It should be understood that sample target analyte 1310 and/or 1312 may contain an upstream and downstream sequence region of the target region, but is understood to at least contain the target region to be amplified and detected. Sample target analyte 1310 and/or 1312 may be contained with a cell, microbe, or virus or could be cell-free. The sample preparation reservoir and/or the reagent ball(s) may include lysis agents to free the target analyte from the cell, microbe, or virus.

Figure 32B:
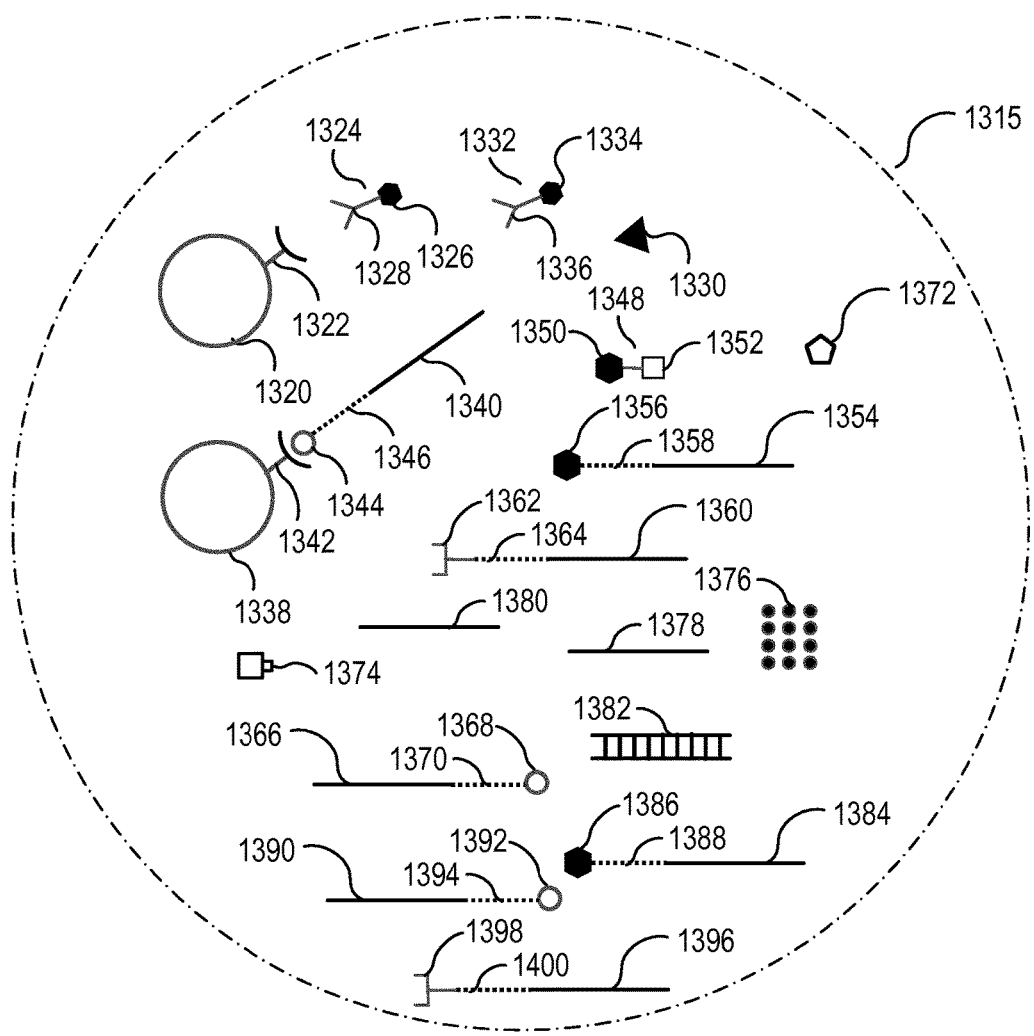

One or more reagent balls may be provided for mixing with the collected sample. The reagent ball(s) may be stored within the cartridge, e.g., within a shuttle stored in the cartridge as described above. Referring to FIG. 32B, reagent ball 1315 may include a plurality of solid particles 1320, a plurality of affinity molecules 1322, a plurality of detector agents 1324 which may each include signaling agent 1326 and affinity molecule 1328, a plurality of control targets 1330, a plurality of control detector agents 1332 which may each include control signaling agent 1334 and control affinity molecule 1336, a plurality of solid particles 1338 pre-conjugated to primers 1340 (e.g., via affinity molecule 1342 pre-bound to capture element 1344 pre-bound to spacer 1346 pre-bound to primer 1340 or through a direct covalent bond), a plurality of detector agents 1348 which may each include signaling agent 1350 and affinity molecule 1352, a plurality of internal control reverse primers 1354 which may each be pre-bound to signaling agent 1356, e.g., each optionally via spacer 1358, a plurality of reverse primers 1360 which may each be pre-bound to label 1362, e.g., via spacer 1364, a plurality of internal control forward primers 1366 which may each be pre-bound to capture element 1368, e.g., via spacer 1370, a plurality of polymerase 1372, a plurality of reverse transcriptases (RT) 1374, a plurality of dNTPs 1376, a plurality of RT specific primers 1378, a plurality of RNA template controls 1380, a plurality of DNA template controls 1382, a plurality of reverse primers 1384 which may each be pre-bound to signaling agent 1386, e.g., via spacer 1388, a plurality of forward primers 1390 which may each be pre-bound to capture element 1392, e.g., via spacer 1394, and/or a plurality of internal control reverse primers 1396 which may each be pre-bound to internal control label 1394, e.g., via internal control spacer 1400. Reagent ball 1315 may be constructed in the manner, and used in a cartridge as, described above with respect to any reagent ball described herein including reagent balls 375, 375', 375'', 375'''.

The plurality of solid particles 1320 may comprise magnetically responsive material such as the magnetic particles, as described herein, or non-magnetically responsive material such as gold nanoparticles. The plurality of solid particles 1320 may be similar to the magnetic particles described above. Preferably, each solid particle 1320 is pre-bound to affinity molecule 1322, as described herein. Affinity molecule 1322 may be any affinity molecule described herein and preferably has an affinity to bind to a sample target analyte(s). Detector agent 1324 having signaling agent 1326 and affinity molecule 1328 may be similar to the respective agent/molecule described herein. For example, signaling agent 1326 may be HRP and affinity molecule 1328 may be streptavidin. The plurality of control targets 1330 may be configured to bind to affinity molecules pre-bound to the surface of the sensor of the cartridge, for example, affinity molecules pre-bound to the positive control working electrode of the sensor (e.g., see FIGS. 7D, 7E, 7F) and/or the working electrode of the sensor (e.g., see FIG. 7D). Control targets 1330 may be a protein. Control affinity molecule 1336 may be any affinity molecule described herein and preferably has an affinity to bind to control target 1330. Control signaling agent 1334 may be similar to the signaling agents described herein, including signal agent 1326. The plurality of solid particles 1338 may comprise magnetically responsive material such as the magnetic particles, as described herein, or non-magnetically responsive material such as gold nanoparticles. The plurality of solid particles 1338 may be similar to the magnetic particles described above. Preferably, each solid particle 1338 is pre-bound to affinity molecule 1342, as described herein. Affinity molecule 1342 may be any affinity molecule described herein and preferably has an affinity to bind to capture element 1344. For example, affinity molecule 1342 may be pre-bound to capture element 1344. Capture element 1344 contains a spacer 1346 and the primer 1340. Detector agent 1348 having signaling agent 1350 and affinity molecule 1352 may be similar to the respective agent/molecule described herein. For example, signaling agent 1350 may be HRP and affinity molecule 1352 may be streptavidin. Affinity molecule 1352 may have an affinity to bind to a label such as label 1362 and/or internal control label 1398. Internal control reverse primers 1354 may be configured to bind to affinity molecules pre-bound to the surface of the sensor of the cartridge, for example, affinity molecules pre-bound to the positive control working electrode of the sensor (e.g., see FIGS. 7D, 7E, 7F) and/or the working electrode of the sensor (e.g., see FIG. 7D). Internal control reverse primers 1354 may bind to affinity molecules pre-bound to the surface of the sensor via capture element 1368 bound to internal control forward primer 1366 (e.g., via spacer 1370). Signaling agent 1356 may be any signaling agent described herein such as HRP. Reverse primers 1360 may be configured to bind to the target analyte(s) and to bind directly or indirectly to a solid particle to localize at the surface of the sensor of the cartridge, for example, via magnetic fields at the working electrode of the sensor. Label 1362 may be any type of label such as biotin and is configured to bind with an affinity molecule, e.g., affinity molecule 1352 bound to signaling agent 1350. Internal control forward primers 1366 may be configured to bind to affinity molecules pre-bound to the surface of the sensor of the cartridge, for example, affinity molecules pre-bound to the positive control working electrode of the sensor (e.g., see FIGS. 7D, 7E, 7F) and/or the working electrode of the sensor (e.g., see FIG. 7D) via, for example, capture element 1368. The plurality of polymerase 1372, the plurality of reverse transcriptases (RT) 1374, the plurality of dNTPs 1376, the plurality of RT specific primers 1378, the plurality of RNA template controls 1380, and/or the plurality of DNA template controls 1382 may be used to amplify the nucleic acid, e.g., RNA and/or DNA, via, for example, isothermal amplification. The plurality of RNA template controls 1380, and/or the plurality of DNA template controls 1382 may be contained with a cell, microbe, or virus or could be free floating. The sample preparation reservoir and/or the reagent ball(s) may include lysis agents to free the template control(s) from the cell, microbe, or virus. Reverse primers 1384 may be configured to bind to a target analyte(s) and to bind directly or indirectly to a solid particle to localize at the surface of the sensor of the cartridge, for example, via magnetic fields at the working electrode of the sensor. Signaling agent 1386 may be any signaling agent described herein such as HRP. Forward primers 1390 may be configured to bind to a target analyte and to bind directly or indirectly to a solid particle to localize at the surface of the sensor of the cartridge, for example, via magnetic fields at the working electrode of the sensor via, for example, capture element 1392. Internal control reverse primers 1396 may be configured to bind to affinity molecules pre-bound to the surface of the sensor of the cartridge, for example, affinity molecules pre-bound to the positive control working electrode of the sensor (e.g., see FIGS. 7D, 7E, 7F) and/or the working electrode of the sensor (e.g., see FIG. 7D). Internal control reverse primers 1396 may bind to affinity molecules pre-bound to the surface of the sensor via capture element 1368 bound to internal control forward primer 1366 (e.g., via spacer 1370). Label 1398 may be any type of label such as biotin and may be configured to bind with an affinity molecule, e.g., affinity molecule 1352 bound to signaling agent 1350.

The molecules may be lyophilized in multiple reagent balls configured to be used with a single cartridge or one reagent ball configured to be used with a single cartridge. The types of molecules may be distributed amongst the reagent balls in a desired manner or randomly. In addition, certain types of molecules may be stored in the fluid within the sample preparation reservoir while other types are stored within a reagent ball(s).

Figure 32C:
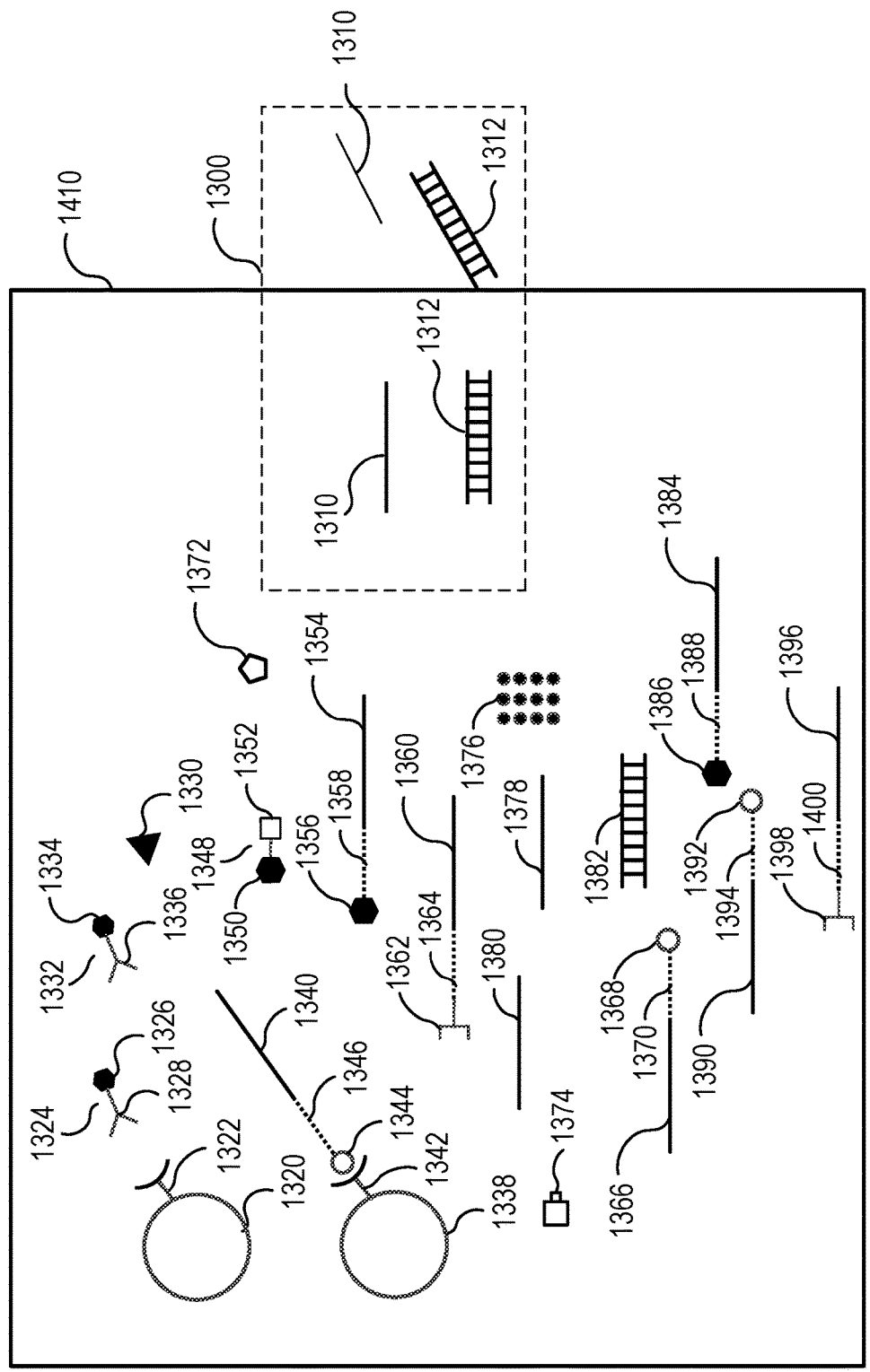

Referring now to FIG. 32C, any combination of the types of particles shown in reagent ball 1315 may be mixed in fluid held in sample preparation reservoir 1290 with a sample collected with sample collection device 1200. The sample may be introduced into sample preparation reservoir 1410 while on the distal portion of sample collection device 1300 or after being released from the distal portion of sample collection device 1300, both of which are described above. The sample may have a plurality of sample target analytes. The types of particles shown in reagent ball 1315 may be pre-stored in the fluid within sample preparation reservoir 1410 or some or all of those molecules may be introduced into the fluid from a reagent ball(s), such as reagent ball 1315. Sample preparation reservoir 1410 may be constructed in the same manner as any sample preparation reservoir described herein including sample preparation reservoirs 317, 317', 317", 317'".

Sample target analyte 1310 and/or 1312 may further mix within sample preparation reservoir 1410. While not necessary, mixing within sample preparation reservoir 1410 may be enhanced by actuation of a sonicator element disposed adjacent sample preparation reservoir 1410, as described above. The mixing within sample preparation reservoir 1410 may amplify nucleic acids, e.g., DNA and/or RNA, within the mixture of fluid within sample preparation reservoir which includes the sample and optionally reagent ball(s). The sample target analyte may be a target nucleic acid, e.g., a RNA for the detection and/or diagnosis of an influenza or HIV infection, and DNA for DNA viruses or bacteria or RNA for the detection of 16s rRNA for bacteria. The amplification proceeds by action of a polymerase beginning at the 3' end of a bound primer (forward or reverse) wherein the polymerase moves along the template strands comprising the target nucleic acid and incorporates nucleotides (dNTP) to synthesize a complementary strand. Since the primer may have a labelled end, these labelled ends are incorporated into the resulting amplicon. In the case of a capture element labelled end, this allow the amplicon to bind to an affinity molecule bound to a solid particle or to a pre-bound surface affinity molecule on a sensor surface while the signaling agent on the other end of the amplicon can be conjugated directly or indirectly to the signaling agent. As used herein, "conjugated" intends a covalent or non-covalently bond, e.g., a biotin-Strepavidin binding complex. And these binding events can happen simultaneously with the amplification. In a further aspect, a separate amplification reaction is simultaneously occurring and lysis of viral particles, bacteria, other microbes, and cells may be occurring freeing the cellular contents, e.g., nucleic acid. In addition to the labeled primers, unlabeled primers designed to amplify at least the same target region but perhaps some sequence flanking the target sequence may be provided to facilitate the amplification reaction simultaneously with the labelled primers. The presence of unlabeled primers can make amplification more efficient since labelled primers may be more sterically hindered as they bind to other elements e.g. solid particles or signaling agents.

This polymerization of the complement strand in the amplifcation can be facilitated by the presence of single stranded binding proteins known to those of ordinary skill in the art such as but not limited to SSB from *E. coli*. Strand displacing polymerases can be used to allow for the polymerization of the complement strand to occur without thermally denaturing the double strand prior to synthesis of complementary strands. Since the primer may have a labelled end, these labelled ends are incorporated into the resulting amplicon. In the case of a capture element labelled end, this allow the amplicon to bind to an affinity molecule bound to a solid particle or to a pre-bound surface affinity molecule on a sensor surface while the signaling agent on the other end of the amplicon can be conjugated directly or indirectly to the signaling agent. As used herein, "conjugated" intends a covalent or non-covalently bond, e.g., a biotin-Strepavidin binding complex. And these binding events can happen simultaneously with the amplification.

Figure 32D:
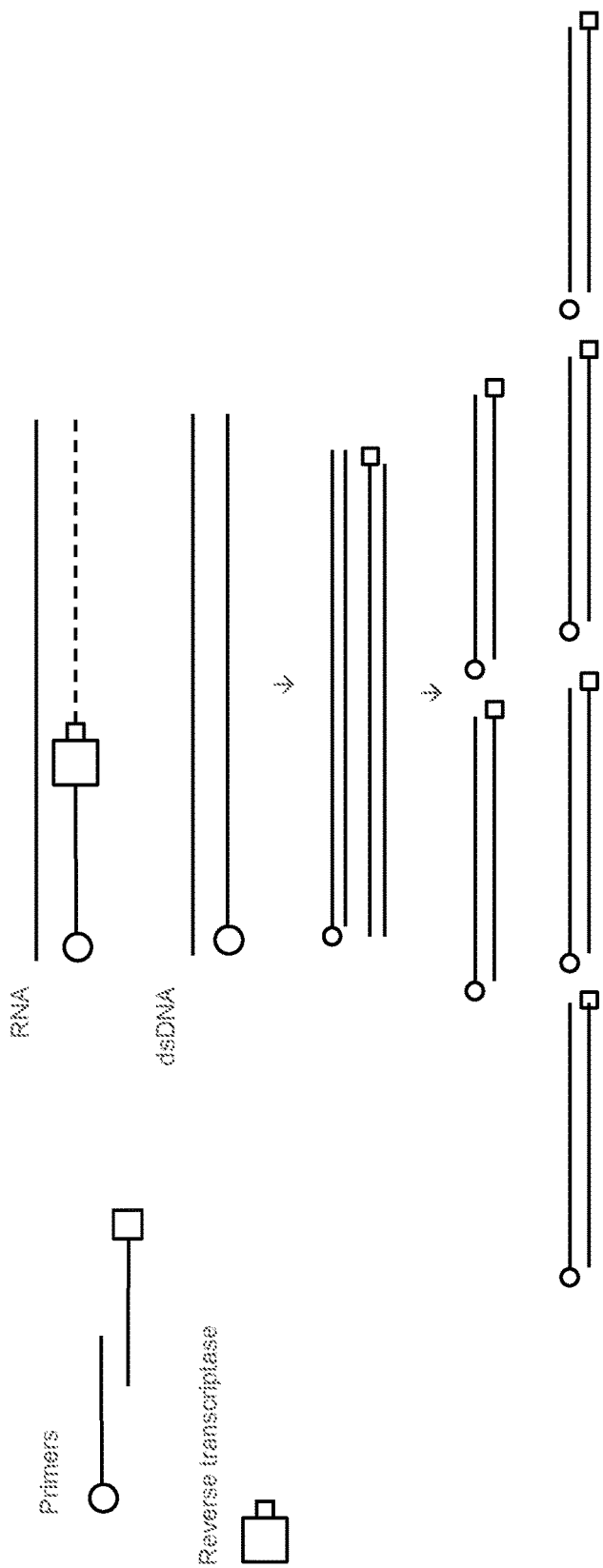
Figure 32E:
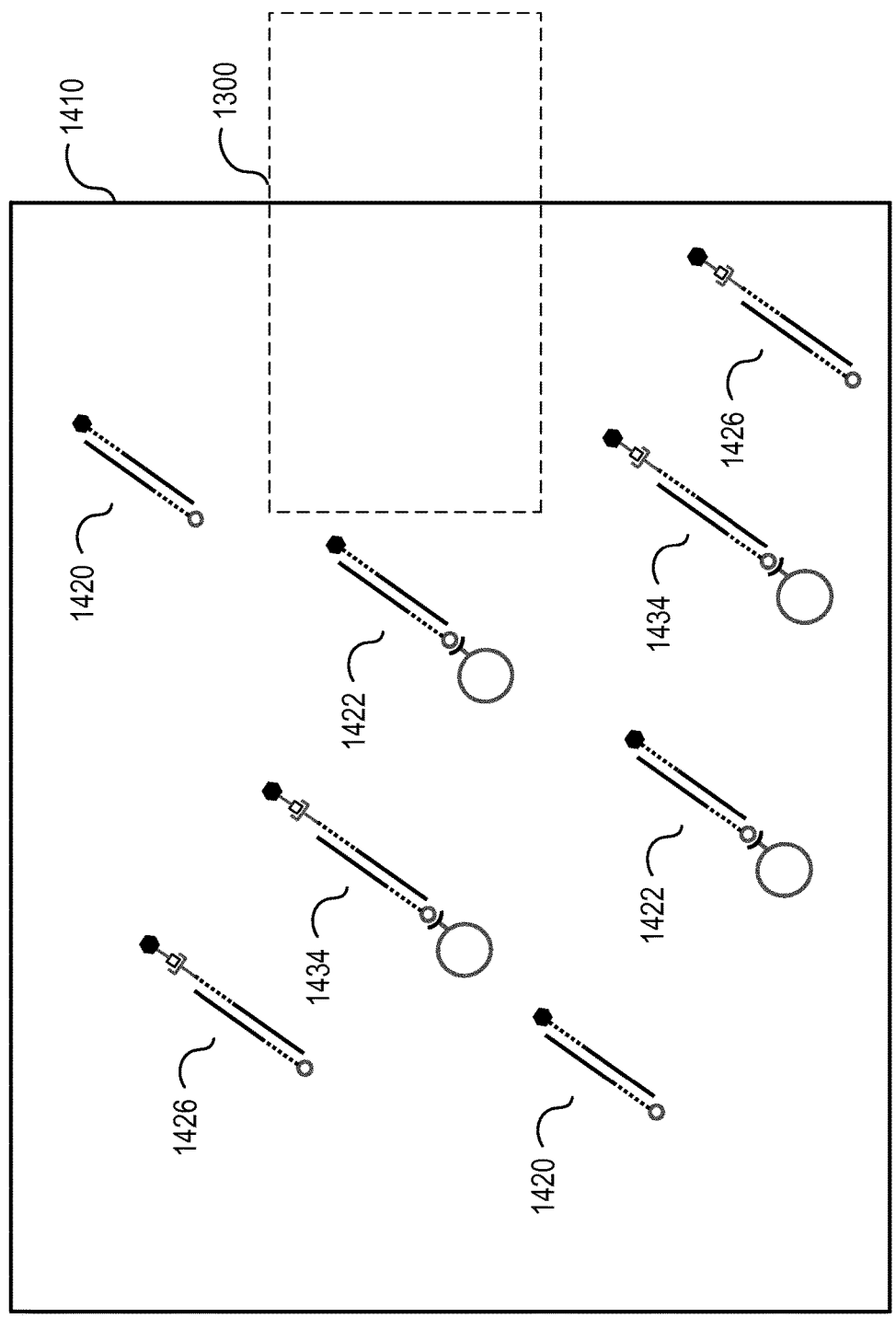

The amplification may be an isothermal reaction such as isothermal amplification. FIG. 32D shows an exemplary process for isothermal amplification of nucleic acids. The amplification of nucleic acids within sample preparation reservoir 1410 generates amplicons as shown in FIG. 32E. Actuation of the sonication element to mix the contents of the sample preparation reservoir may promote the amplification. The amplicons may form sandwich complexes which are labeled amplicon complexes 1422 comprising a capture label and a signaling label, or labeled amplicon complexes 1434. For example, a forward primer and reverse primer amplicon may be bound to a signaling agent and/or bound to a solid particle as a result of the mixing. Amplicon complexes 1422 and 1434 may each include a solid particle configured to be magnetically held over a working electrode in a sensor such that a signaling agent of the complex can react with a substrate from a substrate solution. The amplicons may form partial sandwich complexes which may be unlabeled partial amplicon complexes 1420 or labeled partial amplicon complexes 1426. For example, an internal control forward primer and an internal control reverse primer amplicon may be bound to a signaling agent as a result of the mixing. Partial amplicon complexes 1420 and 1426 may be configured to bind to pre-bound surface affinity molecules over an electrode (e.g., working electrode and/or positive control working electrode) of a sensor.

Pre-conjugated primers (either covalently or through a linkage such as biotin-streptavidin) may be used wherein either the forward or the reverse is conjugated to a particle and the other side (forward if reverse was conjugated to particle and reverse if forward was conjugated to particle) is conjugated to a signaling agent either directly or indirectly and there may also be a population of unlabelled and unconjugated primers that facilitates the reaction to occur more efficiently.

Figure 32F:
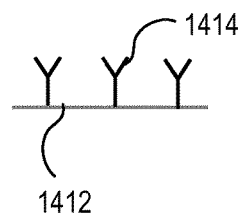

Referring now to FIG. 32F, a surface of a sensor for use in a cartridge device described herein is shown. Sensor surface 1412 may include a plurality of affinity molecules 1414 pre-bound to sensor surface 1412 within the cartridge. Surface affinity molecule 1414 may be any affinity molecule described herein and preferably has an affinity to bind to a partial amplicon complex. For example, surface affinity molecule 1414 may have an affinity to bind to an internal control capture element bound to an internal control forward primer and an internal control reverse primer amplicon bound to a signaling agent. The internal control reverse primer amplicon may be bound to a signaling agent, e.g., via a spacer, or may be bound to a label, e.g., via a spacer, which is bound to an affinity molecule bound to a signaling agent. Sensor surface 1412 is preferably positioned within the analysis channel of the cartridge for exposure to fluid released from the sample preparation reservoir and/or fluid released from the substrate reservoir. FIG. 32F shows sensor surface 1412 prior to exposure to fluid from the reservoir(s). Sensor surface 1412 may be used on any of the sensors described above including sensors 338, 338', 338", 338''', 338''''. Sensor surface 1412 may be used for a working electrode of the sensor such as working electrode 340" and/or may be used for a positive control working electrode of the sensor such as positive control working electrodes 376, 376', 376".

Figure 32G:
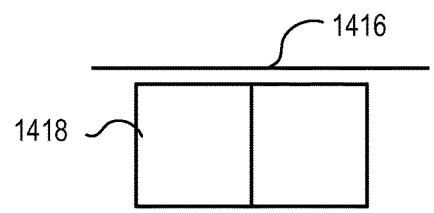

Referring now to FIG. 32G, another surface of a sensor for use in a cartridge device described herein is shown. Sensor surface 1416 may have a self-assembled monolayer such as thiolated ethylene glycol and/or a dithiol such as hexaethylene glycol dithiol for added stability. Sensor surface 1416 is preferably positioned within the analysis channel of the cartridge for exposure to fluid released from the sample preparation reservoir and/or fluid released from the substrate reservoir. FIG. 32G shows sensor surface 1416 prior to exposure of fluid from the reservoir(s). Sensor surface 1416 may be used on any of the sensors described above including sensors 338, 338', 338", 338''', 338''''. Sensor surface 1416 may be used for a working electrode of the sensor such as working electrodes 340, 340', 340''', 340''''. Sensor surface 1416 is configured to be exposed to magnetic fields from magnetic field generator 1418, e.g., when the cartridge is inserted in the reader. For example, magnetic field generator 1418 may be similar to first magnetic generator 406 and second magnetic generator 407 of reader 400 described above.

Figure 32H:
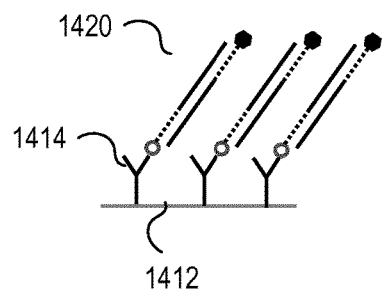

Referring now to FIG. 32H, sensor surface 1414 is shown after exposure to reagents, e.g., from fluid flowing into the analysis channel from the sample preparation reservoir. As shown in FIG. 32H, partial amplicon complexes 1420 of control amplicon molecules may bind to surface affinity molecules 1414 to complete the amplicon complexes. For example, surface affinity molecule 1414 may bind to an internal control capture element bound to an internal control forward primer amplicon and an internal control reverse primer amplicon bound to a signaling agent as shown in FIG. 32H. A chemical reaction may occur when the amplicon complexes are exposed to a substrate, e.g., from substrate reservoir, such that the sensor may detect electrical signals resulting from chemical reactions over the sensor. For example, the mixed fluid from the sample preparation reservoir may be introduced into the analysis channel such that the signaling agents directly or indirectly bound to the amplicon primers from the mixed fluid from the sample preparation reservoir localize over sensor surface 1412 by binding with pre-bound surface affinity molecules 1414, e.g., via capture elements. The chemical reactions may occur when fluid from the substrate reservoir reacts with particles from the mixed fluid from the sample preparation reservoir localized over the sensor. For example, a substrate solution having a substrate may be introduced from the substrate reservoir and the sensor having sensor surface 1412 may detect electrical signals resulting from the reactions between the substrate (e.g., TMB, OPD) and the signaling agents (e.g., HRP, SBP) localized over the sensor. The reactions may cause electrons to be stripped from the substrate by the signaling agents (which electrons may be donated to acceptor molecules from the substrate solution) thereby generating electrical signals detectable by the sensor. If sensor surface 1412 is on a working electrode, such detected electrical signals may be used to generate the signal indicative of the presence, absence, and/or quantity of one or more analytes within the sample. If sensor surface 1412 is on a positive control working electrode, such detected electrical signals may be used for error detection. For example, if a parameter(s), e.g., voltage, current, of the detected electrical signals is not within a predetermined range(s), there may be an error and the test may be rejected. If the parameter(s) is within the predetermined range, electrical signals detected by the working electrode of the sensor may be used to generate the signal indicative of the presence, absence, and/or quantity of one or more analytes within the sample. The signals from the positive control working electrode and/or the working electrode may be transmitted to reader device 400, e.g., via respective electrical connectors of cartridge device 300 and reader device 400.

Figure 32I:
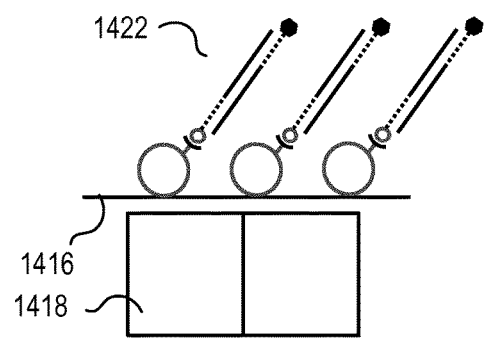

Referring now to FIG. 32I, sensor surface 1416 is shown after exposure to reagents, e.g., from fluid flowing into the analysis channel from the sample preparation reservoir. It should be understood that sensor surface 1416 and sensor surface 1412 or sensor surface 1424 may be exposed to the sample preparation reservoir fluid at substantially the same time, e.g., when sensor surface 1416 corresponds to working electrode 340''' or working electrode 340'''' and sensor surface 1412 corresponds to positive control working electrode 376' of sensor 338''' or positive control working electrode 376" of sensor 338". Similarly, sensor surface 1416 and sensor surface 1412 or sensor surface 1424 may be exposed to the substrate reservoir fluid at substantially the same time, thereby causing reactions to occur between the substrate and reagents (e.g., signaling agents) at substantially the same time.

As shown in FIG. 32I, amplicon complexes 1422 of target amplicon molecules may localize over sensor surface 1416. Target amplicon complexes 1422 may be formed of a solid particle bound to target amplicon primers bound to a signal agent. For example, the solid particle may be bound to an affinity molecule bound to a capture element bound to a target forward primer amplicon and a target reverse primer amplicon bound to the signaling agent as shown in FIG. 32I. A chemical reaction may occur when the target amplicon complexes are exposed to a substrate, e.g., from substrate reservoir, such that the sensor may detect electrical signals resulting from chemical reactions over the sensor. For example, the mixed fluid from the sample preparation reservoir may be introduced into the analysis channel such that signaling agents directly or indirectly bound to target amplicons from the mixed fluid from the sample preparation reservoir localize over sensor surface 1416 responsive to magnetic fields from magnetic field generator 1418 holding the solid particles directly or indirectly bound to the signaling agents. The chemical reactions may occur when fluid from the substrate reservoir reacts with particles from the mixed fluid from the sample preparation reservoir localized over the sensor. For example, a substrate solution having a substrate may be introduced from the substrate reservoir and the sensor having sensor surface 1416 may detect electrical signals resulting from the reactions between the substrate (e.g., TMB, OPD) and the signaling agents (e.g., HRP, SBP) localized over the sensor. The reactions may cause electrons to be stripped from the substrate by the signaling agents (which electrons may be donated to acceptor molecules from the substrate solution) thereby generating electrical signals detectable by the sensor. If sensor surface 1416 is on a working electrode, such detected electrical signals may be used to generate the signal indicative of the presence, absence, and/or quantity of one or more analytes within the sample. The signal from the working electrode may be transmitted to reader device 400, e.g., via respective electrical connectors of cartridge device 300 and reader device 400.

Figure 32J:
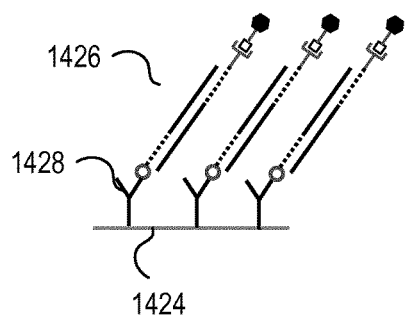

Referring now to FIG. 32J, sensor surface 1424 is similar to sensor surface 1412 of FIG. 32H and the control amplicon complexes are similar to the control amplicon complexes of FIG. 32H except control amplicon complexes 1426 include a label bound to the internal control reverse primer amplicon which is bound to an affinity molecule bound to a signaling agent. For example, surface affinity molecule 1428 may bind to an internal control capture element bound to an internal control forward primer amplicon and an internal control reverse primer amplicon bound to a label bound to an affinity molecule bound to a signaling agent as shown in FIG. 32J. The reaction and signal processing may occur as described above with respect to FIG. 32H.

Figure 32K:
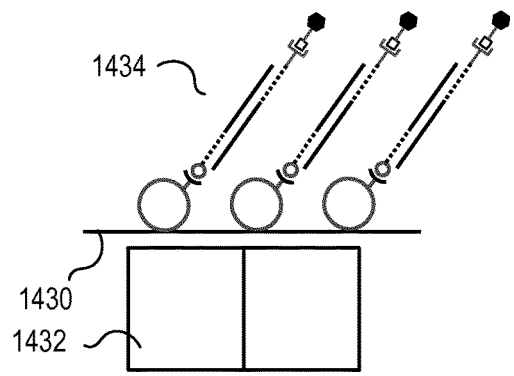

Referring now to FIG. 32K, sensor surface 1430 is similar to sensor surface 1416 and magnetic field generator 1432 is similar to magnetic field generator 1418 of FIG. 32I and the target amplicon complexes are similar to the target amplicon complexes of FIG. 32I except target amplicon complexes 1434 include a label bound to the target reverse primer amplicon which is bound to an affinity molecule bound to a signaling agent. For example, a solid particle may be bound to an affinity molecule bound to a capture element bound to a target forward primer amplicon and a target reverse primer amplicon bound to a label bound to an affinity molecule bound to a signaling agent as shown in FIG. 32K. The reaction and signal processing may occur as described above with respect to FIG. 32I.

As will be readily apparent to one skilled in the art, while one type of molecule may be shown as present in an illustrated reaction, for example, one solid particle 1320 in FIG. 32B, a plurality of the types of molecules may be present. In addition, all the types of molecules shown in FIGS. 32A through 32K need not be included in a reaction.

The sample reagents may include only one population of magnetic particles and one population of detector agents or competitive binding agents. Such embodiments may be tailored for detection of a single target analyte of interest.

In other embodiments, multiple populations of magnetic particles and detector agents and/or competitive binding agents and/or multiple populations of distinct affinity molecules are provided, each population constructed to have its own affinity. For example, each population of magnetic particles has a unique affinity molecule bound to its surface, and each population of magnetic particles is thereby designed to bind with a different target analyte. Similarly, each population of detector agents includes a unique affinity molecule and is thereby designed to bind with a different target analyte. A multiplexing scheme may be used such that a first size of magnetic particles is more magnetically responsive to a first working electrode, and a second size of magnetic particles is more magnetically responsive to a second working electrode, etc. (third, fourth, fifth, etc. sizes and working electrodes may be used). Alternatively or additionally, different surface binding schemes may be used for different working electrodes such that a first set of affinity molecules directed to a first target analyte population is immobilized at the surface of a first working electrode and a second set of affinity molecules directed to a second target analyte population is immobilized at the surface of a second working electrode of the electrochemical cell, etc. (third, fourth, fifth, etc. affinities and working electrodes may be used). In this manner, the respective target analyte population binds to the respective affinity molecules (and signaling agent) and binds to the surface bound affinity molecules on the surface of the respective working electrode. Accordingly, multiple sets of affinity molecules and addressable working electrodes may be used to execute a multiplexing scheme. One or more populations of magnetic particles having unique magnetic properties and/or unique affinity molecules bound thereto, as described above, may be multiplexed with one or more different surface binding schemes. For example, the process of FIGS. 31A-31H may occur at substantially the same time as the process of FIGS. 32A-32K within the same cartridge using the same or different sample preparation reservoirs and the same or different sensors. In embodiments employing the competitive binding approach, each population of competitive binding agents may include a different pre-bound target analyte and is thereby designed to compete with a different target analyte. Such embodiments allow for the detection of a plurality of target analytes, including detection of multiple foodborne pathogens, multiple contaminants, and multiple ailments.

Those skilled in the art will appreciate that the possibilities for forming the magnetic particle-bound complexes are numerous and all such possibilities are contemplated herein. For example, the sample preparation reagents may include a biotin-labelled antibody, which binds to a portion of the target analyte. In some embodiments, antibodies and/or nucleic acids present among the sample preparation reagents may be pre-biotinylated such that a streptavidin conjugated signaling enzyme can bind with the biotinylated detector to form a complex. One such streptavidin conjugated signaling enzyme is HRP. The tagging combination is not limited to biotin-streptavidin. Any suitable tagging scheme will work. In another example, multiple HRP enzymes are conjugated together into a molecule commonly known as a Poly-HRP molecule in order to enhance the signal generating capability of the resultant sandwich complex.

In addition to the components that form the magnetic particle-bound complexes, the sample preparation reagents of various embodiments may include one or more of: (a) agents that facilitate formation of the magnetic particle-bound complexes, such as salts; (b) agents that facilitate access and specificity to target analytes, such as detergents and enzymes for lysis of bacteria or viruses or cutting of large molecules or nucleotides; (c) blocker proteins to decrease nonspecific binding; and (d) stabilizers such as, for example, trehalose, which can improve the shelf life of the sample preparation reagents.

For the sample preparation reagents, salts may be necessary to enhance the likelihood of binding. For example, phosphate buffered saline (PBS) may be the fluid held in the sample preparation reservoir. Any salt which does not interfere with electrochemical detection may be provided within the reagents.

Blocker proteins, such as the well-known Bovine Serum Albumin, casein, fibrinogen, or other blocker protein may be provided to help stabilize the antibodies, enzymes, and/or other proteins present among the sample preparation reagents. Such blocker proteins may also help prevent non-specific binding of signaling enzymes to the magnetic particles and to the walls of the systems and devices described elsewhere herein.

Additionally, for embodiments that require lysis to access the molecules or nucleic acids of interest, detergents may be employed. In various embodiments, nonionic detergents, rather than ionic detergents, are provided to prevent denaturation of the signaling enzyme and/or antibodies. Detergents may enhance lysis of bacteria, but are also useful for gently lysing various viruses, such as the influenza virus. Such lysing may be desirable to improve access to target analytes such as nucleoproteins internal to a virus. Additionally, the sample preparation reagents may include enzymes that enhance lysis and reduce viscosity during lysis; such reagents may be necessary for the preparation of some samples, for example, samples containing bacteria such as *E. coli*. The enzymes that enhance and facilitate lysis may include lysozymes and DNAses that chop up released genomic DNA without disrupting nucleic acid probes on the surface of the magnetic particles.

Enzymes such as RNAses or DNAses, which selectively chop larger nucleotide sequences into smaller sequences, may be useful for generating smaller fragments having favorable binding kinetics. Such enzymes may be present in the sample preparation reagents. Other components also may be included within the sample preparation reagents. For example, a stabilizer agent such as trehalose, may be present; such stabilizer agents help protect proteins from oxidation and thereby increase the shelf-life of the reagents, especially at room temperature.

Figure 33:
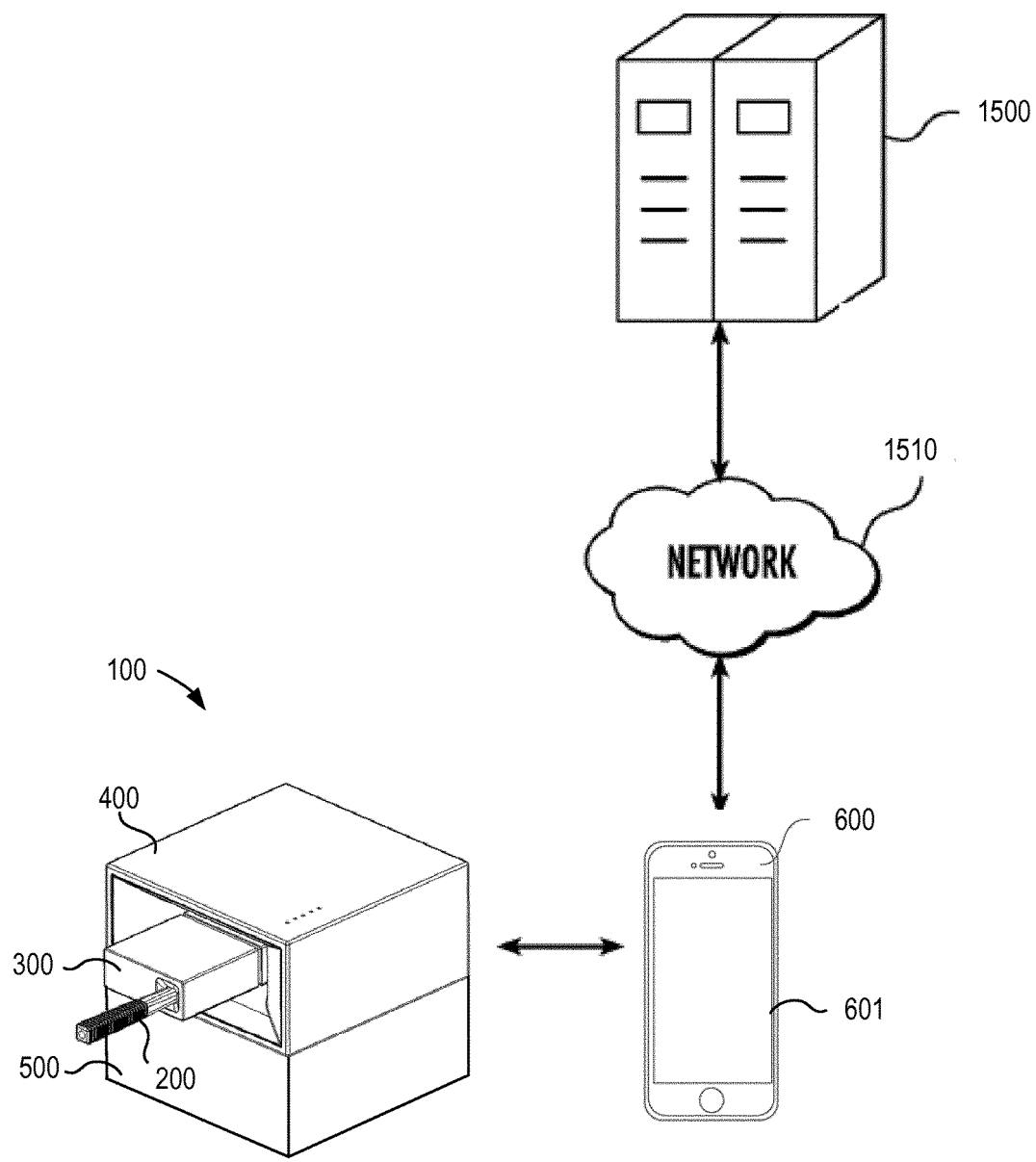
FIG. 33 provides a schematic depiction of the exemplary analyte detection system FIGS. 1A-1B communicatively coupled to one or more servers via a network.

Referring now to FIG. 33, detection system 100 is shown in use where sample collection device 200 is inserted in cartridge device 300 which is inserted in reader device 400. Reader device 400 may transmit signals indicative of the presence, absence, and/or quantity of one or more target analytes to a mobile device running software-based detection interface system 600 such that a user may review and interact with the analyzed results on the presence, absence, and/or quantity of one or more target analytes. Such results may be transmitted to server 1500 via network 1510. Software-based detection interface system 600 may be downloaded onto the mobile device. Software-based detection interface system 600 may be a dedicated application or "app" and may be downloaded from an online store such as iTunes™ (Apple, Inc., Cupertino, Calif.), the App Store (Apple, Inc.), Google™ Play (Google, Inc., Mountain View, Calif.), the Android™ Marketplace (Google, Inc.), Windows™ Phone Store (Microsoft Corp., Redmond, Wash.), or BlackBerry™ World (BlackBerry, Waterloo, Ontario, Canada). Preferably, software-based detection interface system 600 need only be downloaded once—although updates may be downloaded.

Sample collection device 200 may be disposable and configured for one-time use. It may come within removable sterile packaging. Once inserted into the input tunnel of cartridge device 300, sample collection device 200 may be locked into a permanent fixed engagement and cannot be used again. Cartridge device 300 also may be disposable and configured for one-time use. Once sample collection device 200 locks into place within the input tunnel of cartridge 300, cartridge 300 cannot be used again. Cartridge 300, may, however, be removed from the reader 400. Cartridge 300 and reader 400 may be configured to be separably coupled, and cartridge 300 may be inserted and removed from the dock of reader 400 at least before and after implementation of a detection protocol. Reader 400 may include a locking mechanism for temporarily locking cartridge 300 into place, and limiting removal, during the duration of a detection test cycle. Reader 400 of various embodiments is reusable.

Reader 400, and the entire detection system 100, may be configured for non-clinical, consumer-directed use. Accordingly, system 100 is easy to use and generates results quickly. Results of a target analyte detection protocol may be generated in 30 minutes or less from the time a sample from sample collection device 200 is inserted into the system's cartridge 300. Results may be generated in less than 20 minutes, less than 10 minutes, and/or less than 5 minutes. Additionally, the consumer-directed system may be small for an unobtrusive presence within a home, school, office, or other place of employment. Cartridge 300, sample collection device 200, and reader 400 together may be approximately the size of a smartphone or other mobile computing device. System 100 may be sized and configured to be portable. In such embodiments, in addition to a compact, hand-held design, all fluids within the sample are properly sealed and separated such that no leaking or premature oxidation reactions will occur due to jostling of the system components while on the go.

To promote use by lay people in non-clinical settings, system 100 may be designed to be "dummy proof" by including a self-activating and self-run detection protocol. For example, FIG. 33 depicts an example in which cartridge 300 has been placed into the dock of reader 400 and sample collection device 200 has been inserted into the input tunnel of cartridge 300. In the depicted embodiment, loading cartridge 300 into reader 400 may establish an electrical connection between the pins of cartridge 300 and reader 400, thereby completing a circuit within reader 400, which automatically activates reader 400. Upon being activated, reader 400 may determine if sample collection device 200 is properly inserted in cartridge 300, e.g., upon receipt of an electrical signal indicating that the contact switch in cartridge 300 has been activated. Upon detection, reader 400 may initiate a detection protocol automatically without any further human intervention. The automated start ensures that mixing of reagents and sample within the sample preparation reservoir occurs consistently at a fixed time following insertion of sample collection device 200, leading to consistent test results. Alternatively, the testing protocol may initiate when a user presses a "go", "run", "start", or other similar button or icon on reader 400 or computing device 601 running software 600.

In various embodiments, computing device 601 may be included within the system: to provide for more computing power and/or more memory; to provide a wireless transceiver for pulling data from, and transmitting data to, a remote server; and/or to provide a display screen and user interface. Computing device 600 is not needed within every embodiment.

One skilled in the art will appreciate that the embodiment in FIG. 33 is illustrative in nature only and various components may be added, deleted, or substituted and various different hierarchies and modes of communication between the devices may be employed.

Communication network 1510 through which some or all of the various devices communicate with one another. The network may be a local area network (LAN) or a wide area network (WAN). Network 1510 may be a wireless communication network, such as, for example, a mobile WiMAX network, LTE network, Wi-Fi network, or other wireless network. The communication between computing device 601 having a user interface software 600 and server 1500 may occur over the internet via a wired network, such as a DSL cable connection.

Communication between reader 400 and computing device 601 may occur, wirelessly, for example, using Bluetooth®, Wi-Fi, near-field communications, or other radiofrequency technology. Alternatively, transmission of signals between reader 400 and computing device 601 may occur over a cord, cable, or other wired or direct connection. In various embodiments, computing device 601 or other device having a user interface software 600 includes a software application for a front-end, graphical user interface for presenting test results to a user.

Reader 400 may be configured to control the tests and processes needed to detect and/or quantify one or more target analytes within a sample. To do so, a significant amount of information may be stored within the memory of reader 400. Alternatively, some or all of the information may be stored within computing device 601 and/or server 1500 and accessible by reader 400 via the communication network 1510. Such information may include, for example, a database of cartridge keys, which identifies each cartridge type by the signal generated by the cartridge's unique identifier stored in the cartridge's memory. The information also may include test protocols associated with each type of cartridge. The test protocols may specify details such as how long to mix sample preparation reagents through sonication, the frequency of the sonication, when to heat the various heat-sensitive valves, etc. The information may also include correlation tables for each cartridge type, which correlate detected sensor signals to the absence, presence, and/or a specific quantity of a target analyte. Additionally, the information stored by reader 400 and/or server 1500 may include one or more past results. Reader 400 may store test results at least until reader 400 comes into communication with a remote computing device; at such time, the results may be transmitted to the remote computing device (e.g., computing device 601, server 1500) for display and/or long-term storage.

Server 1500 also may store user profiles, which may include biographical information entered into the system by a user through computing device 601 having user interface software 600. A log of test results for each user may also be stored by server 1500 and accessible for viewing by the user through transmission of such data to computing device 601 with user interface software 600.

Definitions

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

The term "about" or "approximately," when used before a numerical designation or range (e.g., pressure or dimensions), indicates approximations which may vary by (+) or (−) 5%, 1% or 0.1%.

As used in the specification and claims, the singular form "a", "an" and "the" include both singular and plural references unless the context clearly dictates otherwise. For example, the term "a molecule" may include, and is contemplated to include, a plurality of molecules. At times, the claims and disclosure may include terms such as "a plurality," "one or more," or "at least one;" however, the absence of such terms is not intended to mean, and should not be interpreted to mean, that a plurality is not conceived.

As used in the specification and claims, "at least one of" means including, but not limited to, one or more of any combination of the following. For example, "at least one of A, B, and C" or "at least one of A, B, or C" means including, but not limited to, A(s) or B(s) or C(s) or A(s) and B(s) or A(s) and C(s) or B(s) and C(s) or A(s) and B(s) and C(s); none of which excludes other elements such as D(s), E(s), etc.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

Although the foregoing has included detailed descriptions of some embodiments by way of illustration and example, it will be readily apparent to those of ordinary skill in the art in light of the teachings of these embodiments that numerous changes and modifications may be made without departing from the spirit or scope of the appended claims.

What is claimed is:

1. A sample analysis cartridge comprising:
   an input tunnel that extends from an aperture, the input tunnel configured to permit insertion of a sample collection device having a distal portion adapted to be exposed to a sample comprising a target nucleic acid;
   a reagent ball comprising reagents for amplification of the target nucleic acid by an amplification reaction;
   a reservoir configured to hold a fluid, the reservoir further configured to receive the sample from the sample collection device and to receive the reagent ball such that the sample is mixed with an effective amount of the reagents for amplification of the target nucleic acid in the fluid of the reservoir to generate amplicons comprising signaling agents;
   an analysis channel configured to receive the fluid comprising the amplicons from the reservoir; and
   a sensor at least partially disposed in the analysis channel such that the amplicons indicative of at least one of a presence, absence, or quantity of the target nucleic acid in the sample localize over the sensor and the sensor senses signals indicative of at least one of the presence, absence, or quantity of the target nucleic acid in the sample based on reactions between a substrate and the signaling agents of the amplicons localized over the sensor.

2. The sample analysis cartridge of claim 1, wherein the reagent ball comprises polymerase, primers for amplification of the target nucleic acid and the signaling agent for the detection of the amplification of the target nucleic acid.

3. The sample analysis cartridge of claim 2, wherein the reagent ball further comprises one or more affinity molecules covalently or non-covalently bound to a solid particle for detection of the target nucleic acid.

4. The sample analysis cartridge of claim 1, wherein the reagent ball is disposed in the input tunnel and not exposed to the fluid in the reservoir in a pre-mixing position, and
wherein the reagent ball is configured to move into the reservoir for mixing with the fluid in the reservoir in a mixing position.

5. The sample analysis cartridge of claim 1, further comprising a shuttle defining a first compartment and a second compartment, the first and second compartments configured to be disposed within the reservoir in a mixing position.

6. The sample analysis cartridge of claim 5, wherein the shuttle is configured to move within the input tunnel such that the first and second compartments are not exposed to the fluid in the reservoir in a pre-mixing position.

7. The sample analysis cartridge of claim 5, further comprising a piezoelectric transducer configured to emit energy into the reservoir to move the fluid in the reservoir between the first and second compartments to mix the fluid, the sample, and the reagents in the reservoir.

8. The sample analysis cartridge of claim 5, wherein the first compartment comprises a reagent ball compartment configured to house the reagent ball and the second compartment comprises a sample compartment configured to receive the sample from the sample collection device.

9. The sample analysis cartridge of claim 1, further comprising a temperature sensor configured to sense temperature indicative of temperature of the fluid in the reservoir.

10. The sample analysis cartridge of claim 9, wherein the temperature sensor is disposed on a printed circuit board positioned adjacent to a piezoelectric transducer.

11. The sample analysis cartridge of claim 10, wherein the piezoelectric transducer is configured to emit energy into the reservoir to move the fluid in the reservoir to mix the fluid, the sample, and the reagents in the reservoir and to emit the energy in a modified manner based on the sensed temperature.

12. The sample analysis cartridge of claim 11, wherein the energy emitted by the piezoelectric transducer is configured to cause the amplification reaction to cure on the target nucleic acid.

13. The sample analysis cartridge of claim 1, further comprising a contact switch configured to indicate insertion of the sample collection device in the input tunnel.

14. The sample analysis cartridge of claim 1, wherein the reagent ball further comprises magnetic particles configured to be magnetically held over a target working electrode of the sensor.

15. The sample analysis cartridge of claim 1, further comprising a substrate reservoir configured to hold a substrate solution comprising the substrate, the substrate reservoir comprising an outlet configured to permit the substrate solution to travel therethrough and into the analysis channel to at least the portion of the sensor such that the substrate reacts with signaling agents localized over the sensor.

16. A sample analysis cartridge comprising:
an input tunnel that extends from an aperture, the input tunnel configured to permit insertion of a sample collection device having a distal portion adapted to be exposed to a sample comprising a target nucleic acid;
a reservoir configured to hold a fluid, the reservoir further configured to receive the sample from the sample collection device such that the sample is mixed with an effective amount of reagents for amplification of the target nucleic acid in the fluid of the reservoir to generate amplicons comprising signaling agents;
a shuttle defining a first compartment and a second compartment, the first and second compartments configured to be disposed within the reservoir in a mixing position;
an analysis channel configured to receive the fluid comprising the amplicons from the reservoir; and
a sensor at least partially disposed in the analysis channel such that the amplicons indicative of at least one of a presence, absence, or quantity of the target nucleic acid in the sample localize over the sensor and the sensor senses signals indicative of at least one of the presence, absence, or quantity of the target nucleic acid in the sample based on reactions between a substrate and the signaling agents of the amplicons localized over the sensor.

17. The sample analysis cartridge of claim 16, further comprising a reagent ball comprising the reagents for amplification of the target nucleic acid by an amplification reaction.

18. The sample analysis cartridge of claim 17, wherein the reagent ball comprises polymerase, primers for amplification of the target nucleic acid and the signaling agent for the detection of the amplification of the target nucleic acid.

19. The sample analysis cartridge of claim 18, wherein the reagent ball further comprises one or more affinity molecules covalently or non-covalently bound to a solid particle for detection of the target nucleic acid.

20. The sample analysis cartridge of claim 17, wherein the reagent ball is disposed in the input tunnel and not exposed to the fluid in the reservoir in a pre-mixing position, and
wherein the reagent ball is configured to move into the reservoir for mixing with the fluid in the reservoir in a mixing position.

21. The sample analysis cartridge of claim 16, wherein the shuttle is configured to move within the input tunnel such that the first and second compartments are not exposed to the fluid in the reservoir in a pre-mixing position.

22. The sample analysis cartridge of claim 16, further comprising a piezoelectric transducer configured to emit energy into the reservoir to move the fluid in the reservoir between the first and second compartments to mix the fluid, the sample, and the reagents in the reservoir.

23. The sample analysis cartridge of claim 16, wherein the first compartment comprises a reagent ball compartment configured to house a reagent ball comprising the reagents for amplification of the target nucleic acid by an amplification reaction and the second compartment comprises a sample compartment configured to receive the sample from the sample collection device.

24. The sample analysis cartridge of claim 16, further comprising a temperature sensor configured to sense temperature indicative of temperature of the fluid in the reservoir.

25. The sample analysis cartridge of claim 24, wherein the temperature sensor is disposed on a printed circuit board positioned adjacent to a piezoelectric transducer.

26. The sample analysis cartridge of claim 25, wherein the piezoelectric transducer is configured to emit energy into the reservoir to move the fluid in the reservoir to mix the fluid, the sample, and the reagents in the reservoir and to emit the energy in a modified manner based on the sensed temperature.

27. The sample analysis cartridge of claim 26, wherein the energy emitted by the piezoelectric transducer is configured to cause an amplification reaction to cure on the target nucleic acid.

28. The sample analysis cartridge of claim 16, further comprising a contact switch configured to indicate insertion of the sample collection device in the input tunnel.

29. The sample analysis cartridge of claim 16, further comprising a reagent ball comprising the reagents for amplification of the target nucleic acid by an amplification reaction, the reagent ball further comprising magnetic particles configured to be magnetically held over a target working electrode of the sensor.

30. The sample analysis cartridge of claim 16, further comprising a substrate reservoir configured to hold a substrate solution comprising the substrate, the substrate reservoir comprising an outlet configured to permit the substrate solution to travel therethrough and into the analysis channel to at least the portion of the sensor such that the substrate reacts with signaling agents localized over the sensor.

\* \* \* \* \*